United States Patent
Zhu et al.

(10) Patent No.: US 9,051,327 B2
(45) Date of Patent: Jun. 9, 2015

(54) PYRIDAZINO[4,5-D]PYRIMIDIN-5(6H)-ONE INHIBITORS OF KINASES

(71) Applicant: AbbVie Inc., North Chicago, IL (US)

(72) Inventors: Gui-Dong Zhu, Gurnee, IL (US); Jane Gong, Deerfield, IL (US); Andrew S. Judd, Grayslake, IL (US); Virajkumar B. Gandhi, Gurnee, IL (US); Alexander R. Shoemaker, Green Oaks, IL (US); Thomas D. Penning, Elmhurst, IL (US); Michael R. Michaelides, Libertyville, IL (US); Chunqiu Lai, Libertyville, IL (US); Keith W. Woods, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/307,680

(22) Filed: Jun. 18, 2014

(65) Prior Publication Data

US 2014/0296220 A1 Oct. 2, 2014

Related U.S. Application Data

(62) Division of application No. 13/552,876, filed on Jul. 19, 2012, now Pat. No. 8,796,289.

(60) Provisional application No. 61/509,226, filed on Jul. 19, 2011.

(51) Int. Cl.
*A01N 43/90* (2006.01)
*A61K 31/519* (2006.01)
*C07D 487/02* (2006.01)
*C07D 487/04* (2006.01)

(52) U.S. Cl.
CPC .................................. *C07D 487/04* (2013.01)

(58) Field of Classification Search
USPC ....................................... 514/262.1; 544/256
See application file for complete search history.

(56) References Cited

U.S. PATENT DOCUMENTS

2007/0254892 A1 11/2007 Sagara et al.

FOREIGN PATENT DOCUMENTS

EP 2168966 A1 3/2010
WO 2009151997 A1 12/2009

OTHER PUBLICATIONS

Vippagunta et al (2001).*
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Glotzer M., et al., "Cyclin is Degraded by the Ubiquitin Pathway," Nature, 1991, vol. 349 (6305), pp. 132-138.
Hashimoto O., et al., "Cell cycle Regulation by the Wee1 Inhibitor PD0166285, Pyrido [2,3-d] Pyimidine, in the B16 Mouse Melanoma Cell Line," Bio Medical Center Cancer, 2006, 6:292.
Hirai H., et al., "Small-molecule Inhibition of Wee1 Kinase by MK-1775 Selectively Sensitizes p53-deficient Tumor Cells to DNA-damaging Agents," Molecular Cancer Therapeutics, 2009, vol. 8 (11), pp. 2992-3000.
International Search Report and Written Opinion for Application No. PCT/US2012/047381, mailed on Aug. 31, 2012, 8 pages.
Leijen S., et al., "Abrogation of the G2 Checkpoint by Inhibition of Wee-1 Kinase Results in Sensitization of p53-deficient Tumor Cells to DNA-damaging Agents," Current Clinical Pharmacology, 2010, vol. 5 (3), pp. 186-191.
Lindqvist A., et al., "The Decision to Enter Mitosis: Feedback and Redundancy in the Mitotic Entry Network," Journal of Cell Biology, 2009, vol. 185 (2), pp. 193-202.
McGowan C.H., et al., "Human Wee1 Kinase Inhibits Cell Division by Phosphorylating p34cdc2 Exclusively on Tyr15," The EMBO Journal, 1993, vol. 12 (1), pp. 75-85.
Nurse P., "Universal Control Mechanism Regulating Onset of M-Phase," Nature, 1990, vol. 344 (6266), pp. 503-508.
O'Connell M.J., et al., "Chk1 is a Wee1 Kinase in the G2 DNA Damage Checkpoint Inhibiting Cdc2 by Y15 Phosphorylation," The EMBO Journal, 1997, vol. 16 (3), pp. 545-554.
Parker L.L., et al., "Inactivation of the p34cdc2-Cyclin B Complex by the Human WEE1 Tyrosine Kinase," Science, 1992, vol. 257 (5078), pp. 1955-1957.
Sabin E.A., et al., "High-Level Expression and in Vivo Processing of Chimeric Ubiquitin Fusion Proteins in *Saccharomyces cerevisiae*," Nature Biotechnology, 1989, vol. 7 (7), pp. 705-709.

(Continued)

*Primary Examiner* — Paul V Ward
(74) *Attorney, Agent, or Firm* — Changxia Sun

(57) ABSTRACT

The present invention relates to compounds of formula (I) or pharmaceutical acceptable salts,

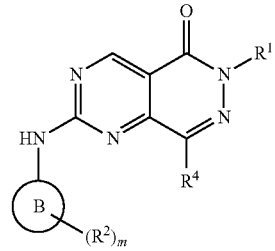

Formula (I)

wherein B, $R^1$, $R^2$, $R^4$, and m are defined in the description. The present invention relates also to compositions containing said compounds which are useful for inhibiting kinases such as wee-1 and methods of treating diseases such as cancer.

10 Claims, No Drawings

(56) References Cited

OTHER PUBLICATIONS

Sancar A., et al., "Molecular Mechanisms of Mammalian DNA Repair and the DNA Damage Checkpoints," Annual Review of Biochemistry, 2004, vol. 73, pp. 39-85.

Stumpff J., et al., "Drosophila Wee1 Kinase Regulates Cdk1 and Mitotic Entry during Embryogenesis," Current Biology, 2004, vol. 14 (23), pp. 2143-2148.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Wang Y., et al., "Knockdown of Chk1, Wee1 and Myt1 by RNA Interference Abrogates G2 Checkpoint and Induces Apoptosis," Cancer Biology & Therapy, 2004, vol. 3 (3), pp. 305-313.

\* cited by examiner

PYRIDAZINO[4,5-D]PYRIMIDIN-5(6H)-ONE INHIBITORS OF KINASES

CROSS-REFERENCE TO RELATED APPLICATIONS

This application is a divisional application of U.S. patent application Ser. No. 13/552,876, filed Jul. 19, 2012, which claims priority to U.S. Provisional Application Ser. No. 61/509,226 filed Jul. 19, 2011, both of which are incorporated by reference in their entirety.

FIELD OF THE INVENTION

This invention pertains to compounds which inhibit the activity of Wee-1 kinase, methods of making the compounds, compositions containing the compounds, and methods of treatment using the compounds.

BACKGROUND OF THE INVENTION

In order to undergo proper cell division, eukaryotic cells must faithfully replicate their genome and then correctly segregate their chromosomes into two daughter cells. This process of cell division, also called the cell cycle, is a step-wise process that is governed by checkpoints to ensure genomic integrity. Upon completion of DNA replication (S-phase), cells enter a growth phase (G2-phase) prior to proceeding into mitosis for chromosome segregation (M-phase). A key regulator of mitosis is the kinase Cdk1 (as called Cdc2) (Nurse, P. (1990) Universal control mechanism regulating onset of M-phase. Nature 344, 503-508). Activation of Cdk1 results in the onset of mitosis, and its subsequent inactivation initiates the exit from mitosis. Cdk1 is activated by the binding of Cyclin A or Cyclin B. Both Cyclin A-Cdk1 and Cyclin B-Cdk1 complexes function to initiate mitosis (Lindqvist, A., et. Al. (2009) The decision to enter mitosis: feedback and redundancy in the mitotic entry network. The Journal of cell biology 185, 193-202). The degradation of Cyclin B triggers the inactivation of Cdk1, resulting in the mitotic exit and entry into a growth (G1) phase prior to beginning a new round of the cell cycle (Glotzer, M., et al. (1991) Cyclin is degraded by the ubiquitin pathway. Nature 349, 132-138).

In addition to Cyclins, Cdk1 is also regulated by Wee1, an atypical tyrosine kinase that phosphorylates Cdk1 on tyrosine 15 (Y15) and inactivates Cdk1 (McGowan, C. H., et al. (1993) Human Wee1 kinase inhibits cell division by phosphorylating p34cdc2 exclusively on Tyr15. The EMBO journal 12, 75-85; Parker, L. L., et al. (1992) Inactivation of the p34cdc2-cyclin B complex by the human WEE1 tyrosine kinase. Science (New York, N.Y. 257, 1955-1957). Wee1 is a critical negative regulator of Cdk1 and functions at the G2-M phase checkpoint to ensure that DNA replication has been completed and the genome is not damaged prior to entering mitosis (O'Connell, et al. (1997) Chk1 is a wee1 kinase in the G2 DNA damage checkpoint inhibiting cdc2 by Y15 phosphorylation. The EMBO journal 16, 545-554). Loss of Wee1 can result in premature entry into mitosis, resulting in mitotic catastrophe and cell death (Stumpff, J., et al. (2004) Drosophila Wee1 kinase regulates Cdk1 and mitotic entry during embryogenesis. Curr Biol 14, 2143-2148). Furthermore, many cancers are defective in their G1-phase checkpoints and are reliant on G2-M phase checkpoints (Sancar, A., et al. (2004) Molecular mechanisms of mammalian DNA repair and the DNA damage checkpoints. Annual review of biochemistry 73, 39-85). Indeed, loss of expression of Wee1 has been shown to lead to the abrogation of the G2-M phase checkpoint and sensitize tumor cells to DNA damage, especially tumors that have lost their G1-phase checkpoint due to a deficiency in the p53 protein (Wang, Y., et al. (2004) Knockdown of Chk1, Wee1 and Myt1 by RNA interference abrogates G2 checkpoint and induces apoptosis. Cancer biology & therapy 3, 305-313).

Inhibitors of Wee1 have the potential to selectively cause lethality in cancerous cells that are defective in other cell cycle checkpoints, while sparing normal tissues that can activate other cell cycle checkpoints. Thus, small molecule inhibitors of Wee1 would be beneficial for therapeutic intervention in cancer and other cell proliferative disorders.

SUMMARY OF THE INVENTION

The present invention has numerous embodiments. One embodiment of this invention, therefore, pertains to compounds that have formula (I) or a pharmaceutically acceptable salt or solvate thereof;

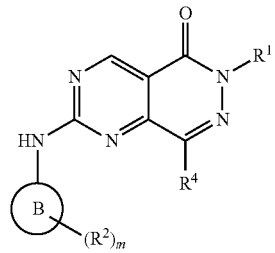

wherein B, $R^1$, $R^2$, $R^4$, and m are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight—or branched—chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight—or branched—chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight—or branched—chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two-or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl(alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4-or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of formula (I) and pharmaceutically acceptable salts and solvates thereof;

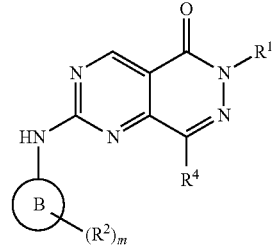

Formula (I)

wherein
B is
(a) phenyl, naphthyl, tetrahydronaphthyl, indenyl, or dihydroindenyl; and m is 1, 2, or 3;
or
(b) 5-16 membered monocyclic, bicyclic, or tricyclic heterocyclyl; and m is 0, 1, 2, or 3;
$R^1$ is hydrogen, $C_{1-6}$ alkyl, $C_{2-6}$ alkenyl, $C_{2-6}$ alkynyl, aryl, heteroaryl, heterocyclyl, cycloalkyl, or cycloalkenyl;

wherein the $R^1$ $C_{1-6}$ alkyl, $C_{2-6}$ alkenyl, and $C_{2-6}$ alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$ alkenyl, $C_{2-6}$ alkynyl, $C_{1-6}$ haloalkyl, —$C_{1-4}$alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$;

$R^2$, at each occurrence, is independently selected from the group consisting of halo, CN, $C_{1-4}$ alkyl, $C_{2-6}$ alkenyl, $C_{2-6}$ alkynyl, $C_{1-4}$-haloalkyl, $C_{1-4}$ hydroxyalkyl, $C_{1-4}$ alkoxy, $C_{1-4}$ haloalkoxy, $C_{1-4}$-thioalkoxy, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $NR^6R^7$—$C_{1-6}$-alkyl-, $OR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$, wherein the $R^2$ cycloalkyl, aryl, heterocycloalkyl, and heteroaryl, alone or part of another group, are optionally substituted with one, two, or three $R^3$;

$R^3$, at each occurrence, is independently selected from the group consisting of halo, $C_{1-4}$ alkyl, $C_{2-6}$ alkenyl, $C_{2-6}$ alkynyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-4}$ alkyl)-, cycloalkyl-($C_{1-4}$ alkyl)-, heteroaryl-($C_{1-4}$ alkyl)-, heterocycloalkyl-($C_{1-4}$ alkyl)-, CN, $NO_2$, $OR^n$, $C(O)R^n$, $C(O)NR^oR^p$, $C(O)OR^n$, $OC(O)R^n$, $OC(O)NR^oR^p$, $NR^oR^p$, $NR^oC(O)R^n$, $S(O)R^n$, $S(O)NR^oR^p$, $S(O)_2R^n$, $NR^oS(O)_2R^n$, and $S(O)_2NR^oR^p$, wherein the $R^3$ aryl, cycloalkyl, heteroaryl, and heterocycloalkyl, alone or as part of another group, are optionally substituted with one, two or three $R^8$;

$R^4$ is hydrogen, $C_{1-6}$ alkyl, $C_{1-6}$ haloalkyl, $C_{1-6}$ alkoxy-$C_{1-6}$-alkyl, $C_{1-6}$ hydroxyalkyl, $C_{2-6}$ alkenyl, $C_{2-6}$ alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$ alkenyl, $C_{1-4}$ haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)R^g$, $OC(O)NR^hR^i$, —$C_{1-6}$ alkyl-$NR^hR^i$, $NR^hR^i$; $NR^hC(O)R^g$, $NR^hNR^iR^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$ alkenyl, and $C_{2-6}$ alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^j$, $OC(O)R^j$, $OC(O)NR^kR^l$, $NR^kR^l$, $NR^kC(O)R^j$, $S(O)R^j$, $S(O)NR^kR^l$, $S(O)_2R^j$, $NR^kS(O)_2R^j$, and $S(O)_2NR^kR^l$;

$R^5$ is independently selected from the group consisting of hydrogen, $C_{1-6}$ alkyl, $C_{1-6}$ hydroxyalkyl, $C_{2-6}$ alkenyl, $C_{2-6}$ alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl; wherein the $R^5$ cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl, $C_{1-4}$ alkoxy, $C_{1-4}$haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl$)_2$;

$R^6$ and $R^7$, at each occurrence, are independently selected from the group consisting of hydrogen, $C_{1-6}$ alkyl, $C_{2-6}$ alkenyl, $C_{2-6}$ alkynyl, $C_{1-6}$-haloalkyl, $C_{1-6}$ hydroxyalkyl, $C_{1-4}$ dialkylamino-$C_{1-4}$ alkyl-, heteroaryl-$C_{1-6}$-alkyl-, heterocycloalkyl-$C_{1-6}$-alkyl-, aryl, cycloalkyl, heteroaryl, and heterocycloalkyl, wherein the $R^6$ and $R^7$ aryl, cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl, $C_{1-4}$ alkoxy, $C_{1-4}$haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl$)_2$;

$R^8$ is independently selected from the group consisting of halo, $C_{1-4}$ alkyl, $C_{1-4}$alkylamino, $C_{1-4}$ dialkylamino-$C_{1-4}$ alkyl-, or 1-methylpiperazinyl;

$R^a$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^a$ aryl, cycloalkyl, heteroaryl, and heterocycloalkyl alone or as part of another group, are optionally substituted with one, two or three substituents independently selected from the group consisting of halo and $C_{1-4}$ alkyl;

$R^b$ and $R^c$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^b$ or $R^c$ aryl, cycloalkyl, heteroaryl, and heterocycloalkyl alone or as part of another group, are optionally substituted with one, two or three substituents independently selected from the group consisting of halo and $C_{1-4}$ alkyl;

$R^d$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^d$ aryl, cycloalkyl, heteroaryl, and heterocycloalkyl, alone or part of another group, are optionally substituted with 1, 2, or 3 substituents independently selected from the group consisting of halo and $C_{1-4}$ alkyl;

$R^e$ and $R^f$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^e$ or $R^f$ aryl, cycloalkyl, heteroaryl, and heterocycloalkyl alone or as part of another group, are optionally substituted with one, two or three substituents independently selected from the group consisting of halo and $C_{1-4}$ alkyl;

$R^g$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$ alkyl;

$R^h$ and $R^i$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl;

$R^j$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^j$ aryl, cycloalkyl, heteroaryl, and heterocycloalkyl alone or as part of another group, are optionally substituted with one, two or three substituents independently selected from the group consisting of halo and $C_{1-4}$ alkyl;

$R^k$ and $R^l$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^k$ or $R^l$ aryl, cycloalkyl, heteroaryl, and heterocycloalkyl alone or as part of another group, are optionally substituted with one, two or three substituents independently selected from the group consisting of halo and $C_{1-4}$ alkyl;

$R^n$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^n$ aryl, cycloalkyl, heteroaryl, and heterocycloalkyl alone or as part of another group, are optionally substituted with one, two or three substituents independently selected from the group consisting of halo and $C_{1-4}$ alkyl;

$R^m$, at each occurrence, is independently selected from the group consisting of hydrogen, $C_{1-6}$ alkyl, $C_{2-6}$ alkenyl, $C_{2-6}$ alkynyl, —C(O)$C_{1-6}$ alkyl, and $C_{1-6}$ haloalkyl; and $R^o$ and $R^p$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^o$ or $R^p$ aryl, cycloalkyl, heteroaryl, and heterocycloalkyl alone or as part of another group, are optionally substituted with one, two or three substituents independently selected from the group consisting of halo and $C_{1-4}$ alkyl.

In one embodiment of formula (I),
B is
(a) phenyl; and m is 1, or 2;
or
(b) 5-16 membered bicyclic, or tricyclic heterocyclyl; and m is 0, 1, 2, or 3;

$R^1$ is hydrogen, $C_{1-6}$ alkyl, $C_{2-6}$ alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$ alkyl, $C_{1-6}$ haloalkyl and $OR^d$;

$R^2$, at each occurrence, is independently selected from the group consisting of $C_{1-4}$ alkyl, $C_{1-4}$ alkoxy, heterocycloalkyl, $NR^6R^7$—$C_{1-6}$-alkyl-, C(O)$R^5$, and S(O)$_2R^5$; wherein the $R^2$ cycloalkyl, aryl, heterocycloalkyl, and heteroaryl, alone or part of another group, are optionally substituted with one, two, or three $R^3$;

$R^3$, at each occurrence, is independently selected $C_{1-4}$ alkyl;

$R^4$ is $C_{1-6}$ alkyl, aryl, cycloalkyl, heteroaryl, heterocycloalkyl, or aryl-$C_{1-6}$-alkyl-; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$ alkenyl, $C_{1-4}$ haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, C(O)$R^g$, C(O)$NR^hR^i$, C(O)$OR^g$, —$C_{1-6}$ $NR^hR^i$, and $NR^hNR^iR^g$;

$R^5$ is heterocycloalkyl;

$R^6$ and $R^7$, at each occurrence, are independently selected $C_{1-6}$ alkyl;

$R^a$, at each occurrence, is hydrogen;

$R^d$, at each occurrence, is independently selected $C_{1-6}$ alkyl;

$R^g$, at each occurrence, is independently selected from the group consisting of hydrogen, $C_{1-6}$ alkyl, aryl, and heterocycloalkyl; wherein the $R^g$ aryl, and heterocycloalkyl are optionally substituted with one, two or three substituents independently selected from the group consisting of halo and $C_{1-4}$ alkyl;

$R^h$ and $R^i$ at each occurrence, are independently selected from the group consisting of hydrogen, $C_{1-6}$ alkyl, and cycloalkyl; and $R^m$, at each occurrence, is independently $C_{1-6}$ alkyl.

In one embodiment of formula (I), B is phenyl, or 5-16 membered monocyclic, 5-16 membered bicyclic, or tricyclic heterocyclyl. In one embodiment of formula (I), B is phenyl. In one embodiment of formula (I), B is 5-16 membered monocyclic, 5-16 membered bicyclic, or tricyclic heterocyclyl.

In one embodiment of formula (I), B is a 4-8 membered monocyclic heterocyclyl. In another embodiment, B is a 4-8 membered heterocycloalkyl or heterocycloalkenyl. In another embodiment, B is a 5-7 membered heteroaryl. In yet another embodiment of formula (I), B is pyrrolidinyl, tetrhydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxopyrrolidinyl, 2-oxopiperidinyl, 4-oxopiperidinyl, or 2,6-dioxopiperidinyl. In yet another embodiment of formula (I), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl.

In one embodiment of formula (I), B is a 4-8 membered monocyclic heterocyclyl; and m is 0, 1, 2, or 3. In another embodiment of formula (I), B is a 4-8 membered monocyclic heterocyclyl; and m is 0. In another embodiment of formula (I), B is a 4-8 membered monocyclic heterocyclyl; and m is 1. In another embodiment of formula (I), B is a 4-8 membered monocyclic heterocyclyl; and m is 2. In another embodiment of formula (I), B is a 4-8 membered monocyclic heterocyclyl; and m is 3.

In one embodiment of formula (I), B is a 7-11 membered bicyclic heterocyclyl. In another embodiment, B is a 4-8 membered heterocycloalkyl or heterocycloalkenyl. In another embodiment, B is a 5-7 membered heteroaryl. In yet another embodiment of formula (I), B is pyrrolidinyl, tetrhydrofuryl, tetrahydrothienyl, imidazolidinyl, pyrazolidinyl, piperidinyl, diazepanyl, tetrahydropyranyl, piperazinyl, dioxanyl, thiazolidin-2-yl, morpholinyl, 2-oxopyrrolidinyl, 4-oxo-1,3-thiazolidin-2-yl, thiomorpholinyl, 2,5-dioxopyrrolidinyl, 2-oxopiperidinyl, 4-oxopiperidinyl, or 2,6-dioxopiperidinyl. In yet another embodiment of formula (I), B is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl. In one embodiment, B is unsubstituted. In another embodiment, B is substituted with one, two, or three $R^2$, and $R^2$ is halo, $C_{1-6}$-alkyl, $C_{1-6}$-haloalkyl, $OR^5$, C(O)$R^5$, $NR^6R^7$, or S(O)$_2R^5$. In one embodiment of formula (I), B is a 7-11 membered bicyclic heterocyclyl; and m is 0, 1, 2, or 3. In another embodiment of formula (I), B is a 7-11 membered bicyclic heterocyclyl; and m is 0. In another embodiment of formula (I), B is a 7-11 membered bicyclic heterocyclyl; and m is 1. In another embodiment of formula (I), B is a 7-11 membered bicyclic heterocyclyl; and m is 2. In another embodiment of formula (I), B is a 7-11 membered bicyclic heterocyclyl; and m is 3.

In one embodiment of formula (I), B is 10-15 membered tricyclic heterocyclyl. In another embodiment, B is a 10-15 membered tricyclic heterocycloalkyl or tricyclic heterocycloalkenyl. In another embodiment, B is a 10-15 membered tricyclic heteroaryl. In one embodiment of formula (I), B is 5-oxo-5,6-dihydroimidazo[1,2-a]pyrimido[5,4-e]pyrimidiny-2-yl or 2',3'-dihydro-1'H-spiro[cyclopropane-1,4'-isoquinolin]-7'-yl. In one embodiment of formula (I), $R^4$ is unsubstituted. In another embodiment of formula (I), B is substituted with one, two, or three $R^2$, and $R^2$ is halo, $C_{1-6}$-alkyl, $C_{1-6}$-haloalkyl, $OR^5$, $C(O)R^5$, $NR^6R^7$, or $S(O)_2R^5$.

In one embodiment of formula (I), B is a 10-15 membered tricyclic heterocyclyl; and m is 0, 1, 2, or 3. In another embodiment of formula (I), B is a 10-15 membered tricyclic heterocyclyl; and m is 0. In another embodiment of formula (I), B is a 10-15 membered tricyclic heterocyclyl; and m is 1. In another embodiment of formula (I), B is a 10-15 membered tricyclic heterocyclyl; and m is 2. In another embodiment of formula (I), B is a 10-15 membered tricyclic heterocyclyl; and m is 3.

In one embodiment of formula (I), B is phenyl. In another embodiment of formula (I), B is phenyl; and m is 1, 2, or 3. In another embodiment of formula (I), B is phenyl; and m is 1. In another embodiment of formula (I), B is phenyl; and m is 2. In another embodiment of formula (I), B is phenyl; and m is 3.

In another embodiment of formula (I), B is phenyl; m is 1, 2, or 3; and $R^2$, at each occurance is independently selected from the group consisting of $C_{1-6}$-alkyl, $C_{1-4}$ alkoxy, heterocycloalkyl, $NR^6R^7$—$C_{1-6}$-alkyl-, $OR^5$, $C(O)R^5$, $C(O)NR^6R^7$, $NR^6R^7$, and $S(O)_2R^5$; wherein the $R^2$ heterocycloalkyl is optionally substituted with one, two, or three $R^3$. In another embodiment of formula (II), B is phenyl; m is 1, 2, or 3; and $R^2$, at each occurance, is independently selected from the group consisting of $C_{1-6}$-alkyl, $C_{1-4}$ alkoxy, heterocycloalkyl, $NR^6R^7$—$C_{1-6}$-alkyl-, $C(O)R^5$, and $S(O)_2R^5$; wherein the $R^2$ heterocycloalkyl is optionally substituted with one, two, or three $R^3$; and $R^3$ is $C_{1-4}$ alkyl. In another embodiment of formula (II), B is phenyl; m is 2; and $R^2$, at each occurance, is independently selected from the group consisting of $C_{1-6}$-alkyl, $C_{1-4}$ alkoxy, and heterocycloalkyl; wherein the $R^2$ heterocycloalkyl is substituted with $R^3$; and $R^3$ is $C_{1-4}$ alkyl. In another embodiment of formula (II), B is phenyl; m is 1; and $R^2$ is heterocycloalkyl; wherein the $R^2$ heterocycloalkyl is unsubstituted. In another embodiment of formula (II), B is phenyl; m is 1; and $R^2$ is heterocycloalkyl; wherein the $R^2$ heterocycloalkyl is substituted with $R^3$; and $R^3$ is $C_{1-4}$ alkyl.

In another embodiment of formula (I), B is

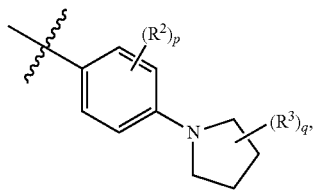

-continued

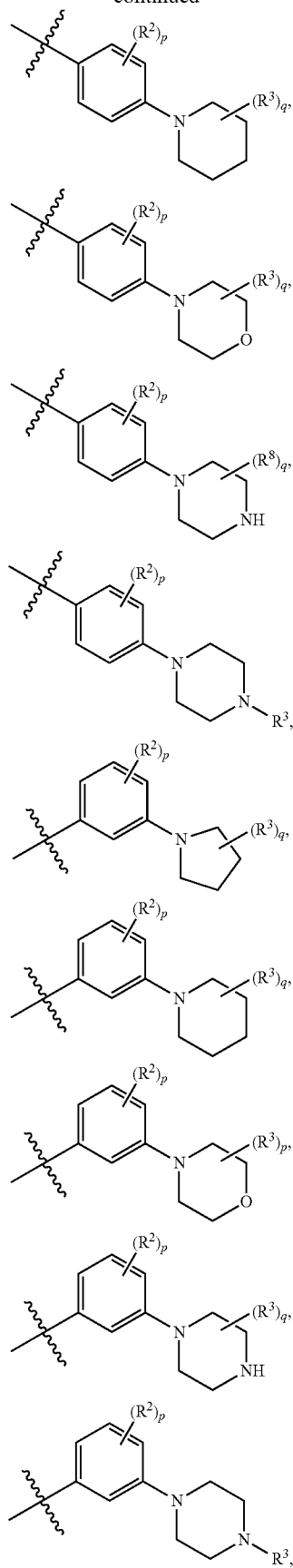

-continued

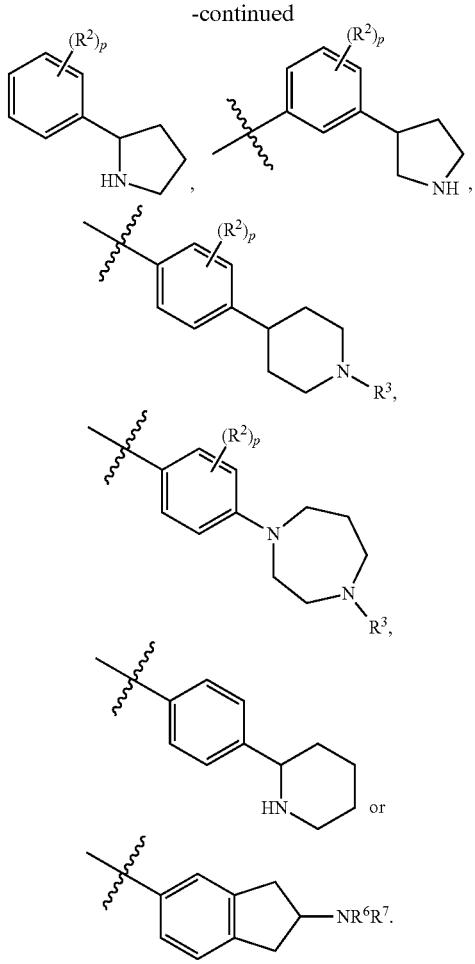

wherein R² and R³ are defined above; p is 0 or 1; and q is 0 or 1.

In one embodiment of formula (I), B is 5-16 membered bicyclic, or tricyclic heterocyclyl; and m is 0, 1, 2, or 3. In another embodiment of formula (I), B is 5-16 membered bicyclic, or tricyclic heterocyclyl; m is 1, 2, or 3; and R², at each occurrence, is independently selected from the group consisting of $C_{1-6}$-alkyl, $C_{1-4}$ alkoxy, heterocycloalkyl, $NR^6R^7$—$C_{1-6}$-alkyl-, $C(O)R^5$, and $S(O)_2R^5$; wherein the R² heterocycloalkyl is optionally substituted with one, two, or three R³.

In one embodiment of formula (I), B is

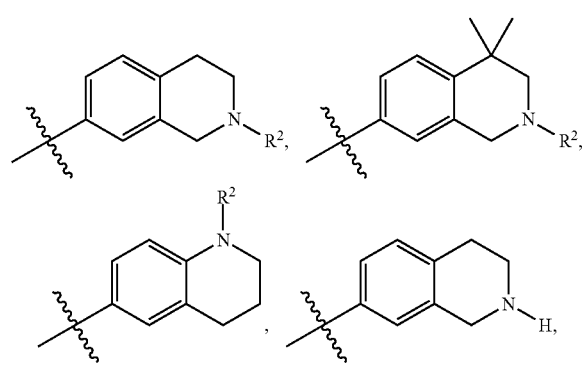

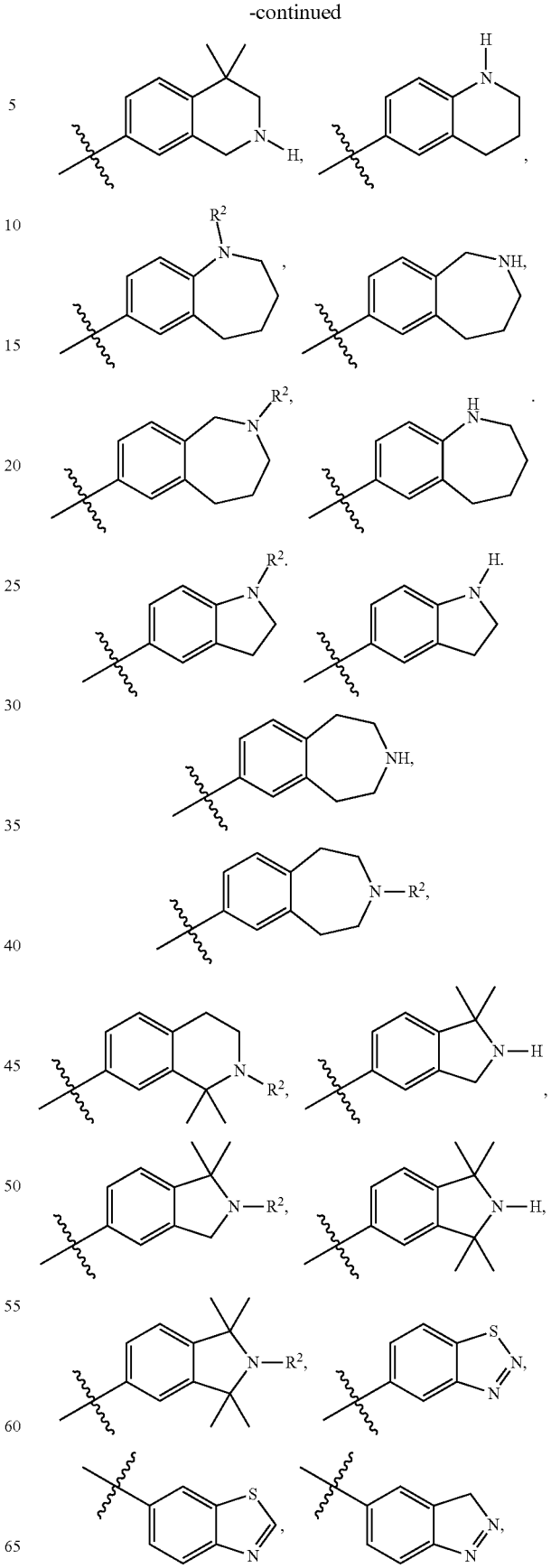

-continued

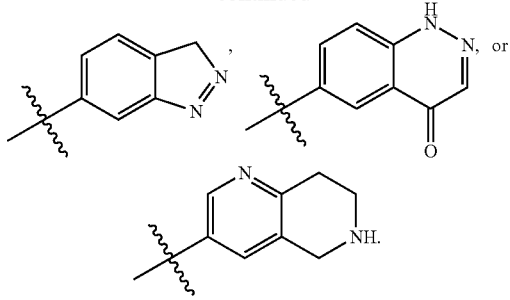

In one embodiment of formula (I), B is

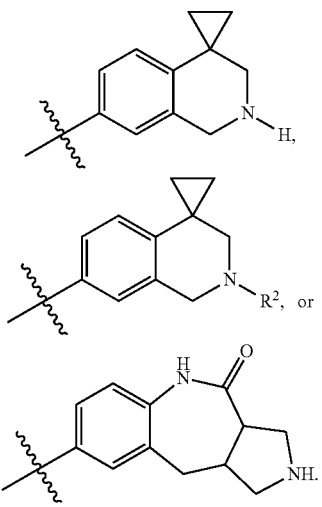

In one embodiment of formula (I), $R^1$ is hydrogen, $C_{1-6}$ alkyl, $C_{2-6}$ alkenyl, $C_{2-6}$ alkynyl, aryl, heterocyclyl, cycloalkyl, or cycloalkenyl; wherein the $R^1$ $C_{1-6}$ alkyl, $C_{2-6}$ alkenyl, and $C_{2-6}$ alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$ alkenyl, $C_{2-6}$ alkynyl, haloalkyl, —$C_{1-4}$alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$.

In another embodiment of formula (I), $R^1$ is hydrogen, $C_{1-6}$ alkyl, $C_{2-6}$ alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$ alkyl, $C_{1-6}$ haloalkyl, and $OR^d$. In another embodiment of formula (I), $R^1$ is aryl; wherein the $R^1$ aryl is optionally substituted with 1, 2, or 3 substituents independently selected from the group consisting of halo, $C_{1-6}$ alkyl, $C_{1-6}$ haloalkyl, and $OR^d$. In another embodiment of formula (I), $R^1$ is aryl; wherein the $R^1$ aryl is optionally substituted with 1, 2, or 3 substituents independently selected from the group consisting of halo, $C_{1-6}$ alkyl, $C_{1-6}$ haloalkyl, and $OR^d$; and $R^d$ is $C_{1-6}$ alkyl. In another embodiment of formula (I), $R^1$ is aryl; wherein the $R^1$ aryl is optionally substituted with 1, 2, or 3 substituents independently selected from the group consisting of halo, $C_{1-6}$ alkyl, $C_{1-6}$ haloalkyl, and $OR^d$; and $R^d$ is $C_{1-6}$ alkyl. In another embodiment of formula (I), $R^1$ is

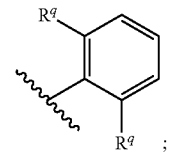

wherein each $R^q$ is as described for substituents on the $R^1$ aryl. In another embodiment of formula (I), $R^1$ is

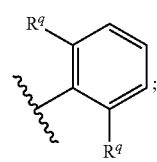

wherein each $R^q$ is independently selected from the group consisting of halo, $C_{1-6}$ alkyl, $C_{1-6}$ haloalkyl, and $OR^d$; and $R^d$ is $C_{1-6}$ alkyl. In another embodiment of formula (I), $R^1$ is

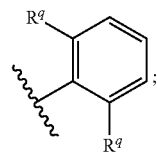

wherein each $R^q$ is independently selected halo. In another embodiment of formula (I), $R^1$ is

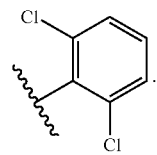

In one embodiment of formula (I), $R^4$ is $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$ alkenyl, $C_{1-4}$ haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$ $NR^hR^i$, $NR^hC(O)R^g$, $NR^hNR^iR^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$ alkenyl, and $C_{2-6}$ alkynyl, alone or part of another group, are optionally substituted with 1, 2, or 3 substituents independently selected from the group consisting of halo, CN, NO$_2$, OR$^j$, SR$^j$, C(O)R$^j$, C(O)NR$^k$R$^i$, C(O)OR$^j$, OC(O)R$^j$, OC(O)NR$^k$R$^i$, NR$^k$R$^i$, NR$^k$C(O)R$^j$, S(O)R$^j$, S(O)NR$^k$R$^i$, S(O)$_2$R$^j$, NR$^k$S(O)$_2$R$^j$, and S(O)$_2$NR$^k$R$^i$; R$^g$, at each occurrence, is independently selected from the group consisting of hydrogen, C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl; wherein the R$^g$ aryl, cycloalkyl, heteroaryl, and heterocycloalkyl alone or as part of another group, are optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl; wherein the R$^h$ or R$^i$ aryl, cycloalkyl, heteroaryl, and heterocycloalkyl alone or as part of another group, are optionally substituted with one, two or three substituents independently selected from the group consisting of halo and C$_{1-4}$ alkyl; and R$^m$, at each occurrence, is independently selected from the group consisting of hydrogen, C$_{1-6}$ alkyl, C$_{2-6}$ alkenyl, C$_{2-6}$ alkynyl, —C(O)C$_{1-6}$ alkyl, and C$_{1-6}$ haloalkyl. In another embodiment of formula (I), R$^4$ is C$_{1-6}$ alkyl, aryl, cycloalkyl, heteroaryl, heterocycloalkyl, or aryl-C$_{1-6}$-alkyl; wherein the R$^4$ aryl, cycloalkyl, heteroaryl, and heterocycloalkyl, alone or part of another group, are optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$ alkyl-NR$^h$R$^i$, NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl and heterocycloalkyl are optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl. In another embodiment of formula (I), R$^4$ is aryl, cycloalkyl, heteroaryl, heterocycloalkyl, or aryl-C$_{1-6}$-alkyl; wherein the R$^4$ aryl, cycloalkyl, heteroaryl, and heterocycloalkyl, alone or part of another group, are optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$ alkyl-NR$^h$R$^i$, NR$^h$R$^i$, and NR$^h$NR$^i$R$^9$; R$^g$, at each occurrence, is independently selected from the group consisting of hydrogen, C$_{1-6}$ alkyl, aryl, and heterocycloalkyl; wherein the R$^g$ aryl and heterocycloalkyl are optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl. In another embodiment of formula (I), R$^4$ is heteroaryl; wherein the heteroaryl is optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$ alkyl-NR$^h$R$^i$, NR$^h$R$^i$, and NR$^h$NR$^i$ R$^g$; R$^g$, at each occurrence, is independently selected from the group consisting of hydrogen, C$_{1-6}$ alkyl, aryl, and heterocycloalkyl;

wherein the R$^g$ aryl, is optionally substituted with one, two or three substituents independently selected from the group consisting of halo and C$_{1-4}$ alkyl; R$^h$ and R$^i$ at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl.

In another embodiment of formula (I), R$^4$ is pyridinyl or pyrazolyl; wherein the pyridinyl and pyrazolyl are optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heterocycloalkyl, heterocycloalkyl-C$_{1-6}$-alkyl-, R$^m$ heterocycloalkyl C$_{1-6}$ alkyl OR$^g$, C(O)R$^g$, C(O)NR$^h$R$^i$, C(O)OR$^g$, —C$_{1-6}$ alkyl-NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl, is optionally substituted with one, two or three independently selected halo; R$^h$ and R$^i$, at each occurrence, are independently selected from the group consisting of hydrogen, and C$_{1-6}$ alkyl; and R$^m$, at each occurrence, is independently selected C$_{1-6}$ alkyl.

Embodiments of Formula (II)

In one embodiment, the present invention is directed, in part, to a class of compounds having a structure of formula (II), and pharmaceutically acceptable salts and solvates thereof

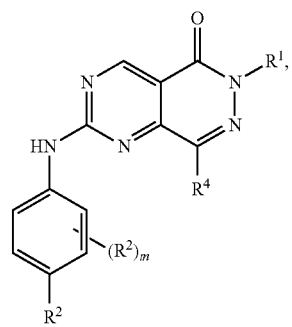

Formula (II)

wherein R$^1$, R$^2$, and R$^4$ are as described in formula (I); and m is 0, 1, or 2.

In one embodiment of formula (II),
m is 0, 1, or 2;
R$^1$ is hydrogen, C$_{1-6}$ alkyl, C$_{2-6}$ alkenyl, C$_{2-6}$ alkynyl, aryl, heterocyclyl, cycloalkyl, or cycloalkenyl; wherein the R$^1$ C$_{1-6}$ alkyl, C$_{2-6}$ alkenyl, and C$_{2-6}$ alkynyl are optionally substituted with 1, 2, or 3 substituents independently selected from the group consisting of halo, CN, NO$_2$, OR$^a$, SR$^a$, C(O)R$^a$, C(O)NR$^b$R$^c$, C(O)OR$^a$, OC(O)R$^a$, OC(O)NR$^b$R$^c$, NR$^b$R$^c$, NR$^b$C(O)R$^a$, S(O)R$^a$, S(O)NR$^b$R$^c$, S(O)$_2$R$^a$, and NR$^b$S(O)$_2$R$^a$; wherein the R$^1$ aryl, heterocyclyl, cycloalkyl, and cycloalkenyl are optionally substituted with 1, 2, or 3 substituents independently selected from the group consisting of halo, C$_{1-6}$ alkyl, C$_{2-6}$ alkenyl, C$_{2-6}$ alkynyl, C$_{1-6}$ haloalkyl, —C$_{1-4}$ alkyl-NR$^e$R$^f$, CN, NO$_2$, OR$^d$, SR$^d$, C(O)R$^d$, C(O)NR$^e$R$^f$, C(O)OR$^d$, OC(O)R$^d$, OC(O)NR$^e$R$^f$, NR$^e$R$^f$, NR$^e$C(O)R$^d$, S(O)R$^d$, S(O)NR$^e$R$^f$, S(O)$_2$R$^d$, NR$^e$S(O)$_2$R$^d$, and S(O)$_2$NR$^e$R$^f$;

$R^2$, at each occurrence, is independently selected from the group consisting of halo, CN, $C_{1-4}$ alkyl, $C_{2-6}$ alkenyl, $C_{2-6}$ alkynyl, $C_{1-4}$-haloalkyl, $C_{1-4}$ alkoxy, $C_{1-4}$haloalkoxy, $C_{1-4}$-thioalkoxy, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $NR^6R^7$—$C_{1-6}$-alkyl-, $OR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$, wherein the $R^2$ cycloalkyl, aryl, heterocycloalkyl, and heteroaryl, alone or part of another group, are optionally substituted with one, two, or three $R^3$;

$R^3$, at each occurrence, is independently selected from the group consisting of halo, $C_{1-4}$ alkyl, $C_{2-6}$ alkenyl, $C_{2-6}$ alkynyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-4}$ alkyl)-, cycloalkyl-($C_{1-4}$ alkyl)-, heteroaryl-($C_{1-4}$ alkyl)-, heterocycloalkyl-($C_{1-4}$ alkyl)-, CN, $NO_2$, $OR^n$, $SR^n$, $C(O)R^n$, $C(O)NR^oR^p$, $C(O)OR^n$, $OC(O)R^n$, $OC(O)NR^oR^p$, $NR^oR^p$, $NR^oC(O)R^n$, $S(O)R^n$, $S(O)NR^oR^p$, $S(O)_2R^n$, $NR^oS(O)_2R^n$, and $S(O)_2NR^oR^p$, wherein the $R^8$ aryl, cycloalkyl, heteroaryl, and heterocycloalkyl, alone or as part of another group, are optionally substituted with one, two or three substituents independently selected from the group consisting of halo and $C_{1-4}$ alkyl;

$R^4$ is $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$ alkenyl, $C_{1-4}$ haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$ $NR^hR^i$, $NR^hR^i$, $NR^hC(O)R^g$, $NR^hNR^i$ $R^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$ alkenyl, and $C_{2-6}$ alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^j$, $OC(O)R^j$, $OC(O)NR^kR^l$, $NR^kR^l$, $NR^k$-$C(O)R^j$, $S(O)R^j$, $S(O)NR^kR^l$, $S(O)_2R^j$, $NR^kS(O)_2R^j$, and $S(O)_2NR^kR^l$;

$R^5$ is independently selected from the group consisting of hydrogen, $C_{1-6}$ alkyl, $C_{2-6}$ alkenyl, $C_{2-6}$ alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl, wherein the $R^5$ cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl $C_{1-4}$alkoxy, $C_{1-4}$haloalkoxy, amino, $C_{1-4}$ alkylamino, $C_{1-4}$ dialkylamino, $C(O)OH$, $C(O)C_{1-4}$ alkyl, $C(O)NH_2$, $C(O)NH(C_{1-4}$ alkyl), or $C(O)N(C_{1-4}$ alkyl)$_2$;

$R^6$ and $R^7$, at each occurrence, are independently selected from the group consisting of hydrogen, $C_{1-6}$ alkyl, $C_{2-6}$ alkenyl, $C_{2-6}$ alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl, wherein the $R^6$ and $R^7$ aryl, cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl, $C_{1-4}$alkoxy, $C_{1-4}$haloalkoxy, amino, $C_{1-4}$ alkylamino, $C_{1-4}$ dialkylamino, $C(O)$ OH, $C(O)C_{1-4}$ alkyl, $C(O)NH_2$, $C(O)NH(C_{1-4}$ alkyl), or $C(O)N(C_{1-4}$ alkyl)$_2$;

$R^a$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^a$ aryl, cycloalkyl, heteroaryl, and heterocycloalkyl alone or as part of another group, are optionally substituted with one, two or three substituents independently selected from the group consisting of halo and $C_{1-4}$ alkyl;

$R^b$ and $R^c$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^b$ or $R^c$ aryl, cycloalkyl, heteroaryl, and heterocycloalkyl alone or as part of another group, are optionally substituted with one, two or three substituents independently selected from the group consisting of halo and $C_{1-4}$ alkyl;

$R^d$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^d$ aryl, cycloalkyl, heteroaryl, and heterocycloalkyl, alone or part of another group, are optionally substituted with 1, 2, or 3 substituents independently selected from the group consisting of halo and $C_{1-4}$ alkyl;

$R^e$ and $R^f$, at each occurrence, are independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the $R^e$ or $R^f$ aryl, cycloalkyl, heteroaryl, and heterocycloalkyl alone or as part of another group, are optionally substituted with one, two or three substituents independently selected from the group consisting of halo and $C_{1-4}$ alkyl;

$R^g$, at each occurrence, is independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$ alkyl;

$R^h$ and $R^i$, at each occurrence, are independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl;

$R^j$, at each occurrence, is independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the $R^j$ aryl, cycloalkyl, heteroaryl, and heterocycloalkyl alone or as part of another group, are optionally substituted with one, two or three substituents independently selected from the group consisting of halo and $C_{1-4}$ alkyl;

$R^k$ and $R^l$, at each occurrence, are independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the $R^k$ or $R^l$ aryl, cycloalkyl, heteroaryl, and heterocycloalkyl alone or as part of another group, are optionally substituted with one, two or three substituents independently selected from the group consisting of halo and $C_{1-4}$ alkyl;

R", at each occurrence, is independently selected from the group consisting of hydrogen, $C_{1-6}$ alkyl, $C_{2-6}$ alkenyl, $C_{2-6}$ alkynyl, $C_{1-6}$haloalkyl, aryl, cycloalkyl, heteroaryl, and heterocycloalkyl; wherein the R" aryl, cycloalkyl, heteroaryl, and heterocycloalkyl alone or as part of another group, are optionally substituted with one, two or three substituents independently selected from the group consisting of halo and $C_{1-4}$ alkyl;

R'", at each occurrence, is independently selected from the group consisting of hydrogen, $C_{1-6}$ alkyl, $C_{2-6}$alkenyl, $C_{2-6}$alkynyl, —C(O)$C_{1-6}$ alkyl, and $C_{1-6}$ haloalkyl; and $R^o$ and $R^p$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^o$ or $R^p$ aryl, cycloalkyl, heteroaryl, and heterocycloalkyl alone or as part of another group, are optionally substituted with one, two or three substituents independently selected from the group consisting of halo and $C_{1-4}$alkyl.

In one embodiment of formula (II), m is 0, 1, or 2;

$R^1$ is hydrogen, $C_{1-6}$alkyl, $C_{2-6}$alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$ alkyl, $C_{1-6}$ haloalkyl and $OR^d$;

$R^2$, at each occurrence, is independently selected from the group consisting of $C_{1-4}$ alkyl, $C_{1-4}$alkoxy, heterocycloalkyl, $NR^6R^7$—$C_{1-6}$-alkyl-, $C(O)R^5$, and $S(O)_2R^5$; wherein the $R^2$ cycloalkyl, aryl, heterocycloalkyl, and heteroaryl, alone or part of another group, are optionally substituted with one, two, or three $R^3$;

$R^3$, at each occurrence, is independently selected $C_{1-4}$ alkyl;

$R^4$ is $C_{1-6}$alkyl, aryl, cycloalkyl, heteroaryl, heterocycloalkyl, or aryl-$C_{1-6}$-alkyl; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, $C(O)R^g$, $C(O)NR^hR^i$, $C(O)OR^g$, —$C_{1-6}$alkyl-$NR^hR^i$, $NR^hR^i$, and $NR^hNR^iR^g$;

$R^5$ is heterocycloalkyl;

$R^6$ and $R^7$, at each occurrence, are independently selected $C_{1-6}$ alkyl;

$R^a$, at each occurrence, is hydrogen;

$R^d$, at each occurrence, is independently selected $C_{1-6}$ alkyl;

$R^g$, at each occurrence, is independently selected from the group consisting of hydrogen, $C_{1-6}$ alkyl, aryl, and heterocycloalkyl; wherein the $R^g$ aryl, and heterocycloalkyl are optionally substituted with one, two or three substituents independently selected from the group consisting of halo and $C_{1-4}$alkyl;

$R^h$ and $R^i$, at each occurrence, are independently selected from the group consisting of hydrogen, $C_{1-6}$ alkyl, and cycloalkyl; and $R^m$, at each occurrence, is independently $C_{1-6}$alkyl.

In one embodiment of formula (II), m is 0, 1, or 2. In another embodiment of formula (II), m is 0. In another embodiment of formula (II), m is 1. In another embodiment of formula (II), m is 2.

In one embodiment of formula (II), m is 0, 1, or 2; and $R^2$, at each occurance, is independently selected from the group consisting of $C_{1-6}$-alkyl, $C_{1-4}$alkoxy, heterocycloalkyl, $NR^6R^7$—$C_{1-6}$-alkyl-, $C(O)R^5$, and $S(O)_2R^5$; wherein the $R^2$ heterocycloalkyl is optionally substituted with one, two, or three $R^3$. In another embodiment of formula (II), m is 0, 1, or 2; and $R^2$, at each occurance, is independently selected from the group consisting of $C_{1-6}$-alkyl, $C_{1-4}$alkoxy, heterocycloalkyl, $NR^6R^7$—$C_{1-6}$-alkyl-, $C(O)R^5$, and $S(O)_2R^5$; wherein the $R^2$ heterocycloalkyl is optionally substituted with one, two, or three $R^3$; and $R^3$ is $C_{1-4}$alkyl.

In another embodiment of formula (II), m is 1; and $R^2$, at each occurance, is independently selected from the group consisting of $C_{1-6}$-alkyl, $C_{1-4}$alkoxy, and heterocycloalkyl; wherein the $R^2$ heterocycloalkyl is substituted with $R^3$; and $R^3$ is $C_{1-4}$ alkyl.

In another embodiment of formula (II), m is 0; and $R^2$ is heterocycloalkyl; wherein the $R^2$ heterocycloalkyl is unsubstituted. In another embodiment of formula (II), m is 0; and $R^2$ is heterocycloalkyl; wherein the $R^2$ heterocycloalkyl is substituted with $R^3$; and $R^3$ is $C_{1-4}$ alkyl.

In one embodiment of formula (II), $R^1$ is hydrogen, $C_{1-6}$alkyl, $C_{2-6}$alkenyl, $C_{2-6}$ alkynyl, aryl, heterocyclyl, cycloalkyl, or cycloalkenyl; wherein the $R^1$ $C_{1-6}$ alkyl, $C_{2-6}$ alkenyl, and $C_{2-6}$alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$alkenyl, $C_{2-6}$alkynyl, $C_{1-6}$haloalkyl, —$C_{1-4}$alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$.

In another embodiment of formula (II), $R^1$ is hydrogen, $C_{1-6}$alkyl, $C_{2-6}$alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$alkyl, $C_{1-6}$haloalkyl, and $OR^d$. In another embodiment of formula (II), $R^1$ is aryl; wherein the $R^1$ aryl is optionally substituted with 1, 2, or 3 substituents independently selected from the group consisting of halo, $C_{1-6}$alkyl, $C_{1-6}$ haloalkyl, and $OR^d$. In another embodiment of formula (II), $R^1$ is aryl; wherein the $R^1$ aryl is optionally substituted with 1, 2, or 3 substituents independently selected from the group consisting of halo, $C_{1-6}$alkyl, $C_{1-6}$haloalkyl, and $OR^d$; and $R^d$ is $C_{1-6}$ alkyl. In another embodiment of formula (II), $R^1$ is aryl; wherein the $R^1$ aryl is optionally substituted with 1, 2, or 3 substituents independently selected from the group consisting of halo, $C_{1-6}$alkyl, $C_{1-6}$ haloalkyl, and $OR^d$; and $R^d$ is $C_{1-6}$alkyl. In another embodiment of formula (II), $R^1$ is

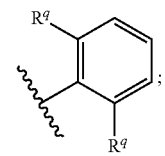

wherein each $R^q$ is as described for substituents on the $R^1$ aryl. In another embodiment of formula (II), $R^1$ is

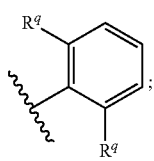

wherein each $R^q$ is independently selected from the group consisting of halo, $C_{1-6}$alkyl, $C_{1-6}$haloalkyl, and $OR^d$; and $R^d$ is $C_{1-6}$alkyl. In another embodiment of formula (II), $R^1$ is

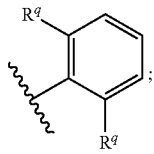

wherein each $R^q$ is independently selected halo. In another embodiment of formula (II), $R^1$ is

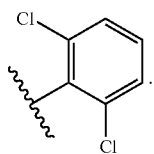

In one embodiment of formula (II), $R^4$ is $C_{1-6}$ alkyl, $C_{2-6}$alkenyl, $C_{2-6}$alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$alkenyl, $C_{1-4}$ haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$alkyl-$NR^hR^i$, $NR^hR^i$, $NR^hC(O)R^g$, $NR^hNR^iR^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$alkenyl, and $C_{2-6}$alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^j$, $OC(O)R^j$, $OC(O)NR^kR^l$, $NR^kR^l$, $NR^kC(O)R^j$, $S(O)R^j$, $S(O)NR^kR^l$, $S(O)_2R^j$, $NR^kS(O)_2R^j$, and $S(O)_2NR^kR^l$; $R^g$, at each occurrence, is independently selected from the group consisting of hydrogen, $C_{1-6}$ alkyl, $C_{2-6}$alkenyl, $C_{2-6}$ alkynyl, $C_{1-6}$haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$ alkyl; $R^h$ and $R^i$, at each occurrence, are independently selected from the group consisting of hydrogen, $C_{1-6}$alkyl, $C_{2-6}$alkenyl, $C_{2-6}$alkynyl, $C_{1-6}$ haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl; and $R^m$, at each occurrence, is independently selected from the group consisting of hydrogen, $C_{1-6}$alkyl, $C_{2-6}$alkenyl, $C_{2-6}$alkynyl, —$C(O)C_{1-6}$alkyl, and $C_{1-6}$haloalkyl. In another embodiment of formula (II), $R^4$ is $C_{1-6}$alkyl, aryl, cycloalkyl, heteroaryl, heterocycloalkyl, or aryl-$C_{1-6}$-alkyl; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, $C(O)R^g$, $C(O)NR^hR^i$, $C(O)OR^g$, —$C_{1-6}$alkyl-$NR^hR^i$, $NR^hR^i$, and $NR^hNR^iR^g$; $R^g$, at each occurrence, is independently selected from the group consisting of hydrogen, $C_{1-6}$ alkyl, aryl, and heterocycloalkyl; wherein the $R^g$ aryl and heterocycloalkyl are optionally substituted with one, two or three substituents independently selected from the group consisting of halo and $C_{1-4}$alkyl; $R^h$ and $R^i$, at each occurrence, are independently selected from the group consisting of hydrogen, $C_{1-6}$ alkyl, cycloalkyl, heteroaryl, and heterocycloalkyl; and $R^m$, at each occurrence, is independently selected $C_{1-6}$ alkyl. In another embodiment of formula (II), $R^4$ is aryl, cycloalkyl, heteroaryl, heterocycloalkyl, or aryl-$C_{1-6}$-alkyl; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$alkenyl, $C_{1-4}$ haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, $C(O)R^g$, $C(O)NR^hR^i$, $C(O)OR^g$, —$C_{1-6}$ alkyl-$NR^hR^i$, $NR^hR^i$, and $NR^hNR^iR^g$; $R^g$, at each occurrence, is independently selected from the group consisting of hydrogen, $C_{1-6}$alkyl, aryl, and heterocycloalkyl; wherein the $R^g$ aryl and heterocycloalkyl are optionally substituted with one, two or three substituents independently selected from the group consisting of halo and $C_{1-4}$alkyl; $R^h$ and $R^i$, at each occurrence, are independently selected from the group consisting of hydrogen, $C_{1-6}$alkyl, cycloalkyl, heteroaryl, and heterocycloalkyl; and $R^m$, at each occurrence, is independently selected $C_{1-6}$ alkyl. In another embodiment of formula (II), $R^4$ is heteroaryl; wherein the heteroaryl is optionally substituted with 1, 2, or 3 substituents independently selected from the group consisting of halo, $C_{1-6}$ alkyl, $C_{2-6}$alkenyl, $C_{1-4}$ haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, $C(O)R^g$, $C(O)NR^hR^i$, $C(O)OR^g$, —$C_{1-6}$alkyl-$NR^hR^i$, $NR^hR^i$, and $NR^hNR^i$ $R^g$; $R^g$, at each occurrence, is independently selected from the group consisting of hydrogen, $C_{1-6}$ alkyl, aryl, and heterocycloalkyl; wherein the $R^g$ aryl, is optionally substituted with one, two or three substituents independently selected from the group consisting of halo and $C_{1-4}$ alkyl; $R^h$ and $R^i$, at each occurrence, are independently selected from the group consisting of hydrogen, $C_{1-6}$ alkyl, cycloalkyl, heteroaryl, and heterocycloalkyl; and $R^m$, at each occurrence, is independently selected $C_{1-6}$alkyl.

In another embodiment of formula (II), $R^4$ is pyridinyl or pyrazolyl; wherein the pyridinyl and pyrazolyl are optionally substituted with 1, 2, or 3 substituents independently selected from the group consisting of halo, $C_{1-6}$ alkyl, $C_{2-6}$alkenyl, $C_{1-4}$ haloalkyl, alkoxy-$C_{1-6}$-alkyl-, hydroxy-$C_{1-6}$-alkyl-, heterocycloalkyl, heterocycloalkyl-$C_{1-6}$-alkyl-, $R^m$-heterocycloalkyl-$C_{1-6}$-alkyl-, $OR^g$, $C(O)R^g$, $C(O)NR^hR^i$, $C(O)OR^g$, —$C_{1-6}$alkyl-$NR^hR^i$, and $NR^hNR^iR^g$; $R^g$, at each occurrence, is independently selected from the group consisting of hydrogen, $C_{1-6}$ alkyl, aryl, and heterocycloalkyl; wherein the $R^g$ aryl, is optionally substituted with one, two or three independently selected halo; $R^h$ and $R^i$, at each occurrence, are independently selected from the group consisting of hydrogen, and $C_{1-6}$alkyl; and $R^m$, at each occurrence, is independently selected $C_{1-6}$ alkyl.

Embodiments of Formula (III)

In one embodiment, the present invention is directed, in part, to a class of compounds having a structure of formula (III), and pharmaceutically acceptable salts and solvates thereof

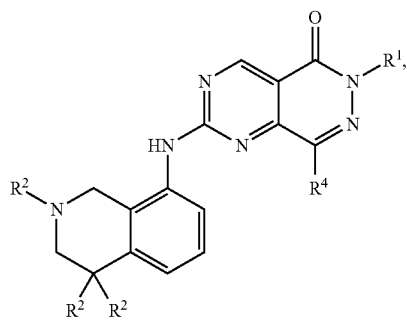

Formula (III)

wherein $R^1$ and $R^4$ are as described in formula (I) and each $R^2$ is independently absent, is as described in formula (I), or are combined, together with the carbon atom to which they are attached, to form a cycloalkyl ring.

In one embodiment of formula (III), $R^1$ is hydrogen, $C_{1-6}$alkyl, $C_{2-6}$alkenyl, $C_{2-6}$alkynyl, aryl, heterocyclyl, cycloalkyl, or cycloalkenyl; wherein the $R^1$ $C_{1-6}$ alkyl, $C_{2-6}$alkenyl, and $C_{2-6}$alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$alkenyl, $C_{2-6}$alkynyl, $C_{1-6}$haloalkyl, —$C_{1-4}$alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$;

$R^2$, at each occurrence, is independently selected from the group consisting of hydrogen, halo, CN, $C_{1-4}$ alkyl, $C_{2-6}$alkenyl, $C_{2-6}$alkynyl, $C_{1-4}$-haloalkyl, $C_{1-4}$alkoxy, $C_{1-4}$ haloalkoxy, $C_{1-4}$-thioalkoxy, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $NR^6R^7$—$C_{1-6}$-alkyl-, $OR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$, wherein the $R^2$ cycloalkyl, aryl, heterocycloalkyl, and heteroaryl, alone or part of another group, are optionally substituted with one, two, or three $R^3$; or two $R^2$ may be combined, together with the carbon atom to which they are attached, to form a cycloalkyl ring;

$R^3$, at each occurrence, is independently selected from the group consisting of halo, $C_{1-4}$alkyl, $C_{2-6}$alkenyl, $C_{2-6}$alkynyl, $C_{1-4}$haloalkyl, amino-$C_{1-4}$-alkyl-, $C_{1-4}$alkylamino-$C_{1-4}$alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-4}$ alkyl)-, cycloalkyl-($C_{1-4}$ alkyl)-, heteroaryl-($C_{1-4}$ alkyl)-, heterocycloalkyl-($C_{1-4}$ alkyl)-, CN, $NO_2$, $OR^n$, $SR^n$, $C(O)R^n$, $C(O)NR^oR^p$, $C(O)OR^n$, $OC(O)R^n$, $OC(O)NR^oR^p$, $NR^oR^p$, $NR^oC(O)R^n$, $S(O)R^n$, $S(O)NR^oR^p$, $S(O)_2R^n$, $NR^oS(O)_2R^n$, and $S(O)_2NR^oR^p$, wherein the $R^8$ aryl, cycloalkyl, heteroaryl, and heterocycloalkyl, alone or as part of another group, are optionally substituted with one, two or three substituents independently selected from the group consisting of halo and $C_{1-4}$alkyl;

$R^4$ is $C_{1-6}$alkyl, $C_{2-6}$alkenyl, $C_{2-6}$alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$ alkyl-$NR^hR^i$, $NR^hR^i$, $NR^hC(O)R^g$, $NR^hNR^iR^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$alkenyl, and $C_{2-6}$ alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^j$, $OC(O)R^j$, $OC(O)NR^kR^l$, $NR^kR^l$, $NR^kC(O)R^j$, $S(O)R^j$, $S(O)NR^kR^l$, $S(O)_2R^j$, $NR^kS(O)_2R^j$, and $S(O)_2NR^kR^l$;

$R^5$ is independently selected from the group consisting of hydrogen, $C_{1-6}$ alkyl, $C_{2-6}$ alkenyl, $C_{2-6}$alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl, wherein the $R^5$ cycloalkyl, heteroaryl, and heterocycloalkyl, alone or as part of another group, are optionally substituted with 1, 2, or 3 substituents independently selected from the group consisting of halo, CN, OH, $C_{1-4}$alkyl, $C_{1-4}$-haloalkyl, $C_{1-4}$alkoxy, $C_{1-4}$ haloalkoxy, amino, $C_{1-4}$alkylamino, $C_{1-4}$ dialkylamino, $C(O)OH$, $C(O)C_{1-4}$alkyl, $C(O)NH_2$, $C(O)NH$ ($C_{1-4}$ alkyl), or $C(O)N(C_{1-4}$ alkyl)$_2$;

$R^6$ and $R^7$, at each occurrence, are independently selected from the group consisting of hydrogen, $C_{1-6}$ alkyl, $C_{2-6}$alkenyl, $C_{2-6}$alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl, wherein the $R^6$ and $R^7$aryl, cycloalkyl, heteroaryl, and heterocycloalkyl, alone or as part of another group, are optionally substituted with 1, 2, or 3 substituents independently selected from the group consisting of halo, CN, OH, $C_{1-4}$alkyl, $C_{1-4}$-haloalkyl, $C_{1-4}$alkoxy, $C_{1-4}$ haloalkoxy, amino, $C_{1-4}$alkylamino, $C_{1-4}$ dialkylamino, $C(O)$ OH, $C(O)C_{1-4}$alkyl, $C(O)NH_2$, $C(O)NH(C_{1-4}$ alkyl), or $C(O)N(C_{1-4}$ alkyl)$_2$;

$R^a$, at each occurrence, is independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^a$ aryl, cycloalkyl, heteroaryl, and heterocycloalkyl alone or as part of another group, are optionally substituted with one, two or three substituents independently selected from the group consisting of halo and $C_{1-4}$ alkyl;

$R^b$ and $R^c$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^b$ or $R^c$ aryl, cycloalkyl, heteroaryl, and heterocycloalkyl alone or as part of another group, are optionally substituted with one, two or three substituents independently selected from the group consisting of halo and $C_{1-4}$ alkyl;

$R^d$, at each occurrence, is independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^d$ aryl, cycloalkyl, heteroaryl, and heterocycloalkyl, alone or part of another group, are optionally substituted with 1, 2, or 3 substituents independently selected from the group consisting of halo and $C_{1-4}$ alkyl;

$R^e$ and $R^f$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^e$ or $R^f$ aryl, cycloalkyl, heteroaryl, and heterocycloalkyl alone or as part of another group, are optionally substituted with one, two or three substituents independently selected from the group consisting of halo and $C_{1-4}$ alkyl;

$R^g$, at each occurrence, is independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$alkyl;

$R^h$ and $R^i$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl;

$R^j$, at each occurrence, is independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^j$ aryl, cycloalkyl, heteroaryl, and heterocycloalkyl alone or as part of another group, are optionally substituted with one, two or three substituents independently selected from the group consisting of halo and $C_{1-4}$ alkyl;

$R^k$ and $R^l$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^k$ or $R^l$ aryl, cycloalkyl, heteroaryl, and heterocycloalkyl alone or as part of another group, are optionally substituted with one, two or three substituents independently selected from the group consisting of halo and $C_{1-4}$ alkyl;

$R^n$, at each occurrence, is independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^n$ aryl, cycloalkyl, heteroaryl, and heterocycloalkyl alone or as part of another group, are optionally substituted with one, two or three substituents independently selected from the group consisting of halo and $C_{1-4}$ alkyl;

$R^m$, at each occurrence, is independently selected from the group consisting of hydrogen, $C_{1-6}$ alkyl, $C_{2-6}$alkenyl, $C_{2-6}$alkynyl, —C(O)$C_{1-6}$ alkyl, and $C_{1-6}$ haloalkyl; and $R^o$ and $R^p$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^o$ or $R^p$ aryl, cycloalkyl, heteroaryl, and heterocycloalkyl alone or as part of another group, are optionally substituted with one, two or three substituents independently selected from the group consisting of halo and $C_{1-4}$ alkyl.

In one embodiment of formula (III), $R^1$ is hydrogen, $C_{1-6}$alkyl, $C_{2-6}$alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$alkyl, $C_{1-6}$ haloalkyl and $OR^d$;

$R^2$, at each occurrence, is independently selected from the group consisting of hydrogen, $C_{1-4}$ alkyl, $C_{1-4}$alkoxy, heterocycloalkyl, $NR^6R^7$—$C_{1-6}$-alkyl-, $C(O)R^5$, and $S(O)_2R^5$; wherein the $R^2$ cycloalkyl, aryl, heterocycloalkyl, and heteroaryl, alone or part of another group, are optionally substituted with one, two, or three $R^3$; or two $R^2$ may be combined, together with the carbon atom to which they are attached, to form a cycloalkyl ring;

$R^3$, at each occurrence, is independently selected $C_{1-4}$ alkyl;

$R^4$ is $C_{1-6}$alkyl, aryl, cycloalkyl, heteroaryl, heterocycloalkyl, or aryl-$C_{1-6}$-alkyl; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, $OR^g$, $C(O)R^g$, $C(O)NR^hR^i$, $C(O)OR^g$, —$C_{1-6}$alkyl-$NR^hR^i$, $NR^hR^i$, and $NR^hNR^iR^g$;

$R^5$ is heterocycloalkyl;

$R^6$ and $R^7$, at each occurrence, are independently selected $C_{1-6}$ alkyl;

$R^a$, at each occurrence, is hydrogen;

$R^d$, at each occurrence, is independently selected $C_{1-6}$ alkyl;

$R^g$, at each occurrence, is independently selected from the group consisting of hydrogen, $C_{1-6}$ alkyl, aryl, and heterocycloalkyl; wherein the $R^g$ aryl, and heterocycloalkyl are optionally substituted with one, two or three substituents independently selected from the group consisting of halo and $C_{1-4}$alkyl;

$R^h$ and $R^i$, at each occurrence, are independently selected from the group consisting of hydrogen, $C_{1-6}$ alkyl, and cycloalkyl; and $R^m$, at each occurrence, is independently $C_{1-6}$ alkyl.

In one embodiment of formula (III), $R^2$, at each occurance, is hydrogen. In one embodiment of formula (III), $R^2$, at each occurance, is independently selected from the group consisting of hydrogen, $C_{1-6}$-alkyl, $C_{1-4}$ alkoxy, heterocycloalkyl, $NR^6R^7$—$C_{1-6}$-alkyl-, $C(O)R^5$, and $S(O)_2R^5$; wherein the $R^2$ heterocycloalkyl is optionally substituted with one, two, or three $R^3$. In another embodiment of formula (III), $R^2$, at each occurance, is independently selected from the group consisting of hydrogen, $C_{1-6}$-alkyl, $C_{1-4}$ alkoxy, heterocycloalkyl, $NR^6R^7$—$C_{1-6}$-alkyl-, $C(O)R^5$, and $S(O)_2R^5$; wherein the $R^2$ heterocycloalkyl is optionally substituted with one, two, or three $R^3$; and $R^3$ is $C_{1-4}$alkyl. In another embodiment of formula (III), $R^2$, at each occurance, is independently selected from the group consisting of hydrogen, $C_{1-6}$-alkyl, $C_{1-4}$alkoxy, and heterocycloalkyl; wherein the $R^2$ heterocycloalkyl is substituted with $R^3$; and $R^3$ is $C_{1-4}$ alkyl.

In another embodiment of formula (III), one $R^2$ is heterocycloalkyl; wherein the $R^2$ heterocycloalkyl is unsubstituted.

In another embodiment of formula (III), one $R^2$ is heterocycloalkyl; wherein the $R^2$ heterocycloalkyl is substituted with $R^3$; and $R^3$ is $C_{1-4}$ alkyl.

In one embodiment of formula (III), $R^1$ is hydrogen, $C_{1-6}$ alkyl, $C_{2-6}$alkenyl, $C_{2-6}$ alkynyl, aryl, heterocyclyl, cycloalkyl, or cycloalkenyl; wherein the $R^1$ $C_{1-6}$ alkyl, $C_{2-6}$ alkenyl, and $C_{2-6}$alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$alkenyl, $C_{2-6}$alkynyl, $C_{1-6}$haloalkyl, —$C_{1-4}$alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$.

In another embodiment of formula (III), $R^1$ is hydrogen, $C_{1-6}$ alkyl, $C_{2-6}$alkenyl, aryl, heterocyclyl, or cycloalkyl; wherein the $R^1$ $C_{1-6}$ alkyl is optionally substituted with 1, 2, or 3 substituents independently selected from the group consisting of halo, CN, and $OR^a$; wherein the $R^1$ aryl is optionally substituted with 1, 2, or 3 substituents independently selected from the group consisting of halo, $C_{1-6}$alkyl, $C_{1-6}$haloalkyl, and $OR^d$. In another embodiment of formula (III), $R^1$ is aryl; wherein the $R^1$ aryl is optionally substituted with 1, 2, or 3 substituents independently selected from the group consisting of halo, $C_{1-6}$ alkyl, $C_{1-6}$ haloalkyl, and $OR^d$. In another embodiment of formula (III), $R^1$ is aryl; wherein the $R^1$ aryl is optionally substituted with 1, 2, or 3 substituents independently selected from the group consisting of halo, $C_{1-6}$alkyl, $C_{1-6}$haloalkyl, and $OR^d$; and $R^d$ is $C_{1-6}$ alkyl. In another embodiment of formula (III), $R^1$ is aryl; wherein the $R^1$ aryl is optionally substituted with 1, 2, or 3 substituents independently selected from the group consisting of halo, $C_{1-6}$ alkyl, $C_{1-6}$ haloalkyl, and $OR^d$; and $R^d$ is $C_{1-6}$alkyl. In another embodiment of formula (III), $R^1$ is

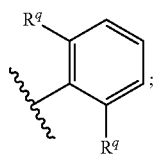

wherein each $R^q$ is as described for substituents on the $R^1$ aryl. In another embodiment of formula (III), $R^1$ is

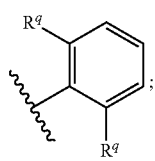

wherein each $R^q$ is independently selected from the group consisting of halo, $C_{1-6}$alkyl, $C_{1-6}$haloalkyl, and $OR^d$; and $R^d$ is $C_{1-6}$alkyl. In another embodiment of formula (III), $R^1$ is

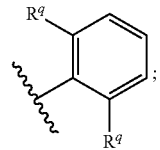

wherein each $R^q$ is independently selected halo. In another embodiment of formula (III), $R^1$

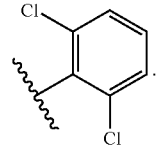

In one embodiment of formula (III), $R^4$ is $C_{1-6}$alkyl, $C_{2-6}$alkenyl, $C_{2-6}$alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$alkyl-$NR^hR^i$, $NR^hR^i$, $NR^hC(O)R^g$, $NR^hNR^iR^g$, $S(O)R^g$, $S(O)NR^hR^i$, $S(O)_2R^g$, $NR^hS(O)_2R^g$, and $S(O)_2NR^hR^i$; wherein the $R^4$ $C_{1-6}$ alkyl, $C_{2-6}$alkenyl, and $C_{2-6}$alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^n$, $OC(O)R^j$, $OC(O)NR^kR^l$, $NR^kR^l$, $NR^kC(O)R^j$, $S(O)R^j$, $S(O)NR^kR^l$, $S(O)_2R^j$, $NR^kS(O)_2R^j$, and $S(O)_2NR^kR^l$; $R^g$, at each occurrence, is independently selected from the group consisting of hydrogen, $C_{1-6}$alkyl, $C_{2-6}$alkenyl, $C_{2-6}$ alkynyl, $C_{1-6}$haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$alkyl; $R^h$ and $R^i$, at each occurrence, are independently selected from the group consisting of hydrogen, $C_{1-6}$ alkyl, $C_{2-6}$alkenyl, $C_{2-6}$alkynyl, $C_{1-6}$ haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl; and $R^m$, at each occurrence, is independently selected from the group consisting of hydrogen, $C_{1-6}$alkyl, $C_{2-6}$alkenyl, $C_{2-6}$alkynyl, —$C(O)C_{1-6}$alkyl, and $C_{1-6}$haloalkyl. In another embodiment of formula (III), $R^4$ is $C_{1-6}$ alkyl, aryl, cycloalkyl, heteroaryl, heterocycloalkyl, or aryl-$C_{1-6}$-alkyl; wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$alkenyl, $C_{1-4}$haloalkyl, alkoxy-$C_{1-6}$-alkyl-, hydroxy-$C_{1-6}$-alkyl-, heteroaryl, heterocycloalkyl, heterocycloalkyl-$C_{1-6}$-alkyl-, $R^m$-heterocycloalkyl-$C_{1-6}$-alkyl-, CN, OR$^g$, C(O)R$^g$, C(O)NR$^h$R$^i$, C(O)OR$^g$, —C$_{1-6}$alkyl-NR$^h$R$^i$, NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl and heterocycloalkyl are optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl. In another embodiment of formula (III), R$^4$ is aryl, cycloalkyl, heteroaryl, heterocycloalkyl, or aryl-C$_{1-6}$-alkyl; wherein the R$^4$ aryl, cycloalkyl, heteroaryl, and heterocycloalkyl, alone or part of another group, are optionally substituted with 1, 2, or 3 substituents independently selected from the group consisting of halo, C$_{1-6}$ alkyl, C$_{2-6}$alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$alkyl-NR$^h$R$^i$, NR$^h$R$^i$, and NR$^h$NR$^i$R$^g$; R$^g$, at each occurrence, is independently selected from the group consisting of hydrogen, C$_{1-6}$alkyl, aryl, and heterocycloalkyl; wherein the R$^g$ aryl and heterocycloalkyl are optionally substituted with one, two or three substituents independently selected from the group consisting of halo and C$_{1-4}$alkyl; R$^h$ and R$^i$, at each occurrence, are independently selected from the group consisting of hydrogen, C$_{1-6}$alkyl, cycloalkyl, heteroaryl, and heterocycloalkyl; and R$^m$, at each occurrence, is independently selected C$_{1-6}$alkyl. In another embodiment of formula (III), R$^4$ is heteroaryl; wherein the heteroaryl is optionally substituted with 1, 2, or 3 substituents independently selected from the group consisting of halo, C$_{1-6}$ alkyl, C$_{2-6}$alkenyl, C$_{1-4}$haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$alkyl-NR$^h$R$^i$, NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl, is optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$alkyl.

In another embodiment of formula (III), R$^4$ is pyridinyl or pyrazolyl; wherein the pyridinyl and pyrazolyl are optionally substituted with 1, 2, or 3 substituents independently selected from the group consisting of halo, C$_{1-6}$ alkyl, C$_{2-6}$alkenyl, C$_{1-4}$ haloalkyl, alkoxy-C$_{1-6}$-alkyl-, hydroxy-C$_{1-6}$-alkyl-, heterocycloalkyl, heterocycloalkyl-C$_{1-6}$-alkyl-, R$^m$-heterocycloalkyl-C$_{1-6}$-alkyl-, OR$^g$, C(O)R$^g$, C(O)NR$^h$R$^i$, C(O)OR$^g$, —C$_{1-6}$alkyl-NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl, is optionally substituted with one, two or three independently selected halo; R$^h$ and R$^i$, at each occurrence, are independently selected from the group consisting of hydrogen, and C$_{1-6}$ alkyl; and R$^m$, at each occurrence, is independently selected C$_{1-6}$ alkyl.

In one embodiment of formula (III), R$^2$, at each occurrence, is hydrogen. In one embodiment of formula (III), R$^2$, at each occurrence, is selected from the group consisting of hydrogen, C$_{1-6}$-alkyl, heterocycloalkyl, NR$^6$R$^7$—C$_{1-6}$-alkyl-, C(O)R$^5$, and S(O)$_2$R$^5$; wherein the R$^2$ heterocycloalkyl is optionally substituted with one, two, or three R$^3$. In one embodiment of formula (III), R$^2$, at each occurrence, is independently selected from the group consisting of hydrogen, C$_{1-6}$-alkyl, heterocycloalkyl, NR$^6$R$^7$—C$_{1-6}$-alkyl-, C(O)R$^5$, and S(O)$_2$R$^5$; wherein the R$^3$ heterocycloalkyl is optionally substituted with one, two, or three R$^3$. In another embodiment of formula (III), R$^2$, at each occurrence, is C$_{1-6}$alkyl. In another embodiment of formula (III), two R$^2$, together with the carbon atom to which they are attached, form a cycloalkyl ring.

Specific embodiments contemplated as part of the invention include, but are not limited to, compounds of formula (I), for example:

6,8-dimethyl-2-{[4-(4-methylpiperazin-1-yl)phenyl]amino}pyrimido[4,5-d]pyridazin-5(6H)-one;

6-allyl-8-methyl-2-{[4-(4-methylpiperazin-1-yl)phenyl]amino}pyrimido[4,5-d]pyridazin-5(6H)-one;

6-methyl-2-{[4-(4-methylpiperazin-1-yl)phenyl]amino}-8-phenylpyrimido[4,5-d]pyridazin-5(6H)-one;

2-{[4-(4-methylpiperazin-1-yl)phenyl]amino}-8-phenylpyrimido[4,5-d]pyridazin-5(6H)-one;

6-allyl-2-{[4-(4-methylpiperazin-1-yl)phenyl]amino}-8-phenylpyrimido[4,5-d]pyridazin-5(6H)-one;

6-methyl-2-{[4-(4-methylpiperazin-1-yl)phenyl]amino}-8-(2-phenylethyl)pyrimido[4,5-d]pyridazin-5(6H)-one;

6-allyl-2-{[4-(4-methylpiperazin-1-yl)phenyl]amino}-8-(2-phenylethyl)pyrimido[4,5-d]pyridazin-5(6H)-one;

3-[2-{[4-(4-methylpiperazin-1-yl)phenyl]amino}-5-oxo-8-(2-phenylethyl)pyrimido[4,5-d]pyridazin-6(5H)-yl]propanenitrile;

2-{[4-(4-methylpiperazin-1-yl)phenyl]amino}-6-phenyl-8-(2-phenylethyl)pyrimido[4,5-d]pyridazin-5(6H)-one;

2-{[4-(4-methylpiperazin-1-yl)phenyl]amino}-8-(2-phenylethyl)-6-(2,2,2-trifluoroethyl)pyrimido[4,5-d]pyridazin-5(6H)-one;

6-methyl-2-{[4-(4-methylpiperazin-1-yl)phenyl]amino}-8-propylpyrimido[4,5-d]pyridazin-5(6H)-one;

6-(2-methylphenyl)-2-{[4-(4-methylpiperazin-1-yl)phenyl]amino}-8-(2-phenylethyl)pyrimido[4,5-d]pyridazin-5(6H)-one;

8-cyclopentyl-6-methyl-2-{[4-(4-methylpiperazin-1-yl)phenyl]amino}pyrimido[4,5-d]pyridazin-5(6H)-one;

8-cyclopentyl-2-{[4-(4-methylpiperazin-1-yl)phenyl]amino}pyrimido[4,5-d]pyridazin-5(6H)-one;

6-allyl-8-cyclopentyl-2-{[4-(4-methylpiperazin-1-yl)phenyl]amino}pyrimido[4,5-d]pyridazin-5(6H)-one;

6-allyl-2-{[4-(4-methylpiperazin-1-yl)phenyl]amino}-8-propylpyrimido[4,5-d]pyridazin-5(6H)-one;

2-{[4-(4-methylpiperazin-1-yl)phenyl]amino}-6-phenyl-8-propylpyrimido[4,5-d]pyridazin-5(6H)-one;

6-(2-methylphenyl)-2-{[4-(4-methylpiperazin-1-yl)phenyl]amino}-8-propylpyrimido[4,5-d]pyridazin-5(6H)-one;

8-benzyl-2-{[4-(4-methylpiperazin-1-yl)phenyl]amino}-6-phenylpyrimido[4,5-d]pyridazin-5(6H)-one;

8-benzyl-6-(2-methylphenyl)-2-{[4-(4-methylpiperazin-1-yl)phenyl]amino}pyrimido[4,5-d]pyridazin-5(6H)-one;

3-[2-{[4-(4-methylpiperazin-1-yl)phenyl]amino}-5-oxo-8-propylpyrimido[4,5-d]pyridazin-6(5H)-yl]propanenitrile;

6-allyl-8-benzyl-2-{[4-(4-methylpiperazin-1-yl)phenyl]amino}pyrimido[4,5-d]pyridazin-5(6H)-one;

2-{[4-(4-methylpiperazin-1-yl)phenyl]amino}-8-propyl-6-(2,2,2-trifluoroethyl)pyrimido[4,5-d]pyridazin-5(6H)-one;

6-(2-chlorophenyl)-2-{[4-(4-methylpiperazin-1-yl)phenyl]amino}-8-(2-phenylethyl)pyrimido[4,5-d]pyridazin-5(6H)-one;

6-(2-chlorophenyl)-2-{[4-(4-methylpiperazin-1-yl)phenyl]amino}-8-propylpyrimido[4,5-d]pyridazin-5(6H)-one;

8-benzyl-6-(2-chlorophenyl)-2-{[4-(4-methylpiperazin-1-yl)phenyl]amino}pyrimido[4,5-d]pyridazin-5(6H)-one;

2-{[4-(4-methylpiperazin-1-yl)phenyl]amino}-6,8-diphenylpyrimido[4,5-d]pyridazin-5(6H)-one;

6-(2-methylphenyl)-2-{[4-(4-methylpiperazin-1-yl)phenyl]amino}-8-phenylpyrimido[4,5-d]pyridazin-5(6H)-one;

6-(2-chlorophenyl)-2-{[4-(4-methylpiperazin-1-yl)phenyl]amino}-8-phenylpyrimido[4,5-d]pyridazin-5(6H)-one;

6-(2-methoxyphenyl)-2-{[4-(4-methylpiperazin-1-yl)phenyl]amino}-8-phenylpyrimido[4,5-d]pyridazin-5(6H)-one;

2-{[4-(4-methylpiperazin-1-yl)phenyl]amino}-8-phenyl-6-[2-(trifluoromethyl)phenyl]pyrimido[4,5-d]pyridazin-5(6H)-one;

8-(2-furyl)-6-(2-methylphenyl)-2-{[4-(4-methylpiperazin-1-yl)phenyl]amino}pyrimido[4,5-d]pyridazin-5(6H)-one;

6-(2-chlorophenyl)-8-(2-furyl)-2-{[4-(4-methylpiperazin-1-yl)phenyl]amino}pyrimido[4,5-d]pyridazin-5(6H)-one;

8-(2-furyl)-2-{[4-(4-methylpiperazin-1-yl)phenyl]amino}-6-phenylpyrimido[4,5-d]pyridazin-5(6H)-one;

6-allyl-8-(2-fluorophenyl)-2-{[4-(4-methylpiperazin-1-yl)phenyl]amino}pyrimido[4,5-d]pyridazin-5(6H)-one;

8-(2-fluorophenyl)-6-(2-methylphenyl)-2-{[4-(4-methylpiperazin-1-yl)phenyl]amino}pyrimido[4,5-d]pyridazin-5(6H)-one;

8-(2-fluorophenyl)-2-{[4-(4-methylpiperazin-1-yl)phenyl]amino}-6-phenylpyrimido[4,5-d]pyridazin-5(6H)-one;

6-(2-chlorophenyl)-8-(2,4-dichlorophenyl)-2-{[4-(4-methylpiperazin-1-yl)phenyl]amino}pyrimido[4,5-d]pyridazin-5(6H)-one;

8-(2,4-dichlorophenyl)-2-{[4-(4-methylpiperazin-1-yl)phenyl]amino}-6-[2-(trifluoromethyl)phenyl]pyrimido[4,5-d]pyridazin-5(6H)-one;

6-(2-chlorophenyl)-8-(2-fluorophenyl)-2-{[4-(4-methylpiperazin-1-yl)phenyl]amino}pyrimido[4,5-d]pyridazin-5(6H)-one;

8-(2,4-dichlorophenyl)-6-(2-methylphenyl)-2-{[4-(4-methylpiperazin-1-yl)phenyl]amino}pyrimido[4,5-d]pyridazin-5(6H)-one;

8-(2,4-dichlorophenyl)-2-{[4-(4-methylpiperazin-1-yl)phenyl]amino}-6-phenylpyrimido[4,5-d]pyridazin-5(6H)-one;

8-(2,4-dichlorophenyl)-6-(2-methoxyphenyl)-2-{[4-(4-methylpiperazin-1-yl)phenyl]amino}pyrimido[4,5-d]pyridazin-5(6H)-one;

6-(3-chlorophenyl)-8-(2,4-dichlorophenyl)-2-{[4-(4-methylpiperazin-1-yl)phenyl]amino}pyrimido[4,5-d]pyridazin-5(6H)-one;

6-(2,6-dichlorophenyl)-8-(2-fluorophenyl)-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-phenylpyrimido[4,5-d]pyridazin-5(6H)-one;

6-allyl-8-(2,4-dichlorophenyl)-2-{[4-(4-methylpiperazin-1-yl)phenyl]amino}pyrimido[4,5-d]pyridazin-5(6H)-one;

6-(2-chlorophenyl)-2-{[4-(4-methylpiperazin-1-yl)phenyl]amino}-8-(2-thienyl)pyrimido[4,5-d]pyridazin-5(6H)-one;

8-cyclopentyl-6-(2-methylphenyl)-2-{[4-(4-methylpiperazin-1-yl)phenyl]amino}pyrimido[4,5-d]pyridazin-5(6H)-one;

8-(3-methylphenyl)-2-{[4-(4-methylpiperazin-1-yl)phenyl]amino}-6-phenylpyrimido[4,5-d]pyridazin-5(6H)-one;

6-(2-chlorophenyl)-8-(3-methylphenyl)-2-{[4-(4-methylpiperazin-1-yl)phenyl]amino}pyrimido[4,5-d]pyridazin-5(6H)-one;

6-(2-methylphenyl)-8-(3-methylphenyl)-2-{[4-(4-methylpiperazin-1-yl)phenyl]amino}pyrimido[4,5-d]pyridazin-5(6H)-one;

6-(2-chlorophenyl)-2-[(2'-methyl-2',3'-dihydro-1'H-spiro[cyclopropane-1,4'-isoquinolin]-7'-yl)amino]-8-phenylpyrimido[4,5-d]pyridazin-5(6H)-one;

8-cyclopentyl-2-{[4-(4-methylpiperazin-1-yl)phenyl]amino}-6-phenylpyrimido[4,5-d]pyridazin-5(6H)-one;

6-(2-chlorophenyl)-8-cyclopentyl-2-{[4-(4-methylpiperazin-1-yl)phenyl]amino}pyrimido[4,5-d]pyridazin-5(6H)-one;

6-(3-chlorophenyl)-8-cyclopentyl-2-{[4-(4-methylpiperazin-1-yl)phenyl]amino}pyrimido[4,5-d]pyridazin-5(6H)-one;

8-cyclopentyl-6-(2-methoxyphenyl)-2-{[4-(4-methylpiperazin-1-yl)phenyl]amino}pyrimido[4,5-d]pyridazin-5(6H)-one;

8-(3-methoxyphenyl)-2-{[4-(4-methylpiperazin-1-yl)phenyl]amino}-6-phenylpyrimido[4,5-d]pyridazin-5(6H)-one;

2-{[4-(4-methylpiperazin-1-yl)phenyl]amino}-6-phenyl-8-[4-(pyrimidin-2-yl)phenyl]pyrimido[4,5-d]pyridazin-5(6H)-one;

6-(2-chlorophenyl)-2-{[4-(4-methylpiperazin-1-yl)phenyl]amino}-8-(pyridin-2-yl)pyrimido[4,5-d]pyridazin-5(6H)-one;

6-(2-chlorophenyl)-2-{[4-(4-methylpiperazin-1-yl)phenyl]amino}-8-[4-(pyrimidin-2-yl)phenyl]pyrimido[4,5-d]pyridazin-5(6H)-one;

6-allyl-2-{[4-(4-methylpiperazin-1-yl)phenyl]amino}-8-[4-(pyrimidin-2-yl)phenyl]pyrimido[4,5-d]pyridazin-5(6H)-one;

6-allyl-8-(3-methoxyphenyl)-2-{[4-(4-methylpiperazin-1-yl)phenyl]amino}pyrimido[4,5-d]pyridazin-5(6H)-one;

6-(2-methylphenyl)-2-{[4-(4-methylpiperazin-1-yl)phenyl]amino}-8-[4-(pyrimidin-2-yl)phenyl]pyrimido[4,5-d]pyridazin-5(6H)-one;

8-(3-bromophenyl)-6-(2-chlorophenyl)-2-{[4-(4-methylpiperazin-1-yl)phenyl]amino}pyrimido[4,5-d]pyridazin-5(6H)-one;

8-(3-bromophenyl)-6-(2-methylphenyl)-2-{[4-(4-methylpiperazin-1-yl)phenyl]amino}pyrimido[4,5-d]pyridazin-5(6H)-one;

8-(3-bromophenyl)-2-{[4-(4-methylpiperazin-1-yl)phenyl]amino}-6-phenylpyrimido[4,5-d]pyridazin-5(6H)-one;

6-allyl-8-(3-bromophenyl)-2-{[4-(4-methylpiperazin-1-yl)phenyl]amino}pyrimido[4,5-d]pyridazin-5(6H)-one;

6-(2,6-dichlorophenyl)-8-(2-furyl)-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-(2-thienyl)pyrimido[4,5-d]pyridazin-5(6H)-one;

6-(2,6-dichlorophenyl)-8-(2-methylphenyl)-2-{[4-(4-methylpiperazin-1-yl)phenyl]amino}pyrimido[4,5-d]pyridazin-5(6H)-one;

8-(3-bromophenyl)-6-(2,6-dichlorophenyl)-2-{[4-(4-methylpiperazin-1-yl)phenyl]amino}pyrimido[4,5-d]pyridazin-5(6H)-one;

8-(6-chloropyridin-2-yl)-2-{[4-(4-methylpiperazin-1-yl)phenyl]amino}-6-phenylpyrimido[4,5-d]pyridazin-5(6H)-one;

8-cyclopentyl-6-(2,6-dichlorophenyl)-2-{[4-(4-methylpiperazin-1-yl)phenyl]amino}pyrimido[4,5-d]pyridazin-5(6H)-one;

8-(6-chloropyridin-2-yl)-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-{6-[2-(2,6-dichlorophenyl)hydrazino]pyridin-2-yl}-2-{[4-(4-methylpiperazin-1-yl)phenyl]amino}pyrimido[4,5-d]pyridazin-5(6H)-one;

6-(2-chlorophenyl)-8-(6-chloropyridin-2-yl)-2-{[4-(4-methylpiperazin-1-yl)phenyl]amino}pyrimido[4,5-d]pyridazin-5(6H)-one;

8-(2-chloropyridin-3-yl)-2-{[4-(4-methylpiperazin-1-yl)phenyl]amino}-6-phenylpyrimido[4,5-d]pyridazin-5(6H)-one;

8-(2-ethoxypyridin-3-yl)-2-{[4-(4-methylpiperazin-1-yl)phenyl]amino}-6-phenylpyrimido[4,5-d]pyridazin-5(6H)-one;

6-(2-chlorophenyl)-8-(2-chloropyridin-3-yl)-2-{[4-(4-methylpiperazin-1-yl)phenyl]amino}pyrimido[4,5-d]pyridazin-5(6H)-one;

8-(2-chloropyridin-3-yl)-6-(2,6-dichlorophenyl)-2-{[4-(4-methylpiperazin-1-yl)phenyl]amino}pyrimido[4,5-d]pyridazin-5(6H)-one;

8-(3-fluorophenyl)-2-{[4-(4-methylpiperazin-1-yl)phenyl]amino}-6-phenylpyrimido[4,5-d]pyridazin-5(6H)-one;

6-(2-chlorophenyl)-8-(3-fluorophenyl)-2-{[4-(4-methylpiperazin-1-yl)phenyl]amino}pyrimido[4,5-d]pyridazin-5(6H)-one;

6-(2,6-dichlorophenyl)-8-(3-fluorophenyl)-2-{[4-(4-methylpiperazin-1-yl)phenyl]amino}pyrimido[4,5-d]pyridazin-5(6H)-one;

2-{[4-(4-methylpiperazin-1-yl)phenyl]amino}-8-(1-methyl-1H-pyrazol-4-yl)-6-phenylpyrimido[4,5-d]pyridazin-5(6H)-one;

6-(2-chlorophenyl)-2-{[4-(4-methylpiperazin-1-yl)phenyl]amino}-8-(1-methyl-1H-pyrazol-4-yl)pyrimido[4,5-d]pyridazin-5(6H)-one;

6-(2,6-dichlorophenyl)-2-{[4-(4-methylpiperazin-1-yl)phenyl]amino}-8-(1-methyl-1H-pyrazol-4-yl)pyrimido[4,5-d]pyridazin-5(6H)-one;

6-(2,6-dichlorophenyl)-8-(6-hydroxypyridin-2-yl)-2-{[4-(4-methylpiperazin-1-yl)phenyl]amino}pyrimido[4,5-d]pyridazin-5(6H)-one;

3-[6-(2,6-dichlorophenyl)-2-{[4-(4-methylpiperazin-1-yl)phenyl]amino}-5-oxo-5,6-dihydropyrimido[4,5-d]pyridazin-8-yl]benzonitrile;

6-(2,6-dichlorophenyl)-8-[3-(dimethylamino)phenyl]-2-{[4-(4-methylpiperazin-1-yl)phenyl]amino}pyrimido[4,5-d]pyridazin-5(6H)-one;

6-(2,6-dichlorophenyl)-8-[3-(1H-imidazol-4-yl)phenyl]-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-[3-(1H-pyrrol-2-yl)phenyl]pyrimido[4,5-d]pyridazin-5(6H)-one;

6-(2,6-dichlorophenyl)-2-{[4-(4-methylpiperazin-1-yl)phenyl]amino}-8-[3-(2-oxopiperidin-1-yl)phenyl]pyrimido[4,5-d]pyridazin-5(6H)-one;

6-(2-chlorophenyl)-8-(3-furyl)-2-{[4-(4-methylpiperazin-1-yl)phenyl]amino}pyrimido[4,5-d]pyridazin-5(6H)-one;

6-(2,6-dichlorophenyl)-8-(3-furyl)-2-{[4-(4-methylpiperazin-1-yl)phenyl]amino}pyrimido[4,5-d]pyridazin-5(6H)-one;

6-(2-chlorophenyl)-2-{[4-(4-methylpiperazin-1-yl)phenyl]amino}-8-(3-thienyl)pyrimido[4,5-d]pyridazin-5(6H)-one;

6-(2,6-dichlorophenyl)-2-{[4-(4-methylpiperazin-1-yl)phenyl]amino}-8-(3-thienyl)pyrimido[4,5-d]pyridazin-5(6H)-one;

6-(2-chlorophenyl)-2-{[4-(4-methylpiperazin-1-yl)phenyl]amino}-8-(pyridin-3-yl)pyrimido[4,5-d]pyridazin-5(6H)-one;

6-(2,6-dichlorophenyl)-2-{[4-(4-methylpiperazin-1-yl)phenyl]amino}-8-(pyridin-3-yl)pyrimido[4,5-d]pyridazin-5(6H)-one;

2-{[4-(4-methylpiperazin-1-yl)phenyl]amino}-6-phenyl-8-(pyridin-3-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-3-yl)pyrimido[4,5-d]pyridazin-5(6H)-one;

2-{[4-(4-methylpiperazin-1-yl)phenyl]amino}-6-phenyl-8-(pyridin-2-yl)pyrimido[4,5-d]pyridazin-5(6H)-one;

6-(2,6-dichlorophenyl)-2-{[4-(4-methylpiperazin-1-yl)phenyl]amino}-8-(pyridin-2-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-2-yl)pyrimido[4,5-d]pyridazin-5(6H)-one;

6-(2,6-dichlorophenyl)-2-{[4-(4-methylpiperazin-1-yl)phenyl]amino}-8-(piperidin-3-yl)pyrimido[4,5-d]pyridazin-5(6H)-one;

2-({4-[(dimethylamino)methyl]phenyl}amino)-8-(2-furyl)-6-(2-methylphenyl)pyrimido[4,5-d]pyridazin-5(6H)-one;

8-(2-furyl)-2-{[4-(4-isopropylpiperazin-1-yl)phenyl]amino}-6-(2-methylphenyl)pyrimido[4,5-d]pyridazin-5(6H)-one;

8-(2-furyl)-6-(2-methylphenyl)-2-{[4-(morpholin-4-ylsulfonyl)phenyl]amino}pyrimido[4,5-d]pyridazin-5(6H)-one;

6-(2-methylphenyl)-2-{[4-(morpholin-4-ylsulfonyl)phenyl]amino}-8-phenylpyrimido[4,5-d]pyridazin-5(6H)-one;

6-allyl-2-{[4-(morpholin-4-ylsulfonyl)phenyl]amino}-8-phenylpyrimido[4,5-d]pyridazin-5(6H)-one;

2-({4-[(dimethylamino)methyl]phenyl}amino)-6-(2-methylphenyl)-8-phenylpyrimido[4,5-d]pyridazin-5(6H)-one;

6-allyl-8-(2-furyl)-2-{[4-(4-isopropylpiperazin-1-yl)phenyl]amino}pyrimido[4,5-d]pyridazin-5(6H)-one;

2-{[4-(4-isopropylpiperazin-1-yl)-3-methoxyphenyl]amino}-6-(2-methylphenyl)-8-phenylpyrimido[4,5-d]pyridazin-5(6H)-one;

6-allyl-2-{[4-(4-isopropylpiperazin-1-yl)-3-methoxyphenyl]amino}-8-phenylpyrimido[4,5-d]pyridazin-5(6H)-one;

6-allyl-2-{[4-(4-isopropyl-1,4-diazepan-1-yl)-3-methylphenyl]amino}-8-phenylpyrimido[4,5-d]pyridazin-5(6H)-one;

2-{[4-(4-isopropyl-1,4-diazepan-1-yl)-3-methylphenyl]amino}-6-(2-methylphenyl)-8-phenylpyrimido[4,5-d]pyridazin-5(6H)-one;

6-allyl-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one;

2-{[4-(4-isopropylpiperazin-1-yl)phenyl]amino}-6-(2-methylphenyl)-8-(2-thienyl)pyrimido[4,5-d]pyridazin-5(6H)-one;

2-{[4-(4-isopropylpiperazin-1-yl)-3-methylphenyl]amino}-6-(2-methylphenyl)-8-(2-thienyl)pyrimido[4,5-d]pyridazin-5(6H)-one;

2-{[4-(4-isopropyl-1,4-diazepan-1-yl)-3-methylphenyl]amino}-6-(2-methylphenyl)-8-(2-thienyl)pyrimido[4,5-d]pyridazin-5(6H)-one;

6-(2-chlorophenyl)-2-{[4-(2-oxopyrrolidin-1-yl)phenyl]amino}-8-(2-thienyl)pyrimido[4,5-d]pyridazin-5(6H)-one;

6-(2-chlorophenyl)-2-{[4-(4-isopropylpiperazin-1-yl)phenyl]amino}-8-(2-thienyl)pyrimido[4,5-d]pyridazin-5(6H)-one;

6-(2-chlorophenyl)-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one;

6-allyl-2-{[4-(2-oxopyrrolidin-1-yl)phenyl]amino}-8-(2-thienyl)pyrimido[4,5-d]pyridazin-5(6H)-one;

6-allyl-2-{[4-(morpholin-4-ylsulfonyl)phenyl]amino}-8-(2-thienyl)pyrimido[4,5-d]pyridazin-5(6H)-one;

6-allyl-2-{[4-(4-isopropylpiperazin-1-yl)phenyl]amino}-8-(2-thienyl)pyrimido[4,5-d]pyridazin-5(6H)-one;

6-allyl-2-{[4-(4-isopropylpiperazin-1-yl)-3-methylphenyl]amino}-8-(2-thienyl)pyrimido[4,5-d]pyridazin-5(6H)-one;

6-(2-methylphenyl)-2-{[4-(2-oxopyrrolidin-1-yl)phenyl]amino}-8-(2-thienyl)pyrimido[4,5-d]pyridazin-5(6H)-one;

6-(2-methylphenyl)-2-{[4-(morpholin-4-ylsulfonyl)phenyl]amino}-8-(2-thienyl)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(2-methylphenyl)-8-(2-thienyl)pyrimido[4,5-d]pyridazin-5(6H)-one;

6-(2-chlorophenyl)-2-{[4-(4-isopropylpiperazin-1-yl)phenyl]amino}-8-phenylpyrimido[4,5-d]pyridazin-5(6H)-one;

2-{[4-(4-isopropylpiperazin-1-yl)-3-methoxyphenyl]amino}-6-(2-methylphenyl)-8-(2-thienyl)pyrimido[4,5-d]pyridazin-5(6H)-one;

8-(2-furyl)-2-{[4-(4-isopropylpiperazin-1-yl)-3-methylphenyl]amino}-6-(2-methylphenyl)pyrimido[4,5-d]pyridazin-5(6H)-one;

2-{[4-(4-isopropylpiperazin-1-yl)phenyl]amino}-6-(2-methylphenyl)-8-phenylpyrimido[4,5-d]pyridazin-5(6H)-one;

8-(2-furyl)-6-(2-methylphenyl)-2-{[4-(2-oxopyrrolidin-1-yl)phenyl]amino}pyrimido[4,5-d]pyridazin-5(6H)-one;

6-allyl-8-(2-furyl)-2-{[4-(4-isopropylpiperazin-1-yl)-3-methoxyphenyl]amino}pyrimido[4,5-d]pyridazin-5(6H)-one;

6-allyl-2-({4-[(dimethylamino)methyl]phenyl}amino)-8-(2-furyl)pyrimido[4,5-d]pyridazin-5(6H)-one;

8-(2-furyl)-2-{[4-(4-isopropylpiperazin-1-yl)-3-methoxyphenyl]amino}-6-(2-methylphenyl)pyrimido[4,5-d]pyridazin-5(6H)-one;

6-allyl-2-{[4-(4-isopropylpiperazin-1-yl)phenyl]amino}-8-phenylpyrimido[4,5-d]pyridazin-5(6H)-one;

6-allyl-8-(2-furyl)-2-{[4-(morpholin-4-ylsulfonyl)phenyl]amino}pyrimido[4,5-d]pyridazin-5(6H)-one;

6-(2-methylphenyl)-2-{[4-(2-oxopyrrolidin-1-yl)phenyl]amino}-8-phenylpyrimido[4,5-d]pyridazin-5(6H)-one;

6-allyl-2-{[4-(2-oxopyrrolidin-1-yl)phenyl]amino}-8-phenylpyrimido[4,5-d]pyridazin-5(6H)-one;

6-allyl-2-({4-[(dimethylamino)methyl]phenyl}amino)-8-phenylpyrimido[4,5-d]pyridazin-5(6H)-one;

6-allyl-8-(2-furyl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-(2-furyl)-2-[(2'-methyl-2',3'-dihydro-1'H-spiro[cyclopropane-1,4'-isoquinolin]-7'-yl)amino]-6-(2-methylphenyl)pyrimido[4,5-d]pyridazin-5(6H)-one;

6-allyl-8-(2-furyl)-2-{[4-(4-isopropylpiperazin-1-yl)-3-methylphenyl]amino}pyrimido[4,5-d]pyridazin-5(6H)-one;

6-(2,6-dichlorophenyl)-8-(1-isopropylpiperidin-3-yl)-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-(piperidin-4-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-4-yl)pyrimido[4,5-d]pyridazin-5(6H)-one;

6-(2,6-dichlorophenyl)-2-{[3-methyl-4-(4-methyl-1,4-diazepan-1-yl)phenyl]amino}-8-(1-methyl-1H-pyrazol-4-yl)pyrimido[4,5-d]pyridazin-5(6H)-one;

6-(2,6-dichlorophenyl)-2-{[4-(4-methylpiperazin-1-yl)phenyl]amino}-8-(1-methyl-1H-pyrazol-3-yl)pyrimido[4,5-d]pyridazin-5(6H)-one;

6-(2,6-dichlorophenyl)-2-{[3-methyl-4-(4-methyl-1,4-diazepan-1-yl)phenyl]amino}-8-(1-methyl-1H-pyrazol-3-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-3-yl)pyrimido[4,5-d]pyridazin-5(6H)-one;

2-{[4-(4-methylpiperazin-1-yl)phenyl]amino}-6-phenyl-8-(pyridin-4-yl)pyrimido[4,5-d]pyridazin-5(6H)-one;

6-(2-chlorophenyl)-2-{[4-(4-methylpiperazin-1-yl)phenyl]amino}-8-(pyridin-4-yl)pyrimido[4,5-d]pyridazin-5(6H)-one;

6-(2,6-dichlorophenyl)-2-{[4-(4-methylpiperazin-1-yl)phenyl]amino}-8-(pyridin-4-yl)pyrimido[4,5-d]pyridazin-5(6H)-one;

6-(2,6-dichlorophenyl)-2-{[4-(4-methylpiperazin-1-yl)phenyl]amino}-8-[3-(piperidin-1-ylmethyl)phenyl]pyrimido[4,5-d]pyridazin-5(6H)-one;

8-{3-[(cyclobutylamino)methyl]phenyl}-6-(2,6-dichlorophenyl)-2-{[4-(4-methylpiperazin-1-yl)phenyl]amino}pyrimido[4,5-d]pyridazin-5(6H)-one;

methyl 6-[6-(2,6-dichlorophenyl)-2-{[4-(4-methylpiperazin-1-yl)phenyl]amino}-5-oxo-5,6-dihydropyrimido[4,5-d]pyridazin-8-yl]pyridine-2-carboxylate;

6-(2,6-dichlorophenyl)-8-[6-(2-hydroxypropan-2-yl)pyridin-2-yl]-2-{[4-(4-methylpiperazin-1-yl)phenyl]amino}pyrimido[4,5-d]pyridazin-5(6H)-one;

6-allyl-2-{[4-(4-isopropylpiperazin-1-yl)-3-methoxyphenyl]amino}-8-(2-thienyl)pyrimido[4,5-d]pyridazin-5(6H)-one;

6-allyl-2-[(2-methyl-1,2,3,4-tetrahydroisoquinolin-7-yl)amino]-8-(2-thienyl)pyrimido[4,5-d]pyridazin-5(6H)-one;

6-allyl-2-{[4-(4-isopropyl-1,4-diazepan-1-yl)-3-methylphenyl]amino}-8-(2-thienyl)pyrimido[4,5-d]pyridazin-5(6H)-one;

6-(2-methylphenyl)-2-[(2-methyl-1,2,3,4-tetrahydroisoquinolin-7-yl)amino]-8-(2-thienyl)pyrimido[4,5-d]pyridazin-5(6H)-one;

6-(2-chlorophenyl)-2-{[4-(morpholin-4-ylsulfonyl)phenyl]amino}-8-(2-thienyl)pyrimido[4,5-d]pyridazin-5(6H)-one;

6-(2-chlorophenyl)-2-{[4-(4-isopropylpiperazin-1-yl)-3-methylphenyl]amino}-8-(2-thienyl)pyrimido[4,5-d]pyridazin-5(6H)-one;

6-(2-chlorophenyl)-2-[(2-methyl-1,2,3,4-tetrahydroisoquinolin-7-yl)amino]-8-(2-thienyl)pyrimido[4,5-d]pyridazin-5(6H)-one;

6-(2-chlorophenyl)-2-{[4-(2-oxopyrrolidin-1-yl)phenyl]amino}-8-phenylpyrimido[4,5-d]pyridazin-5(6H)-one;

6-allyl-2-{[4-(4-isopropylpiperazin-1-yl)-3-methylphenyl]amino}-8-phenylpyrimido[4,5-d]pyridazin-5(6H)-one;

2-{[4-(4-isopropylpiperazin-1-yl)-3-methylphenyl]amino}-6-(2-methylphenyl)-8-phenylpyrimido[4,5-d]pyridazin-5(6H)-one;

6-(2-methylphenyl)-2-[(2-methyl-1,2,3,4-tetrahydroisoquinolin-7-yl)amino]-8-phenylpyrimido[4,5-d]pyridazin-5(6H)-one;

6-allyl-2-[(2'-methyl-2',3'-dihydro-1'H-spiro[cyclopropane-1,4'-isoquinolin]-7'-yl)amino]-8-phenylpyrimido[4,5-d]pyridazin-5(6H)-one;

2-[(2'-methyl-2',3'-dihydro-1'H-spiro[cyclopropane-1,4'-isoquinolin]-7'-yl)amino]-6-(2-methylphenyl)-8-phenylpyrimido[4,5-d]pyridazin-5(6H)-one;

6-(2-chlorophenyl)-2-{[4-(4-isopropylpiperazin-1-yl)-3-methoxyphenyl]amino}-8-(2-thienyl)pyrimido[4,5-d]pyridazin-5(6H)-one;

8-(6-acetylpyridin-2-yl)-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-[6-(3-hydroxypentan-3-yl)pyridin-2-yl]-2-{[4-(4-methylpiperazin-1-yl)phenyl]amino}pyrimido[4,5-d]pyridazin-5(6H)-one;

2-{[4-(4-methylpiperazin-1-yl)phenyl]amino}-6-phenyl-8-(pyrimidin-4-yl)pyrimido[4,5-d]pyridazin-5(6H)-one;

6-(2-chlorophenyl)-2-{[4-(4-methylpiperazin-1-yl)phenyl]amino}-8-(pyrimidin-4-yl)pyrimido[4,5-d]pyridazin-5(6H)-one;

6-(2,6-dichlorophenyl)-2-{[4-(4-methylpiperazin-1-yl)phenyl]amino}-8-(pyrimidin-4-yl)pyrimido[4,5-d]pyridazin-5(6H)-one;

6-(2,6-dichlorophenyl)-2-{[4-(4-methylpiperazin-1-yl)phenyl]amino}-8-[6-(pyrrolidin-1-yl)pyridin-2-yl]pyrimido[4,5-d]pyridazin-5(6H)-one;

6-(2-chlorophenyl)-2-{[4-(4-methylpiperazin-1-yl)phenyl]amino}-8-[6-(pyrrolidin-1-yl)pyridin-2-yl]pyrimido[4,5-d]pyridazin-5(6H)-one;

6-(2-methylphenyl)-2-{[4-(4-methylpiperazin-1-yl)phenyl]amino}-8-[6-(pyrrolidin-1-yl)pyridin-2-yl]pyrimido[4,5-d]pyridazin-5(6H)-one;

6-(2,6-dichlorophenyl)-8-{3-[(methylamino)methyl]phenyl}-2-{[4-(4-methylpiperazin-1-yl)phenyl]amino}pyrimido[4,5-d]pyridazin-5(6H)-one;

6-(2,6-dichlorophenyl)-8-{3-[(dimethylamino)methyl]phenyl}-2-{[4-(4-methylpiperazin-1-yl)phenyl]amino}pyrimido[4,5-d]pyridazin-5(6H)-one;

8-(3-acetylphenyl)-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-{3-[1-(methylamino)ethyl]phenyl}-2-{[4-(4-methylpiperazin-1-yl)phenyl]amino}pyrimido[4,5-d]pyridazin-5(6H)-one;

8-(3,3-difluorocyclobutyl)-6-methyl-2-{[4-(4-methylpiperazin-1-yl)phenyl]amino}pyrimido[4,5-d]pyridazin-5(6H)-one;

methyl 3-[6-(2,6-dichlorophenyl)-2-{[4-(4-methylpiperazin-1-yl)phenyl]amino}-5-oxo-5,6-dihydropyrimido[4,5-d]pyridazin-8-yl]benzoate;

3-[6-(2,6-dichlorophenyl)-2-{[4-(4-methylpiperazin-1-yl)phenyl]amino}-5-oxo-5,6-dihydropyrimido[4,5-d]pyridazin-8-yl]-N,N-dimethylbenzamide;

3-[6-(2,6-dichlorophenyl)-2-{[4-(4-methylpiperazin-1-yl)phenyl]amino}-5-oxo-5,6-dihydropyrimido[4,5-d]pyridazin-8-yl]benzoic acid;

3-[6-(2,6-dichlorophenyl)-2-{[4-(4-methylpiperazin-1-yl)phenyl]amino}-5-oxo-5,6-dihydropyrimido[4,5-d]pyridazin-8-yl]-N-methylbenzamide;

6-(2,6-dichlorophenyl)-8-{3-[(4-methylpiperazin-1-yl)carbonyl]phenyl}-2-{[4-(4-methylpiperazin-1-yl)phenyl]amino}pyrimido[4,5-d]pyridazin-5(6H)-one;

6-(2,6-dichlorophenyl)-2-{[3-methyl-4-(4-methyl-1,4-diazepan-1-yl)phenyl]amino}-8-(pyridin-4-yl)pyrimido[4,5-d]pyridazin-5(6H)-one;

6-(2,6-dichlorophenyl)-2-{[4-(4-methylpiperazin-1-yl)phenyl]amino}-8-[3-(piperidin-1-ylcarbonyl)phenyl]pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-4-yl)pyrimido[4,5-d]pyridazin-5(6H)-one;

8-(3,3-difluorocyclobutyl)-2-{[4-(4-methylpiperazin-1-yl)phenyl]amino}-6-(prop-2-en-1-yl)pyrimido[4,5-d]pyridazin-5(6H)-one;

8-(3,3-difluorocyclobutyl)-2-{[4-(4-methylpiperazin-1-yl)phenyl]amino}-6-(pyridin-2-yl)pyrimido[4,5-d]pyridazin-5(6H)-one;

8-(3,3-difluorocyclobutyl)-6-(2-fluorophenyl)-2-{[4-(4-methylpiperazin-1-yl)phenyl]amino}pyrimido[4,5-d]pyridazin-5(6H)-one;

8-(3,3-difluorocyclobutyl)-6-(3-fluorophenyl)-2-{[4-(4-methylpiperazin-1-yl)phenyl]amino}pyrimido[4,5-d]pyridazin-5(6H)-one;

8-[1-(2-chloroethyl)-1H-pyrazol-4-yl]-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-(1-ethenyl-1H-pyrazol-4-yl)-2-{[4-(4-methylpiperazin-1-yl)phenyl]amino}pyrimido[4,5-d]pyridazin-5(6H)-one;

6-(2,6-dichlorophenyl)-8-{1-[2-(ethylamino)ethyl]-1H-pyrazol-4-yl}-2-{[4-(4-methylpiperazin-1-yl)phenyl]amino}pyrimido[4,5-d]pyridazin-5(6H)-one;

6-(2,6-dichlorophenyl)-8-(1-methyl-1H-imidazol-5-yl)-2-{[4-(4-methylpiperazin-1-yl)phenyl]amino}pyrimido[4,5-d]pyridazin-5(6H)-one;

6-(2-chlorophenyl)-2-({4-[(dimethylamino)methyl]phenyl}amino)-8-phenylpyrimido[4,5-d]pyridazin-5(6H)-one;

6-(2-chlorophenyl)-2-({3-methyl-4-[4-(propan-2-yl)piperazin-1-yl]phenyl}amino)-8-phenylpyrimido[4,5-d]pyridazin-5(6H)-one;

6-(2-chlorophenyl)-2-({3-methyl-4-[4-(propan-2-yl)-1,4-diazepan-1-yl]phenyl}amino)-8-phenylpyrimido[4,5-d]pyridazin-5(6H)-one;

6-(2-chlorophenyl)-2-({3-methoxy-4-[4-(propan-2-yl)piperazin-1-yl]phenyl}amino)-8-phenylpyrimido[4,5-d]pyridazin-5(6H)-one;

2-({4-[(dimethylamino)methyl]phenyl}amino)-6-(2-methylphenyl)-8-(thiophen-2-yl)pyrimido[4,5-d]pyridazin-5(6H)-one;

6-(2-chlorophenyl)-2-({4-[(dimethylamino)methyl]phenyl}amino)-8-(thiophen-2-yl)pyrimido[4,5-d]pyridazin-5(6H)-one;

2-({4-[(dimethylamino)methyl]phenyl}amino)-6-(prop-2-en-1-yl)-8-(thiophen-2-yl)pyrimido[4,5-d]pyridazin-5(6H)-one;

6-(2,6-dichlorophenyl)-8-{1-[2-(methylamino)ethyl]-1H-pyrazol-4-yl}-2-{[4-(4-methylpiperazin-1-yl)phenyl]amino}pyrimido[4,5-d]pyridazin-5(6H)-one;

6-(2,6-dichlorophenyl)-8-{1-[2-(dimethylamino)ethyl]-1H-pyrazol-4-yl}-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-{1-[2-(piperidin-1-yl)ethyl]-1H-pyrazol-4-yl}pyrimido[4,5-d]pyridazin-5(6H)-one;

6-(2,6-dichlorophenyl)-8-{1-[2-(4-methylpiperazin-1-yl) ethyl]-1H-pyrazol-4-yl}-2-{[4-(4-methylpiperazin-1-yl) phenyl]amino}pyrimido[4,5-d]pyridazin-5(6H)-one;

6-(2,6-dichlorophenyl)-8-{3-[(4-methylpiperazin-1-yl)methyl]phenyl}-2-{[4-(4-methylpiperazin-1-yl)phenyl] amino}pyrimido[4,5-d]pyridazin-5(6H)-one;

8-[3-(azetidin-1-ylcarbonyl)phenyl]-6-(2,6-dichlorophenyl)-2-{[4-(4-methylpiperazin-1-yl)phenyl] amino}pyrimido[4,5-d]pyridazin-5(6H)-one;

6-(2,6-dichlorophenyl)-8-(pyridin-2-yl)-2-(1,2,3,4-tetrahydroisoquinolin-7-ylamino)pyrimido[4,5-d]pyridazin-5 (6H)-one;

2-{[4-(piperazin-1-yl)phenyl]amino}-8-(pyridin-2-yl)-6-(pyridin-4-yl)pyrimido[4,5-d]pyridazin-5(6H)-one;

8-(2-acetylpyridin-4-yl)-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-2-{[4-(piperazin-1-yl)phenyl] amino}-8-(pyrazin-2-yl)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one;

methyl 4-[6-(2,6-dichlorophenyl)-2-{[4-(4-methylpiperazin-1-yl)phenyl]amino}-5-oxo-5,6-dihydropyrimido[4, 5-d]pyridazin-8-yl]pyridine-2-carboxylate;

6-(2,6-dichlorophenyl)-2-{[3-methyl-4-(1-methylazepan-4-yl)phenyl]amino}-8-(pyridin-2-yl)pyrimido[4,5-d]pyridazin-5(6H)-one;

6-(2,6-dichlorophenyl)-8-(pyridin-4-yl)-2-(1,2,3,4-tetrahydroisoquinolin-7-ylamino)pyrimido[4,5-d]pyridazin-5 (6H)-one;

6-(2,6-dichlorophenyl)-2-{[4-(4-methylpiperazin-1-yl)phenyl]amino}-8-[2-(pyrrolidin-1-ylcarbonyl)pyridin-4-yl] pyrimido[4,5-d]pyridazin-5(6H)-one;

6-(2,6-dichlorophenyl)-8-(6-fluoropyridin-2-yl)-2-{[4-(piperazin-1-yl)phenyl]amino}pyrimido[4,5-d]pyridazin-5 (6H)-one;

6-(2,6-dichlorophenyl)-8-(6-fluoropyridin-2-yl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-(furan-2-yl)-2-({3-methyl-4-[4-(propan-2-yl)-1,4-diazepan-1-yl]phenyl}amino)-6-(prop-2-en-1-yl)pyrimido[4, 5-d]pyridazin-5(6H)-one;

6-(2,6-dichlorophenyl)-8-[4-(2-oxopyrrolidin-1-yl)phenyl]-2-{[4-(piperazin-1-yl)phenyl]amino}pyrimido[4,5-d]pyridazin-5(6H)-one;

2-[(2-methyl-1,2,3,4-tetrahydroisoquinolin-7-yl)amino]-8-phenyl-6-(prop-2-en-1-yl)pyrimido[4,5-d]pyridazin-5 (6H)-one;

6-(2,6-dichlorophenyl)-2-{[4-(4-methylpiperazin-1-yl)phenyl]amino}-8-(1H-pyrazol-3-yl)pyrimido[4,5-d]pyridazin-5(6H)-one;

6-(2,6-dichlorophenyl)-2-{[4-(4-methylpiperazin-1-yl)phenyl]amino}-8-{1-[2-(piperidin-1-yl)ethyl]-1H-pyrazol-3-yl}pyrimido[4,5-d]pyridazin-5(6H)-one;

8-(furan-2-yl)-6-(2-methylphenyl)-2-[(2-methyl-1,2,3,4-tetrahydroisoquinolin-7-yl)amino]pyrimido[4,5-d]pyridazin-5(6H)-one;

8-[1-(2-chloroethyl)-1H-pyrazol-3-yl]-6-(2,6-dichlorophenyl)-2-{[4-(4-methylpiperazin-1-yl)phenyl] amino}pyrimido[4,5-d]pyridazin-5(6H)-one;

8-[1-(2-aminoethyl)-1H-pyrazol-3-yl]-6-(2,6-dichlorophenyl)-2-{[4-(4-methylpiperazin-1-yl)phenyl] amino}pyrimido[4,5-d]pyridazin-5(6H)-one;

6-(2,6-dichlorophenyl)-8-(1-ethenyl-1H-pyrazol-3-yl)-2-{ [4-(4-methylpiperazin-1-yl)phenyl]amino}pyrimido[4,5-d]pyridazin-5(6H)-one;

6-(2,6-dichlorophenyl)-2-{[4-(piperazin-1-yl)phenyl] amino}-8-[3-(piperidin-1-ylmethyl)phenyl]pyrimido[4,5-d]pyridazin-5(6H)-one;

2-[(4,4-dimethyl-1,2,3,4-tetrahydroisoquinolin-7-yl) amino]-8-(pyridin-2-yl)-6-(pyridin-4-yl)pyrimido[4,5-d] pyridazin-5(6H)-one;

8-(pyridin-2-yl)-6-(pyridin-4-yl)-2-[(2,4,4-trimethyl-1,2,3, 4-tetrahydroisoquinolin-7-yl)amino]pyrimido[4,5-d]pyridazin-5(6H)-one;

6-(2,6-dichlorophenyl)-8-{1-[2-(dimethylamino)ethyl]-1H-pyrazol-3-yl}-2-{[4-(4-methylpiperazin-1-yl)phenyl] amino}pyrimido[4,5-d]pyridazin-5(6H)-one;

6-(2,6-dichlorophenyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2-hydroxyethyl)-8-(pyridin-2-yl)-2-[(2,4,4-trimethyl-1,2, 3,4-tetrahydroisoquinolin-7-yl)amino]pyrimido[4,5-d] pyridazin-5(6H)-one;

6-(2,6-dichlorophenyl)-8-(6-fluoropyridin-2-yl)-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-[4-(2-oxopyrrolidin-1-yl)phenyl]pyrimido [4,5-d]pyridazin-5(6H)-one;

6-(2-chlorophenyl)-2-[(2-methyl-1,2,3,4-tetrahydroisoquinolin-7-yl)amino]-8-phenylpyrimido[4,5-d]pyridazin-5(6H)-one;

8-(furan-2-yl)-6-(2-methylphenyl)-2-({3-methyl-4-[4-(propan-2-yl)-1,4-diazepan-1-yl]phenyl}amino)pyrimido[4, 5-d]pyridazin-5(6H)-one;

6-(2,6-dichlorophenyl)-8-[4-(2-oxopyrrolidin-1-yl)phenyl]-2-(1,2,3,4-tetrahydroisoquinolin-7-ylamino)pyrimido[4, 5-d]pyridazin-5(6H)-one;

4-[6-(2,6-dichlorophenyl)-2-{[4-(4-methylpiperazin-1-yl) phenyl]amino}-5-oxo-5,6-dihydropyrimido[4,5-d]pyridazin-8-yl]-N,N-dimethylpyridine-2-carboxamide;

6-cyclohexyl-2-{[4-(piperazin-1-yl)phenyl]amino}-8-(pyridin-2-yl)pyrimido[4,5-d]pyridazin-5(6H)-one;

6-(2,6-dichlorophenyl)-8-[2-(2-hydroxypropan-2-yl)pyridin-4-yl]-2-{[4-(4-methylpiperazin-1-yl)phenyl] amino}pyrimido[4,5-d]pyridazin-5(6H)-one;

6-(2,6-dichlorophenyl)-8-(pyrazin-2-yl)-2-(1,2,3,4-tetrahydroisoquinolin-7-ylamino)pyrimido[4,5-d]pyridazin-5 (6H)-one;

6-(2,6-dichlorophenyl)-8-[1-(2-methoxyethyl)-1H-pyrazol-3-yl]-2-{[4-(4-methylpiperazin-1-yl)phenyl] amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one;

6-(2,6-dichlorophenyl)-8-[4-(2-oxopyrrolidin-1-yl)phenyl]-2-{[4-(piperidin-4-yl)phenyl]amino}pyrimido[4,5-d]pyridazin-5(6H)-one;

6-(2-chlorophenyl)-2-{[4-(morpholin-4-ylsulfonyl)phenyl] amino}-8-phenylpyrimido[4,5-d]pyridazin-5(6H)-one;

6-(2,6-dichlorophenyl)-8-(pyridin-4-yl)-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(6-fluoropyridin-2-yl)pyrimido[4,5-d]pyridazin-5(6H)-one;

8-(furan-2-yl)-2-[(2-methyl-1,2,3,4-tetrahydroisoquinolin-7-yl)amino]-6-(prop-2-en-1-yl)pyrimido[4,5-d]pyridazin-5(6H)-one;

8-[1-(2-aminoethyl)-1H-pyrazol-3-yl]-6-(2,6-dichlorophenyl)-2-{[4-(piperazin-1-yl)phenyl]amino}pyrimido[4,5-d]pyridazin-5(6H)-one;

8-(2-chloropyridin-4-yl)-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-{1-[2-(methylamino)ethyl]-1H-pyrazol-3-yl}-2-{[4-(4-methylpiperazin-1-yl)phenyl]amino}pyrimido[4,5-d]pyridazin-5(6H)-one;

6-cyclohexyl-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6,8-di(pyridin-2-yl)pyrimido[4,5-d]pyridazin-5(6H)-one;

6-(2,6-dichlorophenyl)-8-(1-methyl-1H-pyrazol-3-yl)-2-{[4-(piperazin-1-yl)phenyl]amino}pyrimido[4,5-d]pyridazin-5(6H)-one;

6-(2,6-dichlorophenyl)-8-(1-methyl-1H-pyrazol-3-yl)-2-(1,2,3,4-tetrahydroisoquinolin-7-ylamino)pyrimido[4,5-d]pyridazin-5(6H)-one;

6-(2-hydroxyethyl)-2-{[4-(piperazin-1-yl)phenyl]amino}-8-(pyridin-2-yl)pyrimido[4,5-d]pyridazin-5(6H)-one;

6-(2,6-dichlorophenyl)-8-[1-(methoxymethyl)-1H-pyrazol-3-yl]-2-{[4-(4-methylpiperazin-1-yl)phenyl]amino}pyrimido[4,5-d]pyridazin-5(6H)-one;

8-(furan-2-yl)-2-{[4-(2-oxopyrrolidin-1-yl)phenyl]amino}-6-(prop-2-en-1-yl)pyrimido[4,5-d]pyridazin-5(6H)-one;

6-(2,6-dichlorophenyl)-8-[1-(2-hydroxyethyl)-1H-pyrazol-3-yl]-2-{[4-(4-methylpiperazin-1-yl)phenyl]amino}pyrimido[4,5-d]pyridazin-5(6H)-one;

6-(2,6-dichlorophenyl)-2-{[4-(4-methylpiperazin-1-yl)phenyl]amino}-8-(pyrazin-2-yl)pyrimido[4,5-d]pyridazin-5(6H)-one;

2-{[4-(4-methylpiperazin-1-yl)phenyl]amino}-6-(propan-2-yl)-8-(pyridin-2-yl)pyrimido[4,5-d]pyridazin-5(6H)-one;

2-{[4-(4-methylpiperazin-1-yl)phenyl]amino}-6-(propan-2-yl)-8-(pyridin-4-yl)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(propan-2-yl)-8-(pyridin-2-yl)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(propan-2-yl)-8-(pyridin-4-yl)pyrimido[4,5-d]pyridazin-5(6H)-one;

8-(4-bromophenyl)-6-(2,6-dichlorophenyl)-2-{[4-(4-methylpiperazin-1-yl)phenyl]amino}pyrimido[4,5-d]pyridazin-5(6H)-one;

methyl 4-[6-(2,6-dichlorophenyl)-2-{[4-(4-methylpiperazin-1-yl)phenyl]amino}-5-oxo-5,6-dihydropyrimido[4,5-d]pyridazin-8-yl]benzoate;

8-cyclobutyl-6-(2,6-dichlorophenyl)-2-{[4-(4-methylpiperazin-1-yl)phenyl]amino}pyrimido[4,5-d]pyridazin-5(6H)-one;

8-cyclobutyl-6-(2,6-dichlorophenyl)-2-{[4-(piperazin-1-yl)phenyl]amino}pyrimido[4,5-d]pyridazin-5(6H)-one;

8-cyclobutyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-cyclobutyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;

6-cyclobutyl-2-{[4-(4-methylpiperazin-1-yl)phenyl]amino}-8-(pyridin-4-yl)pyrimido[4,5-d]pyridazin-5(6H)-one;

2-[(4,4-dimethyl-1,2,3,4-tetrahydroisoquinolin-7-yl)amino]-6-(2-hydroxyethyl)-8-(pyridin-2-yl)pyrimido[4,5-d]pyridazin-5(6H)-one;

6-(2,6-dichlorophenyl)-2-{[4-(piperazin-1-yl)phenyl]amino}-8-(pyridin-2-yl)pyrimido[4,5-d]pyridazin-5(6H)-one;

2-{[4-(piperazin-1-yl)phenyl]amino}-6,8-di(pyridin-2-yl)pyrimido[4,5-d]pyridazin-5(6H)-one;

6-(naphthalen-1-yl)-2-{[4-(piperazin-1-yl)phenyl]amino}-8-(pyridin-2-yl)pyrimido[4,5-d]pyridazin-5(6H)-one;

8-(pyridin-2-yl)-6-(pyridin-3-yl)-2-[(2,4,4-trimethyl-1,2,3,4-tetrahydroisoquinolin-7-yl)amino]pyrimido[4,5-d]pyridazin-5(6H)-one;

6-(2-hydroxypropyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2-hydroxypropyl)-2-{[4-(piperazin-1-yl)phenyl]amino}-8-(pyridin-2-yl)pyrimido[4,5-d]pyridazin-5(6H)-one;

4-[6-(2,6-dichlorophenyl)-2-{[4-(4-methylpiperazin-1-yl)phenyl]amino}-5-oxo-5,6-dihydropyrimido[4,5-d]pyridazin-8-yl]benzoic acid;

4-[6-(2,6-dichlorophenyl)-2-{[4-(4-methylpiperazin-1-yl)phenyl]amino}-5-oxo-5,6-dihydropyrimido[4,5-d]pyridazin-8-yl]-N,N-dimethylbenzamide;

N-cyclobutyl-4-[6-(2,6-dichlorophenyl)-2-{[4-(4-methylpiperazin-1-yl)phenyl]amino}-5-oxo-5,6-dihydropyrimido[4,5-d]pyridazin-8-yl]benzamide;

4-[6-(2,6-dichlorophenyl)-2-{[4-(4-methylpiperazin-1-yl)phenyl]amino}-5-oxo-5,6-dihydropyrimido[4,5-d]pyridazin-8-yl]-N-methylbenzamide;

6-cyclohexyl-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6-(2-hydroxypropyl)-8-(pyridin-2-yl)pyrimido[4,5-d]pyridazin-5(6H)-one;

6-(2-chloro-6-fluorophenyl)-2-{[4-(4-methylpiperazin-1-yl)phenyl]amino}-8-(pyridin-4-yl)pyrimido[4,5-d]pyridazin-5(6H)-one;

6-(2-chloro-6-fluorophenyl)-2-{[4-(piperazin-1-yl)phenyl]amino}-8-(pyridin-4-yl)pyrimido[4,5-d]pyridazin-5(6H)-one;

6-(2-chloro-6-fluorophenyl)-2-{[4-(4-methylpiperazin-1-yl)phenyl]amino}-8-(pyrimidin-4-yl)pyrimido[4,5-d]pyridazin-5(6H)-one;

6-(2-chloro-6-fluorophenyl)-8-(6-ethoxypyridin-2-yl)-2-{[4-(4-methylpiperazin-1-yl)phenyl]amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-methylpyrimido[4,5-d]pyridazin-5(6H)-one;

2-{[4-(4-cyclobutylpiperazin-1-yl)phenyl]amino}-6-(2,6-dichlorophenyl)-8-(pyridin-4-yl)pyrimido[4,5-d]pyridazin-5(6H)-one;

6-(2-chloro-6-fluorophenyl)-2-{[4-(4-methylpiperazin-1-yl)phenyl]amino}-8-(1-methyl-1H-pyrazol-4-yl)pyrimido[4,5-d]pyridazin-5(6H)-one;

6-(2-chloro-6-fluorophenyl)-8-(6-hydroxypyridin-2-yl)-2-{[4-(4-methylpiperazin-1-yl)phenyl]amino}pyrimido[4,5-d]pyridazin-5(6H)-one;

6-(piperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one;

2-[(4,4-dimethyl-1,2,3,4-tetrahydroisoquinolin-7-yl)amino]-6-(piperidin-4-yl)-8-(pyridin-2-yl)pyrimido[4,5-d]pyridazin-5(6H)-one;

2-[(4,4-dimethyl-1,2,3,4-tetrahydroisoquinolin-7-yl)amino]-6-(naphthalen-1-yl)-8-(pyridin-2-yl)pyrimido[4,5-d]pyridazin-5(6H)-one;

6-(2,6-dichlorophenyl)-2-{[4-(4-methylpiperazin-1-yl)phenyl]amino}-8-(1,3-thiazol-5-yl)pyrimido[4,5-d]pyridazin-5(6H)-one;

6-(2-chloro-6-fluorophenyl)-2-(2',3'-dihydro-1'H-spiro[cyclopropane-1,4'-isoquinolin]-7'-ylamino)-8-methylpyrimido[4,5-d]pyridazin-5(6H)-one;

6-(2-chloro-6-fluorophenyl)-2-{[4-(4-methylpiperazin-1-yl)phenyl]amino}-8-(pyridin-2-yl)pyrimido[4,5-d]pyridazin-5(6H)-one;

6-(4-hydroxypyridin-3-yl)-2-{[4-(4-methylpiperazin-1-yl)phenyl]amino}-8-(pyridin-2-yl)pyrimido[4,5-d]pyridazin-5(6H)-one;

6-(2-chloro-6-fluorophenyl)-8-methyl-2-[(2,4,4-trimethyl-1,2,3,4-tetrahydroisoquinolin-7-yl)amino]pyrimido[4,5-d]pyridazin-5(6H)-one;

6-(2-chloro-6-fluorophenyl)-8-methyl-2-{[4-(4-methylpiperazin-1-yl)phenyl]amino}pyrimido[4,5-d]pyridazin-5(6H)-one;

6-(2-chloro-6-fluorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;

6-(2,6-dichlorophenyl)-8-methyl-2-{[4-(4-methylpiperazin-1-yl)phenyl]amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1,3-thiazol-5-yl)pyrimido[4,5-d]pyridazin-5(6H)-one, 6-(2,6-dichlorophenyl)-2-{[4-(4-methylpiperazin-1-yl)phenyl]amino}-8-(1,3-thiazol-2-yl)pyrimido[4,5-d]pyridazin-5(6H)-one, 6-(2,6-dichlorophenyl)-2-[(2'-methyl-2',3'-dihydro-1'H-spiro[cyclopropane-1,4'-isoquinolin]-7'-yl)amino]-8-(1,3-thiazol-5-yl)pyrimido[4,5-d]pyridazin-5(6H)-one;

6-(2,6-dichlorophenyl)-2-(1,2,3,4-tetrahydroisoquinolin-7-ylamino)-8-(1,3-thiazol-5-yl)pyrimido[4,5-d]pyridazin-5(6H)-one;

6-(2,6-dichlorophenyl)-2-{[4-(piperazin-1-yl)phenyl]amino}-8-(1,3-thiazol-5-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1,3-thiazol-2-yl)pyrimido[4,5-d]pyridazin-5(6H)-one;

6-(2,6-dichlorophenyl)-2-({4-[4-(oxetan-3-yl)piperazin-1-yl]phenyl}amino)-8-(pyridin-4-yl)pyrimido[4,5-d]pyridazin-5(6H)-one;

6-(1-methylpiperidin-4-yl)-2-{[4-(piperazin-1-yl)phenyl]amino}-8-(pyridin-2-yl)pyrimido[4,5-d]pyridazin-5(6H)-one;

6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;

6-(2,6-dichlorophenyl)-2-{[4-(piperazin-1-yl)phenyl]amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;

6-(2,6-dichlorophenyl)-2-(1,2,3,4-tetrahydroisoquinolin-7-ylamino)pyrimido[4,5-d]pyridazin-5(6H)-one;

6-(1-methylpiperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one;

2-[(4,4-dimethyl-1,2,3,4-tetrahydroisoquinolin-7-yl)amino]-6-(1-methylpiperidin-4-yl)-8-(pyridin-2-yl)pyrimido[4,5-d]pyridazin-5(6H)-one;

6-(2,6-dimethylcyclohexyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2,6-dimethylcyclohexyl)-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6-(1-methylpiperidin-3-yl)-8-(pyridin-2-yl)pyrimido[4,5-d]pyridazin-5(6H)-one;

6-(2,6-dimethylcyclohexyl)-2-{[4-(piperazin-1-yl)phenyl]amino}-8-(pyridin-2-yl)pyrimido[4,5-d]pyridazin-5(6H)-one;

6-(1-methylpiperidin-3-yl)-2-{[4-(piperazin-1-yl)phenyl]amino}-8-(pyridin-2-yl)pyrimido[4,5-d]pyridazin-5(6H)-one;

6-(2-chloro-6-fluorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one;

6-(3-chloropyridin-2-yl)-2-{[4-(4-methylpiperazin-1-yl)phenyl]amino}-8-(pyridin-4-yl)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one;

6-(2,6-dichlorophenyl)-8-(1-methyl-1H-imidazol-4-yl)-2-{[4-(4-methylpiperazin-1-yl)phenyl]amino}pyrimido[4,5-d]pyridazin-5(6H)-one, 6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one;

6-(2,6-dichlorophenyl)-8-(1-methyl-1H-imidazol-4-yl)-2-{[4-(piperazin-1-yl)phenyl]amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(2,6-dichlorophenyl)-8-(1-methyl-1H-imidazol-4-yl)-2-(1,2,3,4-tetrahydroisoquinolin-7-ylamino)pyrimido[4,5-d]pyridazin-5(6H)-one;

6-(3-chloropyridin-2-yl)-8-(1-methyl-1H-imidazol-4-yl)-2-{[4-(4-methylpiperazin-1-yl)phenyl]amino}pyrimido[4,5-d]pyridazin-5(6H)-one;

6-(2,6-dichlorophenyl)-2-{[4-(piperazin-1-yl)phenyl]amino}-8-(1,3-thiazol-2-yl)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1,3-thiazol-2-yl)pyrimido[4,5-d]pyridazin-5(6H)-one;

6-(2,6-dichlorophenyl)-2-(1,2,3,4-tetrahydroisoquinolin-7-ylamino)-8-(1,3-thiazol-2-yl)pyrimido[4,5-d]pyridazin-5(6H)-one;

6-(3-chloropyridin-2-yl)-2-{[4-(piperazin-1-yl)phenyl]amino}-8-(1,3-thiazol-2-yl)pyrimido[4,5-d]pyridazin-5(6H)-one, 6-(3-chloropyridin-2-yl)-2-{[4-(4-methylpiperazin-1-yl)phenyl]amino}-8-(pyridin-2-yl)pyrimido[4,5-d]pyridazin-5(6H)-one;

6-(3-chloropyridin-2-yl)-2-(2',3'-dihydro-1'H-spiro[cyclopropane-1,4'-isoquinolin]-7'-ylamino)-8-methylpyrimido[4,5-d]pyridazin-5(6H)-one;

6-(3-chloropyridin-2-yl)-8-(1-methyl-1H-imidazol-4-yl)-2-{[4-(piperazin-1-yl)phenyl]amino}pyrimido[4,5-d]pyridazin-5(6H)-one;

6-(3-chloropyridin-2-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;

6-(3-chloropyridin-2-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(3-chloropyridin-2-yl)-8-(1-methyl-1H-imidazol-4-yl)-2-(1,2,3,4-tetrahydroisoquinolin-7-ylamino)pyrimido[4,5-d]pyridazin-5(6H)-one;

6-(2,6-dichlorophenyl)-8-(1-methyl-1H-imidazol-2-yl)-2-{[4-(4-methylpiperazin-1-yl)phenyl]amino}pyrimido[4,5-d]pyridazin-5(6H)-one;

6-(2,6-dichlorophenyl)-8-(1-methyl-1H-imidazol-2-yl)-2-{[4-(piperazin-1-yl)phenyl]amino}pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1-methyl-1H-imidazol-2-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-2-yl)pyrimido[4,5-d]pyridazin-5(6H)-one;

6-(3,5-dichloropyridin-4-yl)-2-{[4-(4-methylpiperazin-1-yl)phenyl]amino}-8-(pyridin-4-yl)pyrimido[4,5-d]pyridazin-5(6H)-one;

6-(3,5-dichloropyridin-4-yl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one;

6-(3,5-dichloropyridin-4-yl)-2-{[4-(4-methylpiperazin-1-yl)phenyl]amino}-8-(1,3-thiazol-5-yl)pyrimido[4,5-d]pyridazin-5(6H)-one, 6-(3,5-dichloropyridin-4-yl)-8-(1-methyl-1H-imidazol-4-yl)-2-{[4-(4-methylpiperazin-1-yl)phenyl]amino}pyrimido[4,5-d]pyridazin-5(6H)-one;

6-(3,5-dichloropyridin-4-yl)-2-{[4-(4-methylpiperazin-1-yl)phenyl]amino}-8-(pyridin-2-yl)pyrimido[4,5-d]pyridazin-5(6H)-one;

6-(2,6-dichlorophenyl)-2-({2-methoxy-4-[4-(4-methylpiperazin-1-yl)piperidin-1-yl]phenyl}amino)-8-methylpyrimido[4,5-d]pyridazin-5(6H)-one;

6-(2,6-dichlorophenyl)-8-methyl-2-[(2,4,4-trimethyl-1,2,3,4-tetrahydroisoquinolin-7-yl)amino]pyrimido[4,5-d]pyridazin-5(6H)-one;

6-(3-chloropyridin-2-yl)-8-methyl-2-[(2,4,4-trimethyl-1,2,3,4-tetrahydroisoquinolin-7-yl)amino]pyrimido[4,5-d]pyridazin-5(6H)-one;

6-(2-chloro-6-fluorophenyl)-2-{[2-(dimethylamino)-2,3-dihydro-1H-inden-5-yl]amino}-8-methylpyrimido[4,5-d]pyridazin-5(6H)-one;

6-(3-chloropyridin-2-yl)-2-{[2-(dimethylamino)-2,3-dihydro-1H-inden-5-yl]amino}-8-methylpyrimido[4,5-d]pyridazin-5(6H)-one;

6-(2-chloro-6-fluorophenyl)-8-methyl-2-{[3-methyl-4-(1-methylazepan-4-yl)phenyl]amino}pyrimido[4,5-d]pyridazin-5(6H)-one;

6-(3-chloropyridin-2-yl)-8-methyl-2-{[3-methyl-4-(1-methylazepan-4-yl)phenyl]amino}pyrimido[4,5-d]pyridazin-5(6H)-one;

6-(2,6-dichlorophenyl)-2-{[4,4-dimethyl-2-(2,2,2-trifluoroethyl)-1,2,3,4-tetrahydroisoquinolin-7-yl]amino}-8-methylpyrimido[4,5-d]pyridazin-5(6H)-one;

6-(2,6-dichlorophenyl)-8-methyl-2-(1,2,3,4-tetrahydroisoquinolin-6-ylamino)pyrimido[4,5-d]pyridazin-5(6H)-one;

6-(3,5-dichloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(3-chloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

2-{[4-(4-acetylpiperazin-1-yl)phenyl]amino}-6-(2,6-dichlorophenyl)-8-(pyridin-2-yl)pyrimido[4,5-d]pyridazin-5(6H)-one;

2-[(2'-acetyl-2',3'-dihydro-1'H-spiro[cyclopropane-1,4'-isoquinolin]-7'-yl)amino]-6-(2,6-dichlorophenyl)-8-(pyridin-2-yl)pyrimido[4,5-d]pyridazin-5(6H)-one;

6-(2,6-dichlorophenyl)-2-({4-[4-(methylsulfonyl)piperazin-1-yl]phenyl}amino)-8-(pyridin-2-yl)pyrimido[4,5-d]pyridazin-5(6H)-one;

6-(2,6-dichlorophenyl)-2-{[2'-(methylsulfonyl)-2',3'-dihydro-1'H-spiro[cyclopropane-1,4'-isoquinolin]-7'-yl]amino}-8-(pyridin-2-yl)pyrimido[4,5-d]pyridazin-5(6H)-one;

2-{[4-(4-acetylpiperazin-1-yl)phenyl]amino}-6-(2,6-dichlorophenyl)-8-(pyridin-4-yl)pyrimido[4,5-d]pyridazin-5(6H)-one;

2-[(2'-acetyl-2',3'-dihydro-1'H-spiro[cyclopropane-1,4'-isoquinolin]-7'-yl)amino]-6-(2,6-dichlorophenyl)-8-(pyridin-4-yl)pyrimido[4,5-d]pyridazin-5(6H)-one;

6-(2,6-dichlorophenyl)-2-({4-[4-(methylsulfonyl)piperazin-1-yl]phenyl}amino)-8-(pyridin-4-yl)pyrimido[4,5-d]pyridazin-5(6H)-one;

6-(2,6-dichlorophenyl)-2-{[2'-(methylsulfonyl)-2',3'-dihydro-1'H-spiro[cyclopropane-1,4'-isoquinolin]-7'-yl]amino}-8-(pyridin-4-yl)pyrimido[4,5-d]pyridazin-5(6H)-one;

6-(3-chloropyridin-4-yl)-2-{[4-(4-methylpiperazin-1-yl)phenyl]amino}-8-(pyridin-4-yl)pyrimido[4,5-d]pyridazin-5(6H)-one;

6-(3-chloropyridin-4-yl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one;

6-(3-chloropyridin-4-yl)-2-{[4-(4-methylpiperazin-1-yl)phenyl]amino}-8-(pyridin-2-yl)pyrimido[4,5-d]pyridazin-5(6H)-one;

6-(3-chloropyridin-4-yl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one;

8-cyclopropyl-6-(2,6-dichlorophenyl)-2-{[4-(4-methylpiperazin-1-yl)phenyl]amino}pyrimido[4,5-d]pyridazin-5(6H)-one;

6-(2,6-dichlorophenyl)-8-(difluoromethyl)-2-{[4-(4-methylpiperazin-1-yl)phenyl]amino}pyrimido[4,5-d]pyridazin-5(6H)-one;

6-(2,6-dichlorophenyl)-8-ethyl-2-{[4-(4-methylpiperazin-1-yl)phenyl]amino}pyrimido[4,5-d]pyridazin-5(6H)-one;

8-cyclopropyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-cyclopropyl-6-(2,6-dichlorophenyl)-2-(1,2,3,4-tetrahydroisoquinolin-7-ylamino)pyrimido[4,5-d]pyridazin-5(6H)-one, 8-cyclopropyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;

8-cyclopropyl-6-(2,6-dichlorophenyl)-2-{[4-(piperazin-1-yl)phenyl]amino}pyrimido[4,5-d]pyridazin-5(6H)-one;

6-(2,6-dichlorophenyl)-8-methyl-2-{[4-(piperazin-1-yl)phenyl]amino}pyrimido[4,5-d]pyridazin-5(6H)-one;
6-(2,6-dichlorophenyl)-8-methyl-2-{[3-methyl-4-(1-methylazepan-4-yl)phenyl]amino}pyrimido[4,5-d]pyridazin-5(6H)-one;
6-(2,6-dichlorophenyl)-8-methyl-2-(1,2,3,4-tetrahydroisoquinolin-7-ylamino)pyrimido[4,5-d]pyridazin-5(6H)-one;
6-(2-chloro-6-fluorophenyl)-8-methyl-2-{[4-(piperazin-1-yl)phenyl]amino}pyrimido[4,5-d]pyridazin-5(6H)-one;
6-(2,6-dichlorophenyl)-2-{[2-(dimethylamino)-2,3-dihydro-1H-inden-5-yl]amino}-8-methylpyrimido[4,5-d]pyridazin-5(6H)-one;
6-(2-chloro-6-fluorophenyl)-8-methyl-2-(1,2,3,4-tetrahydroisoquinolin-7-ylamino)pyrimido[4,5-d]pyridazin-5(6H)-one;
6-(3-chloropyridin-2-yl)-8-methyl-2-{[4-(piperazin-1-yl)phenyl]amino}pyrimido[4,5-d]pyridazin-5(6H)-one;
6-(3-chloropyridin-2-yl)-8-methyl-2-(1,2,3,4-tetrahydroisoquinolin-7-ylamino)pyrimido[4,5-d]pyridazin-5(6H)-one;
6-(2,6-dichlorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;
6-(2,6-dichlorophenyl)-8-ethyl-2-[(2'-methyl-2',3'-dihydro-1'H-spiro[cyclopropane-1,4'-isoquinolin]-7'-yl)amino]pyrimido[4,5-d]pyridazin-5(6H)-one;
6-(2,6-dichlorophenyl)-8-ethyl-2-(1,2,3,4-tetrahydroisoquinolin-7-ylamino)pyrimido[4,5-d]pyridazin-5(6H)-one;
6-(2,6-dichlorophenyl)-2-(2',3'-dihydro-1'H-spiro[cyclopropane-1,4'-isoquinolin]-7'-ylamino)-8-ethylpyrimido[4,5-d]pyridazin-5(6H)-one;
6-(2,6-dichlorophenyl)-8-(difluoromethyl)-2-{[4-(piperazin-1-yl)phenyl]amino}pyrimido[4,5-d]pyridazin-5(6H)-one;
6-(2,6-dichlorophenyl)-2-{[2-(dimethylamino)-2,3-dihydro-1H-inden-5-yl]amino}-8-ethylpyrimido[4,5-d]pyridazin-5(6H)-one;
6-(2,6-dichlorophenyl)-8-(difluoromethyl)-2-(2',3'-dihydro-1'H-spiro[cyclopropane-1,4'-isoquinolin]-7'-ylamino)pyrimido[4,5-d]pyridazin-5(6H)-one;
6-(2,6-dichlorophenyl)-8-(difluoromethyl)-2-{[2-(dimethylamino)-2,3-dihydro-1H-inden-5-yl]amino}pyrimido[4,5-d]pyridazin-5(6H)-one;
6-(2,6-dichlorophenyl)-8-ethyl-2-{[4-(piperazin-1-yl)phenyl]amino}pyrimido[4,5-d]pyridazin-5(6H)-one;
6-(2,6-dichlorophenyl)-8-(difluoromethyl)-2-(1,2,3,4-tetrahydroisoquinolin-7-ylamino)pyrimido[4,5-d]pyridazin-5(6H)-one;
6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
6-(2,6-dichlorophenyl)-2-{[4-(4-methylpiperazin-1-yl)phenyl]amino}-8-(trifluoromethyl)pyrimido[4,5-d]pyridazin-5(6H)-one;
6-(2,6-dichlorophenyl)-2-[(2'-methyl-2',3'-dihydro-1'H-spiro[cyclopropane-1,4'-isoquinolin]-7'-yl)amino]-8-(trifluoromethyl)pyrimido[4,5-d]pyridazin-5(6H)-one;
2-{[4-(4-acetylpiperazin-1-yl)phenyl]amino}-6-(2,6-dichlorophenyl)-8-ethylpyrimido[4,5-d]pyridazin-5(6H)-one;
2-[(2'-acetyl-2',3'-dihydro-1'H-spiro[cyclopropane-1,4'-isoquinolin]-7'-yl)amino]-6-(2,6-dichlorophenyl)-8-(difluoromethyl)pyrimido[4,5-d]pyridazin-5(6H)-one;
7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-carboxamide;
2-[(2'-acetyl-2',3'-dihydro-1'H-spiro[cyclopropane-1,4'-isoquinolin]-7'-yl)amino]-6-(2,6-dichlorophenyl)-8-methylpyrimido[4,5-d]pyridazin-5(6H)-one;
6-(2,6-dichlorophenyl)-2-{[4-(piperazin-1-yl)phenyl]amino}-8-(trifluoromethyl)pyrimido[4,5-d]pyridazin-5(6H)-one;
6-(2,6-dichlorophenyl)-8-(fluoromethyl)-2-{[4-(4-methylpiperazin-1-yl)phenyl]amino}pyrimido[4,5-d]pyridazin-5(6H)-one;
6-(2,6-dichlorophenyl)-2-(2',3'-dihydro-1'H-spiro[cyclopropane-1,4'-isoquinolin]-7'-ylamino)-8-(trifluoromethyl)pyrimido[4,5-d]pyridazin-5(6H)-one;
6-(2,6-dichlorophenyl)-2-(1,2,3,4-tetrahydroisoquinolin-7-ylamino)-8-(trifluoromethyl)pyrimido[4,5-d]pyridazin-5(6H)-one;
6-(2,6-dichlorophenyl)-2-{[4-(pyrrolidin-3-yl)phenyl]amino}-8-(trifluoromethyl)pyrimido[4,5-d]pyridazin-5(6H)-one;
6-(2,6-dichlorophenyl)-8-(methoxymethyl)-2-{[4-(4-methylpiperazin-1-yl)phenyl]amino}pyrimido[4,5-d]pyridazin-5(6H)-one;
6-(2,6-dichlorophenyl)-8-(methoxymethyl)-2-{[4-(piperazin-1-yl)phenyl]amino}pyrimido[4,5-d]pyridazin-5(6H)-one;
6-(2,6-dichlorophenyl)-2-({4-[4-(dimethylamino)piperidin-1-yl]phenyl}amino)-8-methylpyrimido[4,5-d]pyridazin-5(6H)-one;
6-(2,6-dichlorophenyl)-2-{[2'-(hydroxyacetyl)-2',3'-dihydro-1'H-spiro[cyclopropane-1,4'-isoquinolin]-7'-yl]amino}-8-methylpyrimido[4,5-d]pyridazin-5(6H)-one;
6-(2,6-dichlorophenyl)-8-methyl-2-{[2'-(methylsulfonyl)-2',3'-dihydro-1'H-spiro[cyclopropane-1,4'-isoquinolin]-7'-yl]amino}pyrimido[4,5-d]pyridazin-5(6H)-one;
6-(2,6-dichlorophenyl)-2-(2',3'-dihydro-1'H-spiro[cyclopropane-1,4'-isoquinolin]-7'-ylamino)-8-(methoxymethyl)pyrimido[4,5-d]pyridazin-5(6H)-one;
6-(2,6-dichlorophenyl)-8-(methoxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
6-(2,6-dichlorophenyl)-8-(hydroxymethyl)-2-{[4-(piperazin-1-yl)phenyl]amino}pyrimido[4,5-d]pyridazin-5(6H)-one;
6-(2,6-dichlorophenyl)-8-(hydroxymethyl)-2-{[4-(4-methylpiperazin-1-yl)phenyl]amino}pyrimido[4,5-d]pyridazin-5(6H)-one;
6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
6-(2,6-dichlorophenyl)-2-(2',3'-dihydro-1'H-spiro[cyclopropane-1,4'-isoquinolin]-7'-ylamino)-8-(hydroxymethyl)pyrimido[4,5-d]pyridazin-5(6H)-one;
7-{[6-(2,6-dichlorophenyl)-8-methyl-5-oxo-5,6-dihydropyrimido[4,5-d]pyridazin-2-yl]amino}-3,4-dihydroisoquinoline-2(1H)-sulfonamide;
6-(2,6-dichlorophenyl)-8-methyl-2-[(2-methyl-1,2,3,4-tetrahydroisoquinolin-6-yl)amino]pyrimido[4,5-d]pyridazin-5(6H)-one;
7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-sulfonamide;
6-(2,6-dichlorophenyl)-2-{[2-(2-hydroxy-2-methylpropanoyl)-1,2,3,4-tetrahydroisoquinolin-6-yl]amino}-8-methylpyrimido[4,5-d]pyridazin-5(6H)-one;
6-(2,6-dichlorophenyl)-2-[(4,4-dimethyl-1,2,3,4-tetrahydroisoquinolin-7-yl)amino]-8-methylpyrimido[4,5-d]pyridazin-5(6H)-one;

2-[(2-acetyl-4,4-dimethyl-1,2,3,4-tetrahydroisoquinolin-7-yl)amino]-6-(2,6-dichlorophenyl)-8-methylpyrimido[4,5-d]pyridazin-5(6H)-one;

2-{[2-(cyclopropylcarbonyl)-4,4-dimethyl-1,2,3,4-tetrahydroisoquinolin-7-yl]amino}-6-(2,6-dichlorophenyl)-8-methylpyrimido[4,5-d]pyridazin-5(6H)-one;

6-(2,6-dichlorophenyl)-2-{[4,4-dimethyl-2-(methylsulfonyl)-1,2,3,4-tetrahydroisoquinolin-7-yl]amino}-8-methylpyrimido[4,5-d]pyridazin-5(6H)-one;

6-(2,6-dichlorophenyl)-8-methyl-2-{[4-(3-oxopiperazin-1-yl)phenyl]amino}pyrimido[4,5-d]pyridazin-5(6H)-one;

6-(2,6-dichlorophenyl)-8-methyl-2-[(1,1,2-trimethyl-1,2,3,4-tetrahydroisoquinolin-7-yl)amino]pyrimido[4,5-d]pyridazin-5(6H)-one;

6-(2,6-dichlorophenyl)-2-[(1,1-dimethyl-1,2,3,4-tetrahydroisoquinolin-7-yl)amino]-8-methylpyrimido[4,5-d]pyridazin-5(6H)-one;

6-(2,6-dichlorophenyl)-8-methyl-2-({4-[4-(oxetan-3-yl)piperazin-1-yl]phenyl}amino)pyrimido[4,5-d]pyridazin-5(6H)-one;

6-(2,6-dichlorophenyl)-2-{[4-(hexahydropyrrolo[3,4-c]pyrrol-2(1H)-yl)phenyl]amino}-8-methylpyrimido[4,5-d]pyridazin-5(6H)-one;

6-(3,5-dichloropyridin-4-yl)-2-(2',3'-dihydro-1'H-spiro[cyclopropane-1,4'-isoquinolin]-7'-ylamino)-8-methylpyrimido[4,5-d]pyridazin-5(6H)-one;

6-(3,5-dichloropyridin-4-yl)-8-methyl-2-(1,2,3,4-tetrahydroisoquinolin-6-ylamino)pyrimido[4,5-d]pyridazin-5(6H)-one;

2-[(2-acetyl-1,2,3,4-tetrahydroisoquinolin-6-yl)amino]-6-(2,6-dichlorophenyl)-8-methylpyrimido[4,5-d]pyridazin-5(6H)-one;

6-(2,6-dichlorophenyl)-8-methyl-2-{[2-(methylsulfonyl)-1,2,3,4-tetrahydroisoquinolin-6-yl]amino}pyrimido[4,5-d]pyridazin-5(6H)-one;

6-(2,6-dichlorophenyl)-2-(2,3-dihydro-1H-isoindol-5-ylamino)-8-methylpyrimido[4,5-d]pyridazin-5(6H)-one;

6-(2,6-dichlorophenyl)-2-[(1,1-dimethyl-1,2,3,4-tetrahydroisoquinolin-6-yl)amino]-8-methylpyrimido[4,5-d]pyridazin-5(6H)-one;

6-(2,6-dichlorophenyl)-8-methyl-2-[(1,1,2-trimethyl-1,2,3,4-tetrahydroisoquinolin-6-yl)amino]pyrimido[4,5-d]pyridazin-5(6H)-one;

6-(2,6-dichlorophenyl)-8-methyl-2-({4-[(4-methylpiperazin-1-yl)methyl]phenyl}amino)pyrimido[4,5-d]pyridazin-5(6H)-one;

6-(2,6-dichlorophenyl)-8-methyl-2-{[4-(pyrrolidin-2-yl)phenyl]amino}pyrimido[4,5-d]pyridazin-5(6H)-one;

6-(2,6-dichlorophenyl)-8-methyl-2-{[4-(1-methylpiperidin-4-yl)phenyl]amino}pyrimido[4,5-d]pyridazin-5(6H)-one;

2-({4-[(1R,4R)-2,5-diazabicyclo[2.2.1]hept-2-yl]phenyl}amino)-6-(2,6-dichlorophenyl)-8-methylpyrimido[4,5-d]pyridazin-5(6H)-one;

6-(2,6-dichlorophenyl)-8-methyl-2-{[4-(piperidin-4-yl)phenyl]amino}pyrimido[4,5-d]pyridazin-5(6H)-one;

6-(2,6-dichlorophenyl)-8-methyl-2-{[4-(piperidin-3-yl)phenyl]amino}pyrimido[4,5-d]pyridazin-5(6H)-one;

6-(2,6-dichlorophenyl)-8-ethyl-2-[(1,1,2-trimethyl-1,2,3,4-tetrahydroisoquinolin-6-yl)amino]pyrimido[4,5-d]pyridazin-5(6H)-one;

6-(2,6-dichlorophenyl)-8-ethyl-2-[(1,1,2-trimethyl-1,2,3,4-tetrahydroisoquinolin-7-yl)amino]pyrimido[4,5-d]pyridazin-5(6H)-one;

6-(2,6-dichlorophenyl)-2-[(4,4-dimethyl-1,2,3,4-tetrahydroisoquinolin-7-yl)amino]-8-ethylpyrimido[4,5-d]pyridazin-5(6H)-one;

6-(2,6-dichlorophenyl)-2-[(1,1-dimethyl-1,2,3,4-tetrahydroisoquinolin-7-yl)amino]-8-ethylpyrimido[4,5-d]pyridazin-5(6H)-one;

6-(2,6-dichlorophenyl)-8-ethyl-2-[(3-oxo-1,2,3,4-tetrahydroisoquinolin-7-yl)amino]pyrimido[4,5-d]pyridazin-5(6H)-one;

6-(2,6-dichlorophenyl)-8-ethyl-2-({4-[(4-methylpiperazin-1-yl)methyl]phenyl}amino)pyrimido[4,5-d]pyridazin-5(6H)-one;

6-(2,6-dichlorophenyl)-2-[(1,1-dimethyl-1,2,3,4-tetrahydroisoquinolin-6-yl)amino]-8-ethylpyrimido[4,5-d]pyridazin-5(6H)-one;

6-(2,6-dichlorophenyl)-8-methyl-2-[(3-oxo-1,2,3,4-tetrahydroisoquinolin-7-yl)amino]pyrimido[4,5-d]pyridazin-5(6H)-one;

2-({4-[(1R,4R)-2,5-diazabicyclo[2.2.1]hept-2-yl]phenyl}amino)-6-(2,6-dichlorophenyl)-8-ethylpyrimido[4,5-d]pyridazin-5(6H)-one;

6-(2,6-dichlorophenyl)-8-ethyl-2-{[3-methyl-4-(4-methyl-1,4-diazepan-1-yl)phenyl]amino}pyrimido[4,5-d]pyridazin-5(6H)-one;

6-(2,6-dichlorophenyl)-8-ethyl-2-{[4-(3-oxopiperazin-1-yl)phenyl]amino}pyrimido[4,5-d]pyridazin-5(6H)-one;

6-(2,6-dichlorophenyl)-8-methyl-2-[(1,1,2-trimethyl-2,3-dihydro-1H-isoindol-5-yl)amino]pyrimido[4,5-d]pyridazin-5(6H)-one;

2-[(7-chloro-1,2,3,4-tetrahydroisoquinolin-6-yl)amino]-6-(2,6-dichlorophenyl)-8-methylpyrimido[4,5-d]pyridazin-5(6H)-one;

6-(2,6-dichlorophenyl)-8-(difluoromethyl)-2-(1,2,3,4-tetrahydroisoquinolin-6-ylamino)pyrimido[4,5-d]pyridazin-5(6H)-one;

6-(2,6-dichlorophenyl)-8-(difluoromethyl)-2-[(2-methyl-1,2,3,4-tetrahydroisoquinolin-6-yl)amino]pyrimido[4,5-d]pyridazin-5(6H)-one;

6-(2,6-dichlorophenyl)-8-(difluoromethyl)-2-[(2-methyl-1,2,3,4-tetrahydroisoquinolin-7-yl)amino]pyrimido[4,5-d]pyridazin-5(6H)-one;

2-[(2-acetyl-1,2,3,4-tetrahydroisoquinolin-6-yl)amino]-6-(2,6-dichlorophenyl)-8-(difluoromethyl)pyrimido[4,5-d]pyridazin-5(6H)-one;

2-[(2-acetyl-1,2,3,4-tetrahydroisoquinolin-7-yl)amino]-6-(2,6-dichlorophenyl)-8-(difluoromethyl)pyrimido[4,5-d]pyridazin-5(6H)-one;

6-(2,6-dichlorophenyl)-8-(difluoromethyl)-2-[(4,4-dimethyl-1,2,3,4-tetrahydroisoquinolin-7-yl)amino]pyrimido[4,5-d]pyridazin-5(6H)-one;

6-(2,6-dichlorophenyl)-8-(difluoromethyl)-2-{[4-(piperidin-3-yl)phenyl]amino}pyrimido[4,5-d]pyridazin-5(6H)-one;

6-(2,6-dichlorophenyl)-2-[(7-fluoro-1,2,3,4-tetrahydroisoquinolin-6-yl)amino]-8-methylpyrimido[4,5-d]pyridazin-5(6H)-one;

6-(2-chlorophenyl)-8-methyl-2-(1,2,3,4-tetrahydroisoquinolin-6-ylamino)pyrimido[4,5-d]pyridazin-5(6H)-one;

6-(2-chlorophenyl)-2-[(4,4-dimethyl-1,2,3,4-tetrahydroisoquinolin-7-yl)amino]-8-methylpyrimido[4,5-d]pyridazin-5(6H)-one;

6-(2-chlorophenyl)-8-methyl-2-[(2,4,4-trimethyl-1,2,3,4-tetrahydroisoquinolin-7-yl)amino]pyrimido[4,5-d]pyridazin-5(6H)-one;

6-(2-chlorophenyl)-2-{[2-(dimethylamino)-2,3-dihydro-1H-inden-5-yl]amino}-8-methylpyrimido[4,5-d]pyridazin-5(6H)-one;

6-(2,6-dichlorophenyl)-8-(difluoromethyl)-2-[(1,1,2-trimethyl-2,3-dihydro-1H-isoindol-5-yl)amino]pyrimido[4,5-d]pyridazin-5(6H)-one;

6-(2,6-dichlorophenyl)-8-(difluoromethyl)-2-{[4-(1-methylpiperidin-3-yl)phenyl]amino}pyrimido[4,5-d]pyridazin-5(6H)-one;

6-(3,5-dichloropyridin-4-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;

6-(3,5-dichloropyridin-4-yl)-8-methyl-2-[(1,1,2-trimethyl-2,3-dihydro-1H-isoindol-5-yl)amino]pyrimido[4,5-d]pyridazin-5(6H)-one;

6-(2,6-dichlorophenyl)-2-[(1,1-dimethyl-2,3-dihydro-1H-isoindol-5-yl)amino]-8-methylpyrimido[4,5-d]pyridazin-5(6H)-one;

6-(2,6-dichlorophenyl)-8-methyl-2-[(2-methyl-1,2,3,4-tetrahydroisoquinolin-7-yl)amino]pyrimido[4,5-d]pyridazin-5(6H)-one;

6-(2,6-dichlorophenyl)-8-methyl-2-[(2-methyl-2,3-dihydro-1H-isoindol-5-yl)amino]pyrimido[4,5-d]pyridazin-5(6H)-one;

6-(2,6-dichlorophenyl)-8-ethyl-2-[(2-methyl-1,2,3,4-tetrahydroisoquinolin-6-yl)amino]pyrimido[4,5-d]pyridazin-5(6H)-one;

6-(2,6-dichlorophenyl)-8-ethyl-2-[(2-methyl-1,2,3,4-tetrahydroisoquinolin-7-yl)amino]pyrimido[4,5-d]pyridazin-5(6H)-one;

6-(2,6-dichlorophenyl)-8-ethyl-2-[(2-methyl-2,3-dihydro-1H-isoindol-5-yl)amino]pyrimido[4,5-d]pyridazin-5(6H)-one;

6-(2-chloro-6-methylphenyl)-8-methyl-2-(1,2,3,4-tetrahydroisoquinolin-7-ylamino)pyrimido[4,5-d]pyridazin-5(6H)-one;

6-(2-chloro-6-methylphenyl)-8-methyl-2-(1,2,3,4-tetrahydroisoquinolin-6-ylamino)pyrimido[4,5-d]pyridazin-5(6H)-one;

6-(2-chloro-6-methylphenyl)-2-[(4,4-dimethyl-1,2,3,4-tetrahydroisoquinolin-7-yl)amino]-8-methylpyrimido[4,5-d]pyridazin-5(6H)-one;

6-(2-chloro-6-methylphenyl)-8-methyl-2-[(2,4,4-trimethyl-1,2,3,4-tetrahydroisoquinolin-7-yl)amino]pyrimido[4,5-d]pyridazin-5(6H)-one;

6-(2-chloro-6-methylphenyl)-2-{[2-(2-hydroxyethyl)-1,2,3,4-tetrahydroisoquinolin-7-yl]amino}-8-methylpyrimido[4,5-d]pyridazin-5(6H)-one;

6-(2-chloro-6-methylphenyl)-2-[(4-{4-[3-(dimethylamino)propyl]piperazin-1-yl}phenyl)amino]-8-methylpyrimido[4,5-d]pyridazin-5(6H)-one;

6-(2-chloro-6-methylphenyl)-8-methyl-2-({4-[(1-methylpiperidin-4-yl)amino]phenyl}amino)pyrimido[4,5-d]pyridazin-5(6H)-one;

6-(2-chloro-6-methylphenyl)-8-methyl-2-({4-[(1-methylpiperidin-4-yl)oxy]phenyl}amino)pyrimido[4,5-d]pyridazin-5(6H)-one;

6-(2,6-dichlorophenyl)-8-methyl-2-({4-[(1-methylpiperidin-4-yl)oxy]phenyl}amino)pyrimido[4,5-d]pyridazin-5(6H)-one;

6-(2,6-dichlorophenyl)-8-methyl-2-{[3-(piperidin-1-yl)phenyl]amino}pyrimido[4,5-d]pyridazin-5(6H)-one;

6-(2,6-dichlorophenyl)-8-methyl-2-{[3-(morpholin-4-yl)phenyl]amino}pyrimido[4,5-d]pyridazin-5(6H)-one;

6-(2,6-dichlorophenyl)-8-methyl-2-{[3-(piperazin-1-yl)phenyl]amino}pyrimido[4,5-d]pyridazin-5(6H)-one;

2-({3-[4-(3-chloropropyl)piperazin-1-yl]phenyl}amino)-6-(2,6-dichlorophenyl)-8-methylpyrimido[4,5-d]pyridazin-5(6H)-one;

2-{[3-(4-cyclobutylpiperazin-1-yl)phenyl]amino}-6-(2,6-dichlorophenyl)-8-methylpyrimido[4,5-d]pyridazin-5(6H)-one;

6-(2,6-dichlorophenyl)-8-methyl-2-({3-[4-(tetrahydro-2H-pyran-4-yl)piperazin-1-yl]phenyl}amino)pyrimido[4,5-d]pyridazin-5(6H)-one;

6-(2,6-dichlorophenyl)-2-({3-[4-(3-hydroxypropyl)piperazin-1-yl]phenyl}amino)-8-methylpyrimido[4,5-d]pyridazin-5(6H)-one;

6-(2,6-dichlorophenyl)-8-methyl-2-{[3-(4-methylpiperazin-1-yl)phenyl]amino}pyrimido[4,5-d]pyridazin-5(6H)-one;

6-(2,6-dichlorophenyl)-8-methyl-2-({3-[4-(oxetan-3-yl)piperazin-1-yl]phenyl}amino)pyrimido[4,5-d]pyridazin-5(6H)-one;

6-(2,6-dichlorophenyl)-8-methyl-2-[(3-{[2-(morpholin-4-yl)ethyl]amino}phenyl)amino]pyrimido[4,5-d]pyridazin-5(6H)-one;

6-(2,6-dichlorocyclohexa-1,5-dien-1-yl)-2-[(3-{[2-(dimethylamino)ethyl]amino}phenyl)amino]-8-methylpyrimido[4,5-d]pyridazin-5(6H)-one;

6-(2,6-dichlorophenyl)-2-[(3-{4-[3-(dimethylamino)propyl]piperazin-1-yl}phenyl)amino]-8-methylpyrimido[4,5-d]pyridazin-5(6H)-one;

6-(2,6-dichlorophenyl)-8-methyl-2-({3-[(1-methylpiperidin-4-yl)oxy]phenyl}amino)pyrimido[4,5-d]pyridazin-5(6H)-one;

6-(2,6-dichlorophenyl)-2-[(4-{4-[3-(dimethylamino)propyl]piperazin-1-yl}phenyl)amino]-8-methylpyrimido[4,5-d]pyridazin-5(6H)-one;

6-(2-chlorophenyl)-2-[(4-{4-[3-(dimethylamino)propyl]piperazin-1-yl}phenyl)amino]-8-methylpyrimido[4,5-d]pyridazin-5(6H)-one;

6-(2,6-dichlorophenyl)-2-[(3-{[4-(dimethylamino)piperidin-1-yl]carbonyl}phenyl)amino]-8-methylpyrimido[4,5-d]pyridazin-5(6H)-one;

3-{[6-(2,6-dichlorophenyl)-8-methyl-5-oxo-5,6-dihydropyrimido[4,5-d]pyridazin-2-yl]amino}-N-[4-(dimethylamino)cyclohexyl]benzamide;

3-{[6-(2,6-dichlorophenyl)-8-methyl-5-oxo-5,6-dihydropyrimido[4,5-d]pyridazin-2-yl]amino}benzoic acid;

6-(2,6-dichlorophenyl)-8-methyl-2-({3-[(1-methylpiperidin-4-yl)amino]phenyl}amino)pyrimido[4,5-d]pyridazin-5(6H)-one;

3-{[6-(2,6-dichlorophenyl)-8-methyl-5-oxo-5,6-dihydropyrimido[4,5-d]pyridazin-2-yl]amino}-N-(1-methylpiperidin-4-yl)benzamide;

6-(2-chloro-6-methylphenyl)-8-methyl-2-{[4-(piperidin-4-ylamino)phenyl]amino}pyrimido[4,5-d]pyridazin-5(6H)-one;

6-(2,6-dichlorophenyl)-8-methyl-2-{[4-(piperidin-4-ylamino)phenyl]amino}pyrimido[4,5-d]pyridazin-5(6H)-one;

6-(2-chlorophenyl)-8-methyl-2-{[4-(piperidin-4-ylamino)phenyl]amino}pyrimido[4,5-d]pyridazin-5(6H)-one;

6-(2,6-dichlorophenyl)-2-[(3-{[4-(2-hydroxyethyl)piperazin-1-yl]carbonyl}phenyl)amino]-8-methylpyrimido[4,5-d]pyridazin-5(6H)-one;

6-(2,6-dichlorophenyl)-8-methyl-2-({3-[(4-methylpiperazin-1-yl)carbonyl]phenyl}amino)pyrimido[4,5-d]pyridazin-5(6H)-one;

6-(2,6-dichlorophenyl)-2-({3-[(1,1-dioxidothiomorpholin-4-yl)carbonyl]phenyl}amino)-8-methylpyrimido[4,5-d]pyridazin-5(6H)-one;

3-{[6-(2,6-dichlorophenyl)-8-methyl-5-oxo-5,6-dihydropyrimido[4,5-d]pyridazin-2-yl]amino}-N-(piperidin-4-yl)benzamide;

and pharmaceutically acceptable salts and solvates thereof.

Compounds of this invention may contain asymmetrically substituted carbon atoms in the R or S configuration, wherein the terms "R" and "S" are as defined in Pure Appl. Chem.

(1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

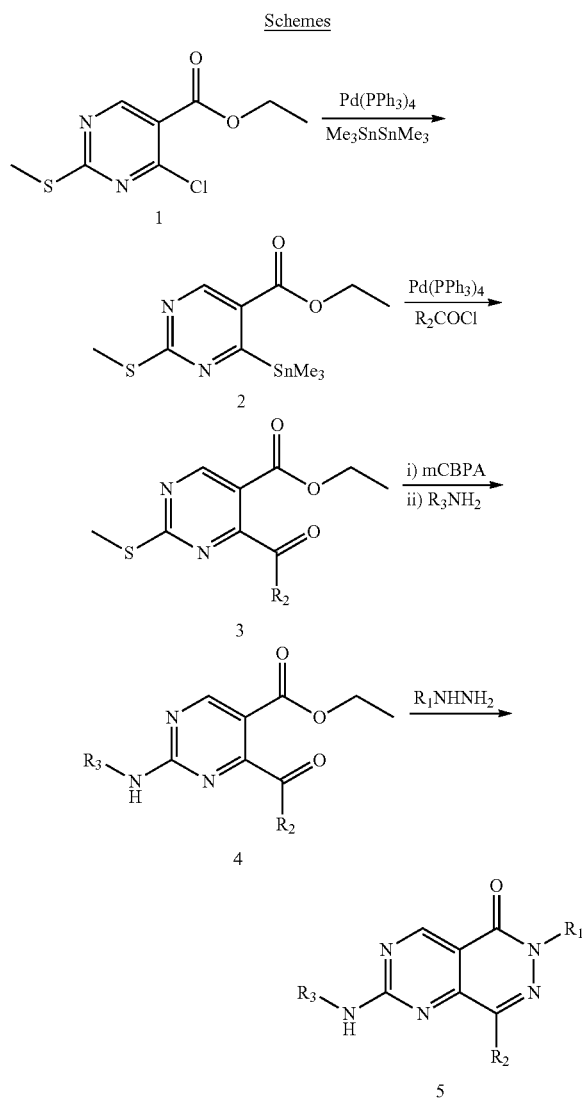

Schemes

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all wee-1 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

In one group of embodiments, diseases and conditions of humans or other animals that can be treated with inhibitors of kinases, include, but are not limited to, tumors that are deficient in the p53 protein. The p53 protein is a tumor suppressor protein that is encoded in humans by the TP53 gene. The p53 protein regulates the cell cycle and therefore functions as a tumor suppressor that is involved in preventing cancer. Inhibition of Wee1 kinases sensitizes tumor cells to DNA damage and/or cell cycle perturbation, especially tumors that have lost their $G_1$-phase checkpoint due to a deficiency in the p53 protein.

A discussion of the loss of expression of Wee1 and how it relates to deficiency in the p53 protein can be found in *Annual Review of Biochemistry*, 2004, 73:39-85.

Involvement of mutations in the p53 gene and human tumor types can be found in *Nature*, 1989, 342:705-708.

A discussion of Wee1 kinase and p53 deficient tumor cells can be found in *Molecular Cancer Therapy*, 2009, 8:11.

A discussion of p53 and Wee1 kinases and anti-cancer therapies can be found in *BMC Cancer* 2006, 6:292.

A discussion of Wee1 kinase and p53 deficient tumor cells can be found in *Current Clinical Pharmacology*, 2010, 5:186-191.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC®(imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE®(piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547, 632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX®(bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents.

Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

6,8-dimethyl-2-{[4-(4-methylpiperazin-1-yl)phenyl]amino}pyrimido[4,5-d]pyridazin-5(6H)-one Example 1A ethyl 4-(1-ethoxyvinyl)-2-(methylthio)pyrimidine-5-carboxylate A solution of ethyl 4-chloro-2-(methylthio)pyrimidine-5-carboxylate (3.0 g, 12.89 mmol), tributyl(1-ethoxyvinyl)stannane (4.79 ml, 14.18 mmol) and bis(triphenylphosphine)palladium dichloride (0.452 g, 0.645 mmol) in N,N-dimethylformamide (43 mL) was heated to 70° C. for 1 hour. The mixture was cooled, treated with a solution of KF (1.5 g in 3 mL water) and stirred overnight at room temperature. The mixture was diluted with water and ether and filtered through diatomaceous earth. The layers were separated and the aqueous layer was extracted into ether. The combined extracts were rinsed with brine, dried over $MgSO_4$, filtered, and concentrated under reduced pressure. The residue was purified by flash chromatography (0-20% gradient ethyl acetate in hexane) to provide the title compound. MS ESI(+) m/z 269.0 $[M+H]^+$.

Example 1B ethyl 4-acetyl-2-(methylthio)pyrimidine-5-carboxylate

A solution of Example 1A (2.0 g, 7.45 mmol) in a solvent mixture of ethanol (24.84 ml) and 10% HCl solution (4.53 ml, 14.91 mmol) was heated to 50° C. for 18 hours. The reaction mixture was cooled, and the majority of the ethanol removed by rotary evaporation. The residue was partitioned between ethyl acetate and water. The layers were separated, and the aqueous layer was extracted with additional ethyl acetate. The combined organics were dried with anhydrous sodium sulfate, filtered, and concentrated under reduced pressure to provide the title compound, which was used in the subsequent step without further purification. MS ESI(+) m/z 241 $[M+H]^+$.

Example 1C 6,8-dimethyl-2-(methylthio)pyrimido[5,4-d]pyridazin-5(6H)-one

A solution of Example 1B (600 mg, 2.497 mmol) and methylhydrazine (0.131 mL, 2.497 mmol) in n-butanol (12.5 mL) was heated to 140° C. by microwave irradiation (Biotage Initiator) for 30 minutes. The reaction mixture was cooled to room temperature, whereupon a solid crystallized from the solution. The solid was filtered, washed with hexane, and air-dried to provide the title compound. MS ESI(+) m/z 223 $[M+H]^+$.

Example 1D 6,8-dimethyl-2-{[4-(4-methylpiperazin-1-yl)phenyl]amino}pyrimido[4,5-d]pyridazin-5(6H)-one To a cold (0° C.) solution of Example IC (100 mg, 0.450 mmol) in dichloromethane (1.5 mL) was added meta-chloroperoxybenzoic acid (122 mg, 0.495 mmol) in a single portion. After 1 hour, the reaction mixture was partitioned between 10% sodium thiosulfate solution and ethyl acetate. The layers were separated, and the organic layer was washed with saturated sodium bicarbonate solution, dried with anhydrous sodium sulfate, filtered and concentrated under reduced pressure. The residue was dissolved in N,N-dimethylformamide (3 mL). Hunig's base (157 µl, 0.900 mmol) and 4-(4-methylpiperazin-1-yl)aniline (86 mg, 0.450 mmol) were added to the solution, and the reaction mixture was heated at 100° C. overnight. The reaction mixture was cooled to room temperature and partitioned between water and ethyl acetate. The organic layer was concentrated under reduced pressure. The crude residue was purified by RP-MPLC (125 g C-18 silica gel), eluting with a gradient of 5 to 50% acetonitrile in water each containing 0.1% TFA, to provide the title compound. MS ESI(+) m/z 366.2 [M+H]$^+$; $^1$H NMR (300 MHz, DMSO-d$_6$): δ ppm 10.33 (s, 1H), 9.22 (s, 1H), 7.77-7.62 (m, 2H), 6.99-6.91 (m, 2H), 3.63 (s, 3H), 3.20-3.02 (m, 4H), 2.46-2.43 (m, 4H), 2.22 (s, 3H).

Example 2

6-allyl-8-methyl-2-{[4-(4-methylpiperazin-1-yl)phenyl]amino}pyrimido[4,5-d]pyridazin-5(6H)-one Example 2A 6-allyl-8-methyl-2-(methylthio)pyrimido[5,4-d]pyridazin-5(6H)-one The title compound was prepared as described in Example 1C, substituting allylhydrazine for methylhydrazine. MS ESI (+) m/z 249.1 [M+H]$^+$.

Example 2B 6-allyl-8-methyl-2-{[4-(4-methylpiperazin-1-yl)phenyl]amino}pyrimido[4,5-d]pyridazin-5(6H)-one The title compound was prepared as described in Example 1D, substituting Example 2A for Example IC. MS ESI(+) m/z 392.2 [M+H]$^+$; $^1$H NMR (300 MHz, DMSO-d$_6$): δ ppm 10.38-10.32 (m, 1H), 9.22 (s, 1H), 7.78-7.43 (m, 2H), 6.99-6.91 (m, 2H), 6.04-5.87 (m, 1H), 5.22-5.09 (m, 2H), 4.68-4.62 (m, 2H), 3.14-3.07 (m, 4H), 2.47-2.41 (m, 4H), 2.22 (s, 3H).

Example 3

6-methyl-2-{[4-(4-methylpiperazin-1-yl)phenyl]amino}-8-phenylpyrimido[4,5-d]pyridazin-5(6H)-one Example 3A ethyl 4-benzoyl-2-(methylthio)pyrimidine-5-carboxylate To a cold (−78° C.) freshly-prepared solution of lithium diisopropylamide (2.62 mmol) in THF (5 mL) was added a solution of 2-phenyl-2-(trimethylsilyloxy)acetonitrile (0.5 ml, 2.382 mmol) in THF (4 mL). The solution was stirred for 2 hours, and a solution of ethyl 4-chloro-2-(methylthio)pyrimidine-5-carboxylate (554 mg, 2.382 mmol) in THF (3 mL) was added dropwise. The cold bath was removed, and the reaction warmed to room temperature. The reaction mixture was quenched by the addition of saturated sodium bicarbonate solution (15 mL) and ethyl acetate (15 mL). The layers were separated, and the aqueous extracted with addition ethyl acetate. The combined organics were dried with anhydrous sodium sulfate, filtered, and concentrated under reduced pressure. The residue was dissolved in THF (15 mL), and a solution of tetrabutyl ammonium fluoride (3.0 mmol, 3.0 mL, 1 M in THF) was added. The reaction mixture was stirred for 1 hour, and quenched by the addition of saturated sodium bicarbonate solution (15 mL) and ethyl acetate (15 mL). The layers were separated, and the aqueous layer extracted with addition ethyl acetate. The combined organics were dried with anhydrous sodium sulfate, filtered, and concentrated under reduced pressure. The residue was purified by chromatography on silica gel, eluting with a gradient of hexane to 30% ethyl acetate in hexane, to give the title compound. MS ESI(+) m/z 302.9 [M+H]$^+$.

Example 3B

Ethyl 4-benzoyl-2-(4-(4-methylpiperazin-1-yl)phenylamino)pyrimidine-5-carboxylate To a cold (0° C.) solution of Example 3A (200 mg, 0.661 mmol) in dichloromethane (2.2 mL) was added meta-chloroperoxybenzoic acid (179 mg, 0.728 mmol) in a single portion. After 1 hour, the reaction mixture was partitioned between 10% sodium thiosulfate solution and ethyl acetate. The layers were separated, and the organic layer was washed with saturated sodium bicarbonate solution, dried with anhydrous sodium sulfate, filtered and concentrated under reduced pressure. The residue was dissolved in N,N-dimethylformamide (3 mL). Hunig's base (231 µl, 1.323 mmol) and 4-(4-methylpiperazin-1-yl)aniline (127 mg, 0.661 mmol) were added to the solution, and the reaction was heated to 45° C. for 3 hours.

The reaction mixture was cooled to room temperature and partitioned between water and ethyl acetate. The organic layer was concentrated under reduced pressure. The crude residue was purified by MPLC (10 g SiO$_2$), eluting with dichloromethane to 10% methanol in dichloromethane, to provide the title compound. MS ESI(+) m/z 446.3 [M+H]$^+$.

Example 3C 6-methyl-2-{[4-(4-methylpiperazin-1-yl)phenyl]amino}-8-phenylpyrimido[4,5-d]pyridazin-5(6H)-one A solution of Example 3B (50 mg, 0.112 mmol) and methylhydrazine (6.50 µl, 0.123 mmol) in n-butanol (12.5 mL) was heated to 170° C. by microwave irradiation (Biotage Initiator) for 3 hour. The reaction mixture was cooled to room temperature, and the solid was filtered and air-dried to provide the title compound. MS ESI(+) m/z 428.2 [M+H]$^+$; $^1$H NMR (300 MHz, DMSO-d$_6$): δ ppm 10.34 (s, 1H), 9.29 (s, 1H), 7.94-7.91 (m, 2H), 7.59-7.48 (m, 5H), 6.84 (d, J=8.7 Hz, 2H), 3.75 (s, 3H), 3.13-3.05 (m, 4H), 2.47-2.44 (m, 4H), 2.22 (s, 3H).

Example 4

2-{[4-(4-methylpiperazin-1-yl)phenyl]amino}-8-phenylpyrimido[4,5-d]pyridazin-5(6H)-one Example 4 was isolated as a by-product during the preparation of Example 5. The mother liquor from the reaction to give Example 5 was purified by RP-MPLC (125 g C-18 silica gel), eluting with a gradient of 5 to 50% acetonitrile in water each containing 0.1% TFA, to provide the title compound as a solid. MS ESI(+) m/z 414.2 [M+H]$^+$; $^1$H NMR (300 MHz, DMSO-d$_6$): δ ppm 12.91 (s, 1H), 10.31 (s, 1H), 9.27 (d, J=12.7 Hz, 1H), 7.99-7.83 (m, 2H), 7.69-7.40 (m, 5H), 6.84 (d, J=8.4 Hz, 2H), 3.11-3.02 (m, 4H), 2.48-2.41 (m, 4H), 2.22 (s, 3H).

Example 5

6-allyl-2-{[4-(4-methylpiperazin-1-yl)phenyl]amino}-8-phenylpyrimido[4,5-d]pyridazin-5(6H)-one The title compound was prepared as described in Example 3, substituting allylhydrazine for methylhydrazine. MS ESI (+) m/z 454.2 [M+H]$^+$; $^1$H NMR (300 MHz, DMSO-d$_6$): δ ppm 10.39 (s, 1H), 9.50 (s, 1H), 9.32 (s, 1H), 7.95-7.90 (m, 2H), 7.68-7.44 (m, 5H), 6.97-6.85 (m, 2H), 6.12-5.95 (m, 1H), 5.26-5.17 (m, 2H), 4.82-4.75 (m, 2H), 3.84-3.73 (m, 2H), 3.58-3.48 (m, 2H), 3.30-3.07 (m, 2H), 3.00-2.82 (m, 5H).

Example 6

6-methyl-2-{[4-(4-methylpiperazin-1-yl)phenyl]amino}-8-(2-phenylethyl)pyrimido[4,5-d]pyridazin-5(6H)-one Example 6A ethyl 2-(methylthio)-4-(trimethylstannyl)pyrimidine-5-carboxylate To a suspension of ethyl 4-chloro-2-(methylthio)pyrimidine-5-carboxylate (4 g, 17.19 mmol) and palladium tetrakis(triphenylphosphine) (600 mg, 0.516 mmol) in anhydrous toluene (20 mL) was added hexamethylditin (5.74 g, 17.53 mmol). The reaction mixture was purged with nitrogen, and heated at 105° C. overnight. After cooling, the mixture was filtered through a short silica column, and eluted with 200 mL of 35% ethyl acetate in hexane. Concentration of the filtrate gave the title compound which was directly used in the next step without further purification. MS (DCI/NH$_3$) m/z 362 (M+H)$^+$.

Example 6B ethyl 2-(methylthio)-4-(3-phenylpropanoyl)pyrimidine-5-carboxylate

To a solution of Example 6A (600 mg, 1.74 mmol) in toluene (20 ml) was added palladium tetrakis(triphenylphosphine) (96 mg, 0.08 mmol) and 3-phenylpropanoyl chloride (0.37 ml, 2.5 mmol). The reaction mixture was purged with nitrogen and heated at 100° C. for 12 hours. After cooling, the reaction mixture was directly separated by flash chromatography which was eluted with 15% ethyl acetate in hexane to provide the title compound. MS (DCI/NH$_3$) m/z 303 (M+H)$^+$.

Example 6C ethyl 2-(4-(4-methylpiperazin-1-yl)phenylamino)-4-(3-phenylpropanoyl)pyrimidine-5-carboxylate A solution of Example 6B (490 mg, 1.5 mmol) in dichloromethane (10 ml) was treated with 3-chlorobenzoperoxoic acid (256 mg, 1.5 mmol) for 2 hours. 4-(4-Methylpiperazin-1-yl)aniline (405 mg, 1.6 mmol) was then added, and the mixture stirred at room temperature overnight. Volatiles were removed on a rotavapor. The residue was partitioned between ethyl acetate and sodium bicarbonate. The organic phase was washed with sodium bicarbonate solution, and concentrated. The residue was separated by flash chromatography on silica gel that was eluted with 15% of methanol in methylene chloride to provide the title compound. MS (DCI/NH$_3$) m/z 474 (M+H)$^+$.

Example 6D 6-methyl-2-{[4-(4-methylpiperazin-1-yl)phenyl]amino}-8-(2-phenylethyl)pyrimido[4,5-d]pyridazin-5(6H)-one A solution of Example 6C (40 mg, 0.09 mmol) and methylhydrazine (21 mg, 0.45 mmol) in ethanol (0.5 ml) was heated at 100° C. overnight. After cooling, the volatiles were removed, and the residue was purified by HPLC (Zorbax C-18, 0.1% TFA/CH$_3$CN/H$_2$O) to yield the title compound as TFA salt. MS (DCI/NH$_3$) m/z 456 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 7

6-allyl-2-{[4-(4-methylpiperazin-1-yl)phenyl]amino}-8-(2-phenylethyl)pyrimido[4,5-d]pyridazin-5(6H)-one The title compound was prepared as described in Example 6D, substituting allylhydrazine for methylhydrazine. MS (DCI/NH$_3$) m/z 482 (M+H)$^+$; $^1$H NMR (300 MHz, DMSO-d$_6$): δ ppm 2.47 (s, 3H), 2.73-2.88 (m, 4H), 2.94-3.04 (m, 2H), 3.12-3.17 (m, 2H), 3.19 (d, J=6.10 Hz, 4H), 4.65 (d, J=5.49 Hz, 2H), 5.09 (dd, J=17.40, 1.53 Hz, 1H), 5.16 (dd, J=10.38, 1.53 Hz, 1H), 5.83-5.99 (m, 1H), 6.92 (d, J=8.85 Hz, 2H), 7.11-7.38 (m, 5H), 7.63-7.79 (m, 2H), 9.24 (s, 1H).

Example 8

3-[2-{[4-(4-methylpiperazin-1-yl)phenyl]amino}-5-oxo-8-(2-phenylethyl)pyrimido[4,5-d]pyridazin-6(5H)-yl]propanenitrile The title compound was prepared as described in Example 6D, substituting 3-hydrazinylpropanenitrile for methylhydrazine. MS (DCI/NH$_3$) m/z 495 (M+H)$^+$; $^1$H NMR (300 MHz, DMSO-d$_6$): δ ppm 2.25 (s, 3H), 2.94 (t, J=6.41 Hz, 4H), 3.02 (m, 2H), 3.08-3.14 (m, 5H), 3.13-3.22 (m, 3H), 4.29 (t, J=6.41 Hz, 2H), 6.89 (d, J=8.85 Hz, 2H), 7.11-7.37 (m, 5H), 7.68 (m, 2H), 9.25 (s, 1H).

Example 9

2-{[4-(4-methylpiperazin-1-yl)phenyl]amino}-6-phenyl-8-(2-phenylethyl)pyrimido[4,5-d]pyridazin-5(6H)-one The title compound was prepared as described in Example 6D, substituting phenylhydrazine for methylhydrazine. MS (DCI/NH$_3$) m/z 518 (M+H)$^+$; $^1$H NMR (300 MHz, DMSO-d$_6$): δ ppm 2.24 (s, 3H), 2.44-2.49 (m, 4H), 3.00-3.07 (m, 2H), 3.08-3.13 (m, 4H), 3.17-3.24 (m, 2H), 6.91 (d, J=8.85 Hz, 2H), 7.18-7.34 (m, 5H), 7.37-7.44 (m, 1H), 7.46-7.54 (m, 4H), 7.72 (s, 2H), 9.29 (s, 1H).

Example 10

2-{[4-(4-methylpiperazin-1-yl)phenyl]amino}-8-(2-phenylethyl)-6-(2,2,2-trifluoroethyl)pyrimido[4,5-d]pyridazin-5(6H)-one The title compound was prepared as described in Example 6D, substituting (2,2,2-trifluoroethyl)hydrazine for methylhydrazine. MS (DCI/NH$_3$) m/z 524 (M+H)$^+$; $^1$H NMR (300 MHz, DMSO-d$_6$): δ ppm 2.23 (s, 3H), 2.42-2.48 (m, 4H), 3.01 (m, 2H), 3.07-3.13 (m, 4H), 3.16 (m, 2H), 4.90 (q, J=9.05 Hz, 2H), 6.88 (d, J=8.24 Hz, 2H), 7.10-7.39 (m, 5H), 7.67 (s, 2H), 9.25 (s, 1H).

Example 11

6-methyl-2-{[4-(4-methylpiperazin-1-yl)phenyl]amino}-8-propylpyrimido[4,5-d]pyridazin-5(6H)-one

Example 11A ethyl 4-butyryl-2-(methylthio)pyrimidine-5-carboxylate

The title compound was prepared as described in Example 6B, substituting butyryl chloride for 3-phenylpropanoyl chloride. MS (DCI/NH$_3$) m/z 269 (M+H)$^+$.

Example 11B ethyl 4-butyryl-2-(4-(4-methylpiperazin-1-yl)phenylamino)pyrimidine-5-carboxylate The title compound was prepared as described in Example 6C, substituting Example 11A for Example 6B. MS (DCI/NH$_3$) m/z 412 (M+H)$^+$.

Example 11C 6-methyl-2-{[4-(4-methylpiperazin-1-yl)phenyl]amino}-8-propylpyrimido[4,5-d]pyridazin-5(6H)-one The title compound was prepared as described in Example 6D, substituting Example 11B for Example 6C. MS (DCI/NH$_3$) m/z 394 (M+H)$^+$; $^1$H NMR (300 MHz, DMSO-d$_6$): δ ppm 1.00 (t, J=7.46 Hz, 3H), 1.63-1.85 (m, 2H), 2.22 (s, 3H), 2.43-2.48 (m, 4H), 2.79-2.90 (m, 2H), 3.06-3.14 (m, 4H), 3.63 (s, 3H), 6.94 (d, J=9.16 Hz, 2H), 7.71 (s, 2H), 9.22 (s, 1H).

Example 12

6-(2-methylphenyl)-2-{[4-(4-methylpiperazin-1-yl)phenyl]amino}-8-(2-phenylethyl)pyrimido[4,5-d]pyridazin-5(6H)-one The title compound was prepared as described in Example 6D, substituting o-tolylhydrazine for methylhydrazine. MS (DCI/NH$_3$) m/z 532 (M+H)$^+$; $^1$H NMR (300 MHz, DMSO-d$_6$): δ ppm 2.01 (s, 3H), 2.88 (s, 3H), 2.91-3.10 (m, 4H), 3.09-3.27 (m, 4H), 3.58 (d, 2H), 3.80 (d, J=13.09 Hz, 2H), 7.01 (d, J=8.72 Hz, 2H), 7.17-7.29 (m, 5H), 7.29-7.34 (m, 1H), 7.34-7.39 (m, 3H), 7.78 (s, 2H), 9.31 (s, 1H).

Example 13

8-cyclopentyl-6-methyl-2-{[4-(4-methylpiperazin-1-yl)phenyl]amino}pyrimido[4,5-d]pyridazin-5(6H)-one The title compound was prepared as described in Example 6, substituting cyclopentanecarbonyl chloride for 3-phenylpropanoyl chloride in Example 6B. MS (DCI/NH$_3$) m/z 420 (M+H)$^+$; $^1$H NMR (300 MHz, DMSO-d$_6$): δ ppm 1.64-1.89 (m, 4H), 1.97-2.08 (m, 4H), 2.22 (s, 3H), 2.43-2.48 (m, 4H), 3.07-3.14 (m, 4H), 3.60-3.72 (m, 1H), 3.63 (s, 3H), 6.94 (d, J=9.16 Hz, 2H), 7.69 (m, 2H), 9.22 (s, 1H), 10.30 (s, 1H).

Example 14

8-cyclopentyl-2-{[4-(4-methylpiperazin-1-yl)phenyl]amino}pyrimido[4,5-d]pyridazin-5(6H)-one The title compound was isolated as a side product in Example 15. MS (DCI/NH$_3$) m/z 406 (M+H)$^+$; $^1$H NMR (300 MHz, DMSO-d$_6$): δ ppm 1.68 (m, 4H), 2.00 (m, 4H), 2.39-2.50 (m, 4H), 2.69-2.78 (m, 2H), 3.04-3.14 (m, 4H), 3.60-3.72 (m, 1H), 6.94 (d, J=9.12 Hz, 2H), 7.70 (m, 2H), 9.18 (s, 1H), 10.29 (br s, 1H).

Example 15

6-allyl-8-cyclopentyl-2-{[4-(4-methylpiperazin-1-yl)phenyl]amino}pyrimido[4,5-d]pyridazin-5(6H)-one The title compound was prepared as described in Example 6, substituting cyclopentanecarbonyl chloride for 3-phenylpropanoyl chloride in Example 6B, and allylhydrazine for methylhydrazine in Example 6D. MS (DCI/NH$_3$) m/z 446 (M+H)$^+$; $^1$H NMR (300 MHz, DMSO-d$_6$): δ ppm 1.64-1.74 (m, 4H), 1.84 (m, 2H), 2.00 (m, 2H), 2.22 (m, 3H), 2.41-2.47 (m, 4H), 3.08-3.13 (m, 4H), 4.65 (d, J=5.55 Hz, 2H), 5.06-5.21 (m, 2H), 5.90-6.02 (m, 1H), 6.95 (d, J=9.12 Hz, 2H), 7.70 (m, 2H), 9.22 (s, 1H).

Example 16

6-allyl-2-{[4-(4-methylpiperazin-1-yl)phenyl]amino}-8-propylpyrimido[4,5-d]pyridazin-5(6H)-one The title compound was prepared as described in Example 6D, substituting Example 11B for Example 6C and allylhydrazine for methylhydrazine. MS (DCI/NH$_3$) m/z 420 (M+H)$^+$; $^1$H NMR (300 MHz, DMSO-d$_6$): δ ppm 0.98 (t, J=7.34 Hz, 3H), 1.68-1.78 (m, 2H), 2.28 (s, 3H), 2.48-2.64 (m, 4H), 2.81-2.90 (m, 2H), 3.04-3.20 (m, 4H), 4.66 (d, J=5.55 Hz, 2H), 5.05-5.22 (m, 2H), 5.79-6.09 (m, 1H), 6.95 (d, J=9.12 Hz, 2H), 7.72 (s, 2H), 9.23 (s, 1H).

Example 17

2-{[4-(4-methylpiperazin-1-yl)phenyl]amino}-6-phenyl-8-propylpyrimido[4,5-d]pyridazin-5(6H)-one The title compound was prepared as described in Example 6D, substituting Example 11B for Example 6C and phenylhydrazine for methylhydrazine. MS (DCI/NH$_3$) m/z 456

(M+H)⁺; ¹H NMR (300 MHz, DMSO-d₆): δ ppm 1.03 (t, J=7.34 Hz, 3H), 1.74-1.84 (m, 2H), 2.43-2.51 (m, J=1.98 Hz, 4H), 2.88 (s, 3H), 2.89-2.96 (m, 2H), 3.32-3.42 (m, 4H), 6.93 (d, J=7.54 Hz, 2H), 7.31 (t, J=7.93 Hz, 1H), 7.51 (t, J=7.74 Hz, 2H), 7.56-7.63 (m, 2H), 7.80 (s, 2H), 9.30 (s, 1H).

Example 18

6-(2-methylphenyl)-2-{[4-(4-methylpiperazin-1-yl) phenyl]amino}-8-propylpyrimido[4,5-d]pyridazin-5 (6H)-one The title compound was prepared as described in Example 6D, substituting Example 11B for Example 6C and o-tolylhydrazine for methylhydrazine. MS (DCI/NH₃) m/z 470 (M+H)⁺; ¹H NMR (300 MHz, DMSO-d₆): δ ppm (ppm 0.99 (t, J=7.34 Hz, 3H), 1.64-1.85 (m, 2H), 2.10 (s, 3H), 2.87 (s, 3H), 2.89-3.03 (m, 2H), 3.09-3.28 (m, 2H), 3.45-3.61 (m, 4H), 3.82 (d, J=12.69 Hz, 2H), 7.05 (d, J=9.12 Hz, 2H), 7.30-7.34 (m, 1H), 7.36-7.42 (m, 2H), 7.51-7.58 (m, 1H), 7.80 (s, 2H), 9.30 (s, 1H).

Example 19

8-benzyl-2-{[4-(4-methylpiperazin-1-yl)phenyl] amino}-6-phenylpyrimido[4,5-d]pyridazin-5(6H)-one Example 19A ethyl 2-(methylthio)-4-(2-phenylacetyl)pyrimidine-5-carboxylate The title compound was prepared as described in Example 6B, substituting 2-phenylacetyl chloride for 3-phenylpropanoyl chloride. MS (DCI/NH₃) m/z 317 (M+H)⁺.

Example 19B ethyl 2-(4-(4-methylpiperazin-1-yl)phenylamino)-4-(2-phenylacetyl)pyrimidine-5-carboxylate The title compound was prepared as described in Example 6C, substituting Example 19A for Example 6B. MS (DCI/NH₃) m/z 460 (M+H)⁺.

Example 19C 8-benzyl-2-{[4-(4-methylpiperazin-1-yl)phenyl] amino}-6-phenylpyrimido[4,5-d]pyridazin-5(6H)-one The title compound was prepared as described in Example 6D, substituting Example 19B for Example 6C and phenylhydrazine for methylhydrazine. MS (DCI/NH₃) m/z 504 (M+H)⁺; ¹H NMR (300 MHz, DMSO-d₆): δ ppm 2.88 (s, 3H), 2.92-3.03 (m, 2H), 3.12-3.28 (m, 2H), 3.54 (d, J=11.90 Hz, 2H), 3.83 (d, J=13.49 Hz, 2H), 4.27 (s, 2H), 7.02 (d, J=9.12 Hz, 2H), 7.19 (t, J=7.14 Hz, 1H), 7.30 (t, J=7.34 Hz, 2H), 7.35 (s, 2H), 7.39-7.46 (m, 1H), 7.52 (t, J=7.54 Hz, 2H), 7.57-7.69 (m, 4H), 9.30 (s, 1H).

Example 20

8-benzyl-6-(2-methylphenyl)-2-{[4-(4-methylpiperazin-1-yl)phenyl]amino}pyrimido[4,5-d]pyridazin-5 (6H)-one The title compound was prepared as described in Example 6D, substituting Example 19B for Example 6C and o-tolylhydrazine for methylhydrazine. MS (DCI/NH₃) m/z 518 (M+H)⁺; ¹H NMR (300 MHz, DMSO-d₆): δ ppm (2.11 (s, 3H), 2.88 (s, 3H), 2.90-3.03 (m, 2H), 3.17 (m, 2H), 3.56 (m, 2H), 3.71-3.88 (m, 2H), 4.25 (s, 2H), 7.02 (d, J=9.12 Hz, 2H), 7.15-7.22 (m, 1H), 7.25-7.34 (m, 4H), 7.34-7.42 (m, 4H), 7.64 (d, J=8.73 Hz, 2H), 9.29 (s, 1H).

Example 21

3-[2-{[4-(4-methylpiperazin-1-yl)phenyl]amino}-5-oxo-8-propylpyrimido[4,5-d]pyridazin-6(5H)-yl] propanenitrile The title compound was prepared as described in Example 6D, substituting Example 11B for Example 6C and 3-hydrazinylpropanenitrile for methylhydrazine. MS (DCI/NH₃) m/z 433 (M+H)⁺; ¹H NMR (300 MHz, DMSO-d₆): δ ppm 1.01 (t, J=7.34 Hz, 3H), 1.65-1.85 (m, 2H), 2.82-2.91 (m, 2H), 2.88 (s, 3H), 3.00 (t, J=6.35 Hz, 2H), 3.09-3.33 (m, 2H), 3.51 (m, 2H), 3.82 (d, J=12.69 Hz, 2H), 4.30 (t, J=6.35 Hz, 2H), 7.03 (d, J=9.12 Hz, 2H), 7.77 (d, J=1.59 Hz, 2H), 9.27 (s, 1H).

Example 22

6-allyl-8-benzyl-2-{[4-(4-methylpiperazin-1-yl)phenyl]amino}pyrimido[4,5-d]pyridazin-5(6H)-one The title compound was prepared as described in Example 6D, substituting Example 19B for Example 6C and allylhydrazine for methylhydrazine. MS (DCI/NH₃) m/z 468 (M+H)⁺; ¹H NMR (300 MHz, DMSO-d₆): δ ppm 2.88 (s, 3H), 2.95 (d, J=12.30 Hz, 2H), 3.20 (m, 2H), 3.52 (m, 2H), 3.82 (d, J=13.49 Hz, 2H), 4.21 (s, 2H), 4.71 (d, J=4.76 Hz, 2H), 5.05-5.29 (m, 2H), 5.86-6.10 (m, 1H), 7.00 (d, J=9.12 Hz, 2H), 7.13-7.22 (m, 1H), 7.23-7.33 (m, 4H), 7.61 (d, J=8.73 Hz, 2H), 9.24 (s, 1H).

Example 23

2-{[4-(4-methylpiperazin-1-yl)phenyl]amino}-8-propyl-6-(2,2,2-trifluoroethyl)pyrimido[4,5-d]pyridazin-5(6H)-one The title compound was prepared as described in Example 6D, substituting Example 11B for Example 6C and (2,2,2-trifluoroethyl)hydrazine for methylhydrazine. MS (DCI/NH₃) m/z 462 (M+H)⁺; ¹H NMR (300 MHz, DMSO-d₆): δ ppm 0.99 (t, J=7.34 Hz, 3H), 1.68-1.78 (m, 2H), 2.22 (s, 3H), 2.41-2.47 (m, 4H), 2.78-2.87 (m, 2H), 3.07-3.15 (m, 4H), 3.25 (s, 2H), 6.94 (d, J=9.12 Hz, 2H), 7.71 (s, 2H), 9.18 (s, 1H).

Example 24

6-(2-chlorophenyl)-2-{[4-(4-methylpiperazin-1-yl) phenyl]amino}-8-(2-phenylethyl)pyrimido[4,5-d] pyridazin-5(6H)-one The title compound was prepared as described in Example 6D, substituting (2-chlorophenyl)hydrazine for methylhydrazine. MS (DCI/NH₃) m/z 553 (M+H)⁺; ¹H NMR (300 MHz, DMSO-d₆): δ ppm 2.88 (s, 3H), 2.92-2.99 (m, 2H), 2.95-3.07 (m, 2H), 3.12-3.26 (m, 4H), 3.55 (d, J=11.87 Hz, 2H), 3.80 (d, J=13.56 Hz, 2H), 7.00 (d, J=9.16 Hz, 2H), 7.15-7.33 (m, 5H), 7.48-7.58 (m, 3H), 7.64-7.69 (m, 1H), 7.76 (m, 2H), 9.31 (s, 1H).

Example 25

6-(2-chlorophenyl)-2-{[4-(4-methylpiperazin-1-yl)phenyl]amino}-8-propylpyrimido[4,5-d]pyridazin-5(6H)-one The title compound was prepared as described in Example 6D, substituting Example 11B for Example 6C and (2-chlorophenyl)hydrazine for methylhydrazine. MS (DCI/NH$_3$) m/z 491 (M+H)$^+$; $^1$H NMR (300 MHz, DMSO-d$_6$): δ ppm 0.99 (t, J=7.34 Hz, 3H), 1.64-1.85 (m, 2H), 2.88 (s, 3H), 2.92-3.03 (m, 2H), 3.05-3.28 (m, 2H), 3.53 (d, J=11.90 Hz, 2H), 3.63-3.95 (m, 4H), 7.05 (d, J=8.72 Hz, 2H), 7.49-7.56 (m, 2H), 7.56-7.63 (m, 1H), 7.63-7.71 (m, 1H), 7.80 (m, 2H), 9.30 (s, 1H).

Example 26

8-benzyl-6-(2-chlorophenyl)-2-{[4-(4-methylpiperazin-1-yl)phenyl]amino}pyrimido[4,5-d]pyridazin-5(6H)-one The title compound was prepared as described in Example 6D, substituting Example 19B for Example 6C and (2-chlorophenyl)hydrazine for methylhydrazine. MS (DCI/NH$_3$) m/z 539 (M+H)$^+$; $^1$H NMR (300 MHz, DMSO-d$_6$): δ ppm 2.88 (s, 3H), 2.91-3.04 (m, 2H), 3.11-3.26 (m, 2H), 3.48-3.61 (m, 2H), 3.84 (d, J=12.21 Hz, 2H), 4.24 (s, 2H), 7.03 (d, J=9.16 Hz, 2H), 7.15-7.23 (m, 1H), 7.25-7.37 (m, 4H), 7.52-7.58 (m, 3H), 7.59-7.67 (m, 2H), 7.67-7.73 (m, 1H), 9.29 (s, 1H).

Example 27

2-{[4-(4-methylpiperazin-1-yl)phenyl]amino}-6,8-diphenylpyrimido[4,5-d]pyridazin-5(6H)-one

Example 27A ethyl 4-benzoyl-2-(methylthio)pyrimidine-5-carboxylate

The title compound was prepared as described in Example 6B, substituting benzoyl chloride for 3-phenylpropanoyl chloride. MS (DCI/NH$_3$) m/z 303 (M+H)$^+$.

Example 27B ethyl 4-benzoyl-2-(4-(4-methylpiperazin-1-yl)phenylamino)pyrimidine-5-carboxylate The title compound was prepared as described in Example 6C, substituting Example 27A for Example 6B. MS (DCI/NH$_3$) m/z 446 (M+H)$^+$.

Example 27C

2-{[4-(4-methylpiperazin-1-yl)phenyl]amino}-6,8-diphenylpyrimido[4,5-d]pyridazin-5(6H)-one The title compound was prepared as described in Example 6D, substituting Example 27B for Example 6C and phenylhydrazine for methylhydrazine. MS (DCI/NH$_3$) m/z 490 (M+H)$^+$; $^1$H NMR (300 MHz, DMSO-d$_6$): δ ppm 2.87 (s, 3H), 2.88-3.00 (m, 2H), 3.14-3.29 (m, 2H), 3.53 (d, J=13.09 Hz, 2H), 3.80 (d, J=13.09 Hz, 2H), 6.95 (d, J=8.33 Hz, 2H), 7.34-7.60 (m, 6H), 7.61-7.75 (m, 4H), 7.91-8.10 (m, 2H), 9.35-9.36 (m, 1H).

Example 28

6-(2-methylphenyl)-2-{[4-(4-methylpiperazin-1-yl)phenyl]amino}-8-phenylpyrimido[4,5-d]pyridazin-5(6H)-one The title compound was prepared as described in Example 6D, substituting Example 27B for Example 6C and o-tolylhydrazine for methylhydrazine. MS (DCI/NH$_3$) m/z 504 (M+H)$^+$; $^1$H NMR (300 MHz, DMSO-d$_6$): δ ppm 2.18 (s, 3H), 2.87 (s, 3H), 2.88-2.98 (m, 2H), 3.10-3.29 (m, 2H), 3.53 (d, J=12.29 Hz, 2H), 3.80 (d, J=12.69 Hz, 2H), 6.95 (d, J=8.33 Hz, 2H), 7.31-7.46 (m, 4H), 7.48-7.55 (m, 3H), 7.67 (d, J=7.93 Hz, 2H), 7.89-7.97 (m, 2H), 9.37 (s, 1H).

Example 29

6-(2-chlorophenyl)-2-{[4-(4-methylpiperazin-1-yl)phenyl]amino}-8-phenylpyrimido[4,5-d]pyridazin-5(6H)-one The title compound was prepared as described in Example 6D, substituting Example 27B for Example 6C and (2-chlorophenyl)hydrazine for methylhydrazine. MS (DCI/NH$_3$) m/z 525 (M+H)$^+$; $^1$H NMR (300 MHz, DMSO-d$_6$): δ ppm 2.87 (s, 3H), 2.89-3.01 (m, 2H), 3.09-3.25 (m, 2H), 3.53 (d, J=11.50 Hz, 2H), 3.80 (d, J=11.90 Hz, 2H), 6.95 (d, J=8.33 Hz, 2H), 7.47-7.61 (m, 5H), 7.61-7.76 (m, 4H), 7.93 (dd, J=6.54, 2.97 Hz, 2H), 9.37 (s, 1H).

Example 30

6-(2-methoxyphenyl)-2-{[4-(4-methylpiperazin-1-yl)phenyl]amino}-8-phenylpyrimido[4,5-d]pyridazin-5(6H)-one The title compound was prepared as described in Example 6D, substituting Example 27B for Example 6C and (2-methoxyphenyl)hydrazine for methylhydrazine. MS (DCI/NH$_3$) m/z 520 (M+H)$^+$; $^1$H NMR (300 MHz, DMSO-d$_6$): δ ppm 2.87 (s, 3H), 2.90-3.00 (m, 2H), 3.18 (d, J=9.16 Hz, 2H), 3.53 (d, J=11.87 Hz, 2H), 3.78 (s, 3H), 3.79-3.88 (m, 2H), 6.95 (d, J=8.82 Hz, 2H), 7.11 (t, J=7.63 Hz, 1H), 7.24 (d, J=7.12 Hz, 1H), 7.42-7.48 (m, 1H), 7.49-7.54 (m, 4H), 7.67 (d, J=8.82 Hz, 2H), 7.90 (d, J=2.03 Hz, 1H), 7.92 (d, J=4.41 Hz, 1H), 9.33 (s, 1H).

Example 31

2-{[4-(4-methylpiperazin-1-yl)phenyl]amino}-8-phenyl-6-[2-(trifluoromethyl)phenyl]pyrimido[4,5-d]pyridazin-5(6H)-one The title compound was prepared as described in Example 6D, substituting Example 27B for Example 6C and (2-(trifluoromethyl)phenyl)hydrazine for methylhydrazine. MS (DCI/NH$_3$) m/z 558 (M+H)$^+$; $^1$H NMR (300 MHz, DMSO-d$_6$): δ ppm 2.87 (s, 3H), 2.89-2.99 (m, 2H), 3.12-3.26 (m, 2H), 3.47-3.60 (m, 2H), 3.80 (d, J=12.55 Hz, 2H), 6.95 (d, J=7.80 Hz, 2H), 7.49-7.53 (m, 3H), 7.66 (d, J=8.14 Hz, 2H), 7.78 (t, J=7.46 Hz, 2H), 7.89 (dd, J=6.44, 3.05 Hz, 3H), 7.97 (d, J=7.80 Hz, 1H), 9.36 (s, 1H).

Example 32

8-(2-furyl)-6-(2-methylphenyl)-2-{[4-(4-methylpiperazin-1-yl)phenyl]amino}pyrimido[4,5-d]pyridazin-5(6H)-one

Example 32A ethyl 4-(furan-2-carbonyl)-2-(methylthio)pyrimidine-5-carboxylate The title compound was prepared as described in Example 6B, substituting furan-2-carbonyl chloride for 3-phenylpropanoyl chloride. MS (DCI/NH$_3$) m/z 293 (M+H)$^+$.

Example 32B ethyl 4-(furan-2-carbonyl)-2-(4-(4-methylpiperazin-1-yl)phenylamino)pyrimidine-5-carboxylate The title compound was prepared as described in Example 6C, substituting Example 32A for Example 6B. MS (DCI/NH$_3$) m/z 436 (M+H)$^+$.

Example 32C 8-(2-furyl)-6-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 32B for Example 6C and o-tolylhydrazine for methylhydrazine. MS (DCI/NH$_3$) m/z 514 (M+H)$^+$; $^1$H NMR (300 MHz, DMSO-d$_6$): δ ppm 2.14 (s, 3H), 2.88 (s, 3H), 2.99 (d, J=11.90 Hz, 2H) 3.08-3.29 (m, 2H), 3.55 (d, J=12.29 Hz, 2H), 3.86 (d, J=12.69 Hz, 2H), 7.08 (d, J=9.12 Hz, 2H), 7.52-7.68 (m, 6H), 7.68-7.74 (m, 2H), 7.87 (d, J=0.79 Hz, 1H), 9.33 (s, 1H).

Example 33

6-(2-chlorophenyl)-8-(2-furyl)-2-{[4-(4-methylpiperazin-1-yl)phenyl]amino}pyrimido[4,5-d]pyridazin-5(6H)-one The title compound was prepared as described in Example 6D, substituting Example 32B for Example 6C and (2-chlorophenyl)hydrazine for methylhydrazine. MS (DCI/NH$_3$) m/z 494 (M+H)$^+$; $^1$H NMR (300 MHz, DMSO-d$_6$): δ ppm 2.14 (s, 3H), 2.88 (s, 3H), 2.98 (d, J=12.70 Hz, 2H), 3.09-3.29 (m, 2H), 3.46-3.63 (m, 2H), 3.75-3.94 (m, 2H), 7.08 (d, J=8.73 Hz, 2H), 7.34-7.47 (m, 6H), 7.63 (d, J=8.73 Hz, 2H), 7.85 (d, J=1.59 Hz, 1H), 9.33 (s, 1H).

Example 34

8-(2-furyl)-2-{[4-(4-methylpiperazin-1-yl)phenyl]amino}-6-phenylpyrimido[4,5-d]pyridazin-5(6H)-one The title compound was prepared as described in Example 6D, substituting Example 32B for Example 6C and phenylhydrazine for methylhydrazine. MS (DCI/NH$_3$) m/z 480 (M+H)$^+$; $^1$H NMR (300 MHz, DMSO-d$_6$): δ ppm 2.88 (s, 3H), 2.98 (d, J=10.71 Hz, 2H), 3.11-3.26 (m, 2H), 3.46-3.62 (m, 2H), 3.78-3.92 (m, 2H), 7.08 (d, J=9.12 Hz, 2H), 7.17-7.23 (m, 1H), 7.41-7.49 (m, 1H), 7.54 (t, J=7.54 Hz, 2H), 7.63 (d, J=8.33 Hz, 5H), 7.85-7.93 (m, 1H), 9.34 (s, 1H).

Example 35

6-allyl-8-(2-fluorophenyl)-2-{[4-(4-methylpiperazin-1-yl)phenyl]amino}pyrimido[4,5-d]pyridazin-5(6H)-one

Example 35A ethyl 4-(2-fluorobenzoyl)-2-(methylthio)pyrimidine-5-carboxylate The title compound was prepared as described in Example 6B, substituting 2-fluorobenzoyl chloride for 3-phenylpropanoyl chloride. MS (DCI/NH$_3$) m/z 321 (M+H)$^+$.

Example 35B ethyl 4-(2-fluorobenzoyl)-2-(4-(4-methylpiperazin-1-yl)phenylamino)pyrimidine-5-carboxylate The title compound was prepared as described in Example 6C, substituting Example 35A for Example 6B. MS (DCI/NH$_3$) m/z 464 (M+H)$^+$.

Example 35C 6-allyl-8-(2-fluorophenyl)-2-{[4-(4-methylpiperazin-1-yl)phenyl]amino}pyrimido[4,5-d]pyridazin-5(6H)-one The title compound was prepared as described in Example 6D, substituting Example 35B for Example 6C and allylhydrazine for methylhydrazine. MS (DCI/NH$_3$) m/z 472 (M+H)$^+$; $^1$H NMR (300 MHz, DMSO-d$_6$): δ ppm 2.86 (s, 3H), 2.87-2.97 (m, 2H), 3.07-3.24 (m, 2H), 3.52 (d, J=11.90 Hz, 2H), 3.75 (d, J=13.48 Hz, 2H), 4.77 (d, J=5.55 Hz, 2H), 5.17-5.21 (m, 1H), 5.24 (s, 1H), 5.93-6.13 (m, 1H), 6.83 (d, J=5.55 Hz, 2H), 7.27-7.48 (m, 2H), 7.49-7.65 (m, 4H), 9.31 (s, 1H).

Example 36

8-(2-fluorophenyl)-6-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 35B for Example 6C and o-tolylhydrazine for methylhydrazine. MS (DCI/NH$_3$) m/z 522 (M+H)$^+$; $^1$H NMR (300 MHz, DMSO-d$_6$): δ ppm 2.18 (s, 3H), 2.87 (s, 3H), 2.87-2.96 (m, 2H), 3.05-3.24 (m, 2H), 3.52 (d, J=11.53 Hz, 2H), 3.76 (d, J=11.87 Hz, 2H), 6.85 (d, J=7.12 Hz, 2H), 7.30-7.48 (m, 5H), 7.51-7.68 (m, 5H), 9.36 (s, 1H).

Example 37

8-(2-fluorophenyl)-2-{[4-(4-methylpiperazin-1-yl)phenyl]amino}-6-phenylpyrimido[4,5-d]pyridazin-5(6H)-one The title compound was prepared as described in Example 6D, substituting Example 35B for Example 6C and phenylhydrazine for methylhydrazine. MS (DCI/NH$_3$) m/z 508 (M+H)$^+$; $^1$H NMR (300 MHz, DMSO-d$_6$): δ ppm 2.87 (s, 3H), 2.87-2.97 (m, 2H), 3.09-3.28 (m, 2H), 3.53 (d, J=13.22 Hz, 2H), 3.76 (d, J=12.89 Hz, 2H), 6.85 (d, J=7.12 Hz, 2H), 7.30-7.50 (m, 3H), 7.49-7.62 (m, 5H), 7.61-7.75 (m, 3H), 9.36 (s, 1H).

Example 38

6-(2-chlorophenyl)-8-(2,4-dichlorophenyl)-2-{[4-(4-methylpiperazin-1-yl)phenyl]amino}pyrimido[4,5-d]pyridazin-5(6H)-one

Example 38A ethyl 4-(2,4-dichlorobenzoyl)-2-(methylthio)pyrimidine-5-carboxylate The title compound was prepared as described in Example 6B, substituting 2,4-dichlorobenzoyl chloride for 3-phenylpropanoyl chloride. MS (DCI/NH$_3$) m/z 372 (M+H)$^+$.

Example 38B ethyl 4-(2,4-dichlorobenzoyl)-2-(4-(4-methylpiperazin-1-yl)phenylamino)pyrimidine-5-carboxylate The title compound was prepared as described in Example 6C, substituting Example 38A for Example 6B. MS (DCI/NH$_3$) m/z 515 (M+H)$^+$.

Example 38C 6-(2-chlorophenyl)-8-(2,4-dichlorophenyl)-2-{[4-(4-methylpiperazin-1-yl)phenyl]amino}pyrimido[4,5-d]pyridazin-5(6H)-one The title compound was prepared as described in Example 6D, substituting Example 38B for Example 6C and (2-chlorophenyl)hydrazine for methylhydrazine. MS (DCI/NH$_3$) m/z 593 (M+H)$^+$; $^1$H NMR (300 MHz, DMSO-d$_6$): δ ppm 2.87 (s, 3H), 2.89-2.99 (m, 2H), 3.08-3.26 (m, 2H), 3.54 (d, J=10.31 Hz, 2H), 3.75 (d, J=12.69 Hz, 2H), 6.81 (d, J=6.35 Hz, 2H), 7.46 (d, J=8.33 Hz, 2H), 7.53-7.58 (m, 3H), 7.61-7.75 (m, 4H), 9.36 (s, 1H).

Example 39

8-(2,4-dichlorophenyl)-2-{[4-(4-methylpiperazin-1-yl)phenyl]amino}-6-[2-(trifluoromethyl)phenyl]pyrimido[4,5-d]pyridazin-5(6H)-one The title compound was prepared as described in Example 6D, substituting Example 38B for Example 6C and (2-(trifluoromethyl)phenyl)hydrazine for methylhydrazine. MS (DCI/NH$_3$) m/z 627 (M+H)$^+$; $^1$H NMR (300 MHz, DMSO-d$_6$): δ ppm 2.87 (s, 3H), 2.94 (d, J=11.90 Hz, 2H), 3.08-3.30 (m, 2H), 3.54 (d, J=9.46 Hz, 2H), 3.75 (d, J=8.55 Hz, 2H), 6.80 (d, J=7.02 Hz, 2H), 7.45 (d, J=8.24 Hz, 2H), 7.52-7.66 (m, 2H), 7.73-7.83 (m, 2H), 7.84-8.01 (m, 3H), 9.35 (s, 1H).

Example 40

6-(2-chlorophenyl)-8-(2-fluorophenyl)-2-{[4-(4-methylpiperazin-1-yl)phenyl]amino}pyrimido[4,5-d]pyridazin-5(6H)-one The title compound was prepared as described in Example 6D, substituting Example 35B for Example 6C and (2-chlorophenyl)hydrazine for methylhydrazine. MS (DCI/NH$_3$) m/z 543 (M+H)$^+$; $^1$H NMR (300 MHz, DMSO-d$_6$): δ ppm 2.87 (s, 3H), 2.89-2.99 (m, 2H), 3.07-3.26 (m, 2H), 3.49-3.58 (m, 2H), 3.77 (d, J=12.82 Hz, 2H), 6.85 (d, J=6.41 Hz, 2H), 7.37 (t, J=7.48 Hz, 1H), 7.43-7.51 (m, 1H), 7.53-7.58 (m, 3H), 7.58-7.64 (m, 2H), 7.67-7.73 (m, 3H), 9.36 (s, 1H).

Example 41

8-(2,4-dichlorophenyl)-6-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 38B for Example 6C and o-tolylhydrazine for methylhydrazine. MS (DCI/NH$_3$) m/z 573 (M+H)$^+$; $^1$H NMR (300 MHz, DMSO-d$_6$): δ ppm 2.18 (s, 3H), 2.87 (s, 3H), 2.90-2.98 (m, 2H), 3.10-3.26 (m, 2H), 3.48-3.60 (m, 2H), 3.74 (d, J=11.29 Hz, 2H), 6.80 (d, J=6.41 Hz, 2H), 7.30-7.44 (m, 4H), 7.47 (d, J=8.54 Hz, 2H), 7.57-7.71 (m, 3H), 9.36 (s, 1H).

Example 42

8-(2,4-dichlorophenyl)-2-{[4-(4-methylpiperazin-1-yl)phenyl]amino}-6-phenylpyrimido[4,5-d]pyridazin-5(6H)-one The title compound was prepared as described in Example 6D, substituting Example 38B for Example 6C and phenylhydrazine for methylhydrazine. MS (DCI/NH$_3$) m/z 559 (M+H)$^+$; $^1$H NMR (300 MHz, DMSO-d$_6$): δ ppm 1H 2.87 (s, 3H) 2.89-3.00, (m, 2H), 3.06-3.26 (m, 2H), 3.46-3.61 (m, 2H), 3.75 (d, J=9.46 Hz, 2H), 6.81 (d, J=5.49 Hz, 2H), 7.41-7.51 (m, 4H), 7.53 (t, J=7.78 Hz, 2H), 7.60-7.67 (m, 3H), 7.69 (s, 1H), 9.37 (s, 1H).

Example 43

8-(2,4-dichlorophenyl)-6-(2-methoxyphenyl)-2-{[4-(4-methylpiperazin-1-yl)phenyl]amino}pyrimido[4,5-d]pyridazin-5(6H)-one The title compound was prepared as described in Example 6D, substituting Example 38B for Example 6C and (2-methoxyphenyl)hydrazine for methylhydrazine. MS (DCI/NH$_3$) m/z 589 (M+H)$^+$; $^1$H NMR (300 MHz, DMSO-d$_6$): δ ppm 2.91 (s, 3H), 2.92-3.07 (m, 2H), 3.13-3.34 (m, 2H), 3.52-3.67 (m, 2H), 3.81 (d, J=17.09 Hz, 2H), 3.84 (s, 3H), 6.99-7.08 (m, 2H), 7.46-7.60 (m, 2H), 7.62-7.73 (m, 4H), 7.91 (d, J=2.14 Hz, 1H), 7.94 (d, J=8.54 Hz, 2H), 9.04 (s, 1H).

Example 44

6-(3-chlorophenyl)-8-(2,4-dichlorophenyl)-2-{[4-(4-methylpiperazin-1-yl)phenyl]amino}pyrimido[4,5-d]pyridazin-5(6H)-one The title compound was prepared as described in Example 6D, substituting Example 38B for Example 6C and (3-chlorophenyl)hydrazine for methylhydrazine. MS (DCI/NH$_3$) m/z 593 (M+H)$^+$; $^1$H NMR (300 MHz, DMSO-d$_6$): δ ppm 2.87 (s, 3H), 2.89-3.01 (m, 2H), 3.07-3.26 (m, 2H), 3.47-3.62 (m, 2H), 3.69-3.85 (m, 2H), 6.81 (d, J=7.32 Hz, 2H), 7.47 (d, J=7.63 Hz, 2H), 7.50-7.54 (m, 2H), 7.57 (t, J=7.93 Hz, 1H), 7.61-7.69 (m, 2H), 7.70 (s, 1H), 7.77 (s, 1H), 9.37 (s, 1H).

Example 45

6-(2,6-dichlorophenyl)-8-(2-fluorophenyl)-2-{[4-(4-methylpiperazin-1-yl)phenyl]amino}pyrimido[4,5-d]pyridazin-5(6H)-one The title compound was prepared as described in Example 6D, substituting Example 35B for Example 6C and (2,6-dichlorophenyl)hydrazine for methylhydrazine. MS (DCI/NH$_3$) m/z 577 (M+H)$^+$; $^1$H NMR (300 MHz, DMSO-d$_6$): δ ppm 2.87 (s, 3H), 3.00 (m, 2H), 3.06-3.21 (m, 2H), 3.45-3.62 (m, 2H), 3.77 (d, J=12.29 Hz, 2H), 6.84 (d, J=8.33 Hz, 2H), 7.38 (t, J=7.54 Hz, 2H), 7.50-7.67 (m, 4H), 7.71-7.78 (m, 3H), 9.38 (s, 1H).

Example 46

6-(2,6-dichlorophenyl)-2-{[4-(4-methylpiperazin-1-yl)phenyl]amino}-8-phenylpyrimido[4,5-d]pyridazin-5(6H)-one The title compound was prepared as described in Example 6D, substituting Example 27B for Example 6C and (2,6-dichlorophenyl)hydrazine for methylhydrazine. MS (DCI/NH$_3$) m/z 559 (M+H)$^+$; $^1$H NMR (300 MHz, CD$_3$OD): δ ppm 2.88 (s, 3H), 2.88-3.02 (m, 2H), 3.18 (d, J=9.91 Hz, 2H), 3.47-3.63 (m, 2H), 3.81 (d, J=12.69 Hz, 2H), 6.90-7.01 (m, 2H), 7.50-7.57 (m, 2H), 7.58-7.72 (m, 3H), 7.75 (m, 2H), 7.77 (m, 1H), 7.92 (dd, J=6.74, 2.78 Hz, 2H), 9.38 (s, 1H).

Example 47

6-allyl-8-(2,4-dichlorophenyl)-2-{[4-(4-methylpiperazin-1-yl)phenyl]amino}pyrimido[4,5-d]pyridazin-5(6H)-one The title compound was prepared as described in Example 6D, substituting Example 38B for Example 6C and allylhydrazine for methylhydrazine. MS (DCI/NH$_3$) m/z 523 (M+H)$^+$; $^1$H NMR (300 MHz, DMSO-d$_6$): δ ppm 2.86 (s, 3H), 2.88-2.97 (m, 2H), 3.10-3.25 (m, 2H), 3.53 (d, J=11.19 Hz, 2H), 3.73 (d, J=12.89 Hz, 2H), 4.76 (d, J=5.09 Hz, 2H), 5.18 (dd, J=9.32, 1.53 Hz, 1H), 5.23 (d, J=1.36 Hz, 1H), 5.84-6.17 (m, 1H), 6.81 (d, J=2.71 Hz, 2H), 7.45 (d, J=8.82 Hz, 2H), 7.54-7.68 (m, 2H), 7.88 (s, 1H), 9.31 (s, 1H).

Example 48

6-(2-chlorophenyl)-2-{[4-(4-methylpiperazin-1-yl)phenyl]amino}-8-(2-thienyl)pyrimido[4,5-d]pyridazin-5(6H)-one

Example 48A ethyl 2-(methylthio)-4-(thiophene-2-carbonyl)pyrimidine-5-carboxylate

The title compound was prepared as described in Example 6B, substituting thiophene-2-carbonyl chloride for 3-phenyl-propanoyl chloride. MS (DCI/NH$_3$) m/z 309 (M+H)$^+$.

Example 48B ethyl 2-(4-(4-methylpiperazin-1-yl)phenylamino)-4-(thiophene-2-carbonyl)pyrimidine-5-carboxylate The title compound was prepared as described in Example 6C, substituting Example 48A for Example 6B. MS (DCI/NH$_3$) m/z 452 (M+H)$^+$.

Example 48C

6-(2-chlorophenyl)-2-{[4-(4-methylpiperazin-1-yl)phenyl]amino}-8-(2-thienyl)pyrimido[4,5-d]pyridazin-5(6H)-one The title compound was prepared as described in Example 6D, substituting Example 48B for Example 6C and (2-chlorophenyl)hydrazine for methylhydrazine. MS (DCI/NH$_3$) m/z 514 (M+H)$^+$; $^1$H NMR (300 MHz, DMSO-d$_6$): δ ppm 2.88 (s, 3H), 2.99 (d, J=11.90 Hz, 2H) 3.08-3.29 (m, 2H), 3.55 (d, J=12.29 Hz, 2H), 3.86 (d, J=12.69 Hz, 2H), 7.08 (d, J=9.12 Hz, 2H), 7.52-7.68 (m, 6H), 7.68-7.74 (m, 2H), 7.87 (d, J=0.79 Hz, 1H), 9.33 (s, 1H).

Example 49

8-cyclopentyl-6-(2-methylphenyl)-2-{[4-(4-methylpiperazin-1-yl)phenyl]amino}pyrimido[4,5-d]pyridazin-5(6H)-one

Example 49A ethyl 4-(cyclopentanecarbonyl)-2-(methylthio)pyrimidine-5-carboxylate

The title compound was prepared as described in Example 6B, substituting cyclopentanecarbonyl chloride for 3-phenyl-propanoyl chloride. MS (DCI/NH$_3$) m/z 295 (M+H)$^+$

Example 49B ethyl 4-(cyclopentanecarbonyl)-2-(4-(4-methylpiperazin-1-yl)phenylamino)pyrimidine-5-carboxylate The title compound was prepared as described in Example 6C, substituting Example 49A for Example 6B. MS (DCI/NH$_3$) m/z 438 (M+H)$^+$.

Example 49C

8-cyclopentyl-6-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 49B for Example 6C and o-tolyl-hydrazine for methylhydrazine. MS (DCI/NH$_3$) m/z 496 (M+H)$^+$; $^1$H NMR (300 MHz, DMSO-d$_6$): δ ppm 1.67 (d, J=5.16 Hz, 4H), 1.74-1.92 (m, 2H), 1.95-2.09 (m, 2H), 2.10 (s, 3H), 2.87 (s, 3H), 2.93-2.99 (m, 2H), 3.06-3.28 (m, 2H), 3.54 (d, J=11.50 Hz, 2H), 3.67-3.90 (m, 3H), 7.05 (d, J=9.12 Hz, 2H), 7.29-7.35 (m, 2H), 7.35-7.42 (m, 2H), 7.79 (s, 2H), 9.29 (s, 1H).

Example 50

8-(3-methylphenyl)-2-{[4-(4-methylpiperazin-1-yl) phenyl]amino}-6-phenylpyrimido[4,5-d]pyridazin-5 (6H)-one

Example 50A ethyl 4-(3-methylbenzoyl)-2-(methylthio)pyrimidine-5-carboxylate The title compound was prepared as described in Example 6B, substituting 3-methylbenzoyl chloride for 3-phenylpropanoyl chloride. MS (DCI/NH$_3$) m/z 317 (M+H)$^+$. Example 50B ethyl 4-(3-methylbenzoyl)-2-(4-(4-methylpiperazin-1-yl)phenylamino)pyrimidine-5-carboxylate The title compound was prepared as described in Example 6C, substituting Example 50A for Example 6B. MS (DCI/NH$_3$) m/z 460 (M+H)$^+$.

Example 50C 8-(3-methylphenyl)-2-{[4-(4-methylpiperazin-1-yl) phenyl]amino}-6-phenylpyrimido[4,5-d]pyridazin-5 (6H)-one The title compound was prepared as described in Example 6D, substituting Example 50B for Example 6C and phenylhydrazine for methylhydrazine. MS (DCI/NH$_3$) m/z 504 (M+H)$^+$; $^1$H NMR (300 MHz, DMSO-d$_6$): δ ppm 2.25 (s, 3H), 2.39 (s, 3H), 3.09 (d, J=4.36 Hz, 4H), 3.26-3.35 (m, 4H), 6.85 (d, J=8.33 Hz, 2H), 7.30-7.37 (m, 1H), 7.38-7.49 (m, 2H), 7.53 (t, J=7.54 Hz, 2H), 7.62 (d, J=7.93 Hz, 2H), 7.67 (d, J=7.54 Hz, 2H), 7.71-7.81 (m, 2H), 9.34 (s, 1H).

Example 51

6-(2-chlorophenyl)-8-(3-methylphenyl)-2-{[4-(4-methylpiperazin-1-yl)phenyl]amino}pyrimido[4,5-d] pyridazin-5(6H)-one The title compound was prepared as described in Example 6D, substituting Example 50B for Example 6C and (2-chlorophenyl)hydrazine for methylhydrazine. MS (DCI/NH$_3$) m/z 539 (M+H)$^+$; $^1$H NMR (300 MHz, DMSO-d$_6$): δ ppm 2.38 (s, 3H), 2.87 (s, 3H), 2.89-2.98 (m, 2H), 3.06-3.29 (m, 2H), 3.45-3.65 (m, 2H), 3.79 (d, J=13.09 Hz, 2H), 6.93 (d, J=8.33 Hz, 2H), 7.22-7.37 (m, 1H), 7.42 (t, J=7.73 Hz, 1H), 7.49-7.61 (m, 2H), 7.62-7.80 (m, 6H), 9.36 (s, 1H).

Example 52

6-(2-methylphenyl)-8-(3-methylphenyl)-2-{[4-(4-methylpiperazin-1-yl)phenyl]amino}pyrimido[4,5-d] pyridazin-5(6H)-one The title compound was prepared as described in Example 6D, substituting Example 50B for Example 6C and o-tolylhydrazine for methylhydrazine. MS (DCI/NH$_3$) m/z 518 (M+H)$^+$; $^1$H NMR (300 MHz, DMSO-d$_6$): δ ppm 2.18 (s, 3H), 2.38 (s, 3H), 2.88 (s, 3H), 2.93 (d, J=8.82 Hz, 2H), 3.03-3.28 (m, 2H), 3.37-3.63 (m, 2H), 3.78 (d, J=11.53 Hz, 2H), 6.82-6.99 (m, 2H), 7.20-7.37 (m, 2H), 7.35-7.55 (m, 4H), 7.60-7.81 (m, 4H), 9.36 (s, 1H).

Example 53

6-(2-chlorophenyl)-2-[(2'-methyl-2',3'-dihydro-1'H-spiro[cyclopropane-1,4'-isoquinolin]-7'-yl)amino]-8-phenylpyrimido[4,5-d]pyridazin-5(6H)-one

Example 53A ethyl 4-benzoyl-2-(2'-methyl-2',3'-dihydro-1'H-spiro [cyclopropane-1,4'-isoquinoline]-7'-ylamino)pyrimidine-5-carboxylate The title compound was prepared as described in Example 6C, substituting Example 27A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline. MS (DCI/NH$_3$) m/z 443 (M+H)$^+$.

Example 53B 6-(2-chlorophenyl)-2-(2'-methyl-2',3'-dihydro-1'H-spiro[cyclopropane-1,4'-isoquinoline]-7'-ylamino)-8-phenylpyrimido[4,5-d]pyridazin-5(6H)-one The title compound was prepared as described in Example 6D, substituting Example 53A for Example 6C and (2-chlorophenyl)hydrazine for methylhydrazine. MS (DCI/NH$_3$) m/z 522 (M+H)$^+$; $^1$H NMR (300 MHz, DMSO-d$_6$): δ ppm 0.92 (d, J=5.16 Hz, 1H), 1.02-1.13 (m, 1H), 1.12-1.25 (m, 1H), 1.28-1.40 (m, 1H), 2.94 (s, 3H), 3.47-3.55 (m, 2H), 4.29 (m, 2H), 6.83 (d, J=8.72 Hz, 1H), 7.51-7.60 (m, 6H), 7.64 (s, 1H), 7.67-7.75 (m, 2H), 7.88 (dd, J=6.54, 2.97 Hz, 2H), 9.43 (s, 1H).

Example 54

8-cyclopentyl-2-{[4-(4-methylpiperazin-1-yl)phenyl] amino}-6-phenylpyrimido[4,5-d]pyridazin-5(6H)-one The title compound was prepared as described in Example 6D, substituting Example 49B for Example 6C and phenylhydrazine for methylhydrazine. MS (DCI/NH$_3$) m/z 522 (M+H)$^+$; $^1$H NMR (300 MHz, DMSO-d$_6$): δ ppm 1.58-1.80 (m, 4H), 1.82-1.95 (m, 2H), 1.99-2.12 (m, 2H), 2.23 (s, 3H), 3.06-3.15 (m, 4H), 3.23-3.37 (m, 4H), 3.64-3.87 (m, 2H), 6.96 (d, J=9.12 Hz, 2H), 7.34-7.42 (m, 1H), 7.51 (t, J=7.73 Hz, 2H), 7.56-7.64 (m, 2H), 7.65-7.84 (m, 2H), 9.28 (s, 1H).

Example 55

6-(2-chlorophenyl)-8-cyclopentyl-2-{[4-(4-methylpiperazin-1-yl)phenyl]amino}pyrimido[4,5-d]pyridazin-5(6H)-one The title compound was prepared as described in Example 6D, substituting Example 49B for Example 6C and (2-chlorophenyl)hydrazine for methylhydrazine. MS (DCI/NH$_3$) m/z 510 (M+H)$^+$; $^1$H NMR (300 MHz, DMSO-d$_6$): δ ppm 1.57-1.73 (m, 4H), 1.73-1.88 (m, 2H), 1.95-2.11 (m, 2H), 2.87 (s, 3H), 2.91-3.03 (m, 2H), 3.03-3.29 (m, 2H), 3.35-3.62 (m, 4H), 3.69-3.90 (m, 1H), 7.05 (d, J=8.72 Hz, 2H), 7.48-7.55 (m, 2H), 7.56-7.62 (m, 1H), 7.63-7.71 (m, 1H), 7.79 (d, J=3.17 Hz, 2H), 9.29 (s, 1H).

Example 56

6-(3-chlorophenyl)-8-cyclopentyl-2-{[4-(4-methylpiperazin-1-yl)phenyl]amino}pyrimido[4,5-d]pyridazin-5(6H)-one The title compound was prepared as described in Example 6D, substituting Example 49B for Example 6C and (3-chlorophenyl)hydrazine for methylhydrazine. MS (DCI/NH$_3$) m/z 510 (M+H)$^+$; $^1$H NMR (300 MHz, DMSO-d$_6$): δ ppm 1.62-1.78 (m, 4H), 1.82-1.96 (m, 2H), 2.05 (t, J=12.04 Hz, 2H), 2.56 (m, 4H), 2.84 (s, 3H), 2.89-2.99 (m, 2H), 3.16-3.28 (m, 2H), 3.76 (t, J=7.63 Hz, 1H), 7.00 (d, J=9.16 Hz, 2H), 7.42-7.51 (m, 1H), 7.55 (t, J=7.80 Hz, 1H), 7.60-7.66 (m, 1H), 7.71-7.77 (m, 3H), 9.29 (s, 1H).

Example 57

8-cyclopentyl-6-(2-methoxyphenyl)-2-{[4-(4-methylpiperazin-1-yl)phenyl]amino}pyrimido[4,5-d]pyridazin-5(6H)-one The title compound was prepared as described in Example 6D, substituting Example 49B for Example 6C and (2-methoxyphenyl)hydrazine for methylhydrazine. MS (DCI/NH$_3$) m/z 512 (M+H)$^+$; $^1$H NMR (300 MHz, DMSO-d$_6$): δ ppm 1.59-1.72 (m, 4H), 1.75-1.91 (m, 2H), 1.92-2.09 (m, 2H), 2.87 (s, 3H), 2.92-3.02 (m, 1H), 3.10-3.28 (m, 2H), 3.53 (d, J=12.21 Hz, 2H), 3.70 (s, 2H), 3.75 (s, 3H), 3.82 (d, J=13.56 Hz, 2H), 7.03-7.10 (m, 3H), 7.20 (d, J=7.46 Hz, 1H), 7.33 (dd, J=7.80, 1.70 Hz, 1H), 7.39-7.50 (m, 1H), 7.71-7.84 (m, 2H), 9.26 (s, 1H).

Example 58

8-(3-methoxyphenyl)-2-{[4-(4-methylpiperazin-1-yl)phenyl]amino}-6-phenylpyrimido[4,5-d]pyridazin-5(6H)-one

Example 58A ethyl 4-(3-methoxybenzoyl)-2-(methylthio)pyrimidine-5-carboxylate The title compound was prepared as described in Example 6B, substituting 3-methoxybenzoyl chloride for 3-phenylpropanoyl chloride. MS (DCI/NH$_3$) m/z 333 (M+H)$^+$.

Example 58B ethyl 4-(3-methoxybenzoyl)-2-(4-(4-methylpiperazin-1-yl)phenylamino)pyrimidine-5-carboxylate The title compound was prepared as described in Example 6C, substituting Example 58A for Example 6B. MS (DCI/NH$_3$) m/z 476 (M+H)$^+$.

Example 58C 8-(3-methoxyphenyl)-2-{[4-(4-methylpiperazin-1-yl)phenyl]amino}-6-phenylpyrimido[4,5-d]pyridazin-5(6H)-one The title compound was prepared as described in Example 6D, substituting Example 58B for Example 6C and phenyldrazine for methylhydrazine. MS (DCI/NH$_3$) m/z 520 (M+H)$^+$; $^1$H NMR (300 MHz, DMSO-d$_6$): δ ppm 2.88 (s, 3H), 2.90-2.99 (m, 2H), 3.10-3.29 (m, 2H), 3.52 (m, 2H), 3.70-3.79 (m, 2H), 3.79 (s, 3H), 6.92 (d, J=8.33 Hz, 2H), 7.11 (d, J=8.33 Hz, 1H), 7.40-7.49 (m, 2H), 7.49-7.59 (m, 4H), 7.68 (d, J=7.93 Hz, 4H), 9.37 (s, 1H).

Example 59

2-{[4-(4-methylpiperazin-1-yl)phenyl]amino}-6-phenyl-8-[4-(pyrimidin-2-yl)phenyl]pyrimido[4,5-d]pyridazin-5(6H)-one

Example 59A ethyl 2-(methylthio)-4-(4-(pyrimidin-2-yl)benzoyl)pyrimidine-5-carboxylate The title compound was prepared as described in Example 6B, substituting 4-(pyrimidin-2-yl)benzoyl chloride for 3-phenylpropanoyl chloride. MS (DCI/NH$_3$) m/z 381 (M+H)$^+$.

Example 59B ethyl 2-(4-(4-methylpiperazin-1-yl)phenylamino)-4-(4-(pyrimidin-2-yl)benzoyl)pyrimidine-5-carboxylate The title compound was prepared as described in Example 6C, substituting Example 59A for Example 6B. MS (DCI/NH$_3$) m/z 524 (M+H)$^+$.

Example 59C 2-(4-(4-methylpiperazin-1-yl)phenylamino)-6-phenyl-8-(4-(pyrimidin-2-yl)phenyl)pyridazino[4,5-d]pyrimidin-5(6H)-one The title compound was prepared as described in Example 6D, substituting Example 59B for Example 6C and phenyldrazine for methylhydrazine. MS (DCI/NH$_3$) m/z 563 (M+H)$^+$; $^1$H NMR (300 MHz, DMSO-d$_6$): δ ppm 2.86 (s, 3H), 2.97 (d, J=12.55 Hz, 2H), 3.04-3.23 (m, 2H), 3.52 (d, J=11.87 Hz, 2H), 3.76 (d, J=12.89 Hz, 2H), 6.94 (d, J=9.16 Hz, 2H), 7.37-7.58 (m, 4H), 7.63 (d, J=9.16 Hz, 2H), 7.67-7.76 (m, 2H), 8.13 (d, J=8.14 Hz, 2H), 8.51 (d, J=8.48 Hz, 2H), 8.97 (d, J=4.75 Hz, 2H), 9.38 (s, 1H).

Example 60

6-(2-chlorophenyl)-2-{[4-(4-methylpiperazin-1-yl)phenyl]amino}-8-(pyridin-2-yl)pyrimido[4,5-d]pyridazin-5(6H)-one

Example 60A ethyl 2-(methylthio)-4-picolinoylpyrimidine-5-carboxylate

To a solution of ethyl 4-chloro-2-(methylthio)pyrimidine-5-carboxylate (1.6 g, 6.88 mmol), picolinaldehyde (0.9 g, 8.25 mmol) and 1,3-dimethyl-1H-imidazol-3-ium iodide (0.5 g, 1.2 mmol) in anhydrous THF (20 ml) was added NaH (60% in mineral oil, 200 mg, 8.25 mmol). The mixture was heated under reflux for 1 hour, and cooled to room temperature. The reaction mixture was then poured into ice-water then parti-

Example 60B ethyl 2-(4-(4-methylpiperazin-1-yl)phenylamino)-4-picolinoylpyrimidine-5-carboxylate The title compound was prepared as described in Example 6C, substituting Example 60A for Example 6B. MS (DCI/NH$_3$) m/z 447 (M+H)$^+$.

Example 60C 6-(2-chlorophenyl)-2-{[4-(4-methylpiperazin-1-yl)phenyl]amino}-8-(pyridin-2-yl)pyrimido[4,5-d]pyridazin-5(6H)-one The title compound was prepared as described in Example 6D, substituting Example 60B for Example 6C and (2-chlorophenyl)hydrazine for methylhydrazine. MS (DCI/NH$_3$) m/z 526 (M+H)$^+$; $^1$H NMR (300 MHz, DMSO-d$_6$): δ ppm 2.87 (s, 3H), 2.89-2.97 (m, 2H), 3.04-3.28 (m, 2H), 3.53 (d, J=11.87 Hz, 2H), 3.79 (d, J=13.22 Hz, 2H), 6.91 (d, J=8.48 Hz, 2H), 7.49-7.61 (m, 3H), 7.65-7.78 (m, 5H), 7.85-7.93 (m, 1H), 7.94-8.03 (m, 1H), 9.37 (s, 1H).

Example 61

6-(2-chlorophenyl)-2-{[4-(4-methylpiperazin-1-yl)phenyl]amino}-8-[4-(pyrimidin-2-yl)phenyl]pyrimido[4,5-d]pyridazin-5(6H)-one The title compound was prepared as described in Example 6D, substituting Example 59B for Example 6C and (2-chlorophenyl)hydrazine for methylhydrazine. MS (DCI/NH$_3$) m/z 603 (M+H)$^+$; $^1$H NMR (300 MHz, DMSO-d$_6$): δ ppm 2.87 (s, 3H), 2.90-2.99 (m, 2H), 3.06-3.36 (m, 2H), 3.53 (d, J=11.90 Hz, 2H), 3.71-4.02 (m, 2H), 6.94 (d, J=6.74 Hz, 2H), 7.51 (t, J=4.96 Hz, 2H), 7.55-7.66 (m, 3H), 7.67-7.81 (m, 2H), 8.08 (d, J=7.93 Hz, 2H), 8.50 (d, J=8.33 Hz, 2H), 8.97 (d, J=5.16 Hz, 2H), 9.38 (s, 1H).

Example 62

6-allyl-2-{[4-(4-methylpiperazin-1-yl)phenyl]amino}-8-[4-(pyrimidin-2-yl)phenyl]pyrimido[4,5-d]pyridazin-5(6H)-one The title compound was prepared as described in Example 6D, substituting Example 59B for Example 6C and allylhydrazine for methylhydrazine. MS (DCI/NH$_3$) m/z 532 (M+H)$^+$; $^1$H NMR (300 MHz, DMSO-d$_6$): δ ppm 2.87 (s, 3H), 2.89-2.99 (m, 2H), 3.06-3.30 (m, 2H), 3.53 (d, J=12.21 Hz, 2H), 3.75-3.94 (m, 2H), 4.81 (d, J=5.43 Hz, 2H), 5.22 (s, 1H), 5.24-5.28 (m, 1H), 5.95-6.16 (m, 1H), 6.93 (d, J=7.12 Hz, 2H), 7.52 (t, J=4.75 Hz, 1H), 7.61 (d, J=9.16 Hz, 2H), 8.08 (d, J=7.80 Hz, 2H), 8.50 (d, J=8.48 Hz, 2H), 8.97 (d, J=5.09 Hz, 2H), 9.33 (s, 1H).

Example 63

6-allyl-8-(3-methoxyphenyl)-2-{[4-(4-methylpiperazin-1-yl)phenyl]amino}pyrimido[4,5-d]pyridazin-5(6H)-one The title compound was prepared as described in Example 6D, substituting Example 58B for Example 6C and allyldrazine for methylhydrazine. MS (DCI/NH$_3$) m/z 484 (M+H)$^+$; $^1$H NMR (300 MHz, DMSO-d$_6$): δ ppm 2.87 (s, 3H), 2.90-3.01 (m, 2H), 3.09-3.36 (m, 2H), 3.46-3.75 (m, 4H), 3.78 (s, 3H), 4.78 (d, J=5.43 Hz, 2H), 5.11-5.30 (m, 2H), 5.85-6.15 (m, 1H), 6.91 (d, J=7.12 Hz, 2H), 7.04-7.16 (m, 1H), 7.39-7.52 (m, 3H), 7.66 (d, J=7.80 Hz, 2H), 9.32 (s, 1H).

Example 64

6-(2-methylphenyl)-2-{[4-(4-methylpiperazin-1-yl)phenyl]amino}-8-[4-(pyrimidin-2-yl)phenyl]pyrimido[4,5-d]pyridazin-5(6H)-one The title compound was prepared as described in Example 6D, substituting Example 59B for Example 6C and o-tolylhydrazine for methylhydrazine. MS (DCI/NH$_3$) m/z 582 (M+H)$^+$; $^1$H NMR (300 MHz, DMSO-d$_6$): δ ppm 2.20 (s, 3H), 2.87 (s, 3H), 2.90-3.01 (m, 2H), 3.07-3.30 (m, 2H), 3.28 (m, 2H), 3.76 (d, J=12.89 Hz, 2H), 6.94 (d, J=6.78 Hz, 2H), 7.34-7.47 (m, 4H), 7.51 (t, J=4.75 Hz, 1H), 7.63 (d, J=8.82 Hz, 2H), 8.09 (d, J=8.14 Hz, 2H), 8.49 (d, J=8.48 Hz, 2H), 8.96 (d, J=5.09 Hz, 2H), 9.38 (s, 1H).

Example 65

8-(3-bromophenyl)-6-(2-chlorophenyl)-2-{[4-(4-methylpiperazin-1-yl)phenyl]amino}pyrimido[4,5-d]pyridazin-5(6H)-one

Example 65A ethyl 4-(3-bromobenzoyl)-2-(methylthio)pyrimidine-5-carboxylate

The title compound was prepared as described in Example 6B, substituting 3-bromobenzoyl chloride for 3-phenylpropanoyl chloride. MS (DCI/NH$_3$) m/z 382 (M+H)$^+$.

Example 65B ethyl 4-(3-bromobenzoyl)-2-(4-(4-methylpiperazin-1-yl)phenylamino)pyrimidine-5-carboxylate The title compound was prepared as described in Example 6C, substituting Example 65A for Example 6B. MS (DCI/NH$_3$) m/z 525 (M+H)$^+$.

Example 65C 8-(3-bromophenyl)-6-(2-chlorophenyl)-2-{[4-(4-methylpiperazin-1-yl)phenyl]amino}pyrimido[4,5-d]pyridazin-5(6H)-one The title compound was prepared as described in Example 6D, substituting Example 65B for Example 6C and (2-chlorophenyl)hydrazine for methylhydrazine. MS (DCI/NH$_3$) m/z 603 (M+H)$^+$; $^1$H NMR (300 MHz, DMSO-d$_6$): δ ppm 2.88 (s, 3H), 2.92-2.98 (m, 2H), 3.18 (d, J=9.83 Hz, 2H), 3.54 (d, J=11.53 Hz, 2H), 3.79 (d, J=13.22 Hz, 2H), 7.00 (d, J=8.82 Hz, 2H), 7.44-7.51 (m, 1H), 7.54-7.59 (m, 2H), 7.65 (d, J=8.14 Hz, 2H), 7.68-7.76 (m, 3H), 7.88 (d, J=7.12 Hz, 1H), 8.13 (s, 1H), 9.37 (s, 1H).

Example 66

8-(3-bromophenyl)-6-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 65B for Example 6C and o-tolylhydrazine for methylhydrazine. MS (DCI/NH$_3$) m/z 583 (M+H)$^+$; $^1$H NMR (300 MHz, DMSO-d$_6$): δ ppm 2.18 (s, 3H), 2.88 (s, 3H), 2.91-3.00 (m, 2H), 3.10-3.26 (m, 2H), 3.54 (d, J=11.87 Hz, 2H), 3.78 (d, J=12.55 Hz, 2H), 6.99 (d, J=9.16 Hz, 2H), 7.34-7.45 (m, 4H), 7.48 (t, J=7.97 Hz, 1H), 7.66 (d, J=8.82 Hz, 2H), 7.71 (d, J=9.16 Hz, 1H), 7.88 (d, J=7.46 Hz, 1H), 8.13 (s, 1H), 9.37 (s, 1H).

Example 67

8-(3-bromophenyl)-2-{[4-(4-methylpiperazin-1-yl)phenyl]amino}-6-phenylpyrimido[4,5-d]pyridazin-5(6H)-one The title compound was prepared as described in Example 6D, substituting Example 65B for Example 6C and phenylhydrazine for methylhydrazine. MS (DCI/NH$_3$) m/z 569 (M+H)$^+$; $^1$H NMR (300 MHz, DMSO-d$_6$): δ ppm 2.88 (s, 3H), 2.90-3.00 (m, 2H), 3.03-3.30 (m, 2H), 3.54 (d, J=12.89 Hz, 2H), 3.78 (d, J=13.90 Hz, 2H), 6.99 (d, J=9.16 Hz, 2H), 7.40-7.58 (m, 4H), 7.62-7.70 (m, 4H), 7.72 (d, J=9.16 Hz, 1H), 7.94 (d, J=7.80 Hz, 1H), 8.17 (s, 1H), 9.37 (s, 1H).

Example 68

6-allyl-8-(3-bromophenyl)-2-{[4-(4-methylpiperazin-1-yl)phenyl]amino}pyrimido[4,5-d]pyridazin-5(6H)-one The title compound was prepared as described in Example 6D, substituting Example 65B for Example 6C and allylhydrazine for methylhydrazine. MS (DCI/NH$_3$) m/z 534 (M+H)$^+$; $^1$H NMR (300 MHz, DMSO-d$_6$): δ ppm 2.87 (s, 3H), 2.91-2.99 (m, 2H), 3.07-3.29 (m, 2H), 3.53 (d, J=12.55 Hz, 2H), 3.77 (d, J=13.90 Hz, 2H), 4.79 (d, J=5.43 Hz, 2H), 5.04-5.32 (m, 2H), 5.87-6.14 (m, 1H), 6.98 (d, J=9.16 Hz, 2H), 7.50 (t, J=7.80 Hz, 1H), 7.63 (d, J=8.82 Hz, 2H), 7.71 (d, J=9.16 Hz, 1H), 7.89 (d, J=7.46 Hz, 1H), 8.13 (s, 1H), 9.32 (s, 1H).

Example 69

6-(2,6-dichlorophenyl)-8-(2-furyl)-2-{[4-(4-methylpiperazin-1-yl)phenyl]amino}pyrimido[4,5-d]pyridazin-5(6H)-one The title compound was prepared as described in Example 6D, substituting Example 32B for Example 6C and (2,6-dichlorophenyl)hydrazine for methylhydrazine. MS (DCI/NH$_3$) m/z 549 (M+H)$^+$; $^1$H NMR (300 MHz, DMSO-d$_6$): δ ppm 2.89 (s, 3H), 2.92-3.05 (m, 2H), 3.11-3.28 (m, 2H), 3.47-3.63 (m, 2H), 3.87 (d, J=12.55 Hz, 2H), 7.08 (d, J=8.82 Hz, 2H), 7.58-7.67 (m, 5H), 7.74 (m, 1H), 7.77 (d, J=1.02 Hz, 1H), 7.85-7.91 (m, 1H), 9.35 (s, 1H).

Example 70

6-(2,6-dichlorophenyl)-2-{[4-(4-methylpiperazin-1-yl)phenyl]amino}-8-(2-thienyl)pyrimido[4,5-d]pyridazin-5(6H)-one The title compound was prepared as described in Example 6D, substituting Example 48B for Example 6C and (2,6-dichlorophenyl)hydrazine for methylhydrazine. MS (DCI/NH$_3$) m/z 565 (M+H)$^+$; $^1$H NMR (300 MHz, DMSO-d$_6$): δ ppm 2.90 (s, 3H), 2.94-3.05 (m, 2H), 3.11-3.28 (m, 2H), 3.48-3.73 (m, 2H), 3.87 (d, J=12.29 Hz, 2H), 7.08 (d, J=9.12 Hz, 2H), 7.12-7.18 (m, 1H), 7.57-7.67 (m, 3H), 7.71 (d, J=4.36 Hz, 1H), 7.75 (m, 2H), 7.77 (m, 1H), 9.36 (s, 1H).

Example 71

6-(2,6-dichlorophenyl)-8-(2-methylphenyl)-2-{[4-(4-methylpiperazin-1-yl)phenyl]amino}pyrimido[4,5-d]pyridazin-5(6H)-one

Example 71A ethyl 4-(2-methylbenzoyl)-2-(methylthio)pyrimidine-5-carboxylate The title compound was prepared as described in Example 6B, substituting 2-methylbenzoyl chloride for 3-phenylpropanoyl chloride. MS (DCI/NH$_3$) m/z 317 (M+H)$^+$.

Example 71B ethyl 4-(2-methylbenzoyl)-2-(4-(4-methylpiperazin-1-yl)phenylamino)pyrimidine-5-carboxylate The title compound was prepared as described in Example 6C, substituting Example 71A for 6B. MS (DCI/NH$_3$) m/z 460 (M+H)$^+$.

Example 71C 6-(2,6-dichlorophenyl)-8-(2-methylphenyl)-2-{[4-(4-methylpiperazin-1-yl)phenyl]amino}pyrimido[4,5-d]pyridazin-5(6H)-one The title compound was prepared as described in Example 6D, substituting Example 71B for Example 6C and 2,6-dichlorophenylhydrazine for methylhydrazine. MS (DCI/NH$_3$) m/z 573 (M+H)$^+$; $^1$H NMR (300 MHz, CD$_3$OD): δ ppm 2.38 (s, 3H), 2.88 (s, 3H), 2.91-3.00 (m, 2H), 3.04-3.28 (m, 2H), 3.53 (d, J=7.46 Hz, 2H), 3.79 (d, J=12.89 Hz, 2H), 6.87-7.01 (m, 2H), 7.31-7.38 (m, 1H), 7.42 (t, J=7.63 Hz, 1H), 7.57-7.67 (m, 3H), 7.70 (d, J=7.46 Hz, 2H), 7.74-7.77 (m, 2H), 9.38 (s, 1H).

Example 72

8-(3-bromophenyl)-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 65B for 6C and 2,6-dichlorophenylhydrazine for methylhydrazine. MS (DCI/NH$_3$) m/z 534 (M+H)$^+$; $^1$H NMR (300 MHz, DMSO-d$_6$): δ ppm 2.88 (s, 3H), 2.91-3.00 (m, 2H), 3.09-3.29 (m, 2H), 3.54 (d, J=12.29 Hz, 2H), 3.79 (d, J=13.09 Hz, 2H), 7.00 (d, J=9.12 Hz, 2H), 7.50 (t, J=7.93 Hz, 1H), 7.58-7.68 (m, 3H), 7.73 (s, 1H), 7.75-7.77 (m, 2H), 7.84 (d, J=7.14 Hz, 1H), 8.14 (s, 1H), 9.39 (s, 1H).

Example 73

8-(6-chloropyridin-2-yl)-2-{[4-(4-methylpiperazin-1-yl)phenyl]amino}-6-phenylpyrimido[4,5-d]pyridazin-5(6H)-one Example 73A ethyl 4-(6-chloropicolinoyl)-2-(methylthio)pyrimidine-5-carboxylate The title compound was prepared as described in Example 6B, substituting 6-chloropicolinoyl chloride for 3-phenylpropanoyl chloride. MS (DCI/NH$_3$) m/z 338 (M+H)$^+$.

Example 73B ethyl 4-(6-chloropicolinoyl)-2-(4-(4-methylpiperazin-1-yl)phenylamino)pyrimidine-5-carboxylate The title compound was prepared as described in Example 6C, substituting Example 73A for Example 6B. MS (DCI/NH$_3$) m/z 481 (M+H)$^+$.

Example 73C 8-(6-chloropyridin-2-yl)-2-{[4-(4-methylpiperazin-1-yl)phenyl]amino}-6-phenylpyrimido[4,5-d]pyridazin-5(6H)-one The title compound was prepared as described in Example 6D, substituting Example 73B for Example 6C and phenylhydrazine for methylhydrazine. MS (DCI/NH$_3$) m/z 526 (M+H)$^+$; $^1$H NMR (300 MHz, CD$_3$OD): δ ppm 2.88 (s, 3H), 2.91-3.03 (m, 2H), 3.06-3.29 (m, 2H), 3.43-3.62 (m, 2H), 3.81 (d, J=13.22 Hz, 2H), 6.98 (d, J=8.48 Hz, 2H), 7.40-7.48 (m, 1H), 7.49-7.61 (m, 5H), 7.65-7.74 (m, 3H), 8.43 (dd, J=8.48, 2.37 Hz, 1H), 9.38 (s, 1H).

Example 74

8-cyclopentyl-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 49B for Example 6C and 2,6-dichlorophenylhydrazine for methylhydrazine. MS (DCI/NH$_3$) m/z 551 (M+H)$^+$; $^1$H NMR (300 MHz, DMSO-d$_6$): δ ppm 1.66 (d, J=5.16 Hz, 4H), 1.72-1.90 (m, 2H), 1.94-2.13 (m, 2H), 2.88 (s, 3H), 2.96 (d, J=11.90 Hz, 2H), 3.04-3.30 (m, 2H), 3.49-3.67 (m, 2H), 3.72-3.90 (m, 3H), 7.05 (d, J=9.12 Hz, 2H), 7.54-7.64 (m, 1H), 7.68-7.75 (m, 2H), 7.75-7.86 (m, 2H), 9.31 (s, 1H).

Example 75

8-(6-chloropyridin-2-yl)-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 73B for Example 6C and (2,6-dichlorophenyl)hydrazine for methylhydrazine. MS (DCI/NH$_3$) m/z 594 (M+H)$^+$; $^1$H NMR (300 MHz, CD$_3$OD): δ ppm 2.87 (s, 3H), 2.94-3.03 (m, 2H), 3.10-3.29 (m, 2H), 3.55 (d, J=12.55 Hz, 2H), 3.82 (d, J=13.56 Hz, 2H), 6.98 (d, J=8.14 Hz, 2H), 7.56 (d, J=9.16 Hz, 2H), 7.59-7.72 (m, 3H), 7.73-7.80 (m, 2H), 8.36 (dd, J=8.48, 2.37 Hz, 1H), 9.39 (s, 1H).

Example 76

6-(2,6-dichlorophenyl)-8-{6-[2-(2,6-dichlorophenyl)hydrazino]pyridin-2-yl}-2-{[4-(4-methylpiperazin-1-yl)phenyl]amino}pyrimido[4,5-d]pyridazin-5(6H)-one The title compound was isolated as a side product during the preparation of Example 75. MS (DCI/NH$_3$) m/z 735 (M+H)$^+$; $^1$H NMR (300 MHz, CD$_3$OD): δ ppm 2.87 (s, 3H), 2.92-3.00 (m, 2H), 3.06-3.25 (m, 2H), 3.53-3.72 (m, 2H), 3.79 (d, J=13.09 Hz, 2H), 6.88-7.05 (m, 4H), 7.29-7.44 (m, 2H), 7.49-7.73 (m, 5H), 7.73-7.80 (m, 2H), 9.37 (s, 1H).

Example 77

6-(2-chlorophenyl)-8-(6-chloropyridin-2-yl)-2-{[4-(4-methylpiperazin-1-yl)phenyl]amino}pyrimido[4,5-d]pyridazin-5(6H)-one The title compound was prepared as described in Example 6D, substituting Example 73B for Example 6C and (2-chlorophenyl)hydrazine for methylhydrazine. MS (DCI/NH$_3$) m/z 735 (M+H)$^+$; $^1$H NMR (300 MHz, CD$_3$OD): δ ppm 2.88 (s, 3H), 2.91-3.03 (m, 2H), 3.11-3.29 (m, 2H), 3.55 (d, J=11.90 Hz, 2H), 3.81 (d, J=12.69 Hz, 2H), 6.98 (d, J=8.33 Hz, 2H), 7.51-7.61 (m, 5H), 7.64-7.76 (m, 3H), 8.37 (dd, J=8.53, 2.58 Hz, 1H), 9.37 (s, 1H).

Example 78

8-(2-chloropyridin-3-yl)-2-{[4-(4-methylpiperazin-1-yl)phenyl]amino}-6-phenylpyrimido[4,5-d]pyridazin-5(6H)-one Example 78A ethyl 4-(2-chloronicotinoyl)-2-(methylthio)pyrimidine-5-carboxylate The title compound was prepared as described in Example 6B, substituting 2-chloronicotinoyl chloride for 3-phenylpropanoyl chloride. MS (DCI/NH$_3$) m/z 338 (M+H)$^+$.

Example 78B ethyl 4-(6-chloropicolinoyl)-2-(4-(4-methylpiperazin-1-yl)phenylamino)pyrimidine-5-carboxylate The title compound was prepared as described in Example 6C, substituting Example 78A for Example 6B. MS (DCI/NH$_3$) m/z 481 (M+H)$^+$.

Example 78C 8-(2-chloropyridin-3-yl)-2-{[4-(4-methylpiperazin-1-yl)phenyl]amino}-6-phenylpyrimido[4,5-d]pyridazin-5(6H)-one The title compound was prepared as described in Example 6D, substituting Example 78B for Example 6C and phenylhydrazine for methylhydrazine. MS (DCI/NH$_3$) m/z 526 (M+H)$^+$; $^1$H NMR (300 MHz, CD$_3$OD): δ ppm 2.87 (s, 3H), 2.90-2.98 (m, 2H), 3.07-3.26 (m, 2H), 3.52 (d, J=12.55 Hz, 2H), 3.74 (d, J=11.87 Hz, 2H), 6.68-6.85 (m, 2H), 7.38-7.58 (m, 5H), 7.58-7.72 (m, 3H), 8.18 (dd, J=7.46, 1.70 Hz, 1H), 8.58-8.65 (m, 1H), 9.38 (s, 1H).

Example 79

8-(2-ethoxypyridin-3-yl)-2-{[4-(4-methylpiperazin-1-yl)phenyl]amino}-6-phenylpyrimido[4,5-d]pyridazin-5(6H)-one The title compound was isolated as a side product during the preparation of Example 78. MS (DCI/NH$_3$) m/z 535 (M+H)$^+$; $^1$H NMR (300 MHz, CD$_3$OD): δ ppm 0.85 (t, J=7.14 Hz, 3H), 2.87 (s, 3H), 2.90-3.00 (m, 2H), 3.04-3.28 (m, 2H), 3.51 (m, 2H), 3.68-4.03 (m, 4H), 7.01 (d, J=9.12 Hz, 2H), 7.24 (dd, J=8.53, 4.16 Hz, 1H), 7.45-7.60 (m, 4H), 7.65 (d, J=9.12 Hz, 2H), 7.90 (d, J=7.93 Hz, 1H), 7.99 (s, 1H), 8.76 (dd, J=3.97, 1.59 Hz, 1H), 10.20 (s, 1H).

Example 80

6-(2-chlorophenyl)-8-(2-chloropyridin-3-yl)-2-{[4-(4-methylpiperazin-1-yl)phenyl]amino}pyrimido[4,5-d]pyridazin-5(6H)-one The title compound was prepared as described in Example 6D, substituting Example 78B for Example 6C and 2-chlorophenylhydrazine for methylhydrazine. MS (DCI/NH$_3$) m/z 560 (M+H)$^+$; $^1$H NMR (300 MHz, CD$_3$OD): δ ppm 2.87 (s, 3H), 2.90-2.98 (m, 2H), 3.07-3.25 (m, 2H), 3.52 (d, J=11.50 Hz, 2H), 3.74 (d, J=12.69 Hz, 2H), 6.67-6.84 (m, 2H), 7.46 (d, J=8.33 Hz, 2H), 7.52-7.61 (m, 2H), 7.60-7.76 (m, 3H), 8.12 (d, J=7.54 Hz, 1H), 8.61 (d, J=3.17 Hz, 1H), 9.38 (s, 1H).

Example 81

8-(2-chloropyridin-3-yl)-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 78B for Example 6C and (2,6-dichlorophenyl)hydrazine for methylhydrazine. MS (DCI/NH$_3$) m/z 594 (M+H)$^+$; $^1$H NMR (300 MHz, CD$_3$OD): δ ppm 2.88 (s, 3H), 2.89-2.98 (m, 2H), 3.03-3.24 (m, 2H), 3.48-3.60 (m, 2H), 3.74 (d, J=11.50 Hz, 2H), 6.76 (d, J=7.14 Hz, 2H), 7.44 (d, J=8.33 Hz, 2H), 7.56-7.70 (m, 2H), 7.71-7.82 (m, 2H), 8.14 (d, J=7.14 Hz, 1H), 8.62 (d, J=2.78 Hz, 1H), 9.39 (s, 1H).

Example 82

8-(3-fluorophenyl)-2-{[4-(4-methylpiperazin-1-yl)phenyl]amino}-6-phenylpyrimido[4,5-d]pyridazin-5(6H)-one Example 82A ethyl 4-(3-fluorobenzoyl)-2-(methylthio)pyrimidine-5-carboxylate The title compound was prepared as described in Example 6B, substituting 3-fluorobenzoyl chloride for 3-phenylpropanoyl chloride. MS (DCI/NH$_3$) m/z 464 (M+H)$^+$.

Example 82B ethyl 4-(3-fluorobenzoyl)-2-(4-(4-methylpiperazin-1-yl)phenylamino)pyrimidine-5-carboxylate The title compound was prepared as described in Example 6C, substituting Example 82A for Example 6B. MS (DCI/NH$_3$) m/z 481 (M+H)$^+$.

Example 82C 8-(3-fluorophenyl)-2-{[4-(4-methylpiperazin-1-yl)phenyl]amino}-6-phenylpyrimido[4,5-d]pyridazin-5(6H)-one The title compound was prepared as described in Example 6D, substituting Example 82B for Example 6C and phenylhydrazine for methylhydrazine. MS (DCI/NH$_3$) m/z 508 (M+H)$^+$; $^1$H NMR (300 MHz, CD$_3$OD): δ ppm 2.87 (s, 3H), 2.90-3.01 (m, 2H), 3.11-3.27 (m, 2H), 3.54 (d, J=12.29 Hz, 2H), 3.78 (d, J=13.48 Hz, 2H), 6.96 (d, J=8.33 Hz, 2H), 7.30-7.40 (m, 1H), 7.45 (t, J=7.34 Hz, 1H), 7.50-7.60 (m, 3H), 7.59-7.73 (m, 3H), 7.81 (m, 1H), 7.83-7.87 (m, 1H), 7.89 (m, 1H), 9.38 (s, 1H).

Example 83

6-(2-chlorophenyl)-8-(3-fluorophenyl)-2-{[4-(4-methylpiperazin-1-yl)phenyl]amino}pyrimido[4,5-d]pyridazin-5(6H)-one The title compound was prepared as described in Example 6D, substituting Example 82B for Example 6C and 2-chlorophenylhydrazine for methylhydrazine. MS (DCI/NH$_3$) m/z 543 (M+H)$^+$; $^1$H NMR (300 MHz, CD$_3$OD): δ ppm 2.88 (s, 3H), 2.91-3.00 (m, 2H), 3.07-3.29 (m, 2H), 3.54 (d, J=11.90 Hz, 2H), 3.79 (d, J=13.88 Hz, 2H), 6.95 (d, J=7.93 Hz, 2H), 7.31-7.39 (m, 1H), 7.51-7.60 (m, 3H), 7.64 (d, J=8.33 Hz, 2H), 7.68-7.78 (m, 3H), 7.80-7.87 (m, 1H), 9.37 (s, 1H).

Example 84

6-(2,6-dichlorophenyl)-8-(3-fluorophenyl)-2-{[4-(4-methylpiperazin-1-yl)phenyl]amino}pyrimido[4,5-d]pyridazin-5(6H)-one The title compound was prepared as described in Example 6D, substituting Example 82B for Example 6C and (2,6-dichlorophenyl)hydrazine for methylhydrazine. MS (DCI/NH$_3$) m/z 577 (M+H)$^+$; $^1$H NMR (300 MHz, CD$_3$OD): δ ppm 2.88 (s, 3H), 2.90-3.03 (m, 2H), 3.11-3.28 (m, 2H), 3.54 (d, J=11.90 Hz, 2H), 3.79 (d, J=12.69 Hz, 2H), 6.95 (d, J=7.93 Hz, 2H), 7.32-7.41 (m, 1H), 7.52-7.60 (m, 1H), 7.59-7.67 (m, 3H), 7.69-7.78 (m, 3H), 7.82 (d, J=9.52 Hz, 1H), 9.39 (s, 1H).

Example 85

2-{[4-(4-methylpiperazin-1-yl)phenyl]amino}-8-(1-methyl-1H-pyrazol-4-yl)-6-phenylpyrimido[4,5-d]pyridazin-5(6H)-one

Example 85A ethyl 4-(1-methyl-1H-pyrazole-4-carbonyl)-2-(methylthio)pyrimidine-5-carboxylate The title compound was prepared as described in Example 6B, substituting 1-methyl-1H-pyrazole-4-carbonyl chloride for 3-phenylpropanoyl chloride. MS (DCI/NH$_3$) m/z 307 (M+H)$^+$.

Example 85B ethyl 4-(1-methyl-1H-pyrazole-4-carbonyl)-2-(4-(4-methylpiperazin-1-yl)phenylamino)pyrimidine-5-carboxylate The title compound was prepared as described in Example 6C, substituting Example 85A for Example 6B. MS (DCI/NH$_3$) m/z 450 (M+H)$^+$.

Example 85C

2-{[4-(4-methylpiperazin-1-yl)phenyl]amino}-8-(1-methyl-1H-pyrazol-4-yl)-6-phenylpyrimido[4,5-d]pyridazin-5(6H)-one The title compound was prepared as described in Example 6D, substituting Example 85B for Example 6C and phenylhydrazine for methylhydrazine. MS (DCI/NH$_3$) m/z 494 (M+H)$^+$; $^1$H NMR (300 MHz, CD$_3$OD): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 86

6-(2-chlorophenyl)-2-{[4-(4-methylpiperazin-1-yl)phenyl]amino}-8-(1-methyl-1H-pyrazol-4-yl)pyrimido[4,5-d]pyridazin-5(6H)-one The title compound was prepared as described in Example 6D, substituting Example 85B for Example 6C and (2-chlorophenyl)hydrazine for methylhydrazine. MS (DCI/NH$_3$) m/z 589 (M+H)$^+$; $^1$H NMR (300 MHz, CD$_3$OD): δ ppm 2.88 (s, 3H), 2.97 (t, J=11.70 Hz, 2H), 3.11-3.27 (m, 2H), 3.55 (d, J=11.50 Hz, 2H), 3.84 (s, 3H), 3.88 (d, J=5.55 Hz, 2H), 7.11 (d, J=7.93 Hz, 2H), 7.52-7.61 (m, 4H), 7.62-7.73 (m, 4H), 9.32 (s, 1H).

Example 87

6-(2,6-dichlorophenyl)-2-{[4-(4-methylpiperazin-1-yl)phenyl]amino}-8-(1-methyl-1H-pyrazol-4-yl)pyrimido[4,5-d]pyridazin-5(6H)-one The title compound was prepared as described in Example 6D, substituting Example 85B for Example 6C and (2,6-dichlorophenyl)hydrazine for methylhydrazine. MS (DCI/NH$_3$) m/z 563 (M+H)$^+$; $^1$H NMR (300 MHz, CD$_3$OD): δ ppm 2.88 (s, 3H), 2.97 (t, J=11.70 Hz, 2H), 3.11-3.27 (m, 2H), 3.55 (d, J=11.50 Hz, 2H), 3.84 (s, 3H), 3.88 (d, J=5.55 Hz, 2H), 7.11 (d, J=7.93 Hz, 2H), 7.52-7.61 (m, 4H), 7.62-7.73 (m, 4H), 9.32 (s, 1H).

Example 88

6-(2,6-dichlorophenyl)-8-(6-hydroxypyridin-2-yl)-2-{[4-(4-methylpiperazin-1-yl)phenyl]amino}pyrimido[4,5-d]pyridazin-5(6H)-one A suspension of Example 75 (50 mg, 0.08 mmol) in dioxane (5 ml) was added LiOH (10 mg, 0.4 mmol) in water (1 mL). The mixture was stirred at 50° C. overnight. After cooling, the volatiles were removed and the residue was purified by HPLC (Zorbax C-18, 0.1% TFA/CH$_3$CN/H$_2$O) to yield the title compound as TFA salt. MS (DCI/NH$_3$) m/z 576 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 89

3-[6-(2,6-dichlorophenyl)-2-{[4-(4-methylpiperazin-1-yl)phenyl]amino}-5-oxo-5,6-dihydropyrimido[4,5-d]pyridazin-8-yl]benzonitrile A 100 mL round bottom fask was charged with Example 72 (150 mg, 0.23 mmol), zinc cyanide (27 mg, 0.23 mmol), tris(dibenzylideneacetone)dipalladium(0) (11 mg, 0.01 mmol) and 1,1'-bis(diphenylphosphino)ferrocene (13 mg, 0.02 mmol), and was purged with nitrogen. Anhydrous N,N-dimethylformamide (20 mL) was added and the solution was purged with nitrogen again. The reaction mixture was stirred at 100° C. overnight. After cooling, the reaction mixture was partitioned between ethyl acetate and brine. The organic phase was washed with water and concentrated. The residue was separated by HPLC (Zorbax C-18, 0.1% TFA/CH$_3$CN/H$_2$O) to yield the title compound as TFA salt. MS (DCI/NH$_3$) m/z 583 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 90

6-(2,6-dichlorophenyl)-8-[3-(dimethylamino)phenyl]-2-{[4-(4-methylpiperazin-1-yl)phenyl]amino}pyrimido[4,5-d]pyridazin-5(6H)-one A solution of Example 72 (30 mg, 0.05 mmol), N,N,1,1,1-pentamethylstannanamine (20 mg, 0.1 mmol) and palladium tetrakis(triphenylphosphine) (3 mg, 0.002 mmol) in anhydrous toluene (5 mL) was purged with N$_2$ and heated at 90° C. overnight. After cooling, the reaction mixture was partitioned between ethyl acetate and brine. The organic phase was washed with water and concentrated. The residue was separated by HPLC (Zorbax C-18, 0.1% TFA/CH$_3$CN/H$_2$O) to yield the title compound as TFA salt. MS (DCI/NH$_3$) m/z 602 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 91

6-(2,6-dichlorophenyl)-8-[3-(1H-imidazol-4-yl)phenyl]-2-{[4-(4-methylpiperazin-1-yl)phenyl]amino}pyrimido[4,5-d]pyridazin-5(6H)-one To a mixture of Example 72 (60 mg, 0.06 mmol), 1H-imidazol-4-ylboronic acid (10 mg, 0.09 mmol) and dichlorobis(triphenylphosphine)palladium (2 mg, 0.003 mmol) in a solvent mixture of 7:3:2 1,2-dimethoxyethane/water/ethanol (2 mL) was added an aqueous sodium carbonate solution (2M, 0.1 mL). The mixture was heated in a microwave reactor (Biotage Initiator) at 150° C. for 15 minutes. After cooling, the mixture was concentrated, and the residue was purified by HPLC (Zorbax C-18, 0.1% TFA/CH$_3$CN/H$_2$O) to yield the title compound as TFA salt. MS (DCI/NH$_3$) m/z 625 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 92

6-(2,6-dichlorophenyl)-2-{[4-(4-methylpiperazin-1-yl)phenyl]amino}-8-[3-(1H-pyrrol-2-yl)phenyl]pyrimido[4,5-d]pyridazin-5(6H)-one The title compound was prepared as described in Example 91, substituting 1H-pyrrol-2-ylboronic acid for 1H-imidazol-4-ylboronic acid. MS (DCI/NH$_3$) m/z 624 (M+H)$^+$; $^1$H NMR (300 MHz, CD$_3$OD): δ ppm 2.88 (s, 3H), 2.97 (t, J=11.70 Hz, 2H), 3.11-3.27 (m, 2H), 3.55 (d, J=11.50 Hz, 2H), 3.84 (s, 3H), 3.88 (d, J=5.55 Hz, 2H), 7.11 (d, J=7.93 Hz, 2H), 7.52-7.61 (m, 4H), 7.62-7.73 (m, 4H), 9.32 (s, 1H).

Example 93

6-(2,6-dichlorophenyl)-2-{[4-(4-methylpiperazin-1-yl)phenyl]amino}-8-[3-(2-oxopiperidin-1-yl)phenyl]pyrimido[4,5-d]pyridazin-5(6H)-one A mixture of Example 72 (30 mg, 0.05 mmol), piperidin-2-one (10 mg, 0.1 mmol) and tris(dibenzylideneacetone)dipalladium(0) (11 mg, 0.01 mmol) in anhydride dioxane (1.5 mL) was heated in a microwave reactor (Biotage Initiator) at 200° C. for 30 minutes. After cooling, the mixture was concentrated, and the residue was separated by HPLC (Zorbax C-18, 0.1% TFA/CH$_3$CN/H$_2$O) to yield the title compound as TFA salt. MS (DCI/NH$_3$) m/z 656 (M+H)$^+$; $^1$H NMR (300 MHz, DMSO-d$_6$): δ ppm 2.23 (s, 3H), 2.44-2.48 (m, 4H), 2.95-3.02 (m, 2H), 3.08-3.11 (m, 4H), 3.11-3.18 (m, 2H), 3.64 (s, 3H), 6.88 (d, J=8.54 Hz, 2H), 7.11-7.39 (m, 5H), 7.68 (s, 2H), 9.24 (s, 1H), 10.34 (s, 1H).

Example 94

6-(2-chlorophenyl)-8-(3-furyl)-2-{[4-(4-methylpiperazin-1-yl)phenyl]amino}pyrimido[4,5-d]pyridazin-5(6H)-one

Example 94A ethyl 4-(furan-3-carbonyl)-2-(methylthio)pyrimidine-5-carboxylate The title compound was prepared as described in Example 6B, substituting furan-3-carbonyl chloride for 3-phenylpropanoyl chloride. MS (DCI/NH$_3$) m/z 293 (M+H)$^+$.

Example 94B ethyl 4-(furan-3-carbonyl)-2-(4-(4-methylpiperazin-1-yl)phenylamino)pyrimidine-5-carboxylate The title compound was prepared as described in Example 6C, substituting Example 94A for Example 6B. MS (DCI/NH$_3$) m/z 436 (M+H)$^+$.

Example 94C 6-(2-chlorophenyl)-8-(3-furyl)-2-{[4-(4-methylpiperazin-1-yl)phenyl]amino}pyrimido[4,5-d]pyridazin-5(6H)-one The title compound was prepared as described in Example 6D, substituting Example 94B for Example 6C and (2-chlorophenyl)hydrazine for methylhydrazine. MS (DCI/NH$_3$) m/z 514 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 95

6-(2,6-dichlorophenyl)-8-(3-furyl)-2-{[4-(4-methylpiperazin-1-yl)phenyl]amino}pyrimido[4,5-d]pyridazin-5(6H)-one The title compound was prepared as described in Example 6D, substituting Example 94B for Example 6C and (2,6-dichlorophenyl)hydrazine for methylhydrazine. MS (DCI/NH$_3$) m/z 545 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 96

6-(2-chlorophenyl)-2-{[4-(4-methylpiperazin-1-yl)phenyl]amino}-8-(3-thienyl)pyrimido[4,5-d]pyridazin-5(6H)-one

Example 96A ethyl 2-(methylthio)-4-(thiophene-3-carbonyl)pyrimidine-5-carboxylate The title compound was prepared as described in Example 6B, substituting thiophene-3-carbonyl chloride for 3-phenylpropanoyl chloride. MS (DCI/NH$_3$) m/z 309 (M+H)$^+$.

Example 96B ethyl 2-(4-(4-methylpiperazin-1-yl)phenylamino)-4-(thiophene-3-carbonyl)pyrimidine-5-carboxylate The title compound was prepared as described in Example 6C, substituting Example 96A for Example 6B. MS (DCI/NH$_3$) m/z 452 (M+H)$^+$.

Example 96C 6-(2-chlorophenyl)-2-{[4-(4-methylpiperazin-1-yl)phenyl]amino}-8-(3-thienyl)pyrimido[4,5-d]pyridazin-5(6H)-one The title compound was prepared as described in Example 6D, substituting Example 96B for Example 6C and (2-chlorophenyl)hydrazine for methylhydrazine. MS (DCI/NH$_3$) m/z 583 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 97

6-(2,6-dichlorophenyl)-2-{[4-(4-methylpiperazin-1-yl)phenyl]amino}-8-(3-thienyl)pyrimido[4,5-d]pyridazin-5(6H)-one The title compound was prepared as described in Example 6D, substituting Example 96B for Example 6C and (2,6-dichlorophenyl)hydrazine for methylhydrazine. MS (DCI/NH$_3$) m/z 565 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 98

6-(2-chlorophenyl)-2-{[4-(4-methylpiperazin-1-yl)phenyl]amino}-8-(pyridin-3-yl)pyrimido[4,5-d]pyridazin-5(6H)-one

Example 98A ethyl 2-(methylthio)-4-nicotinoylpyrimidine-5-carboxylate

The title compound was prepared as described in Example 60A, substituting nicotinaldehyde for picolinaldehyde. MS (DCI/NH$_3$) m/z 304 (M+H)$^+$.

Example 98B ethyl 2-(4-(4-methylpiperazin-1-yl)phenylamino)-4-nicotinoylpyrimidine-5-carboxylate The title compound was prepared as described in Example 6C, substituting Example 98A for Example 6B. MS (DCI/NH$_3$) m/z 447 (M+H)$^+$.

Example 98C 6-(2-chlorophenyl)-2-{[4-(4-methylpiperazin-1-yl)phenyl]amino}-8-(pyridin-3-yl)pyrimido[4,5-d]pyridazin-5(6H)-one The title compound was prepared as described in Example 6D, substituting Example 98B for Example 6C and (2-chlorophenyl)hydrazine for methylhydrazine. MS (DCI/NH$_3$) m/z 526 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 99

6-(2,6-dichlorophenyl)-2-{[4-(4-methylpiperazin-1-yl)phenyl]amino}-8-(pyridin-3-yl)pyrimido[4,5-d]pyridazin-5(6H)-one The title compound was prepared as described in Example 6D, substituting Example 98B for Example 6C and (2,6-dichlorophenyl)hydrazine for methylhydrazine. MS (DCI/NH$_3$) m/z 560 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 100

2-{[4-(4-methylpiperazin-1-yl)phenyl]amino}-6-phenyl-8-(pyridin-3-yl)pyrimido[4,5-d]pyridazin-5(6H)-one The title compound was prepared as described in Example 6D, substituting Example 98B for Example 6C and phenylhydrazine for methylhydrazine. MS (DCI/NH$_3$) m/z 491 (M+H)$^+$; $^1$H NMR (300 MHz, DMSO-d$_6$): δ ppm 2.86 (s, 3H), 3.07 (d, J=11.50 Hz, 2H), 3.12-3.27 (m, 2H), 3.48-3.59 (m, 2H), 3.78-3.88 (m, 2H), 3.87 (s, 3H), 7.13-7.16 (m, 2H), 7.42 (t, J=7.34 Hz, 2H), 7.53 (t, J=7.73 Hz, 3H), 7.58 (d, J=7.14 Hz, 2H), 7.65 (s, 1H), 7.67 (s, 1H), 9.33 (s, 1H).

Example 101

6-(2,6-dichlorophenyl)-2-[(2'-methyl-2',3'-dihydro-1'H-spiro[cyclopropane-1,4'-isoquinolin]-7'-yl)amino]-8-(pyridin-3-yl)pyrimido[4,5-d]pyridazin-5(6H)-one

Example 101A ethyl 2-(2'-methyl-2',3'-dihydro-1'H-spiro[cyclopropane-1,4'-isoquinoline]-7'-ylamino)-4-nicotinoylpyrimidine-5-carboxylate The title compound was prepared as described in Example 6C, substituting Example 98A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline. MS (DCI/NH$_3$) m/z 444 (M+H)$^+$.

Example 101B 6-(2,6-dichlorophenyl)-2-[(2'-methyl-2',3'-dihydro-1'H-spiro[cyclopropane-1,4'-isoquinolin]-7'-yl)amino]-8-(pyridin-3-yl)pyrimido[4,5-d]pyridazin-5(6H)-one The title compound was prepared as described in Example 6D, substituting Example 101A for Example 6C and (2,6-dichlorophenyl)hydrazine for methylhydrazine. MS (DCI/

NH$_3$) m/z 557 (M+H)$^+$; $^1$H NMR (300 MHz, DMSO-d$_6$): δ ppm 0.79-1.02 (m, 1H), 1.13 (d, J=13.49 Hz, 2H), 1.26-1.40 (m, 1H), 2.97 (s, 3H), 3.26 (d, J=12.30 Hz, 1H), 3.53 (m, 1H), 4.16-4.27 (m, 1H), 4.33-4.51 (m, 1H), 6.85 (d, J=8.73 Hz, 1H), 7.48 (d, J=8.33 Hz, 1H), 7.59-7.71 (m, 3H), 7.74-7.80 (m, 2H), 8.27 (d, J=7.54 Hz, 1H), 8.79 (d, J=3.57 Hz, 1H), 9.14 (s, 1H), 9.47 (s, 1H).

Example 102

2-{[4-(4-methylpiperazin-1-yl)phenyl]amino}-6-phenyl-8-(pyridin-2-yl)pyrimido[4,5-d]pyridazin-5(6H)-one The title compound was prepared as described in Example 6D, substituting Example 60B for Example 6C and phenylhydrazine for methylhydrazine. MS (DCI/NH$_3$) m/z 491 (M+H)$^+$; $^1$H NMR (300 MHz, DMSO-d$_6$): δ ppm 2.87 (s, 3H), 2.91-2.98 (m, 2H), 3.10-3.25 (m, 2H), 3.53 (d, J=11.90 Hz, 2H), 3.90-4.05 (m, 2H), 6.91 (d, J=8.33 Hz, 2H), 7.40-7.49 (m, 1H), 7.49-7.60 (m, 4H), 7.61-7.78 (m, 3H), 7.90-7.97 (m, 1H), 7.98-8.06 (m, 1H), 8.83 (s, 1H), 9.37 (s, 1H).

Example 103

6-(2,6-dichlorophenyl)-2-{[4-(4-methylpiperazin-1-yl)phenyl]amino}-8-(pyridin-2-yl)pyrimido[4,5-d]pyridazin-5(6H)-one The title compound was prepared as described in Example 6D, substituting Example 60B for Example 6C and (2,6-dichlorophenyl)hydrazine for methylhydrazine. MS (DCI/NH$_3$) m/z 560 (M+H)$^+$; $^1$H NMR (300 MHz, DMSO-d$_6$): δ ppm 2.84-2.87 (m, 3H), 2.89-2.99 (m, 2H), 3.06-3.27 (m, 2H), 3.53 (d, J=11.50 Hz, 2H), 3.79 (d, J=13.09 Hz, 2H), 6.91 (d, J=8.33 Hz, 2H), 7.57 (dd, J=6.35, 4.76 Hz, 1H), 7.59-7.72 (m, 3H), 7.73-7.78 (m, 2H), 7.85-7.91 (m, 1H), 7.96-8.05 (m, 1H), 8.83 (s, 1H), 9.39 (s, 1H).

Example 104

6-(2,6-dichlorophenyl)-2-[(2'-methyl-2',3'-dihydro-1'H-spiro[cyclopropane-1,4'-isoquinolin]-7'-yl)amino]-8-(pyridin-2-yl)pyrimido[4,5-d]pyridazin-5(6H)-one Example 104A ethyl 2-(2'-methyl-2',3'-dihydro-1'H-spiro[cyclopropane-1,4'-isoquinoline]-7'-ylamino)-4-picolinoylpyrimidine-5-carboxylate The title compound was prepared as described in Example 6C, substituting Example 60A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline. MS (DCI/NH$_3$) m/z 444 (M+H)$^+$.

Example 104B 6-(2,6-dichlorophenyl)-2-[(2'-methyl-2',3'-dihydro-1'H-spiro[cyclopropane-1,4'-isoquinolin]-7'-yl)amino]-8-(pyridin-2-yl)pyrimido[4,5-d]pyridazin-5(6H)-one The title compound was prepared as described in Example 6D, substituting Example 104A for Example 6C and (2,6-dichlorophenyl)hydrazine for methylhydrazine. MS (DCI/NH$_3$) m/z 557 (M+H)$^+$; $^1$H NMR (300 MHz, CD$_3$OD): δ ppm 0.92 (d, J=9.49 Hz, 1H), 1.02-1.11 (m, 1H), 1.11-1.20 (m, 1H), 1.28-1.41 (m, 1H), 2.94 (s, 3H), 3.16-3.26 (m, 1H), 3.44-3.61 (m, 2H), 4.26 (s, 1H), 6.80 (d, J=8.48 Hz, 1H), 7.54 (d, J=2.03 Hz, 1H), 7.58-7.69 (m, 3H), 7.73-7.79 (m, 2H), 7.86 (d, J=7.80 Hz, 1H), 8.01-8.09 (m, 1H), 8.84 (d, J=2.71 Hz, 1H), 9.46 (s, 1H).

Example 105

6-(2,6-dichlorophenyl)-2-{[4-(4-methylpiperazin-1-yl)phenyl]amino}-8-(piperidin-3-yl)pyrimido[4,5-d]pyridazin-5(6H)-one Example 105A ethyl 4-(1-(benzyloxycarbonyl)piperidine-3-carbonyl)-2-(methylthio)pyrimidine-5-carboxylate The title compound was prepared as described in Example 6B, substituting benzyl 3-(chlorocarbonyl)piperidine-1-carboxylate for 3-phenylpropanoyl chloride. MS (DCI/NH$_3$) m/z 444 (M+H)$^+$.

Example 105B ethyl 4-(1-(benzyloxycarbonyl)piperidine-3-carbonyl)-2-(4-(4-methylpiperazin-1-yl)phenylamino)pyrimidine-5-carboxylate The title compound was prepared as described in Example 6C, substituting Example 105A for Example 6B. MS (DCI/NH$_3$) m/z 587 (M+H)$^+$.

Example 105C 6-(2,6-dichlorophenyl)-2-{[4-(4-methylpiperazin-1-yl)phenyl]amino}-8-(piperidin-3-yl)pyrimido[4,5-d]pyridazin-5(6H)-one A solution of Example 105B (130 mg, 0.22 mmol) and (2,6-dichlorophenyl)hydrazine (78 mg, 0.45 mmol) in ethanol (0.5 ml) was heated in a sealed tube at 140° C. overnight. After cooling, the volatiles were removed, and the residue was purified by HPLC (Zorbax C-18, 0.1% TFA/CH$_3$CN/H$_2$O) to yield the title compound as TFA salt. MS (DCI/NH$_3$) m/z 566 (M+H)$^+$; $^1$H NMR (300 MHz, CD$_3$OD): δ ppm 2.88 (s, 3H), 2.97 (d, J=12.69 Hz, 4H), 3.19 (d, J=13.88 Hz, 4H), 3.28 (s, 2H), 3.40-3.49 (m, 2H), 3.55 (d, J=12.29 Hz, 2H), 3.72-3.91 (m, 3H), 7.05 (d, J=8.73 Hz, 2H), 7.56-7.66 (m, 1H), 7.68-7.82 (m, 4H), 9.34 (s, 1H).

Example 106

2-({4-[(dimethylamino)methyl]phenyl}amino)-8-(2-furyl)-6-(2-methylphenyl)pyrimido[4,5-d]pyridazin-5(6H)-one Example 106A ethyl 2-(4-((dimethylamino)methyl)phenylamino)-4-(furan-2-carbonyl)pyrimidine-5-carboxylate The title compound was prepared as described in Example 6C, substituting Example 32A for Example 6B, and 4-((dimethylamino)methyl)aniline for 4-(4-methylpiperazin-1-yl) aniline. MS (DCI/NH$_3$) m/z 395 (M+H)$^+$.

Example 106B 2-({4-[(dimethylamino)methyl]phenyl}amino)-8-(2-furyl)-6-(2-methylphenyl)pyrimido[4,5-d]pyridazin-5(6H)-one The title compound was prepared as described in Example 6D, substituting Example 106A for Example 6C and o-tolylhydrazine for methylhydrazine. MS (DCI/NH$_3$) m/z 453 (M+H)$^+$; $^1$H NMR (400 MHz, DMSO-d$_6$): δ ppm 2.15 (s, 3H), 2.22 (s, 6H), 3.48 (s, 2H), 6.64 (s, 1H), 7.34-7.42 (m, 7H), 7.71 (d, J=8.4 Hz, 2H), 7.84 (d, J=1.2 Hz, 1H), 9.38 (s, 1H), 10.61 (s, 1H).

Example 107

8-(2-furyl)-2-{[4-(4-isopropylpiperazin-1-yl)phenyl]amino}-6-(2-methylphenyl)pyrimido[4,5-d]pyridazin-5(6H)-one The title compound was prepared as described in Example 6, substituting Example 32A for Example 6B and 4-(4-isopropylpiperazin-1-yl)aniline for 4-(4-methylpiperazin-1-yl)aniline in Example 6C and o-tolylhydrazine for methylhydrazine in Example 6D. MS (DCI/NH$_3$) m/z 522 (M+H)$^+$; $^1$H NMR (400 MHz, DMSO-d$_6$): δ ppm 1.06 (s, 6H), 2.15 (s, 3H), 2.51-2.74 (m, 5H), 3.17-3.25 (m, 4H), 6.75 (s, 1H), 6.99 (d, J=8.8 Hz, 2H), 7.36-7.42 (m, 5H), 7.56 (d, J=8.8 Hz, 2H), 7.83 (d, J=1.2 Hz, 1H), 9.31 (s, 1H), 10.42 (s, 1H).

Example 108

8-(2-furyl)-6-(2-methylphenyl)-2-{[4-(morpholin-4-ylsulfonyl)phenyl]amino}pyrimido[4,5-d]pyridazin-5(6H)-one The title compound was prepared as described in Example 6, substituting Example 32A for Example 6B and 4-(morpholinosulfonyl)aniline for 4-(4-methylpiperazin-1-yl)aniline in Example 6C and o-tolylhydrazine for methylhydrazine in Example 6D. MS (DCI/NH$_3$) m/z 545 (M+H)$^+$; $^1$H NMR (400 MHz, DMSO-d$_6$): δ ppm 2.16 (s, 3H), 2.90 (t, J=4.2 Hz, 4H), 3.66 (t, J=4.1 Hz, 4H), 6.73 (d, J=1.2 Hz, 1H), 7.38-7.43 (m, 4H), 7.77 (d, J=8.8 Hz, 2H), 7.77 (s, 1H), 7.90 (s, 1H), 8.08 (d, J=8.8 Hz, 2H), 9.49 (s, 1H), 11.08 (s, 1H).

Example 109

6-(2-methylphenyl)-2-{[4-(morpholin-4-ylsulfonyl)phenyl]amino}-8-phenylpyrimido[4,5-d]pyridazin-5(6H)-one Example 109A ethyl 4-benzoyl-2-(4-(morpholinosulfonyl)phenylamino)pyrimidine-5-carboxylate The title compound was prepared as described in Example 6C, substituting Example 27A for Example 6B, and 4-(morpholinosulfonyl)aniline for 4-(4-methylpiperazin-1-yl) aniline. MS (DCI/NH$_3$) m/z 497 (M+H)$^+$.

Example 109B 6-(2-methylphenyl)-2-{[4-(morpholin-4-ylsulfonyl)phenyl]amino}-8-phenylpyrimido[4,5-d]pyridazin-5(6H)-one The title compound was prepared as described in Example 6D, substituting Example 109A for Example 6C and o-tolylhydrazine for methylhydrazine. MS (DCI/NH$_3$) m/z 555 (M+H)$^+$; $^1$H NMR (400 MHz, DMSO-d$_6$): δ ppm 2.20 (s, 3H), 2.85 (m, 4H), 3.62-3.65 (m, 4H), 7.38-7.47 (m, 4H), 7.55-7.62 (m, 5H), 7.91 (t, J=3.8 Hz, 2H), 8.05 (d, J=8.8 Hz, 2H), 9.52 (s, 1H), 11.08, (s, 1H).

Example 110

6-allyl-2-{[4-(morpholin-4-ylsulfonyl)phenyl]amino}-8-phenylpyrimido[4,5-d]pyridazin-5(6H)-one The title compound was prepared as described in Example 6D, substituting Example 109A for Example 6C and allylhydrazine for methylhydrazine. MS (DCI/NH$_3$) m/z 505 (M+H)$^+$; $^1$H NMR (400 MHz, DMSO-d$_6$): δ ppm 2.82-2.84 (m, 4H), 2.62-3.64 (m, 4H), 4.81 (d, J=5.6 Hz, 2H), 5.22 (s, 1H), 5.25 (dd, J=1.2, 7.2 Hz, 1H), 6.00-6.10 (m, 1H), 7.56-7.60 (m, 6H), 7.88-7.90 (m, 1H), 8.02 (d, J=8.8 Hz, 2H), 9.50 (s, 1H), 11.02 (s, 1H).

Example 111

2-({4-[(dimethylamino)methyl]phenyl}amino)-6-(2-methylphenyl)-8-phenylpyrimido[4,5-d]pyridazin-5(6H)-one The title compound was prepared as described in Example 6, substituting Example 27A for Example 6B and 4-((dimethylamino)methyl)aniline for 4-(4-methylpiperazin-1-yl) aniline in Example 6C and o-tolylhydrazine for methylhydrazine in Example 6D. MS (DCI/NH$_3$) m/z 463 (M+H)$^+$; $^1$H NMR (400 MHz, DMSO-d$_6$): δ ppm 2.20 (s, 3H), 2.22 (s, 6H), 3.48 (s, 2H), 7.23 (d, J=8.0 Hz, 2H), 7.35-7.7.53 (m, 7H), 7.77 (d, J=8.0 Hz, 2H), 7.91-7.93 (m, 2H), 9.42 (s, 1H), 10.68 (s, 1H).

Example 112

6-allyl-8-(2-furyl)-2-{[4-(4-isopropylpiperazin-1-yl)phenyl]amino}pyrimido[4,5-d]pyridazin-5(6H)-one The title compound was prepared as described in Example 6, substituting Example 32A for Example 6B and 4-(4-isopropylpiperazin-1-yl)aniline for 4-((dimethylamino)methyl) aniline in Example 6C and allylhydrazine for methylhydrazine in Example 6D. MS (DCI/NH$_3$) m/z 472 (M+H)$^+$; $^1$H NMR (400 MHz, CDCl$_3$): δ ppm 1.05 (d, J=6.8 Hz, 6H), 2.67-2.71 (m, 5H), 3.18-3.19 (m, 4H), 4.80 (d, J=5.6 Hz, 2H), 5.19 (d, J=6.4 Hz, 1H), 5.24 (d, J=17.2 Hz, 1H), 5.94-6.04 (m, 1H), 6.40 (s, 1H), 6.91 (d, J=9.2 Hz, 2H), 7.41 (d, J=8.4 Hz, 2H), 7.51 (s, 2H), 7.75 (s, 1H), 9.33 (s, 1H).

Example 113

2-{[4-(4-isopropylpiperazin-1-yl)-3-methoxyphenyl]amino}-6-(2-methylphenyl)-8-phenylpyrimido[4,5-d]pyridazin-5(6H)-one The title compound was prepared as described in Example 6, substituting Example 27A for Example 6B and 4-(4-isopropylpiperazin-1-yl)-3-methoxyaniline for 4-(4-methylpiperazin-1-yl)aniline in Example 6C and o-tolylhydrazine for methylhydrazine in Example 6D. MS (DCI/NH$_3$) m/z 562 (M+H)$^+$; $^1$H NMR (400 MHz, DMSO-d$_6$): δ ppm 1.21 (d, J=5.6 Hz, 6H), 2.19 (s, 3H), 2.94-3.00 (m, 9H), 3.44 (m, 3H), 6.81 (d, J=4.0 Hz, 1H), 7.32-7.51 (m, 9H), 7.89 (d, J=5.6 Hz, 2H), 9.39 (s, 1H), 10.54 (s, 1H).

Example 114

6-allyl-2-{[4-(4-isopropylpiperazin-1-yl)-3-methoxyphenyl]amino}-8-phenylpyrimido[4,5-d]pyridazin-5(6H)-one The title compound was prepared as described in Example 6, substituting 4-(4-isopropylpiperazin-1-yl)-3-methoxyaniline for 4-(4-methylpiperazin-1-yl)aniline in Example 6C, and Example 109A for Example 6C and allylhydrazine for methylhydrazine in Example 6D. MS (DCI/NH$_3$) m/z 512 (M+H)$^+$; $^1$H NMR (400 MHz, DMSO-d$_6$): δ ppm 1.09 (d, J=6.0 Hz, 6H), 2.75-2.87 (m, 5H), 2.87-3.00 (m, 4H), 3.45 (s, 3H), 4.76 (d, J=5.2 Hz, 2H), 5.20 (s, 1H), 5.24 (d, J=1.2 Hz, 1H), 6.00-6.07 (m, 1H), 6.75 (d, J=7.2 Hz, 1H), 7.29-7.30 (m, 2H), 7.47-7.53 (m, 3H), 7.87 (d, J=3.6 Hz, 2H), 9.31 (s, 3H), 10.40 (s, 1H).

Example 115

6-allyl-2-{[4-(4-isopropyl-1,4-diazepan-1-yl)-3-methylphenyl]amino}-8-phenylpyrimido[4,5-d]pyridazin-5(6H)-one The title compound was prepared as described in Example 6, substituting 4-(4-isopropyl-1,4-diazepan-1-yl)-3-methylaniline for 4-(4-methylpiperazin-1-yl)aniline in Example 6C, and Example 109A for Example 6C and allylhydrazine for methylhydrazine in Example 6D. MS (DCI/NH$_3$) m/z 510 (M+H)$^+$; $^1$H NMR (400 MHz, DMSO-d$_6$): δ ppm 1.29 (d, J=6.0 Hz, 6H), 2.15 (m, 5H), 3.04-3.48 (m, 13H), 4.75 (d, J=4.8 Hz, 2H), 5.20 (dd, J=1.6, 13.6 Hz, 2H), 5.99-6.06 (m, 1H), 6.97 (d, J=8.4 Hz, 1H), 7.43-7.51 (m, 4H), 7.61 (s, 1H), 7.87 (d, J=3.2 Hz, 2H), 9.29 (s, 1H), 10.41 (s, 1H).

Example 116

2-{[4-(4-isopropyl-1,4-diazepan-1-yl)-3-methylphenyl]amino}-6-(2-methylphenyl)-8-phenylpyrimido[4,5-d]pyridazin-5(6H)-one The title compound was prepared as described in Example 6, substituting 4-(4-isopropyl-1,4-diazepan-1-yl)-3-methylaniline for 4-(4-methylpiperazin-1-yl)aniline in Example 6C, and Example 109A for Example 6C and o-tolylhydrazine for methylhydrazine in Example 6D. MS (DCI/NH$_3$) m/z 560 (M+H)$^+$; $^1$H NMR (400 MHz, DMSO-d$_6$): δ ppm 1.33 (d, J=6.0 Hz, 6H), 2.12 (s, 3H), 2.14 (s, 3H), 3.00-3.09 (m, 2H), 3.21-3.52 (m, 9H), 7.03 (d, J=8.8 Hz, 1H), 7.38-7.54 (m, 8H), 7.70 (s, 1H), 7.93 (d, J=5.2 Hz, 2H), 9.40 (s, 1H), 10.56 (s, 1H). MS: 560 (M+H)$^+$.

Example 117

6-allyl-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline in Example 6C, and allylhydrazine for methylhydrazine in Example 6D. MS (DCI/NH$_3$) m/z 457 (M+H)$^+$; $^1$H NMR (400 MHz, DMSO-d$_6$): δ ppm 0.87 (s, 2H), 0.94 (s, 2H), 2.33 (s, 3H), 2.47 (s, 2H), 3.57 (s, 2H), 4.73 (d, J=4.4 Hz, 2H), 5.20 (d, J=6.0 Hz, 1H), 5.24 (s, 1H), 5.98-6.05 (m, 1H), 6.72 (d, J=8.4 Hz, 1H), 7.15 (s, 1H), 7.32 (s, 1H), 7.57 (s, 1H), 7.69 (d, J=4.8 Hz, 1H), 8.24 (s, 1H), 9.31 (s, 1H), 10.47 (s, 1H).

Example 118

2-{[4-(4-isopropylpiperazin-1-yl)phenyl]amino}-6-(2-methylphenyl)-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)aniline for 4-(4-methylpiperazin-1-yl)aniline in Example 6C, and o-tolylhydrazine for methylhydrazine in Example 6D. MS (DCI/NH$_3$) m/z 538 (M+H)$^+$; $^1$H NMR (400 MHz, DMSO-d$_6$): δ ppm 1.34 (d, J=6.4 Hz, 6H), 2.16 (s, 3H), 3.16-3.25 (m, 4H), 3.50-3.52 (m, 3H), 3.85 (d, J=8.4 Hz, 2H), 7.07 (d, J=8.8 Hz, 2H), 7.13 (s, 1H), 7.36-7.42 (m, 4H), 7.63 (d, J=8.8 Hz, 2H), 7.68 (d, J=4.4 Hz, 1H), 8.24 (s, 1H), 9.34 (s, 1H), 10.53 (s, 1H).

Example 119

2-{[4-(4-isopropylpiperazin-1-yl)-3-methylphenyl]amino}-6-(2-methylphenyl)-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)-3-methylaniline for 4-(4-methylpiperazin-1-yl)aniline in Example 6C, and o-tolylhydrazine for methylhydrazine in Example 6D. MS (DCI/NH$_3$) m/z 552 (M+H)$^+$; $^1$H NMR (400 MHz, DMSO-d$_6$): δ ppm 1.35 (d, J=6.8 Hz, 6H), 2.17 (s, 3H), 2.31 (s, 3H), 3.15-3.26 (m, 6H), 3.39-3.53 (m, 3H), 7.10 (d, J=8.4 Hz, 2H), 7.14 (s, 1H), 7.37-7.42 (m, 4H), 7.68 (d, J=5.2 Hz, 2H), 7.70 (s, 1H), 8.15 (s, 1H), 9.36 (s, 1H), 10.56 (s, 1H).

Example 120

2-{[4-(4-isopropyl-1,4-diazepan-1-yl)-3-methylphenyl]amino}-6-(2-methylphenyl)-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropyl-1,4-diazepan-1-yl)-3-methylaniline for 4-(4-methylpiperazin-1-yl)aniline in Example 6C, and o-tolylhydrazine for methylhydrazine in Example 6D. MS (DCI/NH$_3$) m/z 566 (M+H)$^+$; $^1$H NMR (400 MHz, DMSO-d$_6$): δ ppm 1.33 (d, J=6.4 Hz, 6H), 2.17 (s, 3H), 2.32 (s, 3H), 3.10-3.56 (m, 11H), 7.15 (d, J=8.4 Hz, 2H), 7.37-7.43 (m, 5H), 7.68 (d, J=5.2 Hz, 2H), 8.15 (s, 1H), 9.35 (s, 1H), 10.54 (s, 1H).

Example 121

6-(2-chlorophenyl)-2-{[4-(2-oxopyrrolidin-1-yl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 1-(4-aminophenyl)pyrrolidin-2-one for 4-(4-methylpiperazin-1-yl)aniline in Example 6C, and 2-chlorophenylhydrazine for methylhydrazine in Example 6D. MS (DCI/NH$_3$) m/z 515 (M+H)$^+$; $^1$H NMR (400 MHz, DMSO-d$_6$): δ ppm 2.09-2.13 (m, 2H), 2.53 (s, 2H), 3.87 (t, J=7.2 Hz, 2H), 7.16 (s, 1H), 7.57-7.59 (m, 2H), 7.60-7.89 (m, 7H), 8.25 (d, J=4.4 Hz, 1H), 9.38 (s, 1H), 10.67 (s, 1H).

Example 122

6-(2-chlorophenyl)-2-{[4-(4-isopropylpiperazin-1-yl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)aniline in Example 6C, and 2-chlorophenylhydrazine for methylhydrazine in Example 6D. MS (DCI/NH$_3$) m/z 558 (M+H)$^+$; $^1$H NMR (400 MHz, DMSO-d$_6$): δ ppm 1.34 (d, J=6.4 Hz, 6H), 3.16-3.25 (m, 4H), 3.50-3.52 (m, 3H), 3.84-3.87 (m, 2H), 7.07-7.13 (m, 3H), 7.56-7.73 (m, 7H), 8.23 (s, 1H), 9.34 (s, 1H), 10.57 (s, 1H), 10.74 (d, J=2.4 Hz, 1H).

Example 123

6-(2-chlorophenyl)-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline in Example 6C, and 2-chlorophenylhydrazine for methylhydrazine in Example 6D. MS (DCI/NH$_3$) m/z 527 (M+H)$^+$; $^1$H NMR (400 MHz, DMSO-d$_6$): δ ppm 0.98-1.36 (m, 4H), 2.93 (s, 3H), 3.33 (s, 1H), 3.54 (s, 1H), 4.41-4.54 (m, 2H), 6.93 (d, J=8.4 Hz, 1H), 7.28 (s, 1H), 7.55-7.77 (m, 7H), 8.25 (s, 1H), 9.41 (s, 1H), 10.78 (d, J=3.2 Hz, 1H), 10.83 (s, 1H).

Example 124

6-allyl-2-{[4-(2-oxopyrrolidin-1-yl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 1-(4-aminophenyl)pyrrolidin-2-one for 4-(4-methylpiperazin-1-yl)aniline in Example 6C, and allylhydrazine for methylhydrazine in Example 6D. MS (DCI/NH$_3$) m/z 445 (M+H)$^+$; $^1$H NMR (400 MHz, DMSO-d$_6$): δ ppm 2.04-2.12 (m, 2H), 2.51 (t, J=7.6 Hz, 2H), 3.86 (t, J=6.8 Hz, 2H), 4.73 (d, J=4.4 Hz, 2H), 5.20 (d, J=6.4 Hz, 1H), 5.24 (s, 1H), 5.97-6.07 (m, 1H), 7.16 (s, 1H), 7.66-7.73 (m, 5H), 8.22 (s, 1H), 9.31 (s, 1H), 10.56 (s, 1H).

Example 125

6-allyl-2-{[4-(morpholin-4-ylsulfonyl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(morpholinosulfonyl)aniline for 4-(4-methylpiperazin-1-yl)aniline in Example 6C, and allylhydrazine for methylhydrazine in Example 6D. MS (DCI/NH$_3$) m/z 511 (M+H)$^+$; $^1$H NMR (400 MHz, DMSO-d$_6$): δ ppm 2.88-2.90 (m, 4H), 3.64-3.66 (m, 4H), 4.75 (d, J=5.2 Hz, 2H), 5.23 (dd, J=2.4, 13.2 Hz, 2H), 5.98-6.08 (m, 1H), 7.20 (t, J=4.0 Hz, 1H), 7.72-7.75 (m, 3H), 8.05 (d, J=8.4 Hz, 2H), 8.30 (s, 1H), 9.43 (s, 1H), 11.01 (s, 1H).

Example 126

6-allyl-2-{[4-(4-isopropylpiperazin-1-yl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)aniline for 4-(4-methylpiperazin-1-yl)aniline in Example 6C, and allylhydrazine for methylhydrazine in Example 6D. MS (DCI/NH$_3$) m/z 488 (M+H)$^+$; $^1$H NMR (400 MHz, DMSO-d$_6$): δ ppm 1.08 (d, J=6.0 Hz, 6H), 2.74-2.90 (m, 5H), 3.21-3.34 (m, 4H), 4.72 (d, J=5.6 Hz, 2H), 5.20 (d, J=6.0 Hz, 1H), 5.24 (s, 1H), 5.95-6.08 (m, 1H), 6.98 (d, J=8.8 Hz, 2H), 7.12 (s, 1H), 7.55 (d, J=9.2 Hz, 2H), 7.66 (d, J=5.2 Hz, 1H), 8.21 (s, 1H), 9.27 (s, 1H), 10.37 (s, 1H).

Example 127

6-allyl-2-{[4-(4-isopropylpiperazin-1-yl)-3-methylphenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)-3-methylaniline for 4-(4-methylpiperazin-1-yl)aniline in Example 6C, and allylhydrazine for methylhydrazine in Example 6D. MS (DCI/NH$_3$) m/z 502 (M+H)$^+$; $^1$H NMR (400 MHz, DMSO-d$_6$): δ ppm 1.35 (d, J=6.8 Hz, 1H), 2.30 (s, 3H), 3.20-3.33 (m, 6H), 3.48-3.54 (m, 3H), 4.73 (d, J=4.8 hz, 2H), 5.20 (d, J=7.2 Hz, 1H), 5.24 (s, 1H), 5.98-6.02 (m, 1H), 7.08 (d, J=8.4 Hz, 1H), 7.15 (s, 1H), 7.41 (s, 1H), 7.69 (d, J=4.8 Hz, 2H), 8.11 (s, 1H), 9.31 (s, 1H), 10.49 (s, 1H).

Example 128

6-(2-methylphenyl)-2-{[4-(2-oxopyrrolidin-1-yl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 1-(4-aminophenyl)pyrrolidin-2-one for 4-(4-methylpiperazin-1-yl)aniline in Example 6C, and o-tolylhydrazine for methylhydrazine in Example 6D. MS (DCI/NH$_3$) m/z 495 (M+H)$^+$; $^1$H NMR (400 MHz, DMSO-d$_6$): δ ppm 2.05-2.17 (m, 2H), 2.17 (s, 3H), 2.52 (t, J=7.2 Hz, 2H), 3.87 (t, J=7.2 Hz, 2H), 7.16 (s, 1H), 7.35-7.42 (m, 4H), 7.67-7.76 (m, 5H), 8.12 (s, 1H), 9.37 (s, 1H), 10.64 (s, 1H).

Example 129

6-(2-methylphenyl)-2-{[4-(morpholin-4-ylsulfonyl)phenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(morpholinosulfonyl)aniline for 4-(4-methylpiperazin-1-yl)aniline in Example 6C, and o-tolylhydrazine for methylhydrazine in Example 6D. MS (DCI/NH$_3$) m/z 561 (M+H)$^+$; $^1$H NMR (400 MHz, DMSO-d$_6$): δ ppm 2.18 (s, 3H), 2.90 (m, 4H), 3.64-3.66 (m, 4H), 7.19-7.21 (m, 1H), 7.38-7.44 (m, 5H), 7.72 (d, J=5.2 Hz, 1H), 7.43 (d, J=8.8 Hz, 1H), 8.08 (d, J=8.8 Hz, 2H), 8.15 (s, 1H), 9.50 (s, 1H), 11.09 (s, 1H).

Example 130

2-[(2'-methyl-2',3'-dihydro-1'H-spiro[cyclopropane-1,4'-isoquinolin]-7'-yl)amino]-6-(2-methylphenyl)-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline in Example 6C, and o-tolylhydrazine for methylhydrazine in Example 6D. MS (DCI/NH$_3$) m/z 507 (M+H)$^+$; $^1$H NMR (400 MHz, DMSO-d$_6$): δ ppm 0.98-1.34 (m, 4H), 2.17 (s, 3H), 2.92 (s, 3H), 3.28-3.53 (m, 2H), 4.43-4.49 (m, 2H), 6.92 (d, J=8.4 Hz, 1H), 7.30-7.45 (m, 6H), 7.75 (d, J=4.4 Hz, 2H), 8.12 (s, 1H), 9.40 (s, 1H), 10.74 (s, 1H), 11.31-11.37 (m, 1H).

Example 131

6-(2-chlorophenyl)-2-{[4-(4-isopropylpiperazin-1-yl)phenyl]amino}-8-phenylpyrimido[4,5-d]pyridazin-5(6H)-one The title compound was prepared as described in Example 6, substituting benzoyl chloride for 3-phenylpropanoyl chloride in Example 6B, 4-(4-isopropylpiperazin-1-yl)aniline for 4-(4-methylpiperazin-1-yl)aniline in Example 6C, and 2-chlorophenylhydrazine for methylhydrazine in Example 6D. MS (DCI/NH$_3$) m/z 552 (M+H)$^+$; $^1$H NMR (400 MHz, DMSO-d$_6$): δ ppm 1.13 (d, J=7.2 Hz, 6H), 2.16 (s, 3H), 2.85-3.47 (m, 9H), 6.96 (d, J=8.0 Hz, 1H), 7.48-7.90 (m, 10H), 7.91 (d, J=3.6 Hz, 2H), 9.38 (s, 1H), 10.57 (s, 1H).

Example 132

2-{[4-(4-isopropylpiperazin-1-yl)-3-methoxyphenyl]amino}-6-(2-methylphenyl)-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)-3-methoxyaniline for 4-(4-methylpiperazin-1-yl)aniline in Example 6C, and o-tolylhydrazine for methylhydrazine in Example 6D. MS (DCI/NH$_3$) m/z 568 (M+H)$^+$; $^1$H NMR (400 MHz, DMSO-d$_6$): δ ppm 0.85 (d, J=6.4 Hz, 6H), 2.16 (s, 3H), 2.53-2.89 (m, 5H), 3.02 (s, 4H), 3.36 (s, 4H), 3.77 (s, 3H), 6.91 (d, J=8.4 Hz, 1H), 7.08-7.42 (m, 7H), 7.65 (d, J=4.0 Hz, 1H), 8.12 (s, 1H), 9.35 (s, 1H), 10.50 (s, 1H).

Example 133

8-(2-furyl)-2-{[4-(4-isopropylpiperazin-1-yl)-3-methylphenyl]amino}-6-(2-methylphenyl)pyrimido[4,5-d]pyridazin-5(6H)-one The title compound was prepared as described in Example 6, substituting Example 32A for Example 6B and 4-(4-isopropylpiperazin-1-yl)-3-methylaniline for 4-(4-methylpiperazin-1-yl)aniline in Example 6C and o-tolylhydrazine for methylhydrazine in Example 6D. MS (DCI/NH$_3$) m/z 536 (M+H)$^+$; $^1$H NMR (400 MHz, DMSO-d$_6$): δ ppm 1.02 (d, J=7.6 Hz, 6H), 2.14 (s, 3H), 2.28 (s, 3H), 2.61 (s, 4H), 2.66-2.73 (m, 1H), 2.85 (s, 4H), 6.67 (s, 1H), 7.05 (d, J=8.8 Hz, 1H), 7.34-7.42 (m, 5H), 7.63 (s, 1H), 7.71 (s, 1H), 7.83 (s, 1H), 9.33 (s, 1H), 10.52 (s, 1H).

Example 134

2-{[4-(4-isopropylpiperazin-1-yl)phenyl]amino}-6-(2-methylphenyl)-8-phenylpyrimido[4,5-d]pyridazin-5(6H)-one The title compound was prepared as described in Example 6, substituting benzoyl chloride for 3-phenylpropanoyl chloride in Example 6B, 4-(4-isopropylpiperazin-1-yl)aniline for 4-(4-methylpiperazin-1-yl)aniline in Example 6C, and o-tolylhydrazine for methylhydrazine in Example 6D. MS (DCI/NH$_3$) m/z 532 (M+H)$^+$; $^1$H NMR (400 MHz, DMSO-d$_6$): δ ppm 1.08 (d, J=6.0 Hz, 6H), 2.19 (s, 3H), 2.57-2.90 (m, 5H), 3.38 (m, 4H), 6.87 (d, J=7.2 Hz, 1H), 7.36-7.45 (m, 8H), 7.64 (d, J=6.8 Hz, 2H), 7.93 (t, J=3.4 Hz, 2H), 9.35 (s, 1H), 10.49 (s, 1H).

Example 135

8-(2-furyl)-6-(2-methylphenyl)-2-{[4-(2-oxopyrrolidin-1-yl)phenyl]amino}pyrimido[4,5-d]pyridazin-5(6H)-one The title compound was prepared as described in Example 6, substituting Example 32A for Example 6B and 1-(4-aminophenyl)pyrrolidin-2-one for 4-(4-methylpiperazin-1-yl) aniline in Example 6C and o-tolylhydrazine for methylhydrazine in Example 6D. MS (DCI/NH$_3$) m/z 479 (M+H)$^+$; $^1$H NMR (400 MHz, DMSO-d$_6$): δ ppm 2.06-2.11 (m, 2H), 2.15 (s, 3H), 2.51 (t, J=7.2 Hz, 2H), 3.87 (t, J=7.2 Hz, 2H), 6.62 (s, 1H), 7.37-7.43 (m, 5H), 7.70 (d, J=9.2 Hz, 2H), 7.75 (d, J=8.8 Hz, 2H), 7.85 (d, J=1.2 Hz, 1H), 9.37 (s, 1H), 10.65 (s, 1H).

Example 136

6-allyl-8-(2-furyl)-2-{[4-(4-isopropylpiperazin-1-yl)-3-methoxyphenyl]amino}pyrimido[4,5-d]pyridazin-5(6H)-one The title compound was prepared as described in Example 6, substituting furan-2-carbonyl chloride for 3-phenylpropanoyl chloride in Example 6B, 4-(4-isopropylpiperazin-1-yl)-3-methoxyaniline for 4-(4-methylpiperazin-1-yl)aniline in Example 6C, and allylhydrazine for methylhydrazine in Example 6D. MS (DCI/NH$_3$) m/z 502 (M+H)$^+$; $^1$H NMR (400 MHz, DMSO-d$_6$): δ ppm 1.15 (s, 6H), 2.54-2.78 (m, 5H), 2.96-3.12 (m, 4H), 3.74 (s, 3H), 4.75 (d, J=5.2 Hz, 2H), 5.17 (dd, J=1.2, 8.4 Hz, 1H), 5.22 (s, 1H), 5.96-6.12 (m, 1H), 6.63 (s, 1H), 6.92 (d, J=8.8 Hz, 1H), 7.23 (s, 1H), 7.31 (s, 1H), 7.51 (s, 1H), 7.89 (s, 1H), 9.30 (s, 1H), 10.43 (s, 1H).

Example 137

6-allyl-2-({4-[(dimethylamino)methyl]phenyl}amino)-8-(2-furyl)pyrimido[4,5-d]pyridazin-5(6H)-one The title compound was prepared as described in Example 6, substituting furan-2-carbonyl chloride for 3-phenylpropanoyl chloride in Example 6B, 4-((dimethylamino)methyl)aniline for 4-(4-methylpiperazin-1-yl)aniline in Example 6C, and allylhydrazine for methylhydrazine in Example 6D. MS (DCI/NH$_3$) m/z 403 (M+H)$^+$; $^1$H NMR (400 MHz, DMSO-d$_6$): δ ppm 2.18 (s, 6H), 3.42 (s, 2H), 4.75 (d, J=5.2 Hz, 2H), 5.18-5.22 (m, 2H), 5.97-6.04 (m, 1H), 6.63 (s, 1H), 7.31 (d, J=8.4 Hz, 2H), 7.56 (s, 1H), 7.67 (d, J=8.8 Hz, 2H), 7.89 (s, 1H), 9.33 (s, 1H), 10.54 (s, 1H).

Example 138

8-(2-furyl)-2-{[4-(4-isopropylpiperazin-1-yl)-3-methoxyphenyl]amino}-6-(2-methylphenyl)pyrimido[4,5-d]pyridazin-5(6H)-one The title compound was prepared as described in Example 6, substituting Example 32A for Example 6B and 4-(4-isopropylpiperazin-1-yl)-3-methoxyaniline for 4-(4-methylpiperazin-1-yl)aniline in Example 6C and o-tolylhydrazine for methylhydrazine in Example 6D. MS (DCI/NH$_3$) m/z 552 (M+H)$^+$; $^1$H NMR (400 MHz, DMSO-d$_6$): δ ppm 1.17 (s, 6H), 2.14 (s, 3H), 2.62-2.87 (m, 5H), 2.92-3.11 (m, 4H), 3.75 (s, 3H), 6.62 (s, 1H), 6.93 (d, J=8.8 Hz, 1H), 7.23 (d, J=2.4 Hz, 1H), 7.34-7.43 (m, 5H), 7.55 (s, 1H), 7.83 (s, 1H), 9.35 (s, 1H), 10.50 (s, 1H).

Example 139

6-allyl-2-{[4-(4-isopropylpiperazin-1-yl)phenyl]amino}-8-phenylpyrimido[4,5-d]pyridazin-5(6H)-one The title compound was prepared as described in Example 6, substituting benzoyl chloride for 3-phenylpropanoyl chloride in Example 6B, 4-(4-isopropylpiperazin-1-yl)aniline for 4-(4-methylpiperazin-1-yl)aniline in Example 6C, and allylhydrazine for methylhydrazine in Example 6D. MS (DCI/NH$_3$) m/z 482 (M+H)$^+$; $^1$H NMR (400 MHz, CDCl$_3$): δ ppm 1.10 (d, J=6.4 Hz, 6H), 2.70-2.77 (m, 5H), 3.19 (t, J=4.2 Hz, 4H), 4.86 (d, J=6.0 Hz, 2H), 5.26-5.35 (m, 2H), 6.03-6.13 (m, 1H), 6.87 (d, J=7.2 Hz, 1H), 7.44-7.51 (m, 5H), 7.78 (s, 1H), 7.99 (s, 2H), 9.43 (s, 1H).

Example 140

6-allyl-8-(2-furyl)-2-{[4-(morpholin-4-ylsulfonyl)phenyl]amino}pyrimido[4,5-d]pyridazin-5(6H)-one The title compound was prepared as described in Example 6, substituting furan-2-carbonyl chloride for 3-phenylpropanoyl chloride in Example 6B, 4-(morpholinosulfonyl) aniline for 4-(4-methylpiperazin-1-yl)aniline in Example 6C, and allylhydrazine for methylhydrazine in Example 6D. MS (DCI/NH$_3$) m/z 495 (M+H)$^+$; $^1$H NMR (400 MHz, DMSO-d$_6$): δ ppm 2.91 (m, 4H), 3.67 (t, J=4.0 Hz, 4H), 4.77 (d, J=5.2 Hz, 2H), 5.21 (s, 1H), 5.23 (d, J=4.4 Hz, 1H), 5.99-6.06 (m, 1H), 6.68 (d, J=1.2 Hz, 1H), 7.58 (s, 1H), 7.73 (d, J=8.4 Hz, 2H), 7.89 (s, 1H), 8.06 (d, J=8.8 Hz, 2H), 9.42 (s, 1H), 10.97 (s, 1H).

Example 141

6-(2-methylphenyl)-2-{[4-(2-oxopyrrolidin-1-yl)phenyl]amino}-8-phenylpyrimido[4,5-d]pyridazin-5(6H)-one The title compound was prepared as described in Example 6, substituting benzoyl chloride for 3-phenylpropanoyl chloride in Example 6B, 1-(4-aminophenyl)pyrrolidin-2-one for 4-(4-methylpiperazin-1-yl)aniline in Example 6C, and o-tolylhydrazine for methylhydrazine in Example 6D. MS (DCI/NH$_3$) m/z 489 (M+H)$^+$; $^1$H NMR (400 MHz, DMSO-d$_6$): δ ppm 2.03-2.11 (m, 2H), 2.19 (s, 3H), 2.47 (t, J=6.8 Hz, 2H), 3.83 (t, J=7.2 Hz, 2H), 7.35-7.43 (m, 4H), 7.49-7.57 (m, 5H), 7.77 (d, J=8.8 Hz, 2H), 7.72-7.94 (m, 2H), 9.40 (s, 1H), 10.62 (s, 1H).

Example 142

6-allyl-2-{[4-(2-oxopyrrolidin-1-yl)phenyl]amino}-8-phenylpyrimido[4,5-d]pyridazin-5(6H)-one The title compound was prepared as described in Example 6, substituting benzoyl chloride for 3-phenylpropanoyl chloride in Example 6B, 1-(4-aminophenyl)pyrrolidin-2-one for 4-(4-methylpiperazin-1-yl)aniline in Example 6C, and allylhydrazine for methylhydrazine in Example 6D. MS (DCI/NH$_3$) m/z 439 (M+H)$^+$; $^1$H NMR (400 MHz, DMSO-d$_6$): δ ppm 2.03-2.10 (m, 2H), 2.47 (t, J=6.0 Hz, 2H), 3.82 (t, J=7.2 Hz, 2H), 4.78 (d, J=4.8 Hz, 2H), 5.21 (s, 1H), 5.24 (dd, J=1.2, 6.0 Hz, 1H), 6.00-6.08 (m, 1H), 7.52-7.55 (m, 5H), 7.74 (d, J=9.2 Hz, 2H), 7.92 (dd, J=2.4, 6.4 Hz, 2H), 9.35 (s, 1H), 10.54 (s, 1H).

Example 143

6-allyl-2-({4-[(dimethylamino)methyl]phenyl}amino)-8-phenylpyrimido[4,5-d]pyridazin-5(6H)-one The title compound was prepared as described in Example 6, substituting benzoyl chloride for 3-phenylpropanoyl chloride in Example 6B, 4-((dimethylamino)methyl)aniline for 4-(4-methylpiperazin-1-yl)aniline in Example 6C, and allylhydrazine for methylhydrazine in Example 6D. MS (DCI/NH$_3$) m/z 413 (M+H)$^+$; $^1$H NMR (400 MHz, DMSO-d$_6$): δ ppm 2.38 (s, 6H), 3.75 (s, 2H), 4.77 (d, J=5.6 Hz, 2H), 5.21 (s, 1H), 5.23 (dd, J=1.6, 6.0 Hz, 1H), 5.99-6.07 (m, 1H), 7.30 (d, J=8.4 Hz, 2H), 7.51-53 (m, 3H), 7.77 (d, J=8.4 Hz, 2H), 7.88-7.90 (m, 2H), 9.34 (s, 1H), 10.60 (s, 1H).

Example 144

6-allyl-8-(2-furyl)-2-[(2'-methyl-2',3'-dihydro-1'H-spiro[cyclopropane-1,4'-isoquinolin]-7'-yl)amino] pyrimido[4,5-d]pyridazin-5(6H)-one The title compound was prepared as described in Example 6, substituting furan-2-carbonyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline in Example 6C, and allylhydrazine for methylhydrazine in Example 6D. MS (DCI/NH$_3$) m/z 441 (M+H)$^+$; $^1$H NMR (400 MHz, CDCl$_3$): δ ppm 1.04-1.09 (m, 4H), 2.97 (s, 3H), 3.24-3.31 (m, 2H), 4.44 (s, 2H), 4.77 (d, J=5.6 Hz, 2H), 5.16-5.24 (m, 2H), 5.97-6.06 (m, 1H), 6.78 (s, 1H), 6.93 (d, J=8.8 Hz, 1H), 7.51 (s, 1H), 7.57 (d, J=8.4 Hz, 1H), 7.64 (s, 1H), 7.91 (s, 1H), 9.34 (s, 1H).

Example 145

8-(2-furyl)-2-[(2'-methyl-2',3'-dihydro-1'H-spiro [cyclopropane-1,4'-isoquinolin]-7'-yl)amino]-6-(2-methylphenyl)pyrimido[4,5-d]pyridazin-5(6H)-one The title compound was prepared as described in Example 6, substituting Example 32A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline in Example 6C and o-tolylhydrazine for methylhydrazine in Example 6D. MS (DCI/NH$_3$) m/z 491 (M+H)$^+$; $^1$H NMR (400 MHz, DMSO-d$_6$): δ ppm 1.01-1.16 (m, 4H), 2.15 (s, 3H), 2.92 (s, 3H), 3.49-3.51 (m, 2H), 4.45-4.49 (m, 2H), 6.82 (s, 1H), 6.93 (d, J=8.8 Hz, 1H), 7.35-7.70 (m, 7H), 7.87 (s, 1H), 9.38 (s, 1H), 10.71 (s, 1H), 11.22 (s, 1H).

Example 146

6-allyl-8-(2-furyl)-2-{[4-(4-isopropylpiperazin-1-yl)-3-methylphenyl]amino}pyrimido[4,5-d]pyridazin-5 (6H)-one The title compound was prepared as described in Example 6, substituting furan-2-carbonyl chloride for 3-phenylpropanoyl chloride in Example 6B, 4-(4-isopropylpiperazin-1-yl)-3-methylaniline for 4-(4-methylpiperazin-1-yl)aniline in Example 6C, and allylhydrazine for methylhydrazine in Example 6D. MS (DCI/NH$_3$) m/z 486 (M+H)$^+$; $^1$H NMR (400 MHz, DMSO-d$_6$): δ ppm 0.35 (d, J=7.2 Hz, 6H), 2.31 (s, 3H), 3.25-3.32 (m, 6H), 3.45-3.56 (m, 3H), 4.75 (d, J=5.2 Hz, 2H), 5.18 (dd, J=1.6, 7.6 Hz, 1H), 5.22 (s, 1H), 5.99-6.07 (m, 1H), 6.66 (s, 1H), 7.09 (d, J=8.8 Hz, 1H), 7.45-7.75 (m, 3H), 7.89 (d, J=0.8 Hz, 1H), 9.31 (s, 1H), 10.46 (s, 1H).

Example 147

6-(2,6-dichlorophenyl)-8-(1-isopropylpiperidin-3-yl)-2-{[4-(4-methylpiperazin-1-yl)phenyl] amino}pyrimido[4,5-d]pyridazin-5(6H)-one A solution of Example 105 (50 mg, 0.09 mmol) and acetone (25 mg, 0.4 mmol) in methanol (0.5 mL) was heated at 40° C. for 30 minutes. NaCNBH$_3$ (8 mg, 0.13 mmol) was then added, and the mixture was stirred at the same temperature overnight. The volatiles were removed, and the residue was separated purified by HPLC (Zorbax C-18, 0.1% TFA/CH$_3$CN/H$_2$O) to yield the title compound as TFA salt. MS (DCI/NH$_3$) m/z 608 (M+H)$^+$; $^1$H NMR (300 MHz, DMSO-d$_6$): δ ppm 1.24 (t, J=6.95 Hz, 6H), 1.92-2.11 (m, 2H), 2.23-2.39 (m, 1H), 2.88 (s, 3H), 2.98 (d, J=12.89 Hz, 4H), 3.10-3.28 (m, 4H), 3.36-3.48 (m, 2H), 3.80 (d, J=12.89 Hz, 4H), 3.85-3.99 (m, 1H), 7.07 (d, J=9.16 Hz, 2H), 7.57-7.64 (m, 2H), 7.68-7.79 (m, 3H), 9.35 (s, 1H).

Example 148

6-(2,6-dichlorophenyl)-2-{[4-(4-methylpiperazin-1-yl)phenyl]amino}-8-(piperidin-4-yl)pyrimido[4,5-d] pyridazin-5(6H)-one Example 148A ethyl 4-(1-(benzyloxycarbonyl)piperidine-4-carbonyl)-2-(methylthio)pyrimidine-5-carboxylate The title compound was prepared as described in Example 6B, substituting benzyl 4-(chlorocarbonyl)piperidine-1-carboxylate for 3-phenylpropanoyl chloride. MS (DCI/NH$_3$) m/z 444 (M+H)$^+$ Example 148B ethyl 4-(1-(benzyloxycarbonyl)piperidine-4-carbonyl)-2-(4-(4-methylpiperazin-1-yl)phenylamino) pyrimidine-5-carboxylate The title compound was prepared as described in Example 6C, substituting Example 148A for Example 6B. MS (DCI/NH$_3$) m/z 587 (M+H)$^+$ Example 148C 6-(2,6-dichlorophenyl)-2-{[4-(4-methylpiperazin-1-yl)phenyl]amino}-8-(piperidin-4-yl)pyrimido[4,5-d] pyridazin-5(6H)-one The title compound was prepared as described in Example 6D, substituting Example 148B for Example 6C and (2,6-dichlorophenyl)hydrazine for methylhydrazine. MS (DCI/NH$_3$) m/z 566 (M+H)$^+$; $^1$H NMR (300 MHz, CD$_3$OD): δ ppm 1.68-1.94 (m, 2H), 2.17 (d, J=12.69 Hz, 2H), 2.87 (s, 3H), 2.98 (d, J=11.90 Hz, 2H), 3.04-3.23 (m, 4H), 3.32-3.46 (m, 2H), 3.54 (d, J=8.33 Hz, 2H), 3.68 (t, J=1.30 Hz, 2H), 3.80 (d, J=11.10 Hz, 2H), 7.07 (d, J=8.73 Hz, 2H), 7.54-7.67 (m, 2H), 7.69-7.87 (m, 3H), 9.34 (s, 1H).

Example 149

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-4-yl)pyrimido[4,5-d]pyridazin-5(6H)-one Example 149A ethyl 4-(1-methyl-1H-pyrazole-4-carbonyl)-2-(2'-methyl-2',3'-dihydro-1'H-spiro[cyclopropane-1,4'-isoquinoline]-7'-ylamino)pyrimidine-5-carboxylate The title compound was prepared as described in Example 6C, substituting Example 85A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline. MS (DCI/NH$_3$) m/z 447 (M+H)$^+$.

Example 149B 6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-4-yl)pyrimido[4,5-d]pyridazin-5(6H)-one The title compound was prepared as described in Example 6D, substituting Example 149A for Example 6C and (2,6-dichlorophenyl)hydrazine for methylhydrazine. MS (DCI/NH$_3$) m/z 560 (M+H)$^+$; $^1$H NMR (300 MHz, CD$_3$OD): δ ppm 0.90-1.03 (m, 1H), 1.05-1.28 (m, 2H), 1.31-1.43 (m, 1H), 2.97 (s, 3H), 3.46-3.66 (m, 2H), 3.89 (s, 3H), 4.37-4.53 (m, 1H), 4.54-4.69 (m, 1H), 6.97 (d, J=8.73 Hz, 1H), 7.52-7.66 (m, 5H), 7.71-7.79 (m, 2H), 9.41 (s, 1H).

Example 150

6-(2,6-dichlorophenyl)-2-{[3-methyl-4-(4-methyl-1,4-diazepan-1-yl)phenyl]amino}-8-(1-methyl-1H-pyrazol-4-yl)pyrimido[4,5-d]pyridazin-5(6H)-one Example 150A ethyl 4-(1-methyl-1H-pyrazole-4-carbonyl)-2-(2'-methyl-2',3'-dihydro-1'H-spiro[cyclopropane-1,4'-isoquinoline]-7'-ylamino)pyrimidine-5-carboxylate The title compound was prepared as described in Example 6C, substituting Example 85A for Example 6B and 3-methyl-4-(4-methyl-1,4-diazepan-1-yl)aniline for 4-(4-methylpiperazin-1-yl)aniline. MS (DCI/NH$_3$) m/z 448 (M+H)$^+$.

Example 150B 6-(2,6-dichlorophenyl)-2-{[3-methyl-4-(4-methyl-1,4-diazepan-1-yl)phenyl]amino}-8-(1-methyl-1H-pyrazol-4-yl)pyrimido[4,5-d]pyridazin-5(6H)-one The title compound was prepared as described in Example 6D, substituting Example 150A for Example 6C and (2,6-dichlorophenyl)hydrazine for methylhydrazine. MS (DCI/NH$_3$) m/z 591 (M+H)$^+$; $^1$H NMR (300 MHz, CD$_3$OD): δ ppm 1.97-2.22 (m, 4H), 2.33 (s, 3H), 2.92 (s, 3H), 3.09-3.19 (m, 2H), 3.44-3.61 (m, 2H), 3.79-3.92 (m, 5H), 7.19 (d, J=8.82 Hz, 2H), 7.48-7.66 (m, 4H), 7.73 (s, 1H), 7.75 (d, J=1.02 Hz, 1H), 9.36 (s, 1H).

Example 151

6-(2,6-dichlorophenyl)-2-{[4-(4-methylpiperazin-1-yl)phenyl]amino}-8-(1-methyl-1H-pyrazol-3-yl)pyrimido[4,5-d]pyridazin-5(6H)-one Example 151A ethyl 4-(1-methyl-1H-pyrazole-3-carbonyl)-2-(methylthio)pyrimidine-5-carboxylate The title compound was prepared as described in Example 6B, substituting 1-methyl-1H-pyrazole-3-carbonyl chloride for 3-phenylpropanoyl chloride. MS (DCI/NH$_3$) m/z 307 (M+H)$^+$.

Example 151B ethyl 4-(1-methyl-1H-pyrazole-3-carbonyl)-2-(4-(4-methylpiperazin-1-yl)phenylamino)pyrimidine-5-carboxylate The title compound was prepared as described in Example 6C, substituting Example 151A for Example 6B. MS (DCI/NH$_3$) m/z 450 (M+H)$^+$.

Example 151C 6-(2,6-dichlorophenyl)-2-{[4-(4-methylpiperazin-1-yl)phenyl]amino}-8-(1-methyl-1H-pyrazol-3-yl)pyrimido[4,5-d]pyridazin-5(6H)-one The title compound was prepared as described in Example 6D, substituting Example 151B for Example 6C and 2,6-dichlorophenylhydrazine for methylhydrazine. MS (DCI/NH$_3$) m/z 494 (M+H)$^+$; $^1$H NMR (300 MHz, CD$_3$OD): δ ppm 0.84 (s, 3H), 2.95-3.11 (m, 2H), 3.10-3.25 (m, 2H), 3.39-3.59 (m, 2H), 3.81 (d, J=11.10 Hz, 2H), 3.97 (s, 3H), 7.01 (d, J=8.72 Hz, 2H), 7.54-7.68 (m, 2H), 7.74 (s, 1H), 7.77 (s, 1H), 7.83 (d, J=1.98 Hz, 3H), 9.36 (s, 1H).

Example 152

6-(2,6-dichlorophenyl)-2-{[3-methyl-4-(4-methyl-1,4-diazepan-1-yl)phenyl]amino}-8-(1-methyl-1H-pyrazol-3-yl)pyrimido[4,5-d]pyridazin-5(6H)-one Example 152A ethyl 4-(1-methyl-1H-pyrazole-3-carbonyl)-2-(3-methyl-4-(4-methyl-1,4-diazepan-1-yl)phenylamino)pyrimidine-5-carboxylate The title compound was prepared as described in Example 6C, substituting Example 151A for Example 6B and 3-methyl-4-(4-methyl-1,4-diazepan-1-yl)aniline for 4-(4-methylpiperazin-1-yl)aniline. MS (DCI/NH$_3$) m/z 448 (M+H)$^+$.

Example 152B 6-(2,6-dichlorophenyl)-2-{[3-methyl-4-(4-methyl-1,4-diazepan-1-yl)phenyl]amino}-8-(1-methyl-1H-pyrazol-3-yl)pyrimido[4,5-d]pyridazin-5(6H)-one The title compound was prepared as described in Example 6D, substituting Example 152A for Example 6C and (2,6-dichlorophenyl)hydrazine for methylhydrazine. MS (DCI/NH$_3$) m/z 591 (M+H)$^+$; $^1$H NMR (300 MHz, CD$_3$OD): δ ppm 2.01-2.18 (m, 2H), 2.28 (s, 3H), 2.92 (s, 3H), 3.03-3.15 (m, 2H), 3.20-3.38 (m, 3H), 3.40-3.61 (m, 3H), 3.94 (s, 3H), 7.10 (d, J=8.48 Hz, 2H), 7.57-7.72 (m, 3H), 7.74 (s, 1H), 7.77 (d, J=1.36 Hz, 1H), 7.83 (d, J=2.03 Hz, 1H), 9.38 (s, 1H).

Example 153

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-3-yl)pyrimido[4,5-d]pyridazin-5(6H)-one

Example 153A ethyl 4-(1-methyl-1H-pyrazole-3-carbonyl)-2-(2'-methyl-2',3'-dihydro-1'H-spiro[cyclopropane-1,4'-isoquinoline]-7'-ylamino)pyrimidine-5-carboxylate The title compound was prepared as described in Example 6C, substituting Example 151A for Example 6B and 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2(1H)-one derivative. WO 2009151997) for 4-(4-methylpiperazin-1-yl)aniline. MS (DCI/NH$_3$) m/z 447 (M+H)$^+$.

Example 153B 6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-3-yl)pyrimido[4,5-d]pyridazin-5(6H)-one The title compound was prepared as described in Example 6D, substituting Example 153A for Example 6C and (2,6-dichlorophenyl)hydrazine for methylhydrazine. MS (DCI/NH$_3$) m/z 560 (M+H)$^+$; $^1$H NMR (300 MHz, CD$_3$OD): δ ppm 0.97 (t, J=11.53 Hz, 1H) 1.03-1.25 (m, 2H), 1.27-1.45 (m, 1H), 2.95 (s, 3H), 3.40-3.66 (m, 2H), 3.96 (s, 3H), 4.24-4.59 (m, 2H), 6.88 (d, J=8.48 Hz, 2H), 7.57-7.71 (m, 3H), 7.75 (s, 1H), 7.77 (d, J=1.36 Hz, 1H), 7.92 (d, J=2.37 Hz, 1H), 9.42 (s, 1H).

Example 154

2-{[4-(4-methylpiperazin-1-yl)phenyl]amino}-6-phenyl-8-(pyridin-4-yl)pyrimido[4,5-d]pyridazin-5(6H)-one

Example 154A ethyl 4-isonicotinoyl-2-(methylthio)pyrimidine-5-carboxylate

The title compound was prepared as described in Example 60A, substituting isonicotinaldehyde for picolinaldehyde. MS (DCI/NH$_3$) m/z 304 (M+H)$^+$.

Example 154B ethyl 4-isonicotinoyl-2-(4-(4-methylpiperazin-1-yl)phenylamino)pyrimidine-5-carboxylate The title compound was prepared as described in Example 6C, substituting Example 154A for Example 6B. MS (DCI/NH$_3$) m/z 447 (M+H)$^+$.

Example 154C

2-{[4-(4-methylpiperazin-1-yl)phenyl]amino}-6-phenyl-8-(pyridin-4-yl)pyrimido[4,5-d]pyridazin-5(6H)-one The title compound was prepared as described in Example 6D, substituting Example 154B for Example 6C and phenylhydrazine for methylhydrazine. MS (DCI/NH$_3$) m/z 526 (M+H)$^+$; $^1$H NMR (300 MHz, DMSO-d$_6$): δ ppm 2.23 (s, 3H), 2.41-2.54 (m, 4H), 3.08-3.16 (m, 4H), 6.91 (d, J=9.12 Hz, 2H), 7.45 (t, J=7.14 Hz, 2H), 7.49-7.62 (m, 3H), 7.69 (d, J=7.93 Hz, 2H), 7.89-8.06 (m, 2H), 8.67-8.80 (m, 2H), 9.35 (s, 1H).

Example 155

6-(2-chlorophenyl)-2-{[4-(4-methylpiperazin-1-yl)phenyl]amino}-8-(pyridin-4-yl)pyrimido[4,5-d]pyridazin-5(6H)-one The title compound was prepared as described in Example 6D, substituting Example 154B for Example 6C and 2-chlorophenylhydrazine for methylhydrazine. MS (DCI/NH$_3$) m/z 526 (M+H)$^+$; $^1$H NMR (300 MHz, DMSO-d$_6$): δ ppm 2.85 (s, 3H), 3.00 (t, J=12.10 Hz, 2H), 3.10-3.26 (m, 2H), 3.52 (d, J=11.50 Hz, 2H), 3.82 (d, J=13.09 Hz, 2H), 7.00 (d, J=9.12 Hz, 2H), 7.49-7.66 (m, 4H), 7.67-7.80 (m, 2H), 7.94 (d, J=3.97 Hz, 2H), 8.74 (d, J=5.95 Hz, 2H), 9.38 (s, 1H).

Example 156

6-(2,6-dichlorophenyl)-2-{[4-(4-methylpiperazin-1-yl)phenyl]amino}-8-(pyridin-4-yl)pyrimido[4,5-d]pyridazin-5(6H)-one The title compound was prepared as described in Example 6D, substituting Example 154B for Example 6C and 2,6-dichlorophenylhydrazine for methylhydrazine. MS (DCI/NH$_3$) m/z 560 (M+H)$^+$; $^1$H NMR (300 MHz, DMSO-d$_6$): δ ppm 2.88 (s, 3H), 2.92-3.02 (m, 2H), 3.09-3.27 (m, 2H), 3.55 (d, J=11.87 Hz, 2H), 3.84 (d, J=12.89 Hz, 2H), 7.00 (d, J=8.82

Hz, 2H), 7.57-7.65 (m, 3H), 7.73-7.81 (m, 2H), 7.96 (d, J=3.73 Hz, 2H), 8.72-8.79 (m, 2H), 9.40 (s, 1H).

Example 157

6-(2,6-dichlorophenyl)-2-{[4-(4-methylpiperazin-1-yl)phenyl]amino}-8-[3-(piperidin-1-ylmethyl)phenyl]pyrimido[4,5-d]pyridazin-5(6H)-one

Example 157A ethyl 2-(methylthio)-4-(3-(piperidin-1-ylmethyl)benzoyl)pyrimidine-5-carboxylate The title compound was prepared as described in Example 60A, substituting 3-(piperidin-1-ylmethyl)benzaldehyde for picolinaldehyde. MS (DCI/NH$_3$) m/z 400 (M+H)$^+$.

Example 157B ethyl 2-(4-(4-methylpiperazin-1-yl)phenylamino)-4-(3-(piperidin-1-ylmethyl)benzoyl)pyrimidine-5-carboxylate The title compound was prepared as described in Example 6C, substituting Example 157A for Example 6B. MS (DCI/NH$_3$) m/z 543 (M+H)$^+$.

Example 157C 6-(2,6-dichlorophenyl)-2-{[4-(4-methylpiperazin-1-yl)phenyl]amino}-8-[3-(piperidin-1-ylmethyl)phenyl]pyrimido[4,5-d]pyridazin-5(6H)-one The title compound was prepared as described in Example 6D, substituting Example 157B for Example 6C and 2,6-dichlorophenylhydrazine for methylhydrazine. MS (DCI/NH$_3$) m/z 656 (M+H)$^+$; $^1$H NMR (300 MHz, CD$_3$OD): δ ppm 1.27-1.44 (m, 1H), 1.48-1.70 (m, 3H), 1.78 (d, J=11.90 Hz, 2H), 2.89 (s, 3H), 2.90-3.03 (m, 2H), 3.07-3.25 (m, 2H), 3.32 (d, J=11.10 Hz, 2H), 3.54 (d, J=11.50 Hz, 2H), 3.66-4.00 (m, 4H), 4.34 (d, J=2.78 Hz, 2H), 6.94 (d, J=7.14 Hz, 2H), 7.57-7.71 (m, 5H), 7.73-7.80 (m, 2H), 7.90 (s, 1H), 8.15 (d, J=5.95 Hz, 1H) 9.41 (s, 1H).

Example 158

8-{3-[(cyclobutylamino)methyl]phenyl}-6-(2,6-dichlorophenyl)-2-{[4-(4-methylpiperazin-1-yl)phenyl]amino}pyrimido[4,5-d]pyridazin-5(6H)-one

Example 158A ethyl 4-(3-(dimethoxymethyl)benzoyl)-2-(methylthio)pyrimidine-5-carboxylate The title compound was prepared as described in Example 60A, substituting 3-(dimethoxymethyl)benzaldehyde for picolinaldehyde. MS (DCI/NH$_3$) m/z 377 (M+H)$^+$.

Example 158B ethyl 4-(3-(dimethoxymethyl)benzoyl)-2-(4-(4-methylpiperazin-1-yl)phenylamino)pyrimidine-5-carboxylate The title compound was prepared as described in Example 6C, substituting Example 158A for Example 6B. MS (DCI/NH$_3$) m/z 520 (M+H)$^+$.

Example 158C ethyl 4-(3-formylbenzoyl)-2-(4-(4-methylpiperazin-1-yl)phenylamino)pyrimidine-5-carboxylate A solution of Example 158B (200 mg, 0.4 mmol) in dichloromethane (10 ml) was treated with TFA (5 mL) at 40° C. overnight. The volatiles were removed and the residue was directly used in the next step without further purification. MS (DCI/NH$_3$) m/z 474 (M+H)$^+$.

Example 158D ethyl 4-(3-((cyclobutylamino)methyl)benzoyl)-2-(4-(4-methylpiperazin-1-yl)phenylamino)pyrimidine-5-carboxylate A mixture of Example 158C (100 mg, 0.2 mmol), cyclobutanamine (30 mg, 0.4 mmol) and NaCNBH$_3$ (13 mg, 0.2 mmol) in dioxane (5 mL) was heated at 70° C. for two days. The volatiles were removed, and the residue was purified by HPLC (Zorbax C-18, Mobile phase A: 0.1% TFA in H$_2$O; B: 0.1% TFA in CH$_3$CN; 0-100% gradient) to provide the title compound. MS (DCI/NH$_3$) m/z 529 (M+H)$^+$.

Example 158E

8-{3-[(cyclobutylamino)methyl]phenyl}-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 158D for Example 6C and 2,6-dichlorophenylhydrazine for methylhydrazine. MS (DCI/NH$_3$) m/z 642 (M+H)$^+$; $^1$H NMR (300 MHz, CD$_3$OD): δ ppm 1.61-1.88 (m, 2H), 2.13 (d, J=6.71 Hz, 4H), 2.89 (s, 3H), 2.93-3.05 (m, 2H), 3.14-3.29 (m, 2H), 3.55 (d, J=11.29 Hz, 3H), 4.02-4.17 (m, 2H), 6.93 (d, J=9.77 Hz, 2H), 7.58-7.69 (m, 5H), 7.74-7.79 (m, 2H), 7.87 (s, 1H), 8.09 (s, 1H), 9.41 (s, 1H).

Example 159 methyl 6-[6-(2,6-dichlorophenyl)-2-{[4-(4-methylpiperazin-1-yl)phenyl]amino}-5-oxo-5,6-dihydropyrimido[4,5-d]pyridazin-8-yl]pyridine-2-carboxylate

Example 159A ethyl 4-(6-chloropicolinoyl)-2-(methylthio)pyrimidine-5-carboxylate The title compound was prepared as described in Example 6B, substituting 6-chloropicolinoyl chloride for 3-phenylpropanoyl chloride. MS (DCI/NH$_3$) m/z 338 (M+H)$^+$.

Example 159B 8-(6-chloropyridin-2-yl)-6-(2,6-dichlorophenyl)-2-(methylthio)pyrimido[4,5-d]pyridazin-5(6H)-one To a suspension of Example 159A (512 mg, 1.516 mmol) in 2,2,2-trifluoroethanol (15 mL) was added 2,6-dichlorophenylhydrazine hydrochloride (324 mg, 1.516 mmol). This mixture was heated in a sealed tube at 108° C. overnight. The mixture was partitioned between ethyl acetate and brine. The organic phase was concentrated, and the residue was purified by flash chromatography (15-50% ethyl acetate in hexane) to provide the title compound. MS (DCI/NH$_3$) m/z 451 (M+H)$^+$.

Example 159C methyl 6-(6-(2,6-dichlorophenyl)-2-(methylthio)-5-oxo-5,6-dihydropyrimido[4,5-d]pyridazin-8-yl)picolinate Example 159B (235 mg, 0.521 mmol) in methanol (20 mL) was added to [1,1'-bis(diphenylphosphino)ferrocene]palladium(II) dichloride (Heraeus) (38.1 mg, 0.052 mmol) and triethylamine (0.145 ml, 1.043 mmol) in a 50 mL pressure bottle. The mixture was pressurized with carbon monoxide (60 psi), and stirred at 80° C. for 4 hours. The mixture was filtered, and the filtrate was concentrated and the residue was purifed by flash chromatography (20-70-% ethyl acetate in hexane) to provide the title compound. MS (DCI/NH$_3$) m/z 475 (M+H)$^+$.

Example 159D methyl 6-[6-(2,6-dichlorophenyl)-2-{[4-(4-methylpiperazin-1-yl)phenyl]amino}-5-oxo-5,6-dihydropyrimido[4,5-d]pyridazin-8-yl]pyridine-2-carboxylate The title compound was prepared as described in Example 6C, substituting Example 159C for Example 6B. MS (DCI/NH$_3$) m/z 617 (M+H)$^+$; $^1$H NMR (400 MHz, DMSO-d$_6$): δ ppm 2.28 (s, 3H), 2.52-2.55 (m, 4H), 3.11-3.15 (m, 4H), 3.93 (s, 3H), 6.86 (d, J=8.54 Hz, 2H), 7.48 (d, J=8.54 Hz, 2H), 7.62-7.66 (m, 1H), 7.75-7.79 (m, 1H), 8.16 (d, J=8.85 Hz, 1H), 8.43-8.49 (m, 1H), 9.13 (s, 1H), 9.38 (s, 1H), 10.61 (s, 1H).

Example 160

6-(2,6-dichlorophenyl)-8-[6-(2-hydroxypropan-2-yl)pyridin-2-yl]-2-{[4-(4-methylpiperazin-1-yl)phenyl]amino}pyrimido[4,5-d]pyridazin-5(6H)-one To a solution of Example 159D (50 mg, 0.081 mmol) in anhydrous THF (3 mL) was added methylmagnesium bromide (3 M solution, 0.108 mL, 0.324 mmol) at room temperature. The mixture was stirred for 1 hour, and quenched by the addition of water. The volatiles were removed, and the residue was separated by HPLC (Zorbax C-18, Mobile phase A: 0.1% TFA in H$_2$O; B: 0.1% TFA in CH$_3$CN; 0-100% gradient) to provide the title compound as TFA salt. MS (DCI/NH$_3$) m/z 617 (M+H)$^+$; $^1$H NMR (500 MHz, DMSO-d$_6$): δ ppm 1.51 (s, 6H), 2.86 (s, 3H), 2.93 (m, 2H), 3.14-3.19 (m, 2H), 3.52 (m, 2H), 3.76 (m, 2H), 6.90 (d, J=7.02 Hz, 1H), 7.53-7.60 (m, 2H), 7.73-7.75 (m, 2H), 7.83 (d, J=8.24 Hz, 1H), 8.25 (d, J=7.32 Hz, 1H), 8.96 (s, 1H), 9.38 (s, 1H), 9.84 (s, 1H), 10.66 (s, 1H).

Example 161

6-allyl-2-{[4-(4-isopropylpiperazin-1-yl)-3-methoxyphenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)-3-methoxyaniline for 4-(4-methylpiperazin-1-yl) aniline in Example 6C, and allylhydrazine for methylhydrazine in Example 6D. MS (DCI/NH$_3$) m/z 518 (M+H)$^+$; $^1$H NMR (400 MHz, CDCl$_3$): δ ppm 1.13 (d, J=6.4 Hz, 6H), 2.61-2.75 (m, 5H), 3.02-3.22 (m, 4H), 3.80 (s, 3H), 4.83 (d, J=6.0 Hz, 2H), 5.28 (d, J=10.4 Hz, 1H), 5.34 (d, J=16.8 Hz, 1H), 5.99-6.09 (m, 1H), 6.97 (d, J=8.4 Hz, 1H), 7.04 (s, 1H), 7.11 (dd, J=1.6, 8.4 Hz, 1H), 7.19 (s, 1H), 7.38 (d, J=3.6 Hz, 1H), 7.71 (s, 1H), 8.25 (d, J=2.4 Hz, 1H), 9.44 (s, 1H).

Example 162

6-allyl-2-[(2-methyl-1,2,3,4-tetrahydroisoquinolin-7-yl)amino]-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 2-methyl-1,2,3,4-tetrahydroisoquinolin-7-amine for 4-(4-methylpiperazin-1-yl) aniline in Example 6C, and allylhydrazine for methylhydrazine in Example 6D. MS (DCI/NH$_3$) m/z 431 (M+H)$^+$; $^1$H NMR (400 MHz, CDCl$_3$): δ ppm 2.50 (s, 3H), 2.76 (t, J=6.0 Hz, 2H), 2.96 (t, J=6.0 Hz, 2H), 3.63 (s, 2H), 4.83 (d, J=5.6 Hz, 2H), 2.98 (d, J=10.0 Hz, 1H), 5.34 (d, J=12.6 Hz, 1H), 6.03-6.10 (m, 1H), 7.09-7.15 (m, 1H), 7.29 (s, 1H), 7.42 (d, J=4.4 Hz, 1H), 7.52 (s, 1H), 7.63 (s, 1H), 8.26 (d, J=3.2 Hz, 1H), 9.44 (s, 1H).

Example 163

6-allyl-2-{[4-(4-isopropyl-1,4-diazepan-1-yl)-3-methylphenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropyl-1,4-diazepan-1-yl)-3-methylaniline for 4-(4-methylpiperazin-1-yl) aniline in Example 6C, and allylhydrazine for methylhydrazine in Example 6D. MS (DCI/NH$_3$) m/z 516 (M+H)$^+$; $^1$H NMR (400 MHz, DMSO-d$_6$): δ ppm 1.30 (d, J=4.8 Hz, 6H), 2.02-2.22 (m, 2H), 2.31 (s, 3H), 3.10-3.18 (m, 2H), 3.34-3.64 (m, 7H), 4.73 (d, J=5.2 Hz, 2H), 5.20 (d, J=8.4 Hz, 1H), 5.24 (s, 1H), 5.95-6.06 (m, 1H), 7.02 (s, 1H), 7.12 (s, 1H), 7.27 (s, 1H), 7.41 (s, 1H), 7.69 (d, J=4.8 Hz, 1H), 8.24 (s, 1H), 9.44 (s, 1H), 10.46 (s, 1H).

Example 164

6-(2-methylphenyl)-2-[(2-methyl-1,2,3,4-tetrahydroisoquinolin-7-yl)amino]-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 2-methyl-1,2,3,4-tetrahydroisoquinolin-7-amine for 4-(4-methylpiperazin-1-yl) aniline in Example 6C, and o-tolylhydrazine for methylhydrazine in Example 6D. MS (DCI/NH$_3$) m/z 481 (M+H)$^+$; $^1$H NMR (400 MHz, DMSO-d$_6$): δ ppm 2.17 (s, 3H), 2.92 (s, 3H), 2.99-3.05 (m, 1H), 3.20-3.32 (m, 1H), 3.32-3.41 (m, 1H), 3.55-3.65 (m, 1H), 4.28-4.39 (m, 2H), 7.29 (d, J=84 Hz, 2H), 7.36-7.43 (m, 4H), 7.57 (d, J=8.4 Hz, 1H), 7.75 (d, J=5.2 Hz, 2H), 8.28 (s, 1H), 9.41 (s, 1H), 10.74 (s, 1H), 11.05 (s, 1H).

Example 165

6-(2-chlorophenyl)-2-{[4-(morpholin-4-ylsulfonyl) phenyl]amino}-8-(2-thienyl)pyrimido[4,5-d]pyridazin-5(6H)-one The title compound was prepared as described in Example 6, substituting thiophene-2-carbonyl chloride for 3-phenyl-propanoyl chloride in Example 6B, 4-(morpholinosulfonyl) aniline for 4-(4-methylpiperazin-1-yl)aniline in Example 6C, and 2-chlorophenylhydrazine for methylhydrazine in Example 6D. MS (DCI/NH$_3$) m/z 581 (M+H)$^+$; $^1$H NMR (400 MHz, DMSO-d$_6$): δ ppm 2.78-2.95 (m, 4H), 3.55-3.65 (m, 4H), 7.21 (t, J=4.4 Hz, 1H), 7.56-7.61 (m, 2H), 7.68-7.779 (m, 5H), 8.08 (d, J=8.8 Hz, 2H), 8.18 (s, 1H), 9.51 (s, 1H), 11.13 (s, 1H).

Example 166

6-(2-chlorophenyl)-2-{[4-(4-isopropylpiperazin-1-yl)-3-methylphenyl]amino}-8-(2-thienyl)pyrimido[4,5-d]pyridazin-5(6H)-one The title compound was prepared as described in Example 6, substituting thiophene-2-carbonyl chloride for 3-phenyl-propanoyl chloride in Example 6B, 4-(4-isopropylpiperazin-1-yl)-3-methylaniline for 4-(4-methylpiperazin-1-yl)aniline in Example 6C, and 2-chlorophenylhydrazine for methylhydrazine in Example 6D. MS (DCI/NH$_3$) m/z 457 (M+H)$^+$; $^1$H NMR (400 MHz, DMSO-d$_6$): δ ppm 1.35 (d, J=6.4 Hz, 6H), 2.31 (s, 3H), 3.08-3.16 (m, 6H), 3.48-3.54 (m, 3H), 7.10 (d, J=8.4 Hz, 1H), 7.14 (s, 1H), 7.43 (d, J=2.4 Hz, 1H), 7.55-7.60 (m, 2H), 7.67-7.73 (m, 4H), 8.26 (s, 1H), 9.36 (s, 1H), 10.50 (s, 1H), 10.63 (d, J=1.6 Hz, 1H).

Example 167

6-(2-chlorophenyl)-2-[(2-methyl-1,2,3,4-tetrahy-droisoquinolin-7-yl)amino]-8-(2-thienyl)pyrimido[4,5-d]pyridazin-5(6H)-one The title compound was prepared as described in Example 6, substituting thiophene-2-carbonyl chloride for 3-phenyl-propanoyl chloride in Example 6B, 2-methyl-1,2,3,4-tetrahy-droisoquinolin-7-amine for 4-(4-methylpiperazin-1-yl) aniline in Example 6C, and 2-chlorophenylhydrazine for methylhydrazine in Example 6D. MS (DCI/NH$_3$) m/z 501 (M+H)$^+$; $^1$H NMR (400 MHz, DMSO-d$_6$): δ ppm 2.93 (s, 3H), 3.01-3.08 (m, 1H), 3.17-3.25 (m, 1H), 3.34 (s, 1H), 3.66 (d, J=10.0 hz, 1H), 4.27-4.41 (m, 2H), 7.30 (d, J=8.8 Hz, 2H), 7.57-7.59 (m, 3H), 7.67-7.77 (m, 4H), 8.16 (s, 1H), 9.41 (s, 1H), 10.78 (s, 1H).

Example 168

6-(2-chlorophenyl)-2-{[4-(2-oxopyrrolidin-1-yl)phe-nyl]amino}-8-phenylpyrimido[4,5-d]pyridazin-5(6H)-one The title compound was prepared as described in Example 6, substituting benzoyl chloride for 3-phenylpropanoyl chlo-ride in Example 6B, 1-(4-aminophenyl)pyrrolidin-2-one for 4-(4-methylpiperazin-1-yl)aniline in Example 6C, and 2-chlorophenylhydrazine for methylhydrazine in Example 6D. MS (DCI/NH$_3$) m/z 509 (M+H)$^+$; $^1$H NMR (400 MHz, DMSO-d$_6$): δ ppm 2.03-2.10 (m, 2H), 2.49 (t, J=7.6 Hz, 2H), 3.82 (t, J=6.8 Hz, 2H), 7.52-7.57 (m, 7H), 7.66-7.78 (m, 4H), 7.93 (d, J=4.4 Hz, 2H), 9.41 (s, 1H), 10.70 (s, 1H).

Example 169

6-allyl-2-{[4-(4-isopropylpiperazin-1-yl)-3-meth-ylphenyl]amino}-8-phenylpyrimido[4,5-d]pyridazin-5(6H)-one The title compound was prepared as described in Example 6, substituting benzoyl chloride for 3-phenylpropanoyl chlo-ride in Example 6B, 4-(4-isopropylpiperazin-1-yl)-3-methy-laniline for 4-(4-methylpiperazin-1-yl)aniline in Example 6C, and allylhydrazine for methylhydrazine in Example 6D. MS (DCI/NH$_3$) m/z 496 (M+H)$^+$; $^1$H NMR (400 MHz, DMSO-d$_6$): δ ppm 1.02 (s, 6H), 2.14 (s, 3H), 2.55-3.31 (m, 9H), 4.77 (d, J=5.2 Hz, 2H), 5.20 (s, 1H), 5.23 (d, J=3.6 Hz, 1H), 5.96-6.07 (m, 1H), 6.92 (d, J=8.4 Hz, 1H), 7.45 (d, J=8.8 Hz, 1H), 7.50-7.60 (m, 4H), 7.89 (d, J=3.6 Hz, 2H), 9.31 (s, 1H), 10.38 (d, J=1.6 Hz, 1H).

Example 170

2-{[4-(4-isopropylpiperazin-1-yl)-3-methylphenyl] amino}-6-(2-methylphenyl)-8-phenylpyrimido[4,5-d]pyridazin-5(6H)-one The title compound was prepared as described in Example 6, substituting benzoyl chloride for 3-phenylpropanoyl chlo-ride in Example 6B, 4-(4-isopropylpiperazin-1-yl)-3-methy-laniline for 4-(4-methylpiperazin-1-yl)aniline in Example 6C, and o-tolylhydrazine for methylhydrazine in Example 6D. MS (DCI/NH$_3$) m/z 546 (M+H)$^+$; $^1$H NMR (400 MHz, DMSO-d$_6$): δ ppm 1.10 (s, 6H), 2.15 (s, 3H), 2.19 (s, 3H), 2.76-2.99 (m, 9H), 6.94 (d, J=8.4 Hz, 1H), 7.37-7.51 (m, 8H), 7.64 (s, 1H), 7.91 (d, J=3.2 Hz, 2H), 9.37 (s, 1H), 10.49 (s, 1H).

Example 171

6-(2-methylphenyl)-2-[(2-methyl-1,2,3,4-tetrahy-droisoquinolin-7-yl)amino]-8-phenylpyrimido[4,5-d] pyridazin-5(6H)-one The title compound was prepared as described in Example 6, substituting benzoyl chloride for 3-phenylpropanoyl chlo-ride in Example 6B, 2-methyl-1,2,3,4-tetrahydroisoquinolin-7-amine for 4-(4-methylpiperazin-1-yl)aniline in Example 6C, and o-tolylhydrazine for methylhydrazine in Example 6D. MS (DCI/NH$_3$) m/z 475 (M+H)$^+$; $^1$H NMR (400 MHz, DMSO-d$_6$): δ ppm 2.19 (s, 3H), 2.89 (s, 3H), 2.86-2.98 (m, 1H), 3.15-3.25 (m, 2H), 3.55-3.62 (m, 1H), 4.13 (s, 2H), 7.16 (d, J=8.4 Hz, 1H), 7.38-7.45 (m, 4H), 7.58-7.66 (m, 5H), 7.88 (d, J=4.8 Hz, 2H), 9.43 (s, 1H), 10.71 (s, 1H), 11.30 (s, 1H).

Example 172

6-allyl-2-[(2'-methyl-2',3'-dihydro-1'H-spiro[cyclo-propane-1,4'-isoquinolin]-7'-yl)amino]-8-phenylpy-rimido[4,5-d]pyridazin-5(6H)-one The title compound was prepared as described in Example 6, substituting benzoyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2 (1H)-one derivative. WO 2009151997) for 4-(4-methylpiperazin-1-yl)aniline in Example 6C, and allylhydrazine for methylhydrazine in Example 6D. MS (DCI/NH$_3$) m/z 451 (M+H)$^+$; $^1$H NMR (400 MHz, DMSO-d$_6$): δ ppm 0.91-1.26 (m, 4H), 2.89 (s, 3H), 3.21-3.30 (m, 1H), 3.41-3.51 (m, 1H), 4.22 (s, 2H), 4.78 (d, J=5.2 Hz, 2H), 5.21 (s, 1H), 5.24 (d, J=2.8 Hz, 1H), 6.01-6.08 (m, 1H), 6.79 (d, J=8.4 Hz, 1H), 7.53 (d, J=8.4 Hz, 1H), 7.54-7.62 (m, 3H), 7.65 (s, 1H), 7.86 (d, J=6.4 Hz, 2H), 9.37 (s, 1H), 10.63 (s, 1H), 11.07 (s, 1H).

Example 173

2-[(2'-methyl-2',3'-dihydro-1'H-spiro[cyclopropane-1,4'-isoquinolin]-7'-yl)amino]-6-(2-methylphenyl)-8-phenylpyrimido[4,5-d]pyridazin-5(6H)-one The title compound was prepared as described in Example 6, substituting benzoyl chloride for 3-phenylpropanoyl chloride in Example 6B, 2'-methyl-2',3'-dihydro-1'H-spiro[cyclopropane-1,4'-isoquinolin]-7'-amine (Furukawa, S.; Ikeno, T.; Kato, S.; Kawasaki, M.; Kojima, H.; Minagawa, W.; Sawada, N.; Yamamoto, F.; Lohani, S.; Wang, Y. Process for preparation of a 3,4-dihydro-4-imino-pyrimido[4,5-d]pyrimidin-2 (1H)-one derivative. WO 2009151997) for 4-(4-methylpiperazin-1-yl)aniline in Example 6C, and o-tolylhydrazine for methylhydrazine in Example 6D. MS (DCI/NH$_3$) m/z 501 (M+H)$^+$; $^1$H NMR (400 MHz, DMSO-d$_6$): δ ppm 1.04-1.25 (m, 4H), 2.19 (s, 3H), 3.35-3.47 (m, 2H), 4.23 (s, 2H), 6.80 (d, J=8.4 Hz, 1H), 7.38-7.45 (m, 4H), 7.52-7.59 (m, 4H), 7.69 (s, 1H), 7.88 (d, J=4.0 Hz, 2H), 9.42 (s, 1H), 10.71 (s, 1H), 11.33 (s, 1H).

Example 174

6-(2-chlorophenyl)-2-{[4-(4-isopropylpiperazin-1-yl)-3-methoxyphenyl]amino}-8-(2-thienyl)pyrimido[4,5-d]pyridazin-5(6H)-one The title compound was prepared as described in Example 6, substituting thiophene-2-carbonyl chloride for 3-phenylpropanoyl chloride in Example 6B, 4-(4-isopropylpiperazin-1-yl)-3-methoxyaniline for 4-(4-methylpiperazin-1-yl) aniline in Example 6C, and 2-chlorphenylhydrazine for methylhydrazine in Example 6D. MS (DCI/NH$_3$) m/z 588 (M+H)$^+$; $^1$H NMR (400 MHz, CDCl$_3$): δ ppm 1.16 (s, 6H), 2.55-2.85 (m, 5H), 3.05-3.17 (m, 4H), 3.81 (s, 3H), 6.98 (d, J=8.4 Hz, 1H), 7.04 (s, 1H), 7.13 (d, J=7.6 Hz, 1H), 7.22 (s, 1H), 7.40-7.60 (m, 5H), 8.24 (s, 1H), 9.48 (s, 1H).

Example 175

8-(6-acetylpyridin-2-yl)-6-(2,6-dichlorophenyl)-2-{[4-(4-methylpiperazin-1-yl)phenyl]amino}pyrimido[4,5-d]pyridazin-5(6H)-one Example 175A ethyl 4-(6-chloropicolinoyl)-2-(methylthio)pyrimidine-5-carboxylate The title compound was prepared as described in Example 6B, substituting 6-chloropicolinoyl chloride for 3-phenylpropanoyl chloride. MS (DCI/NH$_3$) m/z 338 (M+H)$^+$.

Example 175B 8-(6-chloropyridin-2-yl)-6-(2,6-dichlorophenyl)-2-(methylthio)pyrimido[4,5-d]pyridazin-5(6H)-one To a suspension of Example 175A (512 mg, 1.52 mmol) in 2,2,2-trifluoroethanol (15 mL) was added 2,6-dichlorophenylhydrazine hydrochloride (324 mg, 1.516 mmol). The mixture was heated in a sealed tube at 108° C. overnight. After cooling, the mixture was partitioned between ethyl acetate and brine. The organic phase was concentrated. The residue was separated by flash chromatography (15-50% gradient ethyl acetate in hexane) to provide the title compound. MS (DCI/NH$_3$) m/z 451 (M+H)$^+$.

Example 175C methyl 6-(6-(2,6-dichlorophenyl)-2-(methylthio)-5-oxo-5,6-dihydropyrimido[4,5-d]pyridazin-8-yl)picolinate A solution of Example 175B (235 mg, 0.521 mmol) in methanol (20 ml) was added to a mixture of Pd-dppf (Heraeus, 38.1 mg, 0.052 mmol) and triethylamine (0.145 mL, 1.043 mmol) in a 50 mL pressure bottle. The mixture was pressurized with carbon monoxide (60 psi), and stirred at 80° C. for 4 hours. After cooling, the mixture was concentrated, and the residue was separated by flash chromatography (20-70% gradient ethyl acetate in hexane) to provide the title compound. MS (DCI/NH$_3$) m/z 474 (M+H)$^+$.

Example 175D methyl 6-(6-(2,6-dichlorophenyl)-2-(4-(4-methylpiperazin-1-yl)phenylamino)-5-oxo-5,6-dihydropyrimido[4,5-d]pyridazin-8-yl)picolinate To a solution of Example 175C (160 mg, 0.337 mmol) in methylene chloride (6 mL) was added 3-chloroperoxybenzoic acid (113 mg, 0.506 mmol) and the solution was stirred at room temperature for 2 h. 4-(4-Methylpiperazino)aniline (129 mg, 0.675 mmol) and Hunig's base (0.236 mL, 1.349 mmol) were then added. This mixture was stirred at room temperature overnight, and was partitioned between ethyl acetate and brine. The organic phase was concentrated, and the residue was separated by flash chromatography (0-15% gradient methanol in methylene chloride) to provide the title compound. MS (DCI/NH$_3$) m/z 617 (M+H)$^+$.

Example 175E 8-(6-acetylpyridin-2-yl)-6-(2,6-dichlorophenyl)-2-(4-(4-methylpiperazin-1-yl)phenylamino)pyrimido[4,5-d]pyridazin-5(6H)-one To a solution of Example 175D (50 mg, 0.081 mmol) in anhydrous THF (3 mL) was added methylmagnesium bromide (3 M solution, 0.108 mL, 0.324 mmol) at room temperature. The solution was stirred at the same temperature for 1 hour. Water (1 mL) was then added, and the mixture was concentrated. The residue was separated by HPLC (Zorbax, C-18, 250×2.54 column, Mobile phase A: 0.1% TFA in H$_2$O; B: 0.1% TFA in CH$_3$CN; 0-100% gradient) to provide the title compound as TFA salt. MS (DCI/NH$_3$) m/z 602 (M+H)$^+$; $^1$H NMR (500 MHz, DMSO-d$_6$): δ 2.69 (s, 3H), 2.86 (s, 3H), 2.91-2.98 (m, 2H), 3.14-3.20 (m, 2H), 3.52 (m, 2H), 3.78 (m, 2H), 6.94 (d, J=7.63 Hz, 1H), 7.55-7.58 (m, 2H), 7.63 (dd, J=8.85, 7.63 Hz, 1H), 7.75-7.77 (m, 2H), 8.07 (d, J=8.24 Hz, 1H), 8.44 (d, J=7.32 Hz, 1H), 9.20 (s, 1H), 9.39 (s, 1H), 9.73 (s, 1H), 10.68 (s, 1H).

Example 176

6-(2,6-dichlorophenyl)-8-[6-(3-hydroxypentan-3-yl)pyridin-2-yl]-2-{[4-(4-methylpiperazin-1-yl)phenyl]amino}pyrimido[4,5-d]pyridazin-5(6H)-one To a solution of Example 175D (35 mg, 0.057 mmol) in anhydrous THF (3 mL) was added ethylmagnesium bromide (3 M solution in diethylether, 0.076 mL, 0.227 mmol) at room temperature. The solution was stirred at the same temperature for 1 hour. Water (1 mL) was then added and the mixture was concentrated. The residue was separated by HPLC (Zorbax, C-18, 250×2.54 column, Mobile phase A: 0.1% TFA in H$_2$O; B: 0.1% TFA in CH$_3$CN; 0-100% gradient) to provide the title compound as a TFA salt. MS (DCI/NH$_3$) m/z 646 (M+H)$^+$; $^1$H NMR (500 MHz, DMSO-d$_6$): δ 0.92 (t, J=7.48 Hz, 3H), 1.12 (t, J=7.32 Hz, 3H), 1.58-1.75 (m, 4H), 2.87 (s, 3H), 2.88-2.94 (m, 2H), 3.13-3.21 (m, 4H), 3.52 (m, 2H), 6.92 (d, J=8.54 Hz, 2H), 7.25 (d, J=9.15 Hz, 2H), 7.54-7.59 (m, 1H), 7.67-7.72 (m, 2H), 7.97 (d, J=8.24 Hz, 1H), 8.30 (dd, J=7.93, 2.14 Hz, 1H), 9.05 (d, J=1.53 Hz, 1H), 9.76 (s, 1H).

The following Examples were prepared essentially as described in Example 6, substituting the appropriate acid chloride in Example 6B, the appropriate anilines in Example 6C and the appropriate hydrazines in Example 6D. Some products were purified by flash chromatography while others were purified by reverse-phase HPLC. Accordingly, some Examples were isolated as trifluoroacetic acid salts.

TABLE 1

| Ex | Name | $^1$H NMR | MS |
|---|---|---|---|
| 177 | 2-{[4-(4-methylpiperazin-1-yl)phenyl]amino}-6-phenyl-8-(pyrimidin-4-yl)pyrimido[4,5-d]pyridazin-5(6H)-one | $^1$H NMR (400 MHz, CDCl$_3$): δ 2.88 (s, 3 H), 2.90-3.00 (m, 2 H), 3.08-3.26 (m, 2 H), 3.54 (d, J = 11.87 Hz, 2 H), 3.82 (d, J = 13.22 Hz, 2 H), 6.98 (d, J = 8.82 Hz, 2 H), 7.42-7.61 (m, 5 H), 7.61-7.79 (m, 3 H), 8.09 (d, J = 4.75 Hz, 1 H), 9.03 (d, J = 5.09 Hz, 1 H), 9.38 (s, 1 H). | MS (DCI/NH$_3$) m/z 492 (M + H)$^+$ |
| 178 | 6-(2-chlorophenyl)-2-{[4-(4-methylpiperazin-1-yl)phenyl]amino}-8-(pyrimidin-4-yl)pyrimido[4,5-d]pyridazin-5(6H)-one | $^1$H NMR (300 MHz, DMSO-d$_6$): δ 2.88 (d, J = 3.17 Hz, 3 H), 2.91-3.00 (m, 2 H), 3.08-3.33 (m, 2 H), 3.54 (d, J = 11.51 Hz, 2 H), 3.82 (d, J = 13.09 Hz, 2 H), 6.98 (d, J = 8.73 Hz, 2 H), 7.56-7.74 (m, 3 H), 7.74-7.85 (m, 2 H), 8.06 (d, J = 4.76 Hz, 1 H), 9.03 (d, J = 5.16 Hz, 1 H), 9.40 (s, 1 H), 9.46 (s, 1 H). | MS (DCI/NH$_3$) m/z 526 (M + H)$^+$ |
| 179 | 6-(2,6-dichlorophenyl)-2-{[4-(4-methylpiperazin-1-yl)phenyl]amino}-8-(pyrimidin-4-yl)pyrimido[4,5-d]pyridazin-5(6H)-one | $^1$H NMR (400 MHz, CDCl$_3$): δ 2.88 (s, 3 H), 2.90-2.99 (m, 2 H), 3.04-3.31 (m, 2 H), 3.54 (d, J = 11.51 Hz, 2 H), 3.82 (d, J = 13.09 Hz, 2 H), 6.98 (d, J = 8.73 Hz, 2 H), 7.57-7.72 (m, 3 H), 7.73-7.85 (m, 3 H), 8.06 (d, J = 4.76 Hz, 1 H), 9.03 (d, J = 5.16 Hz, 1 H), 9.40 (s, 1 H). | MS (DCI/NH$_3$) m/z 560 (M + H)$^+$ |
| 180 | 6-(2,6-dichlorophenyl)-2-{[4-(4-methylpiperazin-1-yl)phenyl]amino}-8-[6-(pyrrolidin-1-yl)pyridin-2-yl]pyrimido[4,5-d]pyridazin-5(6H)-on | $^1$H NMR (400 MHz, CDCl$_3$): δ 1.77-2.00 (m, 4 H), 2.84 (s, 3 H), 3.01 (t, J = 11.90 Hz, 2 H), 3.06-3.23 (m, 2 H), 3.40-3.67 (m, 6 H), 3.73 (d, J = 11.11 Hz, 2 H), 6.80 (d, J = 7.93 Hz, 2 H), 7.63 (dd, J = 8.93, 7.34 Hz, 4 H), 7.68-7.88 (m, 4 H), 9.39 (s, 1 H) | MS (DCI/NH$_3$) m/z 628 (M + H)$^+$ |
| 181 | 6-(2-chlorophenyl)-2-{[4-(4-methylpiperazin-1-yl)phenyl]amino}-8-[6-(pyrrolidin-1-yl)pyridin-2-yl]pyrimido[4,5-d]pyridazin-5(6H)-one | $^1$H NMR (400 MHz, CDCl$_3$): δ 1.79-1.98 (m, 4 H), 2.86 (s, 3 H), 2.93 (t, J = 13.29 Hz, 2 H), 3.08-3.23 (m, 2 H), 3.33-3.60 (m, 6 H), 3.72 (d, J = 11.90 Hz, 2 H), 6.79 (d, J = 7.54 Hz, 2 H), 7.50-7.64 (m, 4 H), 7.64-7.80 (m, 5 H), 9.36 (s, 1 H) | MS (DCI/NH$_3$) m/z 594 (M + H)$^+$ |
| 182 | 6-(2-methylphenyl)-2-{[4-(4-methylpiperazin-1-yl)phenyl]amino}-8-[6-(pyrrolidin-1-yl)pyridin-2-yl]pyrimido[4,5-d]pyridazin-5(6H)-one | $^1$H NMR (400 MHz, CDCl$_3$): δ 1.85-1.98 (m, 4 H), 2.19 (s, 3 H), 2.84 (s, 3 H), 3.01 (t, J = 13.22 Hz, 2 H), 3.09-3.26 (m, 2 H), 3.29-3.60 (m, 4 H), 3.56-3.96 (m, 4 H), 6.73-6.91 (m, 2 H), 7.33-7.51 (m, 6 H), 7.52-7.74 (m, 3 H), 9.37 (s, 1 H) | MS (DCI/NH$_3$) m/z 574 (M + H)$^+$ |
| 183 | 6-(2,6-dichlorophenyl)-8-{3-[(methylamino)methyl]phenyl}-2-{[4-(4-methylpiperazin-1-yl)phenyl]amino}pyrimido[4,5-d]pyridazin-5(6H)-one | $^1$H NMR (400 MHz, CDCl$_3$): δ 2.58 (s, 3 H), 2.87 (s, 3 H), 2.97 (d, J = 11.19 Hz, 1 H), 3.09-3.25 (m, 3 H), 3.23-3.30 (m, 2 H), 3.42-3.65 (m, 2 H), 3.71-3.92 (m, 2 H), 4.19 (s, 2 H), 6.93 (d, J = 8.14 Hz, 2 | MS (DCI/NH$_3$) m/z 601 (M + H)$^+$ |

TABLE 1-continued

| Ex | Name | $^1$H NMR | MS |
|---|---|---|---|
| | | H), 7.53-7.72 (m, 5 H), 7.72-7.82 (m, 2 H), 7.86 (s, 1 H), 8.13 (d, J = 6.78 Hz, 1 H), 9.40 (s, 1 H) | |
| 184 | 6-(2,6-dichlorophenyl)-8-{3-[(dimethylamino)methyl]phenyl}-2-{[4-(4-methylpiperazin-1-yl)phenyl]amino}pyrimido[4,5-d]pyridazin-5(6H)-one | $^1$H NMR (400 MHz, CDCl$_3$): δ 2.83 (s, 6 H), 2.99 (s, 3 H), 3.21-3.29 (m, 2 H), 3.31-3.40 (m, 2 H), 3.51-3.69 (m, 2 H), 3.73-3.93 (m, 2 H), 4.37 (s, 2 H), 6.99 (d, J = 6.35 Hz, 2 H), 7.49-7.59 (m, 2 H), 7.60-7.69 (m, 6 H), 8.25-8.38 (m, 1 H), 9.41 (s, 1 H) | MS (DCI/NH$_3$) m/z 615 (M + H)$^+$ |
| 185 | 8-(3-acetylphenyl)-6-(2,6-dichlorophenyl)-2-{[4-(4-methylpiperazin-1-yl)phenyl]amino}pyrimido[4,5-d]pyridazin-5(6H)-one | $^1$H NMR (400 MHz, CDCl$_3$): δ 2.87 (s, 3 H), 2.89-2.99 (m, 2 H), 3.09-3.25 (m, 2 H), 3.35 (s, 3 H), 3.54 (d, J = 11.11 Hz, 2 H), 3.75 (d, J = 13.09 Hz, 2 H), 6.83 (d, J = 7.93 Hz, 2 H), 7.54-7.65 (m, 3 H), 7.70 (t, J = 7.74 Hz, 2 H), 7.74-7.79 (m, 2 H), 8.06-8.15 (m, 2 H), 9.40 (s, 1 H) | MS (DCI/NH$_3$) m/z 600 (M + H)$^+$ |
| 186 | 6-(2,6-dichlorophenyl)-8-{3-[1-(methylamino)ethyl]phenyl}-2-{[4-(4-methylpiperazin-1-yl)phenyl]amino}pyrimido[4,5-d]pyridazin-5(6H)-one | $^1$H NMR (400 MHz, CDCl$_3$): δ 1.53 (d, J = 6.10 Hz, 3 H), 2.46 (s, 3 H), 2.88 (s, 3 H), 2.89-3.01 (m, 2 H), 3.07-3.29 (m, 2 H), 3.54 (d, J = 11.19 Hz, 2 H), 3.80 (d, J = 11.53 Hz, 2 H), 4.37 (d, J = 10.51 Hz, 1 H), 6.92 (s, 2 H), 7.60-7.71 (m, 4 H), 7.70-7.88 (m, 4 H), 8.10 (s, 1 H), 9.40 (s, 1 H) | MS (DCI/NH$_3$) m/z 615 (M + H)$^+$ |
| 187 | 8-(3,3-difluorocyclobutyl)-6-methyl-2-{[4-(4-methylpiperazin-1-yl)phenyl]amino}pyrimido[4,5-d]pyridazin-5(6H)-one | $^1$H NMR (300 MHz, CDCl$_3$): δ 2.45 (s, 3H), 2.61 (m, 4H), 2.98 (m, 4H), 3.24 (m, 4H), 3.82 (s, 3H), 3.85 (m, 1H), 7.00 (d, J = 8.2 Hz, 2H), 7.55 (m, 3H), 9.40 (s, 1H). | MS (DCI/NH$_3$) m/z 442 (M + H)$^+$ |
| 188 | methyl 3-[6-(2,6-dichlorophenyl)-2-{[4-(4-methylpiperazin-1-yl)phenyl]amino}-5-oxo-5,6-dihydropyrimido[4,5-d]pyridazin-8-yl]benzoate | $^1$H NMR (400 MHz, CDCl$_3$): δ 2.87 (s, 3 H), 2.92-2.99 (m, 2 H), 3.08-3.27 (m, 2 H), 3.54 (d, J = 10.71 Hz, 2 H), 3.69-3.81 (m, 2 H), 3.84 (s, 3 H), 6.85 (d, J = 7.93 Hz, 2 H), 7.55-7.67 (m, 4 H), 7.66-7.80 (m, 3 H), 8.12 (d, J = 7.93 Hz, 2 H), 9.39 (s, 1 H) | MS (DCI/NH$_3$) m/z 616 (M + H)$^+$ |
| 189 | 3-[6-(2,6-dichlorophenyl)-2-{[4-(4-methylpiperazin-1-yl)phenyl]amino}-5-oxo-5,6-dihydropyrimido[4,5-d]pyridazin-8-yl]-N,N-dimethylbenzamide | $^1$H NMR (400 MHz, CDCl$_3$): δ 2.87 (s, 3 H), 2.90-3.06 (m, 2 H), 3.10-3.27 (m, 2 H), 3.48 (s, 6 H), 3.51-3.62 (m, 2 H), 3.80 (d, J = 13.09 Hz, 2 H), 6.96 (d, J = 8.33 Hz, 2 H), 7.51-7.69 (m, 6 H), 7.71-7.82 (m, 2 H), 7.90 (s, 1 H), 9.39 (s, 1 H) | MS (DCI/NH$_3$) m/z 629 (M + H)$^+$ |
| 193 | 6-(2,6-dichlorophenyl)-2-{[3-methyl-4-(4-methyl-1,4-diazepan-1-yl)phenyl]amino}-8-(pyridin-4-yl)pyrimido[4,5-d]pyridazin-5(6H)-one | $^1$H NMR (300 MHz, DMSO-d$_6$) δ 2.03-2.29 (m, 4 H), 2.91 (s, 3 H), 3.02-3.13 (m, 2 H), 3.17 (s, 3 H), 3.20-3.37 (m, 2 H), 3.38-3.58 (m, 2 H), 7.03-7.11 (m, 1 H), 7.44 (dd, J = 8.53, 2.18 Hz, 1 H), 7.57-7.68 (m, 2 H), 7.74-7.80 (m, 2 H), 7.88-8.02 (m, 2 H), 8.74 (d, J = 5.95 Hz, 2 H), 9.42 (s, 1 H) | MS (DCI/NH$_3$) m/z 684 (M + H)$^+$ |
| 194 | 6-(2,6-dichlorophenyl)-2-{[4-(4-methylpiperazin-1-yl)phenyl]amino}-8-[3-(piperidin-1-ylcarbonyl)phenyl]pyrimido[4,5-d]pyridazin-5(6H)-one | $^1$H NMR (300 MHz, DMSO-d$_6$) δ 2.88 (s, 3 H), 2.92-3.02 (m, 2 H), 3.05-3.39 (m, 2 H), 3.42-3.91 (m, 14 H), 6.97 (d, J = 8.33 Hz, 2 H), 7.50-7.70 (m, 4 H), 7.73-7.79 (m, 3 H), 8.03 (d, J = 7.54 Hz, 2 H), 9.39 (s, 1 H) | MS (DCI/NH$_3$) m/z 669 (M + H)$^+$ |
| 195 | 6-(2,6-dichlorophenyl)-2-[(2'-methyl-2',3'-dihydro-1'H-spiro[cyclopropane-1,4'-isoquinolin]-7'-yl)amino]-8-(pyridin-4-yl)pyrimido[4,5-d]pyridazin-5(6H)-one | $^1$H NMR (300 MHz, DMSO-d$_6$) δ 2.94 (d, J = 3.39 Hz, 2 H), 3.17 (s, 3 H), 3.22-3.33 (m, 1 H), 3.43-3.64 (m, 1 H), 3.76 (m, 1 H), 3.97 (s, 1 H), 4.06-4.74 (m, 2 H), 6.88 (d, J = 8.82 Hz, 1 H), 7.23-7.31 (m, 1 H), 7.51-7.69 (m, 3 H), 7.75-7.80 (m, 2 H), 7.94 (d, J = 1.36 Hz, 2 H), 8.80 (t, J = 5.26 Hz, 1 H), 9.47 (s, 1 H) | MS (DCI/NH$_3$) m/z 669 (M + H)$^+$ |

TABLE 1-continued

| Ex | Name | ¹H NMR | MS |
|---|---|---|---|
| 196 | 8-(3,3-difluorocyclobutyl)-2-{[4-(4-methylpiperazin-1-yl)phenyl]amino}-6-(prop-2-en-1-yl)pyrimido[4,5-d]pyridazin-5(6H)-one | ¹H NMR (300 MHz, CDCl₃): δ 2.36-2.42 (m, 2 H), 2.63 (s, 2 H), 2.92-3.02 (m, 4 H), 3.25 (s, 4 H), 3.81-3.89 (m, 1 H), 4.78 (s, 2 H), 5.22-5.29 (m, 1 H), 5.97-6.08 (m, 1 H), 6.98 (d, J = 4.52 Hz, 2 H), 7.26 (d, J = 4.52 Hz, 3 H), 7.44-7.60 (m, 3 H), 9.37 (s, 1 H). | MS (DCI/NH₃) m/z 467 (M + H)⁺ |
| 197 | 8-(3,3-difluorocyclobutyl)-2-{[4-(4-methylpiperazin-1-yl)phenyl]amino}-6-(pyridin-2-yl)pyrimido[4,5-d]pyridazin-5(6H)-one | ¹H NMR (400 MHz, CDCl₃): δ 1.57 (m, 2 H), 2.43 (s, 3 H), 2.68 (m, 2 H), 2.97-3.04 (m, 4 H), 3.29 (m, 4 H), 3.89 (t, J = 8.5 Hz, 1 H), 7.00 (d, J = 9.03 Hz, 2 H), 7.38-7.43 (m, 1 H), 7.56 (d, 2 H), 7.62 (d, J = 8.28 Hz, 1 H), 7.88-7.94 (m, 1 H), 8.67-8.70 (m, 1 H), 9.41 (s, 1 H). | MS (DCI/NH₃) m/z 505 (M + H)⁺ |
| 198 | 8-(3,3-difluorocyclobutyl)-6-(2-fluorophenyl)-2-{[4-(4-methylpiperazin-1-yl)phenyl]amino}pyrimido[4,5-d]pyridazin-5(6H)-one | ¹H NMR (400 MHz, CDCl₃): δ 2.39 (s, 3 H), 2.62-2.65 (m, 4 H), 2.93-3.03 (m, 4 H), 3.23-3.29 (m, 4 H), 3.86-3.94 (m, 1 H), 7.00 (d, J = 8.78 Hz, 2 H), 7.23-7.33 (m, 2 H), 7.43-7.51 (m, 2 H), 7.53-7.59 (m, 2 H), 9.41 (s, 1 H). | MS (DCI/NH₃) m/z 522 (M + H)⁺ |
| 199 | 8-(3,3-difluorocyclobutyl)-6-(3-fluorophenyl)-2-{[4-(4-methylpiperazin-1-yl)phenyl]amino}pyrimido[4,5-d]pyridazin-5(6H)-one | ¹H NMR (400 MHz, CDCl₃): δ 2.38 (s, 3 H), 2.64 (m, 4 H), 2.96-3.06 (m, 4 H), 3.24-3.30 (m, 4 H), 3.87-3.96 (m, 1 H), 7.00 (d, J = 8.78 Hz, 2 H), 7.08-7.14 (m, 1 H), 7.42-7.49 (m, 2 H), 7.49-7.60 (m, 3 H), 9.42 (s, 1 H) | MS (DCI/NH₃) m/z 522 (M + H)⁺ |
| 201 | 6-(2,6-dichlorophenyl)-8-(1-ethenyl-1H-pyrazol-4-yl)-2-{[4-(4-methylpiperazin-1-yl)phenyl]amino}pyrimido[4,5-d]pyridazin-5(6H)-one | ¹H NMR (300 MHz, DMSO-d₆) δ 2.89 (s, 3 H), 2.98 (t, J = 12.04 Hz, 2 H), 3.12-3.29 (m, 2 H), 3.56 (d, J = 11.87 Hz, 2 H), 3.86 (d, J = 13.22 Hz, 2 H), 4.96 (d, J = 8.14 Hz, 1 H), 5.49 (d, J = 15.26 Hz, 1 H), 5.76 (d, 1 H), 7.09 (d, J = 8.82 Hz, 2 H), 7.56-7.61 (m, 4 H), 7.70-7.80 (m, 3 H),, 9.36 (s, 1 H) | MS (DCI/NH₃) m/z 574 (M + H)⁺ |
| 203 | 6-(2,6-dichlorophenyl)-8-(1-methyl-1H-imidazol-5-yl)-2-{[4-(4-methylpiperazin-1-yl)phenyl]amino}pyrimido[4,5-d]pyridazin-5(6H)-one | ¹H NMR (300 MHz, DMSO-d₆) δ 2.89 (s, 3 H), 2.99 (d, J = 12.55 Hz, 2 H), 3.18 (d, J = 5.43 Hz, 2 H), 3.55 (d, J = 10.17 Hz, 2 H), 3.73-3.91 (m, 5 H), 7.02 (d, J = 7.80 Hz, 2 H), 7.52-7.70 (m, 4 H), 7.74-7.82 (m, 3 H), 9.40 (s, 1 H) | MS (DCI/NH₃) m/z 562 (M + H)⁺ |
| 204 | 6-(2-chlorophenyl)-2-({4-[(dimethylamino)methyl]phenyl}amino)-8-phenylpyrimido[4,5-d]pyridazin-5(6H)-one | ¹H NMR (400 MHz, DMSO-d₆) δ 10.80 (s, 1 H), 9.45 (s, 1 H), 7.92-7.94 (m, 2 H), 7.83 (d, J = 8.4 Hz, 2 H), 7.71-7.7.74 (m, 2 H), 7.54-7.59 (m, 5 H), 7.39 (d, J = 8.0 Hz, 2 H), 3.88 (s, 2 H), 2.46 (s, 6 H) | MS (ESI) m/z 483 (M + H)⁺ |
| 205 | 6-(2-chlorophenyl)-2-({3-methyl-4-[4-(propan-2-yl)piperazin-1-yl]phenyl}amino)-8-phenylpyrimido[4,5-d]pyridazin-5(6H)-one | ¹H NMR (400 MHz, DMSO-d₆) δ 10.57 (s, 1 H), 9.38 (s, 1 H), 7.91 (d, J = 3.6 Hz, 2 H), 7.65-7.73 (m, 3 H), 7.48-7.59 (m, 6 H), 6.96 (d, J = 8.0 Hz, 1 H), 3.02-3.03 (m, 9 H), 2.16 (s, 3 H), 1.12 (s, 6 H). | MS (ESI) m/z 566 (M + H)⁺ |
| 206 | 6-(2-chlorophenyl)-2-({3-methyl-4-[4-(propan-2-yl)-1,4-diazepan-1-yl]phenyl}amino)-8-phenylpyrimido[4,5-d]pyridazin-5(6H)-one | ¹H NMR (400 MHz, DMSO-d₆) δ 10.56 (s, 1 H), 9.38 (s, 1 H), 7.91 (d, J = 7.2 Hz, 2 H), 7.70-7.73 (m, 2 H), 7.64 (s, 1 H), 7.03-7.59 (m, 6 H), 7.02 (d, J = 8.0 Hz, 1 H), 3.07-3.51 (m, 9 H), 2.17 (s, 3 H), 2.05 (s, 2 H), 1.28 (s, 6 H). | MS (ESI) m/z 580 (M + H)⁺ |
| 207 | 6-(2-chlorophenyl)-2-({3-methoxy-4-[4-(propan-2-yl)piperazin-1-yl]phenyl}amino)-8-phenylpyrimido[4,5-d]pyridazin-5(6H)-one | ¹H NMR (400 MHz, DMSO-d6) δ 10.57 (s, 1 H), 9.39 (s, 1 H), 7.89 (d, J = 7.0 Hz, 2 H), 7.70-7.72 (m, 2 H), 7.46-7.58 (m, 5 H), 7.31-7.36 (m, 2 H), 6.81 (d, J = 7.2 Hz, 1 H), 3.44 (m, 3 H), 3.07-3.35 (m, 9 H), 1.23 (d, J = 4.0 Hz, 6 H). | MS (ESI) m/z 582 (M + H)⁺ |
| 208 | 2-({4-[(dimethylamino)methyl]phenyl}amino)-6-(2-methylphenyl)-8-(thiophen-2-yl)pyrimido[4,5-d]pyridazin-5(6H)-one | ¹H NMR (400 MHz, DMSO-d₆) δ 10.71 (s, 1 H), 9.40 (s, 1 H), 8.30 (s, 1 H), 7.77 (d, J = 4.4 Hz, 2 H), 7.68 (d, J = 4.8 Hz, 1 H), 7.37-7.47 (m, 6 H), 7.17 (s, 1 H), | MS (ESI) m/z 469 (M + H)⁺ |

TABLE 1-continued

| Ex | Name | ¹H NMR | MS |
|---|---|---|---|
| | | 3.78 (s, 2 H), 2.40 (s, 6 H), 2.17 (s, 3 H). | |
| 209 | 6-(2-chlorophenyl)-2-({4-[(dimethylamino)methyl]phenyl}amino)-8-(thiophen-2-yl)pyrimido[4,5-d]pyridazin-5(6H)-one | ¹H NMR (400 MHz, DMSO-d₆) δ 10.81 (s, 1 H), 9.41 (s, 1 H), 8.30 (s, 1H), 7.80 (d, J = 8.4 Hz, 2 H), 7.67-7.73 (m, 3 H), 7.53-7.60 (m, 4 H), 7.19 (t, J = 4.0 Hz, 1 H), 3.99 (s, 2 H), 2.53 (s, 6 H). | MS (ESI) m/z 489 (M + H)⁺ |
| 210 | 2-({4-[(dimethylamino)methyl]phenyl}amino)-6-(prop-2-en-1-yl)-8-(thiophen-2-yl)pyrimido[4,5-d]pyridazin-5(6H)-one | ¹H NMR (400 MHz, DMSO-d₆) δ 10.56 (s, 1 H), 9.34 (s, 1 H), 8.25 (s, 1 H), 7.67-7.70 (m, 3 H), 7.33 (d, J = 8.0 Hz, 2 H), 7.13 (s, 1 H), 5.97-6.07 (m, 1 H), 5.24 (s, 1H), 5.20 (d, J = 6.0 Hz, 1 H), 4.73 (d, J = 5.6 Hz, 2 H), 3.50 (s, 2 H), 2.24 (s, 6 H). | MS (ESI) m/z 419 (M + H)⁺ |
| 217 | 6-(2,6-dichlorophenyl)-8-(pyridin-2-yl)-2-(1,2,3,4-tetrahydroisoquinolin-7-ylamino)pyrimido[4,5-d]pyridazin-5(6H)-one | ¹H NMR (300 MHz, DMSO-d₆) δ 2.94 (t, J = 6.10 Hz, 2 H), 3.38 (d, J = 4.41 Hz, 2 H), 4.02-4.15 (m, 2 H), 7.14 (d, J = 8.14 Hz, 2 H), 7.53-7.68 (m, 3 H), 7.74-7.80 (m, 2 H), 7.87 (d, J = 7.80 Hz, 1 H), 7.99-8.07 (m, 1 H), 8.82 (d, J = 4.41 Hz, 1 H), 9.46 (s, 1 H) | MS (DCI/NH₃) m/z 516 (M + H)⁺ |
| 220 | 6-(2,6-dichlorophenyl)-2-{[4-(piperazin-1-yl)phenyl]amino}-8-(pyrazin-2-yl)pyrimido[4,5-d]pyridazin-5(6H)-one | ¹H NMR (300 MHz, DMSO-d₆) δ 3.13-3.32 (m, 4 H), 3.37-3.71 (m, 4 H), 6.90 (d, J = 8.14 Hz, 2 H), 7.58-7.68 (m, 4 H), 7.72-7.81 (m, 3 H), 8.81 (d, J = 2.71 Hz, 1 H), 9.40 (s, 1 H) | MS (DCI/NH₃) m/z 546 (M + H)⁺ |
| 221 | 6-(2,6-dichlorophenyl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one | ¹H NMR (300 MHz, DMSO-d₆) δ 1.07 (s, 4 H), 3.81-4.29 (m, 4 H), 6.79 (d, J = 8.48 Hz, 1 H), 7.48-7.69 (m, 4 H), 7.73-7.80 (m, 2 H), 7.89 (d, J = 7.80 Hz, 1 H), 8.00-8.13 (m, 1 H), 8.83 (d, J = 4.41 Hz, 1 H), 9.45 (s, 1 H) | MS (DCI/NH₃) m/z 542 (M + H)⁺ |
| 223 | 6-(2,6-dichlorophenyl)-2-(3-methyl-4-(4-methyl-1,4-diazepan-1-yl)phenylamino)-8-(pyridin-2-yl)pyridazino[4,5-d]pyrimidin-5(6H)-one | ¹H NMR (300 MHz, DMSO-d₆) δ 2.03-2.11 (m, 2 H), 2.14 (s, 3 H), 2.91 (s, 3 H), 3.01-3.09 (m, 2 H), 3.15-3.36 (m, 4 H), 3.36-3.58 (m, 3 H), 7.00 (d, J = 8.33 Hz, 1 H), 7.45-7.67 (m, 4 H), 7.73-7.80 (m, 3 H), 7.95-8.04 (m, 1 H), 8.79 (d, J = 4.36 Hz, 1 H), 9.41 (s, 1 H) | MS (DCI/NH₃) m/z 587 (M + H)⁺ |
| 224 | 6-(2,6-dichlorophenyl)-8-(pyridin-4-yl)-2-(1,2,3,4-tetrahydroisoquinolin-7-ylamino)pyrimido[4,5-d]pyridazin-5(6H)-one | ¹H NMR (300 MHz, DMSO-d₆) δ 2.98 (t, J = 6.15 Hz, 2 H), 3.33-3.48 (m, 2 H), 4.03-4.24 (m, 2 H), 7.22 (d, J = 8.72 Hz, 1 H), 7.51-7.70 (m, 3 H), 7.72-7.82 (m, 2 H), 7.95 (d, J = 3.97 Hz, 2 H), 8.79 (d, J = 5.55 Hz, 2 H), 9.47 (s, 1 H) | MS (DCI/NH₃) m/z 516 (M + H)⁺ |
| 226 | 6-(2,6-dichlorophenyl)-8-(6-fluoropyridin-2-yl)-2-{[4-(piperazin-1-yl)phenyl]amino}pyrimido[4,5-d]pyridazin-5(6H)-one | ¹H NMR (300 MHz, DMSO-d₆) δ 1.70-1.85 (m, 1 H), 1.82-1.99 (m, 1 H), 2.70-2.89 (m, 2 H), 2.92-3.10 (m, 2 H), 3.34-3.43 (m, 2 H), 7.14 (d, J = 8.33 Hz, 2 H), 7.40 (dd, J = 8.33, 2.38 Hz, 1 H), 7.59-7.70 (m, 1 H), 7.72-7.96 (m, 5 H), 8.19 (q, J = 8.33 Hz, 1 H), 9.44 (s, 1 H) | MS (DCI/NH₃) m/z 563 (M + H)⁺ |
| 227 | 6-(2,6-dichlorophenyl)-8-(6-fluoropyridin-2-yl)-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (300 MHz, DMSO-d₆) δ 0.78-1.41 (m, 4 H), 2.95 (s, 3 H), 3.23 (d, J = 12.29 Hz, 2 H), 4.31 (s, 2 H), 6.80 (d, J = 8.72 Hz, 1 H), 7.44 (d, J = 5.95 Hz, 1 H), 7.58-7.81 (m, 5 H), 7.89 (dd, J = 7.54, 1.98 Hz, 1 H), 8.25 (q, J = 8.20 Hz, 1 H), 9.46 (s, 1 H) | MS (DCI/NH₃) m/z 574 (M + H)⁺ |
| 228 | 8-(furan-2-yl)-2-({3-methyl-4-[4-(propan-2-yl)-1,4-diazepan-1-yl]phenyl}amino)-6-(prop-2-en-1-yl)pyrimido[4,5-d]pyridazin-5(6H)-one | ¹H NMR (400 MHz, DMSO-d₆) δ 10.43 (s, 1 H), 9.28 (s, 1 H), 7.88 (d, J = 1.2 Hz, 1 H), 7.39-7.67 (m, 3 H), 7.12 (d, J = 8.4 Hz, 1 H), 6.67 (s, 1 H), 5.95-6.05 (m, 1 H), 5.22 (s, 1 H), 5.17-5.19 (m, 1 H), 4.75 (d, J = 4.8 Hz, 2 H), | MS (ESI) m/z 500 (M + H)⁺ |

TABLE 1-continued

| Ex | Name | ¹H NMR | MS |
|---|---|---|---|
| | | 3.12-3.66 (m, 9 H), 2.30 (s, 3 H), 2.00-2.03 (m, 2 H), 1.31 (d, J = 5.6 Hz, 6 H) | |
| 229 | 6-(2,6-dichlorophenyl)-8-[4-(2-oxopyrrolidin-1-yl)phenyl]-2-{[4-(piperazin-1-yl)phenyl]amino}pyrimido[4,5-d]pyridazin-5(6H)-one | ¹H NMR (300 MHz, DMSO-d₆) 2.00-2.20 (m, 2 H), 2.40-2.61 (m, 4 H), 3.22-3.45 (m, 6 H), 3.89 (q, J = 6.74 Hz, 2 H), 6.99 (d, J = 8.33 Hz, 2 H), 7.56-7.66 (m, 2 H), 7.72-7.85 (m, 4 H), 7.90-8.00 (m, 3 H), 9.37 (s, 1 H) | MS (DCI/NH₃) m/z 627 (M + H)⁺ |
| 230 | 2-[(2-methyl-1,2,3,4-tetrahydroisoquinolin-7-yl)amino]-8-phenyl-6-(prop-2-en-1-yl)pyrimido[4,5-d]pyridazin-5(6H)-one | ¹H NMR (400 MHz, DMSO-d₆): 10.46 (s, 1 H), 9.32 (s, 1 H) 7.83 (d, J = 2.4 Hz, 2 H), 7.46-7.52 (m, 4 H), 7.40 (d, J = 8.4 Hz, 1 H), 6.98 (d, J = 8.4 Hz, 1 H), 5.98-6.07 (m, 1 H), 5.23 (d, J = 3.6 Hz, 1 H), 5.20 (s, 1 H), 4.76 (d, J = 5.2 Hz, 2 H), 3.35 (s, 2 H), 2.54-2.77 (m, 4 H), 2.38 (s, 3 H) | MS (ESI) m/z 425 (M + H)⁺ |
| 231 | 6-(2,6-dichlorophenyl)-2-{[4-(4-methylpiperazin-1-yl)phenyl]amino}-8-(1H-pyrazol-3-yl)pyrimido[4,5-d]pyridazin-5(6H)-one | ¹H NMR (300 MHz, DMSO-d₆) δ 2.87 (d, 3 H), 2.98 (d, J = 11.90 Hz, 2 H), 3.11-3.27 (m, 2 H), 3.55 (d, J = 12.69 Hz, 2 H), 3.84 (d, J = 13.09 Hz, 2 H), 7.06 (d, J = 8.73 Hz, 2 H), 7.54-7.67 (m, 4 H), 7.72-7.81 (m, 3 H), 9.37 (s, 1 H) | MS (DCI/NH₃) m/z 548 (M + H)⁺ |
| 232 | 6-(2,6-dichlorophenyl)-2-{[4-(4-methylpiperazin-1-yl)phenyl]amino}-8-{1-[2-(piperidin-1-yl)ethyl]-1H-pyrazol-3-yl}pyrimido[4,5-d]pyridazin-5(6H)-one | ¹H NMR (300 MHz, DMSO-d₆) δ 1.41-1.82 (m, 6 H), 2.85-2.97 (m, 6 H), 2.88 (s, 3 H), 2.97-3.07 (m, 4 H), 3.09-3.28 (m, 2 H), 3.83 (d, J = 13.48 Hz, 2 H), 4.64 (t, J = 6.35 Hz, 2 H), 7.02 (d, J = 8.33 Hz, 2 H), 7.50-7.70 (m, 4 H), 7.72-7.83 (m, 3 H), 9.38 (s, 1 H) | MS (DCI/NH₃) m/z 659 (M + H)⁺ |
| 233 | 8-(furan-2-yl)-6-(2-methylphenyl)-2-[(2-methyl-1,2,3,4-tetrahydroisoquinolin-7-yl)amino]pyrimido[4,5-d]pyridazin-5(6H)-one | ¹H NMR (400 MHz, DMSO-d₆ + D₂O): 9.39 (d, J = 2.4 Hz, 1 H), 7.83 (s, 1 H), 7.68 (s, 1 H), 7.63 (d, J = 8.4 Hz, 1 H), 7.35-7.46 (m, 6 H), 6.77 (s, 1 H), 4.39 (s, 2 H), 3.54-3.56 (m, 2 H), 3.16 (s, 2 H), 2.99 (s, 3 H), 2.14 (s, 3 H) | MS (ESI) m/z 465 (M + H)⁺ |
| 234 | 8-[1-(2-chloroethyl)-1H-pyrazol-3-yl]-6-(2,6-dichlorophenyl)-2-{[4-(4-methylpiperazin-1-yl)phenyl]amino}pyrimido[4,5-d]pyridazin-5(6H)-one | ¹H NMR (300 MHz, DMSO-d₆) δ 2.88 (s, 3 H), 2.97 (d, J = 11.90 Hz, 2 H), 3.15-3.23 (m, 2 H), 3.54 (d, J = 11.90 Hz, 2 H), 3.82 (d, J = 13.09 Hz, 2 H), 4.05 (t, J = 5.75 Hz, 2 H), 4.59 (s, 2 H), 7.00 (d, J = 8.33 Hz, 2 H), 7.56-7.70 (m, 2 H), 7.72-7.78 (m, 2 H), 7.84 (d, J = 7.14 Hz, 2 H), 7.95 (s, 1 H), 9.36 (s, 1 H) | MS (DCI/NH₃) m/z 610 (M + H)⁺ |
| 236 | 6-(2,6-dichlorophenyl)-8-(1-ethenyl-1H-pyrazol-3-yl)-2-{[4-(4-methylpiperazin-1-yl)phenyl]amino}pyrimido[4,5-d]pyridazin-5(6H)-one | 1H NMR (300 MHz, DMSO-d₆) δ 2.90 (s, 3 H), 2.91-3.05 (m, 2 H), 3.08-3.30 (m, 2 H), 3.45-3.62 (m, 2 H), 3.80 (d, J = 13.09 Hz, 2 H), 5.01 (d, J = 9.12 Hz, 1 H), 5.70 (d, J = 15.86 Hz, 1 H), 6.92-7.00 (m, 2 H), 7.25-7.45 (m, 1 H), 7.51-7.68 (m, 2 H), 7.72-7.81 (m, 3 H), 7.80-7.98 (m, 1 H), 8.18-8.31 (m, 1 H), 9.37 (s, 1 H) | MS (DCI/NH3) m/z 574 (M + H)⁺ |
| 238 | 2-[(4,4-dimethyl-1,2,3,4-tetrahydroisoquinolin-7-yl)amino]-8-(pyridin-2-yl)-6-(pyridin-4-yl)pyrimido[4,5-d]pyridazin-5(6H)-one | ¹H NMR (400 MHz, CD₃OD): δ 9.26 (s, 1 H), 8.70-8.68 (m, 1 H), 8.55 (d, J = 6.4 Hz, 2 H), 7.97-7.91 (m, 2 H), 7.89 (d, J = 6.4 Hz, 2 H), 7.56-7.54 (m, 1 H), 7.30-7.24 (m, 2 H), 7.15-7.13 (m, 1 H), 3.64 (s, 2 H), 2.74 (s, 2 H), 1.17 (s, 6 H) | MS (ESI) m/z 477 (M + H)⁺ |
| 239 | 8-(pyridin-2-yl)-6-(pyridin-4-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, CD₃OD): δ 9.30 (s, 1 H), 8.70 (s, 1 H), 8.61-8.56 (m, 1 H), 7.96-7.86 (m, 4 H), 7.55 (s, 1 H), 7.34-7.12 (m, 3 H), 3.19-3.21 (m, 2 H), 2.34-2.31 (m, 5 H), 1.19-1.10 (m, 6 H) | MS (ESI) m/z 491 (M + H)⁺ |
| 240 | 6-(2,6-dichlorophenyl)-8-{1-[2-(dimethylamino)ethyl]-1H-pyrazol-3-yl}-2-{[4-(4- | 1H NMR (300 MHz, DMSO-d₆) δ 2.80 (s, 6 H), 2.89 (s, 3 H), 2.98 (d, | MS (DCI/NH3) |

TABLE 1-continued

| Ex | Name | ¹H NMR | MS |
|----|------|--------|-----|
|  | methylpiperazin-1-yl)phenyl]amino}pyrimido[4,5-d]pyridazin-5(6H)-one | J = 12.89 Hz, 2 H), 3.10-3.26 (m, 2 H), 3.49-3.67 (m, 4 H), 3.82 (d, J = 12.55 Hz, 2 H), 4.63 (t, J = 6.61 Hz, 2 H), 7.01 (d, J = 8.48 Hz, 2 H), 7.55-7.67 (m, 3 H), 7.69-7.82 (m, 3 H), 8.00 (d, J = 2.03 Hz, 1 H), 9.37 (s, 1 H) | m/z 619 (M + H)⁺ |
| 241 | 6-(2,6-dichlorophenyl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, DMSO-d₆): δ 10.87 (br s, 1 H), 10.63 (br, 1 H), 9.47 (s, 1 H), 8.86 (s, 1 H), 8.10 (s, 1 H), 7.89-7.87 (m, 1 H), 7.78-7.76 (m, 2 H), 7.66-7.62 (m, 3 H), 7.53 (s, 1 H), 7.42-7.40 (m, 1 H), 4.13-3.97 (m, 2 H), 3.46-3.42 (m, 1 H), 3.25-3.19 (m, 1 H), 2.95-2.94 (m, 3 H), 1.45 (s, 3 H), 1.31 (s, 3 H) | MS (ESI) m/z 558 (M + H)⁺ |
| 242 | 6-(2-hydroxyethyl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, DMSO-d₆): δ 10.42 (br s, 1 H), 9.33 (s, 1 H), 8.81-8.80 (m, 1 H), 8.02-7.99 (m, 1 H), 7.83-7.78 (m, 1 H), 7.58-7.55 (m, 1 H), 7.46-7.41 (m, 2 H), 7.22-7.20 (m, 1 H), 4.83 (br, 1 H), 4.24-4.21 (m, 2 H), 3.78-3.77 (m, 2 H), 3.26-3.17 (m, 2 H), 2.42-2.35 (m, 5 H), 1.21 (m, 6 H) | MS (ESI) m/z 458 (M + H)⁺ |
| 243 | 6-(2,6-dichlorophenyl)-8-(6-fluoropyridin-2-yl)-2-{[4-(4-methylpiperazin-1-yl)phenyl]amino}pyrimido[4,5-d]pyridazin-5(6H)-one | ¹H NMR (300 MHz, DMSO-d₆) δ 2.88 (s, 3 H), 2.90-2.98 (m, 2 H), 3.06-3.28 (m, 2 H), 3.53 (d, J = 12.30 Hz, 2 H), 3.77 (d, J = 11.50 Hz, 2 H), 6.92 (d, J = 8.33 Hz, 2 H), 7.13 (d, J = 7.54 Hz, 1 H), 7.38 (dd, J = 8.33, 1.98 Hz, 1 H), 7.59-7.66 (m, 1 H), 7.70-7.77 (m, 3 H), 7.83-7.94 (m, 1 H), 8.20 (q, J = 8.33 Hz, 1 H), 9.39 (s, 1 H) | MS (DCI/NH3) m/z 577 (M + H)⁺ |
| 244 | 6-(2,6-dichlorophenyl)-2-{[4-(4-methylpiperazin-1-yl)phenyl]amino}-8-[4-(2-oxopyrrolidin-1-yl)phenyl]pyrimido[4,5-d]pyridazin-5(6H)-one | ¹H NMR (300 MHz, DMSO-d₆): δ 1.91-2.01 (m, 2 H), 2.00-2.16 (m, 4 H), 2.52-2.61 (m, 2 H), 2.85 (s, 3 H), 2.95-3.22 (m, 2 H), 3.84 (t, J = 7.14 Hz, 2 H), 3.90 (t, J = 7.14 Hz, 2 H), 6.99 (d, J = 8.73 Hz, 2 H), 7.46 (d, J = 8.33 Hz, 2 H), 7.53-7.59 (m, 2 H), 7.62-7.72 (m, 2 H), 7.73-7.83 (m, 1 H), 7.93 (d, J = 7.93 Hz, 2 H), 9.41 (s, 1 H) | MS (DCI/NH₃) m/z 641 (M + H)⁺ |
| 245 | 6-(2-chlorophenyl)-2-[(2-methyl-1,2,3,4-tetrahydroisoquinolin-7-yl)amino]-8-phenylpyrimido[4,5-d]pyridazin-5(6H)-one | ¹H NMR (400 MHz, DMSO-d₆): δ 11.60 (s, 1 H), 9.40 (s, 1 H), 7.88 (d, J = 4.8 Hz, 1 H), 7.70-7.736 (m, 2 H), 7.52-7.59 (m, 6 H), 7.42 (d, J = 7.6 Hz, 1 H), 7.02 (d, J = 8.4 Hz, 1 H), 3.32 (s, 2 H), 2.76-2.77 (m, 2 H), 2.67 (s, 2 H), 2.36 (s, 3 H) | MS (ESI) m/z 495 (M + H)⁺ |
| 246 | 8-(furan-2-yl)-6-(2-methylphenyl)-2-({3-methyl-4-[4-(propan-2-yl)-1,4-diazepan-1-yl]phenyl}amino)pyrimido[4,5-d]pyridazin-5(6H)-one | ¹H NMR (400 MHz, DMSO-d₆): δ 10.54 (s, 1 H), 9.34 (s, 1 H), 7.85 (d, J = 1.2 Hz, 1 H), 7.62-7.71 (m, 2 H), 7.35-7.45 (m, 5 H), 7.15 (d, J = 8.8 Hz, 1 H), 6.69 (s, 1 H), 3.13-3.59 (m, 9 H), 2.32 (s, 3 H), 2.15 (s, 5 H), 1.31 (d, J = 5.6 Hz, 6 H) | MS (ESI) m/z 550 (M + H)⁺ |
| 247 | 6-(2,6-dichlorophenyl)-8-[4-(2-oxopyrrolidin-1-yl)phenyl]-2-(1,2,3,4-tetrahydroisoquinolin-7-ylamino)pyrimido[4,5-d]pyridazin-5(6H)-one | ¹H NMR (300 MHz, DMSO-d₆): δ 2.13 (t, J = 7.63 Hz, 2 H), 2.54-2.63 (m, 2 H), 2.97 (t, J = 5.93 Hz, 2 H), 3.35-3.41 (m, 2 H), 3.91 (t, J = 6.95 Hz, 2 H), 4.16 (s, 2 H), 7.21 (d, J = 8.48 Hz, 1 H), 7.56 (dd, J = 8.31, 2.20 Hz, 1 H), 7.59-7.66 (m, 1 H), 7.74-7.79 (m, 2 H), 7.76-7.85 (m, 3 H), 7.91-7.96 (m, 2 H), 9.45 (s, 1 H) | MS (DCI/NH₃) m/z 598 (M + H)⁺ |
| 249 | 6-cyclohexyl-2-{[4-(piperazin-1-yl)phenyl]amino}-8-(pyridin-2-yl)pyrimido[4,5-d]pyridazin-5(6H)-one | ¹HNMR (400 MHz, DMSO-d₆): δ 10.36 (br s, 1 H), 9.29 (s, 1 H), 8.83 (s, 1 H), 8.01-7.98 (m, 1 H), 7.85-7.83 (m, 1 H), 7.66-7.54 (m, 3 H), 6.80-6.78 (m, 2 H), 4.90-4.85 (m, 1 H), 3.17 (s, 1 H), 3.00-2.99 (m, 4 H), 2.88-2.86 (m, 4 H), | MS (ESI) m/z 483 (M + H)⁺ |

TABLE 1-continued

| Ex | Name | ¹H NMR | MS |
|---|---|---|---|
| | | 1.90-1.66 (m, 7 H), 1.48-1.39 (m, 2 H), 1.23-1.17 (m, 1 H) | |
| 251 | 6-(2,6-dichlorophenyl)-8-(pyrazin-2-yl)-2-(1,2,3,4-tetrahydroisoquinolin-7-ylamino)pyrimido[4,5-d]pyridazin-5(6H)-one | ¹H NMR (300 MHz, DMSO-$d_6$): δ 2.95 (t, J = 6.10 Hz, 2 H), 3.34-3.42 (m, 2 H), 4.14 (s, 2 H), 7.16 (d, J = 8.14 Hz, 1 H), 7.53 (dd, J = 8.48, 2.03 Hz, 1 H), 7.64 (dd, J = 9.16, 7.12 Hz, 2 H), 7.74-7.82 (m, 2 H), 8.83 (d, J = 2.37 Hz, 1 H), 8.90 (s, 1 H), 9.25 (s, 1 H), 9.48 (s, 1 H) | MS (DCI/NH$_3$) m/z 517M + H)⁺ |
| 252 | 6-(2,6-dichlorophenyl)-8-[1-(2-methoxyethyl)-1H-pyrazol-3-yl]-2-{[4-(4-methylpiperazin-1-yl)phenyl]amino}pyrimido[4,5-d]pyridazin-5(6H)-one | ¹H NMR (300 MHz, DMSO-$d_6$): δ 2.88 (s, 3 H), 2.93 (s, 3 H), 2.97 (s, 2 H), 3.10-3.27 (m, 2 H), 3.47-3.58 (m, 4 H), 3.82 (d, J = 12.21 Hz, 2 H), 4.40 (d, J = 3.73 Hz, 2 H), 6.95 (d, J = 8.48 Hz, 2 H), 7.56-7.70 (m, 4 H), 7.74-7.81 (m, 3 H), 9.38 (s, 1 H) | MS (DCI/NH$_3$) m/z 606 (M + H)⁺ |
| 253 | 6-(2,6-dichlorophenyl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one | ¹H NMR (300 MHz, DMSO-$d_6$): δ 1.11 (s, 4 H), 3.26 (s, 2 H), 4.24 (s, 2 H), 6.88 (d, J = 8.48 Hz, 1 H), 7.50-7.58 (m, 2 H), 7.61-7.71 (m, 1 H), 7.74-7.82 (m, 2 H), 8.13 (d, J = 1.70 Hz, 2 H), 8.89 (d, J = 6.10 Hz, 2 H), 9.47 (s, 1 H) | MS (DCI/NH$_3$) m/z 542 (M + H)⁺ |
| 254 | 6-(2,6-dichlorophenyl)-8-[4-(2-oxopyrrolidin-1-yl)phenyl]-2-{[4-(piperidin-4-yl)phenyl]amino}pyrimido[4,5-d]pyridazin-5(6H)-one | ¹H NMR (300 MHz, DMSO-$d_6$): δ 1.70-1.89 (m, 2 H), 1.91-2.00 (m, 2 H), 2.07-2.17 (m, 2 H), 2.57 (t, J = 8.13 Hz, 2 H), 2.77-2.89 (m, 1 H), 3.01 (d, J = 11.10 Hz, 2 H), 3.27-3.50 (m, 2 H), 3.91 (t, J = 6.94 Hz, 2 H), 7.20 (d, J = 8.33 Hz, 2 H), 7.58-7.67 (m, 1 H), 7.69-7.76 (m, 3 H), 7.76-7.84 (m, 3 H), 7.96 (d, J = 8.33 Hz, 2 H), 9.42 (s, 1 H). | MS (DCI/NH$_3$) m/z 626 (M + H)⁺ |
| 255 | 6-(2-chlorophenyl)-2-{[4-(morpholin-4-ylsulfonyl)phenyl]amino}-8-phenylpyrimido[4,5-d]pyridazin-5(6H)-one | ¹H NMR (400 MHz, DMSO-$d_6$) δ 11.12, (s, 1 H), 9.52 (s, 1 H), 8.05 (d, J = 8.8 Hz, 2 H), 7.90-7.92 (m, 2 H), 7.72-7.74 (m, 2 H), 7.60-7.63 (m, 2 H), 7.55-7.59 (m, 5H), 3.63 (s, 4 H), 2.85 (m, 4 H) | MS (ESI) m/z 575 (M + H)⁺ |
| 256 | 6-(2,6-dichlorophenyl)-8-(pyridin-4-yl)-2-[(2,4,4-trimethyl-1,2,3,4-tetrahydroisoquinolin-7-yl)amino]pyrimido[4,5-d]pyridazin-5(6H)-one | ¹H NMR (300 MHz, DMSO-$d_6$): δ 1.39 (s, 6 H), 3.00 (s, 3 H), 3.27 (t, J = 11.30 Hz, 2 H), 3.50 (d, J = 12.29 Hz, 2 H), 7.49 (d, J = 1.98 Hz, 1 H), 7.61-7.71 (m, 3 H), 7.74-7.81 (m, 2 H), 7.94 (d, J = 3.97 Hz, 2 H), 8.80 (d, J = 5.55 Hz, 2 H), 9.48 (s, 1 H) | MS (DCI/NH$_3$) m/z 558 (M + H)⁺ |
| 257 | 6-(2,6-dichlorophenyl)-2-(2',3'-dihydro-1'H-spiro[cyclopropane-1,4'-isoquinolin]-7'-ylamino)-8-(6-fluoropyridin-2-yl)pyrimido[4,5-d]pyridazin-5(6H)-one | ¹H NMR (300 MHz, DMSO-$d_6$): δ 1.08 (s, 4 H), 3.27 (s, 2 H), 4.19 (s, 2 H), 6.79 (d, J = 8.72 Hz, 1 H), 7.38 (dd, J = 8.33, 2.38 Hz, 1 H), 7.54 (d, J = 1.98 Hz, 1 H), 7.60-7.71 (m, 2 H), 7.73-7.81 (m, 2 H), 7.89 (d, J = 6.35 Hz, 1 H), 8.23 (q, J = 8.33 Hz, 1 H), 9.45 (s, 1 H) | MS (DCI/NH$_3$) m/z 560 (M + H)⁺ |
| 258 | 8-(furan-2-yl)-2-[(2-methyl-1,2,3,4-tetrahydroisoquinolin-7-yl)amino]-6-(prop-2-en-1-yl)pyrimido[4,5-d]pyridazin-5(6H)-one | ¹H NMR (400 MHz, DMSO-$d_6$) δ 11.31 (s, 1 H), 10.64 (s, 1 H), 9.33 (s, 1 H), 7.91 (s, 1 H), 7.57-7.68 (m, 3 H), 7.28 (d, J = 8.4 Hz, 1 H), 6.82 (s, 1 H), 5.96-6.05 (m, 1 H), 5.22 (s, 1 H), 5.19 (d, J = 5.6 Hz, 1 H), 4.76 (d, J = 4.8 Hz, 2 H), 4.29-4.38 (m, 2 H), 3.65 (m, 1 H), 3.28 (d, J = 2.0 Hz, 2 H), 3.00-3.03 (m, 1 H), 2.91 (s, 3 H) | MS (ESI) m/z 415 (M + H)⁺ |
| 262 | 6-cyclohexyl-8-(pyridin-2-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, CD$_3$OD) δ 9.52 (s, 1 H), 9.20-8.72 (m, 3 H), 8.12 (s, 1 H), 7.80-7.56 (m, 3 H), 5.05-4.99 (m, 1 H), 4.70-4.44 (m, 2 H), 3.60-3.57 (m, 1 H), 3.40-3.3 (m, 1 H), 3.14 (s, 3 H), 2.02-1.87 (m, 7 H), 1.60-1.38 (m, 9 H) | MS (ESI) m/z 496 (M + H)⁺ |

TABLE 1-continued

| Ex | Name | ¹H NMR | MS |
|---|---|---|---|
| 263 | 6-(2,6-dichlorophenyl)-2-[(4,4-dimethyl-1,2,3,4-tetrahydroisoquinolin-7-yl)amino]-8-(pyridin-2-yl)pyrimido[4,5-d]pyridazin-5(6H)-one | ¹HNMR (400 MHz, DMSO-$d_6$): δ 10.70 (br s, 1 H), 9.43 (s, 1 H), 8.81-8.80 (m, 1 H), 8.04-8.00 (m, 1 H), 7.88-7.86 (m, 1 H), 7.77-7.85 (m, 2 H), 7.65-7.58 (m, 2 H), 7.47-7.46 (m, 2 H), 7.27-7.25 (m, 1 H), 3.69 (s, 2 H), 2.78 (s, 2 H) 1.22 (s, 6 H) | MS (ESI) m/z 544 (M + H)⁺ |
| 264 | 2-[(4,4-dimethyl-1,2,3,4-tetrahydroisoquinolin-7-yl)amino]-6,8-di(pyridin-2-yl)pyrimido[4,5-d]pyridazin-5(6H)-one | ¹HNMR (400 MHz, CD₃OD): δ 9.24 (s, 1 H), 8.64 (s, 1 H), 8.51-8.50 (m, 1 H), 7.98-7.89 (m, 3 H), 7.68-7.66 (m, 1 H), 7.51-7.42 (m, 2 H), 7.30-7.24 (m, 2 H), 7.13-7.11 (m, 1 H), 3.62 (s, 2 H), 2.73 (s, 2 H), 1.16 (s, 6 H) | MS (ESI) m/z 477 (M + H)⁺ |
| 265 | 6-(2,6-dichlorophenyl)-8-(1-methyl-1H-pyrazol-3-yl)-2-{[4-(piperazin-1-yl)phenyl]amino}pyrimido[4,5-d]pyridazin-5(6H)-one | ¹H NMR (300 MHz, DMSO-$d_6$): δ 2.99 (t, J = 5.95 Hz, 2 H) 3.35-3.51 (m, 2 H), 3.96 (s, 3 H), 4.22 (s, 2 H), 7.23 (d, J = 8.33 Hz, 1 H), 7.58-7.68 (m, 2 H), 7.68-7.81 (m, 4 H), 7.89 (d, J = 1.98 Hz, 1 H), 9.43 (s, 1 H) | MS (DCI/NH₃) m/z 519 (M + H)⁺ |
| 267 | 6-(2-hydroxyethyl)-2-{[4-(piperazin-1-yl)phenyl]amino}-8-(pyridin-2-yl)pyrimido[4,5-d]pyridazin-5(6H)-one | ¹HNMR (400 MHz, DMSO-$d_6$): δ 10.36 (br s, 1 H), 9.29 (s, 1 H), 8.81 (s, 1 H), 8.01-7.97 (m, 1 H), 7.86-7.84 (m, 1 H), 7.64-7.54 (m, 3 H), 6.80-6.78 (m, 2 H), 4.87-4.86 (m, 1 H), 4.23 (t, J = 5.6 Hz, 2 H), 3.78 (t, J = 5.6 Hz, 2 H), 2.97 (s, 4 H), 2.83 (s, 4 H) | MS (ESI) m/z 445 (M + H)⁺ |
| 268 | 6-(2,6-dichlorophenyl)-8-[1-(methoxymethyl)-1H-pyrazol-3-yl]-2-{[4-(4-methylpiperazin-1-yl)phenyl]amino}pyrimido[4,5-d]pyridazin-5(6H)-one | ¹H NMR (300 MHz, DMSO-$d_6$): δ 2.89 (s, 3 H), 2.91-3.04 (m, 2 H), 3.09-3.30 (m, 2 H), 3.55 (d, J = 10.51 Hz, 2 H), 3.61-3.68 (m, 5 H), 3.84 (d, J = 13.22 Hz, 2 H), 7.06 (d, J = 8.82 Hz, 2 H), 7.55-7.68 (m, 3 H), 7.68-7.82 (m, 4 H), 9.37 (s, 1 H) | MS (DCI/NH₃) m/z 592 (M + H)⁺ |
| 269 | 8-(furan-2-yl)-2-{[4-(2-oxopyrrolidin-1-yl)phenyl]amino}-6-(prop-2-en-1-yl)pyrimido[4,5-d]pyridazin-5(6H)-one | ¹H NMR (400 MHz, DMSO-$d_6$): δ 10.55 (s, 1 H), 9.31 (s, 1 H), 7.89 (d, J = 0.4 Hz, 1 H), 7.66-7.73 (m, 5 H), 6.67 (s, 1 H) 5.97-6.04 (m, 1 H), 5.22 (s, 1 H), 5.19 (dd, J = 1.2, 8.0 Hz, 1 H), 4.75 (d, J = 5.2 Hz, 2 H), 3.88 (t, J = 7.2 Hz, 2 H), 2.51 (t, J = 7.2 Hz, 2 H), 2.05-2.12 (m, 2 H) | MS (ESI) m/z 429 (M + H)⁺ |
| 272 | 2-{[4-(4-methylpiperazin-1-yl)phenyl]amino}-6-(propan-2-yl)-8-(pyridin-2-yl)pyrimido[4,5-d]pyridazin-5(6H)-one | ¹NMR (300 MHz, DMSO-$d_6$): δ 1.36 (d, J = 6.35 Hz, 6 H), 2.87 (s, 3 H), 2.88-3.03 (m, 2 H), 3.07-3.28 (m, 2 H), 3.53 (d, J = 11.90 Hz, 2 H), 3.78 (d, J = 13.09 Hz, 2 H), 5.11-5.42 (m, 1 H), 6.91 (d, J = 8.73 Hz, 2 H), 7.51-7.61 (m, 1 H), 7.72 (d, J = 5.95 Hz, 2 H), 7.90 (d, J = 7.54 Hz, 1 H), 7.97-8.11 (m, 1 H), 8.85 (d, J = 3.17 Hz, 1 H), 9.32 (s, 1 H) | MS (DCI/NH₃) m/z 457 (M + H)⁺ |
| 273 | 2-{[4-(4-methylpiperazin-1-yl)phenyl]amino}-6-(propan-2-yl)-8-(pyridin-4-yl)pyrimido[4,5-d]pyridazin-5(6H)-one | ¹NMR (300 MHz, DMSO-$d_6$): δ 1.38 (d, J = 6.35 Hz, 6 H), 2.88 (s, 3 H), 2.91-3.05 (m, 2 H), 3.08-3.32 (m, 2 H), 3.54 (d, J = 11.90 Hz, 2 H), 3.75 (m, 2 H), 5.11-5.41 (m, 1 H), 7.00 (d, J = 8.73 Hz, 2 H), 7.61 (d, J = 8.73 Hz, 2 H), 8.10 (m, 2 H), 8.78 (d, J = 6.35 Hz, 2 H), 9.33 (s, 1 H) | MS (DCI/NH₃) m/z 457 (M + H)⁺ |
| 274 | 2-[(2'-methyl-2',3'-dihydro-1'H-spiro[cyclopropane-1,4'-isoquinolin]-7'-yl)amino]-6-(propan-2-yl)-8-(pyridin-2-yl)pyrimido[4,5-d]pyridazin-5(6H)-one | ¹NMR (300 MHz, DMSO-$d_6$): δ 0.83-0.94 (m, 1 H), 1.00-1.10 (m, 1 H), 1.11-1.20 (m, 1 H), 1.27-1.33 (m, 1 H), 1.36 (d, J = 6.35 Hz, 6 H), 2.94 (s, 2 H), 4.28 (s, 2 H), 5.15-5.39 (m, 1 H), 6.79 (d, J = 8.73 Hz, 1 H), 7.51-7.70 (m, 3 H), 7.87 (d, J = 7.93 Hz, 1 H), 8.02-8.13 (m, 1 H), 8.87 (d, J = 4.76 Hz, 1 H), 9.38 (s, 1 H) | MS (DCI/NH₃) m/z 454 (M + H)⁺ |

TABLE 1-continued

| Ex | Name | ¹H NMR | MS |
|----|------|--------|-----|
| 275 | 2-[(2'-methyl-2',3'-dihydro-1'H-spiro[cyclopropane-1,4'-isoquinolin]-7'-yl)amino]-6-(propan-2-yl)-8-(pyridin-4-yl)pyrimido[4,5-d]pyridazin-5(6H)-one | ¹NMR (300 MHz, DMSO-$d_6$): δ 0.92 (d, J = 7.54 Hz, 1 H), 1.04-1.13 (m, 1 H), 1.13-1.23 (m, 1 H), 1.34 (m, 1 H), 1.38 (d, J = 6.35 Hz, 6 H), 2.94 (s, 2 H), 4.39 (s, 2 H), 5.18-5.43 (m, 1 H), 6.88 (d, J = 8.73 Hz, 1 H), 7.39-7.70 (m, 2 H), 8.09 (s, 2 H), 8.83 (d, J = 5.95 Hz, 2 H), 9.40 (s, 1 H) | MS (DCI/NH$_3$) m/z 454 (M + H)⁺ |
| 276 | 8-(4-bromophenyl)-6-(2,6-dichlorophenyl)-2-{[4-(4-methylpiperazin-1-yl)phenyl]amino}pyrimido[4,5-d]pyridazin-5(6H)-one | ¹NMR (300 MHz, DMSO-$d_6$): δ 2.84 (s, 3 H), 3.05 (d, J = 11.50 Hz, 2 H), 3.22 (d, J = 19.84 Hz, 2 H), 3.46 (dd, J = 14.48, 7.34 Hz, 2 H), 3.81 (d, J = 9.92 Hz, 2 H), 6.99 (d, J = 8.73 Hz, 2 H), 7.53-7.68 (m, 3 H), 7.68-7.79 (m, 4 H), 7.86 (d, J = 8.33 Hz, 2 H), 9.38 (s, 1 H) | MS (DCI/NH$_3$) m/z 638 (M + H)⁺ |
| 277 | methyl 4-[6-(2,6-dichlorophenyl)-2-{[4-(4-methylpiperazin-1-yl)phenyl]amino}-5-oxo-5,6-dihydropyrimido[4,5-d]pyridazin-8-yl]benzoate | ¹NMR (300 MHz, DMSO-$d_6$): δ 2.89 (s, 3 H), 2.92-3.03 (m, 2 H), 3.13-3.24 (m, 2 H), 3.55 (d, J = 12.30 Hz, 2 H), 3.81 (d, J = 13.09 Hz, 2 H), 3.91 (s, 3 H), 6.95 (d, J = 7.93 Hz, 2 H), 7.52-7.61 (m, 3 H), 7.62-7.68 (m, 1 H), 7.74-7.80 (m, 2 H), 8.06 (s, 3 H), 9.39 (s, 1 H) | MS (DCI/NH$_3$) m/z 617 (M + H)⁺ |
| 278 | 8-cyclobutyl-6-(2,6-dichlorophenyl)-2-{[4-(4-methylpiperazin-1-yl)phenyl]amino}pyrimido[4,5-d]pyridazin-5(6H)-one | ¹NMR (300 MHz, DMSO-$d_6$): δ 1.79-1.93 (m, 1 H), 1.97-2.14 (m, 1 H), 2.18-2.31 (m, 2 H), 2.29-2.41 (m, 2 H), 2.88 (s, 3 H), 2.97 (d, J = 12.30 Hz, 2 H), 3.09-3.27 (m, 2 H), 3.54 (d, J = 11.50 Hz, 2 H), 3.85 (d, J = 13.09 Hz, 2 H), 4.00-4.17 (m, 1 H), 7.08 (d, J = 8.33 Hz, 2 H), 7.52-7.65 (m, 2 H), 7.71-7.76 (m, 2 H), 7.74-7.84 (m, 1 H), 9.30 (s, 1 H) | MS (DCI/NH$_3$) m/z 536 (M + H)⁺ |
| 279 | 8-cyclobutyl-6-(2,6-dichlorophenyl)-2-{[4-(piperazin-1-yl)phenyl]amino}pyrimido[4,5-d]pyridazin-5(6H)-one | ¹NMR (300 MHz, DMSO-$d_6$): δ 1.76-1.95 (m, 1 H), 1.92-2.14 (m, 1 H), 2.15-2.28 (m, 2 H), 2.28-2.43 (m, 2 H), 3.27 (s, 3 H), 3.34 (d, J = 5.55 Hz, 4 H), 3.99-4.25 (m, 2 H), 7.06 (d, J = 8.33 Hz, 2 H), 7.41-7.65 (m, 2 H), 7.65-7.87 (m, 3 H), 9.30 (s, 1 H) | MS (DCI/NH$_3$) m/z 520 (M + H)⁺ |
| 280 | 8-cyclobutyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one | ¹NMR (300 MHz, DMSO-$d_6$): δ 0.98 (d, J = 6.74 Hz, 1 H), 1.14 (d, J = 11.90 Hz, 2 H), 1.25-1.41 (m, 1 H), 1.73-1.94 (m, 1 H), 2.00-2.19 (m, 1 H), 2.17-2.31 (m, 2 H), 2.29-2.43 (m, 2 H), 2.95 (s, 3 H), 3.32 (s, 2 H), 4.06-4.22 (m, 1 H), 4.59 (s, 2 H), 6.94 (d, J = 8.73 Hz, 1 H), 7.55-7.66 (m, 2 H), 7.69-7.82 (m, 3 H), 9.36 (s, 1 H) | MS (DCI/NH$_3$) m/z 533 (M + H)⁺ |
| 281 | 8-cyclobutyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one | ¹NMR (300 MHz, DMSO-$d_6$): δ 1.00-1.21 (m, 4 H), 1.78-1.95 (m, 1 H), 1.97-2.14 (m, 1 H), 2.17-2.30 (m, 2 H), 2.29-2.43 (m, 2 H), 3.28 (s, 2 H), 4.04-4.23 (m, 1 H), 4.43 (s, 2 H), 6.92 (d, J = 8.72 Hz, 1 H), 7.52-7.68 (m, 2 H), 7.68-7.81 (m, 3 H), 9.36 (s, 1 H) | MS (DCI/NH$_3$) m/z 519 (M + H)⁺ |
| 282 | 6-cyclobutyl-2-{[4-(4-methylpiperazin-1-yl)phenyl]amino}-8-(pyridin-4-yl)pyrimido[4,5-d]pyridazin-5(6H)-one | ¹NMR (300 MHz, DMSO-$d_6$): δ 1.78-1.92 (m, 1 H), 2.24-2.39 (m, 1 H), 2.52-2.63 (m, 2 H), 2.82-2.89 (m, 2 H), 2.89 (s, 3 H), 2.90-3.05 (m, 2 H), 3.08-3.29 (m, 2 H), 3.52 (t, J = 11.11 Hz, 2 H), 3.80 (t, J = 13.49 Hz, 2 H), 5.39-5.57 (m, 1 H), 7.00 (d, J = 9.12 Hz, 2 H), 7.61 (d, J = 8.73 Hz, 2 H), 8.81 (d, J = 6.35 Hz, 2 H), 8.85 (d, J = 5.95 Hz, 2 H), 9.31 (s, 1 H) | MS (DCI/NH$_3$) m/z 469 (M + H)⁺ |
| 283 | 2-[(4,4-dimethyl-1,2,3,4-tetrahydroisoquinolin-7-yl)amino]-6-(2-hydroxyethyl)-8-(pyridin-2-yl)pyrimido[4,5-d]pyridazin-5(6H)-one | ¹HNMR (400 MHz, DMSO-$d_6$): δ 10.44 (br s, 1 H), 9.35 (s, 1 H), 8.81-8.80 (m, 1 H), 8.03-7.99 (m, 1 H), 7.85-7.83 (m, 1 H), | MS (ESI) m/z 444 (M + H)⁺ |

TABLE 1-continued

| Ex | Name | ¹H NMR | MS |
|---|---|---|---|
| | | 7.58-7.55 (m, 1 H), 7.45-7.43 (m, 2 H), 7.24-7.22 (m, 1 H), 4.88-4.87 (m, 1 H), 4.23 (d, J = 5.6 Hz, 2 H), 3.78 (d, J = 5.6 Hz, 2 H), 3.69 (s, 2 H), 2.75 (s, 2 H), 1.20 (s, 6 H) | |
| 284 | 6-(2,6-dichlorophenyl)-2-{[4-(piperazin-1-yl)phenyl]amino}-8-(pyridin-2-yl)pyrimido[4,5-d]pyridazin-5(6H)-one | ¹HNMR (400 MHz, DMSO-$d_6$): δ 10.60 (br s, 1 H), 9.36 (s, 1 H), 8.82 (s, 1 H), 8.01-8.00 (m, 1 H), 7.88-7.85 (m, 1 H), 7.76-7.74 (m, 2 H), 7.64-7.57 (m, 4 H), 6.82-6.80 (m, 2 H), 3.17 (s, 1 H), 3.03-3.01 (m, 4 H), 2.89-2.88 (m, 4 H) | MS (ESI) m/z 545 (M + H)⁺ |
| 285 | 2-{[4-(piperazin-1-yl)phenyl]amino}-6,8-di(pyridin-2-yl)pyrimido[4,5-d]pyridazin-5(6H)-one | ¹HNMR (400 MHz, DMSO-$d_6$): δ 10.50 (br s, 1 H), 9.34 (s, 1 H), 8.80 (s, 1 H), 8.64-8.63 (m, 1 H), 8.08-7.98 (m, 2 H), 7.89-7.87 (m, 1 H), 7.73-7.71 (m, 1 H), 7.57-7.54 (m, 4 H), 6.81-6.79 (m, 2 H), 3.02-3.01 (m, 4 H), 2.90-2.87 (m, 4 H) | MS (ESI) m/z 478 (M + H)⁺ |
| 286 | 6-(naphthalen-1-yl)-2-{[4-(piperazin-1-yl)phenyl]amino}-8-(pyridin-2-yl)pyrimido[4,5-d]pyridazin-5(6H)-one | ¹HNMR (400 MHz, DMSO-$d_6$): δ 10.51 (br s, 1 H), 9.36 (s, 1 H), 8.78 (s, 1 H), 8.13-8.08 (m, 2 H), 7.98-7.95 (m, 2 H), 7.75-7.54 (m, 8 H), 6.84-6.82 (m, 2 H), 3.17 (s, 1 H), 3.05-3.04 (m, 4 H), 2.92-2.90 (m, 4 H) | MS (ESI) m/z 527 (M + H)⁺ |
| 287 | 6,8-di(pyridin-2-yl)-2-(2,4,4-trimethyl-1,2,3,4-tetrahydroisoquinolin-7-ylamino)pyrimido[4,5-d]pyridazin-5(6H)-one | ¹HNMR (400 MHz, DMSO-$d_6$): δ 10.58 (br s, 1 H), 9.39 (s, 1 H), 8.80-8.79 (m, 1 H), 8.64-8.63 (m, 1 H), 8.08-7.99 (m, 2 H), 7.86 (d, J = 7.6 Hz, 1 H), 7.72 (d, J = 8.0 Hz, 1 H), 7.59-7.54 (m, 2 H), 7.47 (br, 1 H), 7.41-7.39 (m, 1 H), 7.22-7.20 (m, 1 H), 3.18 (br, 2 H), 2.33 (s, 3 H), 2.29 (s, 2 H), 1.20 (s, 6 H) | MS (ESI) m/z 491 (M + H)⁺ |
| 288 | 6-(2-hydroxypropyl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, DMSO-$d_6$): δ 10.43 (br s, 1 H), 9.34 (s, 1 H), 8.81-8.80 (m, 1 H), 8.02-7.98 (m, 1 H), 7.82-7.80 (m, 1 H), 7.58-7.55 (m, 1 H), 7.47-4.39 (m, 2 H), 7.21-7.19 (m, 1 H), 4.87-4.86 (m, 1 H), 4.18-4.11 (m, 2 H), 4.02-3.99 (m, 1 H), 3.19 (s, 2 H), 2.33 (s, 3 H), 2.28 (s, 2 H), 1.20 (s, 6 H), 1.13 (d, J = 6.0 Hz, 3 H) | MS (ESI) m/z 472 (M + H)⁺ |
| 289 | 6-(2-hydroxypropyl)-2-{[4-(piperazin-1-yl)phenyl]amino}-8-(pyridin-2-yl)pyrimido[4,5-d]pyridazin-5(6H)-one | ¹HNMR (400 MHz, DMSO-$d_6$): δ 10.36 (br s, 1 H), 9.29 (s, 1 H), 8.82 (s, 1 H), 8.01-7.97 (m, 1 H), 7.85-7.83 (m, 1 H), 7.64-7.54 (m, 3 H), 6.80-6.78 (m, 2 H), 4.88-4.87 (m, 1 H), 4.16-4.14 (m, 2 H), 4.01-3.99 (m, 1 H), 2.97-2.96 (m, 4 H), 2.84-2.82 (m, 4 H), 1.13 (t, J = 5.6 Hz, 3 H) | MS (ESI) m/z 459 (M + H)⁺ |
| 294 | 6-cyclohexyl-2-[(4,4-dimethyl-1,2,3,4-tetrahydroisoquinolin-7-yl)amino]-8-(pyridin-2-yl)pyrimido[4,5-d]pyridazin-5(6H)-one | ¹HNMR (400 MHz, DMSO-$d_6$): δ 10.42 (br s, 1 H), 9.34 (s, 1 H), 8.82-8.81 (m, 1 H), 8.02-7.98 (m, 1 H), 7.84-7.82 (m, 2 H), 7.58-7.55 (m, 1 H), 7.44-7.42 (m, 1 H), 7.22-7.20 (m, 1 H), 4.90-4.85 (m, 1 H), 3.66 (s, 2 H), 2.70 (s, 2 H), 1.85-1.65 (m, 7 H), 1.48-1.38 (m, 2 H), 1.22-1.13 (m, 7 H) | MS (ESI) m/z 482 (M + H)⁺ |
| 295 | 2-[(4,4-dimethyl-1,2,3,4-tetrahydroisoquinolin-7-yl)amino]-6-(2-hydroxypropyl)-8-(pyridin-2-yl)pyrimido[4,5-d]pyridazin-5(6H)-one | ¹HNMR (400 MHz, DMSO-$d_6$): δ 10.46 (br s, 1 H), 9.35 (s, 1 H), 8.81-8.80 (m, 1 H), 8.03-7.99 (m, 1 H), 7.84-7.82 (m, 1 H), 7.58-7.55 (m, 1 H), 7.47-7.45 (m, 2 H), 7.25-7.23 (m, 1 H), 4.89-4.87 (m, 1 H), 4.19-4.11 (m, 2 H), 4.04-4.00 (m, 1 H), 3.72 (s, 2 H), 2.80 (s, 2 H), 1.22 (s, 6 H), 1.14 (d, J = 6.0 Hz, 3 H) | MS (ESI) m/z 458 (M + H)⁺ |
| 296 | 6-(2-chloro-6-fluorophenyl)-2-{[4-(4-methylpiperazin-1-yl)phenyl]amino}-8-(pyridin-4-yl)pyrimido[4,5-d]pyridazin-5(6H)-one | ¹NMR (300 MHz, DMSO-$d_6$): δ 2.88 (s, 3 H), 2.91-3.01 (m, 2 H), 3.19 (d, J = 10.71 Hz, 2 H), 3.54 (d, J = 11.11 Hz, 2 H), 3.84 (d, J = 13.49 Hz, 2 H), 6.99 (d, J = 8.73 Hz, 2 H), | MS (DCI/NH₃) m/z 543 (M + H)⁺ |

TABLE 1-continued

| Ex | Name | ¹H NMR | MS |
|---|---|---|---|
| | | 7.48-7.75 (m, 5 H), 7.94 (d, J = 3.57 Hz, 2 H), 8.75 (d, J = 5.95 Hz, 2 H), 9.39 (s, 1 H) | |
| 297 | 6-(2-chloro-6-fluorophenyl)-2-{[4-(piperazin-1-yl)phenyl]amino}-8-(pyridin-4-yl)pyrimido[4,5-d]pyridazin-5(6H)-one | ¹NMR (300 MHz, DMSO-d₆): δ 3.19-3.39 (m, 4 H), 3.74-4.25 (m, 4 H), 6.98 (d, J = 8.82 Hz, 2 H), 7.48-7.74 (m, 3 H), 7.95 (d, J = 3.73 Hz, 2 H), 8.62-8.75 (m, 2 H), 8.72-8.80 (m, 2 H), 9.38 (s, 1 H) | MS (DCI/NH₃) m/z 529 (M + H)⁺ |
| 298 | 6-(2-chloro-6-fluorophenyl)-2-{[4-(4-methylpiperazin-1-yl)phenyl]amino}-8-(pyrimidin-4-yl)pyrimido[4,5-d]pyridazin-5(6H)-one | ¹NMR (300 MHz, DMSO-d₆): δ 2.87 (s, 3 H), 2.89-3.03 (m, 2 H), 3.18 (d, J = 8.72 Hz, 2 H), 3.41-3.62 (m, 2 H), 3.82 (d, J = 13.09 Hz, 2 H), 6.97 (d, J = 8.72 Hz, 2 H), 7.48-7.61 (m, 1 H), 7.62-7.72 (m, 4 H), 8.07 (d, J = 4.36 Hz, 1 H), 9.03 (d, J = 5.16 Hz, 2 H), 9.39 (s, 1 H) | MS (DCI/NH₃) m/z 543 (M + H)⁺ |
| 301 | 2-{[4-(4-cyclobutylpiperazin-1-yl)phenyl]amino}-6-(2,6-dichlorophenyl)-8-(pyridin-4-yl)pyrimido[4,5-d]pyridazin-5(6H)-one | ¹NMR (300 MHz, DMSO-d₆): δ 1.68-1.88 (m, 2 H), 2.12-2.32 (m, 4 H), 2.89-3.04 (m, 4 H), 3.47 (d, J = 9.83 Hz, 2 H), 3.73-3.93 (m, 2 H), 4.69 (q, J = 7.01 Hz, 1 H), 7.01 (d, J = 8.82 Hz, 2 H), 7.52-7.75 (m, 3 H), 7.93 (d, J = 2.37 Hz, 2 H), 8.74 (d, J = 6.10 Hz, 2 H), 9.22 (d, J = 5.76 Hz, 2 H), 9.40 (s, 1 H) | MS (DCI/NH₃) m/z 600 (M + H)⁺ |
| 302 | 6-(2-chloro-6-fluorophenyl)-2-{[4-(4-methylpiperazin-1-yl)phenyl]amino}-8-(1-methyl-1H-pyrazol-4-yl)pyrimido[4,5-d]pyridazin-5(6H)-one | ¹NMR (300 MHz, DMSO-d₆): δ 2.88 (s, 3 H), 3.00 (d, J = 12.21 Hz, 2 H), 3.13-3.29 (m, 2 H), 3.51-3.61 (m, 2 H), 3.76-3.98 (m, 2 H), 3.84 (s, 3 H), 7.11 (d, J = 7.12 Hz, 2 H), 7.45-7.70 (m, 5 H), 7.96 (s, 1 H), 8.31 (s, 1 H), 9.33 (s, 1 H) | MS (DCI/NH₃) m/z 546 (M + H)⁺ |
| 304 | 6-(piperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹HNMR (400 MHz, DMSO-d₆): δ 10.44 (br s, 1 H), 9.35 (s, 1 H), 8.82-8.81 (m, 1 H), 8.03-7.99 (m, 1 H), 7.83-7.71 (m, 1 H), 7.59-7.56 (m, 1 H), 7.47-7.40 (m, 2 H), 7.21-7.19 (m, 1 H), 4.97-4.95 (m, 1 H), 3.19 (s, 2 H), 3.06-3.03 (m, 2 H), 2.64-2.58 (m, 2 H), 2.33 (s, 3 H), 2.28 (s, 2 H), 1.85-1.72 (m, 4 H), 1.20 (m, 6 H) | MS (ESI) m/z 497 (M + H)⁺ |
| 305 | 2-[(4,4-dimethyl-1,2,3,4-tetrahydroisoquinolin-7-yl)amino]-6-(piperidin-4-yl)-8-(pyridin-2-yl)pyrimido[4,5-d]pyridazin-5(6H)-one | ¹HNMR (400 MHz, DMSO-d₆): δ 10.42 (br s, 1 H), 9.34 (s, 1 H), 8.81-8.80 (m, 1 H), 8.02-7.98 (m, 1 H), 7.85-7.83 (m, 1 H), 7.58-7.55 (m, 1 H), 7.42-7.40 (m, 2 H), 7.21-7.19 (m, 1 H), 5.00-4.95 (m, 1 H), 3.62 (s, 2 H), 3.09-3.06 (m, 2 H), 2.68-2.62 (m, 4 H), 1.90-1.75 (m, 4 H), 1.17 (s, 6 H) | MS (ESI) m/z 483 (M + H)⁺ |
| 306 | 2-[(4,4-dimethyl-1,2,3,4-tetrahydroisoquinolin-7-yl)amino]-6-(naphthalen-1-yl)-8-(pyridin-2-yl)pyrimido[4,5-d]pyridazin-5(6H)-one | ¹HNMR (400 MHz, DMSO-d₆): δ 10.56 (br s, 1 H), 9.41 (s, 1 H), 8.76-8.75 (m, 1 H), 8.13-8.08 (m, 2 H), 8.00-7.96 (m, 1 H), 7.89-7.87 (m, 1 H), 7.76-7.67 (m, 3 H), 7.64-7.53 (m, 3 H), 7.46-7.44 (m, 2 H), 7.24-7.22 (m, 1 H), 3.63 (s, 2 H), 2.67 (s, 2 H), 1.19 (s, 6 H) | MS (ESI) m/z 526 (M + H)⁺ |
| 307 | 6-(2,6-dichlorophenyl)-2-{[4-(4-methylpiperazin-1-yl)phenyl]amino}-8-(1,3-thiazol-5-yl)pyrimido[4,5-d]pyridazin-5(6H)-one | ¹H NMR (300 MHz, DMSO-d₆): δ 2.88 (s, 3 H), 2.99 (t, J = 11.50 Hz, 2 H), 3.12-3.29 (m, 2 H), 3.39-3.67 (m, 2 H), 3.86 (d, J = 12.30 Hz, 2 H), 7.09 (d, J = 9.12 Hz, 2 H), 7.52-7.69 (m, 3 H), 7.71-7.83 (m, 2 H), 8.85 (s, 1 H), 9.18 (s, 1 H), 9.38 (s, 1 H) | MS (DCI/NH₃) m/z 566 (M + H)⁺ |
| 309 | 6-(2-chloro-6-fluorophenyl)-2-{[4-(4-methylpiperazin-1-yl)phenyl]amino}-8-(pyridin-2-yl)pyrimido[4,5-d]pyridazin-5(6H)-one | ¹H NMR (300 MHz, DMSO-d₆): δ 2.86 (s, 3 H), 2.90-3.04 (m, 2 H), 3.08-3.25 (m, 2 H), 3.52 (d, J = 11.90 Hz, 2 H), 3.79 (d, J = 13.48 Hz, 2 H), 6.90 (d, J = 7.54 Hz, 2 H), 7.46-7.61 (m, 3 H), 7.59-7.74 (m, 3 H), 7.84-7.95 (m, 1 H), | MS (DCI/NH₃) m/z 543 (M + H)⁺ |

TABLE 1-continued

| Ex | Name | ¹H NMR | MS |
|----|------|--------|-----|
| | | 7.94-8.08 (m, 1 H), 8.82 (s, 1 H), 9.37 (s, 1 H) | |
| 310 | 6-(4-hydroxypyridin-3-yl)-2-{[4-(4-methylpiperazin-1-yl)phenyl]amino}-8-(pyridin-2-yl)pyrimido[4,5-d]pyridazin-5(6H)-one | ¹H NMR (300 MHz, DMSO-d$_6$): δ 2.84 (s, 3 H), 2.91-3.03 (m, 2 H), 3.08-3.26 (m, 2 H), 3.50 (d, J = 11.10 Hz, 2 H), 3.77 (d, J = 13.09 Hz, 2 H), 6.61 (d, J = 7.14 Hz, 1 H), 6.91 (d, J = 7.54 Hz, 2 H), 7.50-7.63 (m, 1 H), 7.67 (m, 2 H), 7.79-7.94 (m, 1 H), 7.94-8.13 (m, 2 H), 8.34 (s, 1 H), 8.83 (d, J = 4.36 Hz, 1 H), 9.34 (s, 1 H) | MS (DCI/NH$_3$) m/z 508 (M + H)$^+$ |
| 315 | 6-(2,6-dichlorophenyl)-2-(2',3'-dihydro-1'H-spiro[cyclopropane-1,4'-isoquinolin]-7'-ylamino)-8-(1,3-thiazol-5-yl)pyrimido[4,5-d]pyridazin-5(6H)-one | ¹H NMR (300 MHz, DMSO-d$_6$): δ 1.14 (d, J = 7.54 Hz, 4 H), 3.30 (s, 2 H), 4.42 (s, 2 H), 6.94 (d, J = 8.73 Hz, 1 H), 7.43-7.58 (m, 1 H), 7.60-7.69 (m, 2 H), 7.74-7.82 (m, 2 H), 9.26 (s, 1 H), 9.31 (s, 1 H), 9.44 (s, 1 H) | MS (DCI/NH$_3$) m/z 549 (M + H)$^+$; |
| 316 | 6-(2,6-dichlorophenyl)-2-{[4-(4-methylpiperazin-1-yl)phenyl]amino}-8-(1,3-thiazol-2-yl)pyrimido[4,5-d]pyridazin-5(6H)-one | ¹H NMR (300 MHz, DMSO-d$_6$): δ 2.88 (s, 3 H), 2.98 (d, J = 11.90 Hz, 2 H), 3.09-3.27 (m, 2 H), 3.55 (d, J = 12.69 Hz, 2 H), 3.86 (d, J = 13.09 Hz, 2 H), 7.06 (d, J = 9.12 Hz, 2 H), 7.62-7.69 (m, 1 H), 7.76-7.80 (m, 2 H), 7.85-7.93 (m, 2 H), 7.99 (d, J = 4.36 Hz, 1 H), 8.19 (d, J = 1.19 Hz, 1 H), 9.39 (s, 1 H) | MS (DCI/NH$_3$) m/z 566 (M + H)$^+$ |
| 317 | 6-(2,6-dichlorophenyl)-2-[(2'-methyl-2',3'-dihydro-1'H-spiro[cyclopropane-1,4'-isoquinolin]-7'-yl)amino]-8-(1,3-thiazol-5-yl)pyrimido[4,5-d]pyridazin-5(6H)-one | ¹H NMR (300 MHz, DMSO-d$_6$): δ 0.93-1.06 (m, 1 H), 1.09-1.30 (m, 2 H), 1.32-1.44 (m, 1 H), 2.97 (d, J = 3.57 Hz, 3 H), 3.33 (s, 2 H), 4.47 (s, 2 H), 6.87-7.00 (m, 1 H), 7.50-7.59 (m, 1 H), 7.59-7.70 (m, 2 H), 7.75-7.81 (m, 2 H), 8.89 (s, 1 H), 9.27 (s, 1 H), 9.44 (s, 1 H) | MS (DCI/NH$_3$) m/z 563 (M + H)$^+$ |
| 318 | 6-(2,6-dichlorophenyl)-2-(1,2,3,4-tetrahydroisoquinolin-7-ylamino)-8-(1,3-thiazol-5-yl)pyrimido[4,5-d]pyridazin-5(6H)-one | ¹H NMR (300 MHz, DMSO-d$_6$): δ 3.03 (t, J = 5.95 Hz, 2 H), 3.40 (m, 2 H), 4.32 (s, 2 H), 7.30 (d, J = 8.33 Hz, 1 H), 7.54 (d, J = 3.97 Hz, 1 H), 7.61-7.68 (m, 1 H), 7.75-7.82 (m, 2 H), 9.13 (s, 2 H), 9.25 (s, 1 H), 9.45 (s, 1 H) | MS (DCI/NH$_3$) m/z 523 (M + H)$^+$ |
| 319 | 6-(2,6-dichlorophenyl)-2-{[4-(piperazin-1-yl)phenyl]amino}-8-(1,3-thiazol-5-yl)pyrimido[4,5-d]pyridazin-5(6H)-one | ¹H NMR (300 MHz, DMSO-d$_6$): δ 3.20-3.39 (m, 8 H), 7.07 (d, J = 8.73 Hz, 2 H), 7.58 (d, J = 7.14 Hz, 2 H), 7.59-7.68 (m, 1 H), 7.72-7.80 (m, 2 H), 8.79 (s, 1 H), 9.18 (s, 1 H), 9.38 (s, 1 H) | MS (DCI/NH$_3$) m/z 552 (M + H)$^+$ |
| 320 | 6-(2,6-dichlorophenyl)-2-[(2'-methyl-2',3'-dihydro-1'H-spiro[cyclopropane-1,4'-isoquinolin]-7'-yl)amino]-8-(1,3-thiazol-2-yl)pyrimido[4,5-d]pyridazin-5(6H)-one | ¹H NMR (300 MHz, DMSO-d$_6$): δ 0.78-1.05 (m, 4 H), 2.42 (s, 3 H), 2.59 (s, 2 H), 3.69 (s, 2 H), 6.76 (d, J = 8.33 Hz, 1 H), 7.64-7.72 (m, 1 H), 7.76-7.80 (m, 2 H), 7.86-7.92 (m, 2 H), 8.05 (d, J = 2.78 Hz, 1 H), 8.13 (d, J = 2.78 Hz, 1 H), 9.41 (s, 1 H) | MS (DCI/NH$_3$) m/z 563 (M + H)$^+$ |
| 321 | 6-(2,6-dichlorophenyl)-2-({4-[4-(oxetan-3-yl)piperazin-1-yl]phenyl}amino)-8-(pyridin-4-yl)pyrimido[4,5-d]pyridazin-5(6H)-one | ¹H NMR (300 MHz, DMSO-d$_6$): δ 3.17 (m, 1 H), 3.32 (m, 8 H), 4.65 (m, 4 H), 6.96 (d, J = 6.35 Hz, 2 H), 7.59 (d, J = 10.71 Hz, 2 H), 7.63 (dd, J = 8.92, 7.34 Hz, 1 H), 7.73-7.81 (m, 2 H), 7.91 (d, J = 3.97 Hz, 2 H), 8.73 (d, J = 5.55 Hz, 2 H), 9.38 (s, 1 H) | MS (DCI/NH$_3$) m/z 602 (M + H)$^+$ |
| 322 | 6-(1-methylpiperidin-4-yl)-2-{[4-(piperazin-1-yl)phenyl]amino}-8-(pyridin-2-yl)pyrimido[4,5-d]pyridazin-5(6H)-one | ¹H NMR (400 MHz, DMSO-d$_6$) δ 10.38 (br s, 1 H), 9.30 (s, 1 H), 8.84 (s, 1 H), 8.02-7.98 (m, 1 H), 7.87-7.85 (m, 1 H), 7.68-7.54 (m, 3 H), 6.82-6.80 (m, 2 H), 4.87-4.83 (m, 1 H), 3.02 (s, 4 H), 2.88 (s, 6 H), 2.20 (s, 3 H), 2.10-1.96 (m, 4 H), 1.79-1.77 (m, 2 H) | MS (ESI) m/z 498 (M + H)$^+$ |
| 328 | 6-(1-methylpiperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-d$_6$): δ 10.43 (br s, 1 H), 9.34 (s, 1 H), 8.82-8.81 (m, 1 H), 8.03-7.99 (m, 1 H), 7.84-7.82 (m, 1 H), 7.59-7.56 (m, 1 H), 7.47-7.41 (m, 2 H), | MS (ESI) m/z 511 (M + H)$^+$ |

TABLE 1-continued

| Ex | Name | ¹H NMR | MS |
|---|---|---|---|
| | | 7.21-7.19 (m, 1 H), 4.90-4.84 (m, 1 H), 3.23-3.19 (m, 2 H), 2.94-2.91 (m, 2 H), 2.33 (s, 3 H), 2.28 (s, 2 H), 2.20 (s, 3 H), 2.15-1.97 (m, 4 H), 1.81-1.78 (m, 2 H), 1.20 (s, 6 H) | |
| 329 | 2-[(4,4-dimethyl-1,2,3,4-tetrahydroisoquinolin-7-yl)amino]-6-(1-methylpiperidin-4-yl)-8-(pyridin-2-yl)pyrimido[4,5-d]pyridazin-5(6H)-one | ¹H NMR (400 MHz, DMSO-d₆): δ 10.60 (br s, 1 H), 9.39 (s, 1 H), 8.85-8.84 (m, 1 H), 8.07-8.03 (m, 1 H), 7.87-7.85 (m, 1 H), 7.61-7.55 (m, 3 H), 7.37-7.35 (m, 1 H), 5.11-5.05 (m, 1 H), 3.98 (s, 2 H), 3.14 (s, 2 H), 2.92-2.88 (m, 3 H), 2.65-2.59 (m, 4 H), 2.25-2.17 (m, 2 H), 2.00-1.98 (m, 2 H), 1.32 (s, 6 H) | MS (ESI): m/z 497.3 (M + H)⁺ |
| 330 | 6-(2,6-dimethylcyclohexyl)-8-(pyridin-2-yl)-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-d₆): δ 10.41 (br s, 1 H), 9.34 (s, 1 H), 8.83-8.82 (m, 1 H), 8.03-7.99 (m, 1 H), 7.76-7.74 (m, 1 H), 7.58-7.55 (m, 1 H), 7.48-7.43 (m, 2 H), 7.21-7.19 (m, 1 H), 4.67-4.64 (m, 1 H), 3.20-3.18 (m, 2 H), 2.33-2.28 (m, 3 H), 1.84-1.81 (m, 1 H), 1.68-1.42 (m, 5 H), 1.23-1.13 (m, 8 H), 0.89 (d, J = 6.4 Hz, 3 H), 0.74 (d, J = 6.4 Hz, 3 H) | MS (ESI): m/z 524.4 (M + H)⁺ |
| 331 | 6-(2,6-dimethylcyclohexyl)-2-[(4,4-dimethyl-1,2,3,4-tetrahydroisoquinolin-7-yl)amino]-8-(pyridin-2-yl)pyrimido[4,5-d]pyridazin-5(6H)-one | ¹H NMR (400 MHz, DMSO-d₆): δ 10.39 (br s, 1 H), 9.34 (s, 1 H), 8.82-8.81 (m, 1 H), 8.02-7.98 (m, 1 H), 7.78-7.76 (m, 1 H), 7.57-7.54 (m, 1 H), 7.45-7.43 (m, 2 H), 7.21-7.19 (m, 1 H), 4.67-4.63 (m, 1 H), 3.63 (s, 2 H), 2.66 (s, 2 H), 2.32-2.28 (m, 2 H), 1.85-1.82 (m, 1 H), 1.68-1.42 (m, 5 H), 1.23-1.13 (m, 8 H), 0.89 (d, J = 7.2 Hz, 3 H), 0.74 (d, J = 6.4 Hz, 3 H) | MS (ESI): m/z 510.3 (M + H)⁺ |
| 332 | 2-[(4,4-dimethyl-1,2,3,4-tetrahydroisoquinolin-7-yl)amino]-6-(1-methylpiperidin-3-yl)-8-(pyridin-2-yl)pyrimido[4,5-d]pyridazin-5(6H)-one | ¹H NMR (400 MHz, DMSO-d₆): δ 10.42 (br s, 1 H), 9.35 (s, 1 H), 8.82-8.80 (m, 1 H), 8.02-7.98 (m, 1 H), 7.83-7.81 (m, 1 H), 7.58-7.55 (m, 1 H), 7.43-7.41 (m, 2 H), 7.22-7.20 (m, 1 H), 5.01-4.96 (m, 1 H), 3.65 (s, 2 H), 2.92-2.90 (m, 1 H), 2.78-2.75 (m, 1 H), 2.69 (s, 2 H), 2.21 (s, 3 H), 2.18-2.12 (m, 2 H), 1.90-1.62 (m, 5 H), 1.18 (s, 6 H) | MS (ESI): m/z 497.3 (M + H)⁺ |
| 333 | 6-(2,6-dimethylcyclohexyl)-2-{[4-(piperazin-1-yl)phenyl]amino}-8-(pyridin-2-yl)pyrimido[4,5-d]pyridazin-5(6H)-one | ¹H NMR (400 MHz, DMSO-d₆): δ 10.34 (br s, 1 H), 9.30 (s, 1 H), 8.85, 8.02-7.98 (m, 1 H), 7.79-7.77 (m, 1 H), 7.70-7.69 (m, 2 H), 7.57-7.54 (m, 1 H), 6.81-6.79 (m, 2 H), 4.66-4.63 (m, 1 H), 3.00-2.99 (m, 4 H), 2.87-2.86 (m, 4 H), 2.33-2.30 (m, 2 H), 1.85-1.82 (m, 1 H), 1.69-1.44 (m, 4 H), 1.20-1.16 (m, 1 H), 0.90 (d, J = 7.2 Hz, 3 H), 0.74 (d, J = 7.2 Hz, 3 H) | MS (ESI): m/z 511.4 (M + H)⁺ |
| 334 | 6-(1-methylpiperidin-3-yl)-2-{[4-(piperazin-1-yl)phenyl]amino}-8-(pyridin-2-yl)pyrimido[4,5-d]pyridazin-5(6H)-one | ¹H NMR (400 MHz, DMSO-d₆): δ 10.36 (br s, 1 H), 9.29 (s, 1 H), 8.83 (s, 1 H), 8.00-7.98 (m, 1 H), 7.84-7.82 (m, 1 H), 7.64-7.54 (m, 3 H), 6.80-6.78 (m, 2 H), 5.01-4.96 (m, 1 H), 2.97-2.96 (m, 4 H), 2.94-2.90 (m, 1 H), 2.84-2.82 (m, 4 H), 2.79-2.75 (m, 1 H), 2.21 (s, 3 H), 2.19-2.12 (m, 2 H), 1.88-1.64 (m, 4 H) | MS (ESI): m/z 498.3 (M + H)⁺ |
| 335 | 6-(2-chloro-6-fluorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one | ¹H NMR (400 MHz, CD₃OD): δ 1.16-1.20 (m, 2 H), 1.26-1.29 (m, 2 H), 1.52 (d, J = 6.41 Hz, 6 H), 3.40 (s, 2 H), 4.50 (s, 2 H), 4.54-4.61 (m, 1 H), 6.97 (d, J = 8.85 Hz, 1 H), 7.32-7.38 (m, 1 H), 7.47-7.52 (m, 1 H), 7.56 (dd, J = 8.39, 5.65 Hz, 2 H), 7.73 (s, 1 H), 8.34 (s, 1 H), 9.41 (s, 1 H) | MS (ESI): m/z 557 (M + H)⁺ |

TABLE 1-continued

| Ex | Name | ¹H NMR | MS |
|---|---|---|---|
| 336 | 6-(3-chloropyridin-2-yl)-2-{[4-(4-methylpiperazin-1-yl)phenyl]amino}-8-(pyridin-4-yl)pyrimido[4,5-d]pyridazin-5(6H)-one | ¹H NMR (300 MHz, DMSO-d₆): δ 2.85 (s, 3 H), 2.92-3.08 (m, 2 H), 3.11-3.26 (m, 2 H), 3.43-3.60 (m, 2 H), 3.82 (d, J = 11.87 Hz, 2 H), 6.99 (d, J = 8.82 Hz, 2 H), 7.61 (d, J = 8.82 Hz, 2 H,) 7.71 (dd, J = 8.14, 4.75 Hz, 1 H), 7.91 (d, J = 4.07 Hz, 2 H), 8.30 (dd, J = 7.97, 1.53 Hz, 1 H), 8.65 (dd, J = 4.58, 1.53 Hz, 1 H), 8.71-8.76 (m, 2 H), 9.38 (s, 1 H) | MS (DCI/NH₃) m/z 526 (M + H)⁺ |
| 337 | 6-(2,6-dichlorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one | ¹H NMR (400 MHz, CD₃OD): δ 1.16-1.21 (m, 2 H), 1.27-1.30 (m, 2 H), 1.52 (d, J = 6.71 Hz, 6 H), 3.40 (s, 2 H), 4.50 (s, 2 H), 4.55-4.62 (m, 1 H), 6.97 (d, J = 8.54 Hz, 1 H), 7.51-7.56 (m, 2 H), 7.60-7.65 (m, 2 H), 7.71-7.75 (m, 1 H), 8.35 (s, 1 H), 9.42 (s, 1 H) | MS (ESI): m/z 574 (M + H)⁺ |
| 338 | 6-(2,6-dichlorophenyl)-8-(1-methyl-1H-imidazol-4-yl)-2-{[4-(4-methylpiperazin-1-yl)phenyl]amino}pyrimido[4,5-d]pyridazin-5(6H)-one | ¹H NMR (300 MHz, DMSO-d₆): δ 2.84 (s, 3 H), 3.15 (d, J = 9.49 Hz, 2 H), 3.26-3.37 (m, 2 H), 3.45-3.60 (m, 2 H), 3.71 (s, 3 H), 3.79-3.96 (m, 2 H), 7.15 (d, J = 5.09 Hz, 2 H), 7.54 (d, J = 8.14 Hz, 2 H), 7.59-7.68 (m, 2 H), 7.72-7.79 (m, 2 H), 8.00 (s, 1 H), 9.36 (s, 1 H) | MS (DCI/NH₃) m/z 562 (M + H)⁺ |
| 339 | 6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one | ¹H NMR (300 MHz, DMSO-d₆): δ 0.89-1.40 (m, 4 H), 2.93 (d, J = 3.73 Hz, 3 H), 3.48 (s, 2 H), 3.96 (s, 3 H), 4.36 (s, 2 H), 6.97 (d, J = 6.44 Hz, 1 H), 7.61-7.69 (m, 2 H), 7.73 (s, 1 H), 7.75-7.81 (m, 3 H), 9.15 (s, 1 H), 9.44 (s, 1 H) | MS (DCI/NH₃) m/z 560 (M + H)⁺ |
| 340 | 6-(2,6-dichlorophenyl)-8-(1-methyl-1H-imidazol-4-yl)-2-{[4-(piperazin-1-yl)phenyl]amino}pyrimido[4,5-d]pyridazin-5(6H)-one | ¹H NMR (300 MHz, DMSO-d₆): δ 3.26 (d, J = 2.03 Hz, 8 H), 3.77 (s, 3 H), 7.15 (d, J = 8.48 Hz, 2 H), 7.54 (d, J = 8.82 Hz, 2 H), 7.60-7.70 (m, 1 H), 7.73-7.85 (m, 2 H), 8.07 (s, 1 H), 9.04 (s, 1 H), 9.38 (s, 1 H) | MS (DCI/NH₃) m/z 549 (M + H)⁺ |
| 341 | 6-(2,6-dichlorophenyl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one | ¹H NMR (300 MHz, DMSO-d₆): δ 1.07-1.20 (m, 4 H), 3.27 (s, 2 H), 3.96 (s, 3 H), 4.40 (s, 2 H), 6.96 (s, 1 H), 7.60-7.74 (m, 4 H), 7.74-7.82 (m, 2 H), 9.13 (s, 1 H), 9.44 (s, 1 H) | MS (DCI/NH₃) m/z 546 (M + H)⁺ |
| 342 | 6-(2,6-dichlorophenyl)-8-(1-methyl-1H-imidazol-4-yl)-2-(1,2,3,4-tetrahydroisoquinolin-7-ylamino)pyrimido[4,5-d]pyridazin-5(6H)-one | ¹H NMR (300 MHz, DMSO-d₆): δ 0.98-1.18 (m, 2 H), 3.03 (m, 2 H), 3.94 (s, 3 H), 4.30 (s, 2 H), 7.33 (s, 1 H), 7.58-7.73 (m, 4 H), 7.74-7.83 (m, 2 H), 9.32 (s, 1 H), 9.45 (s, 1 H) | MS (DCI/NH₃) m/z 520 (M + H)⁺ |
| 343 | 6-(3-chloropyridin-2-yl)-8-(1-methyl-1H-imidazol-4-yl)-2-{[4-(4-methylpiperazin-1-yl)phenyl]amino}pyrimido[4,5-d]pyridazin-5(6H)-one | ¹H NMR (300 MHz, DMSO-d₆): δ 2.25 (s, 3 H), 3.12-3.24 (m, 8 H), 3.62 (s, 3 H), 7.06 (d, J = 7.80 Hz, 2 H), 7.50 (m, 2 H) 7.69 (dd, J = 8.14, 4.75 Hz, 2 H), 7.95 (s, 1 H), 8.27 (dd, J = 8.14, 1.70 Hz, 1 H), 8.64 (dd, J = 4.75, 1.70 Hz, 1 H), 9.30 (s, 1 H) | MS (DCI/NH₃) m/z 529 (M + H)⁺ |
| 344 | 6-(2,6-dichlorophenyl)-2-{[4-(piperazin-1-yl)phenyl]amino}-8-(1,3-thiazol-2-yl)pyrimido[4,5-d]pyridazin-5(6H)-one | ¹H NMR (300 MHz, DMSO-d₆): δ 2.88-3.01 (m, 4 H), 3.09-3.19 (m, 4 H), 6.97 (d, J = 9.16 Hz, 2 H), 7.58-7.69 (m, 1 H), 7.73-7.85 (m, 4 H), 7.99 (s, 1 H), 8.15 (s, 1 H), 9.36 (s, 1 H) | MS (DCI/NH₃) m/z 552 (M + H)⁺ |
| 345 | 6-(2,6-dichlorophenyl)-2-(2',3'-dihydro-1'H-spiro[cyclopropane-1,4'-isoquinolin]-7'-ylamino)-8-(1,3-thiazol-2-yl)pyrimido[4,5-d]pyridazin-5(6H)-one | ¹H NMR (300 MHz, DMSO-d₆): δ 0.97-1.08 (m, 4 H), 3.28 (s, 2 H), 4.29 (s, 2 H), 6.88 (d, J = 8.82 Hz, 1 H), 7.59-7.72 (m, 3 H), 7.81 (s, 2 H), 8.13 (s, 1 H), 8.37 (d, J = 3.05 Hz, 1 H), 9.44 (s, 1 H) | MS (DCI/NH₃) m/z 549 (M + H)⁺ |
| 346 | 6-(2,6-dichlorophenyl)-2-(1,2,3,4-tetrahydroisoquinolin-7-ylamino)-8-(1,3-thiazol-2-yl)pyrimido[4,5-d]pyridazin-5(6H)-one | ¹H NMR (300 MHz, DMSO-d₆): δ 1.05 (t, J = 6.95 Hz, 2 H), 3.01 (t, J = 6.10 Hz, 2 H), 4.29 (s, 2 H), 7.27 (d, J = 8.48 Hz, 1 H), 7.60-7.75 (m, 2 H), 7.76-7.83 (m, 2 H), 8.05 (d, | MS (DCI/NH₃) m/z 522 (M + H)⁺ |

TABLE 1-continued

| Ex | Name | $^1$H NMR | MS |
|---|---|---|---|
| | | J = 3.05 Hz, 1 H), 8.17 (d, J = 3.05 Hz, 1 H), 8.96 (s, 1 H), 9.46 (s, 1 H) | |
| 347 | 6-(3-chloropyridin-2-yl)-2-{[4-(piperazin-1-yl)phenyl]amino}-8-(1,3-thiazol-2-yl)pyrimido[4,5-d]pyridazin-5(6H)-one | $^1$H NMR (300 MHz, DMSO-d$_6$): δ 3.14-3.26 (m, 4 H), 3.27-3.32 (m, 4 H), 7.03 (d, J = 9.16 Hz, 2 H), 7.73 (dd, J = 8.14, 4.41 Hz, 1 H), 7.86 (d, J = 5.76 Hz, 2 H), 7.99 (s, 1 H), 8.16 (s, 1 H), 8.31 (dd, J = 8.14, 1.36 Hz, 1 H), 8.67 (dd, J = 4.75, 1.36 Hz, 1 H), 9.36 (s, 1 H) | MS (DCI/NH$_3$) m/z 518 (M + H)$^+$ |
| 348 | 6-(3-chloropyridin-2-yl)-2-{[4-(4-methylpiperazin-1-yl)phenyl]amino}-8-(pyridin-2-yl)pyrimido[4,5-d]pyridazin-5(6H)-one | $^1$H NMR (300 MHz, DMSO-d$_6$): δ 2.19-2.29 (m, 4 H), 3.09 (m, 4 H), 3.29 (s, 3 H), 6.81 (d, J = 8.48 Hz, 2 H), 7.48-7.66 (m, 3 H), 7.69 (dd, J = 8.14, 4.75 Hz, 1 H), 7.83-7.93 (m, 1 H), 7.92-8.07 (m, 1 H), 8.29 (dd, J = 7.97, 1.53 Hz, 1 H), 8.64 (dd, J = 4.75, 1.36 Hz, 1 H), 8.79 (d, J = 3.73 Hz, 1 H), 9.35 (s, 1 H) | MS (DCI/NH$_3$) m/z 526 (M + H)$^+$ |
| 350 | 6-(3-chloropyridin-2-yl)-8-(1-methyl-1H-imidazol-4-yl)-2-{[4-(piperazin-1-yl)phenyl]amino}pyrimido[4,5-d]pyridazin-5(6H)-one | $^1$H NMR (300 MHz, DMSO-d$_6$): δ 2.83-3.00 (m, 4 H), 3.17 (d, J = 9.12 Hz, 4 H), 3.54 (d, J = 11.90 Hz, 3 H), 6.94 (d, J = 9.52 Hz, 2 H), 7.47-7.88 (m, 7 H), 9.41 (s, 1 H) | MS (DCI/NH$_3$) m/z 515 (M + H)$^+$ |
| 352 | 6-(3-chloropyridin-2-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one | $^1$H NMR (300 MHz, DMSO-d$_6$): δ 1.02-1.21 (m, 4 H), 3.28 (s, 3 H), 3.94 (s, 2 H), 4.41 (s, 2 H), 6.97 (d, J = 6.44 Hz, 1 H), 7.62-7.77 (m, 3 H), 8.32 (dd, J = 8.14, 1.70 Hz, 1 H), 8.67 (dd, J = 4.75, 1.36 Hz, 1 H), 9.09 (s, 1 H), 9.25 (s, 1 H), 9.42 (s, 1 H) | MS (DCI/NH$_3$) m/z 512 (M + H)$^+$ |
| 353 | 6-(3-chloropyridin-2-yl)-8-(1-methyl-1H-imidazol-4-yl)-2-(1,2,3,4-tetrahydroisoquinolin-7-ylamino)pyrimido[4,5-d]pyridazin-5(6H)-one | $^1$H NMR (300 MHz, DMSO-d$_6$): δ 2.95-3.13 (m, 2 H), 3.38 (s, 2 H), 3.92 (s, 3 H), 4.31 (s, 2 H), 7.33 (d, J = 5.55 Hz, 1 H), 7.61-7.81 (m, 3 H), 8.29-8.36 (m, 1 H), 8.67 (dd, J = 4.76, 1.59 Hz, 1 H), 9.29 (s, 2 H), 9.43 (s, 1 H) | MS (DCI/NH$_3$) m/z 486 (M + H)$^+$ |
| 354 | 6-(2,6-dichlorophenyl)-8-(1-methyl-1H-imidazol-2-yl)-2-{[4-(4-methylpiperazin-1-yl)phenyl]amino}pyrimido[4,5-d]pyridazin-5(6H)-one | $^1$H NMR (300 MHz, DMSO-d$_6$): δ 3.04 (m, 4 H), 3.25 (d, J = 7.54 Hz, 3 H), 3.45 (m, 4 H), 3.72 (s, 3 H), 6.94 (d, J = 9.12 Hz, 2 H), 7.56 (t, J = 8.73 Hz, 3 H), 7.73-7.82 (m, 2 H), 8.02 (s, 1 H), 8.92 (s, 1 H), 10.28 (s, 1 H) | MS (DCI/NH$_3$) m/z 563 (M + H)$^+$ |
| 355 | 6-(2,6-dichlorophenyl)-8-(1-methyl-1H-imidazol-2-yl)-2-{[4-(piperazin-1-yl)phenyl]amino}pyrimido[4,5-d]pyridazin-5(6H)-one | $^1$H NMR (300 MHz, DMSO-d$_6$): δ 3.24 (m, 4 H), 3.35 (m, 4 H), 3.82 (s, 3 H), 6.94 (d, J = 8.48 Hz, 2 H), 7.58-7.71 (m, 2 H), 7.74-7.88 (m, 3 H), 9.06 (s, 1 H), 9.12 (s, 1 H), 9.42 (s, 1 H) | MS (DCI/NH$_3$) m/z 549 (M + H)$^+$ |
| 356 | 6-(2,6-dichlorophenyl)-2-(2',3'-dihydro-1'H-spiro[cyclopropane-1,4'-isoquinolin]-7'-ylamino)-8-(1-methyl-1H-imidazol-2-yl)pyrimido[4,5-d]pyridazin-5(6H)-one | $^1$H NMR (300 MHz, DMSO-d$_6$): δ 0.97-1.21 (m, 4 H), 3.25 (s, 2 H), 3.82 (s, 3 H), 4.29 (s, 2 H), 6.83 (d, J = 6.35 Hz, 1 H), 7.45-7.56 (m, 1 H), 7.61-7.72 (m, 2 H), 7.73-7.86 (m, 2 H), 9.41 (s, 2 H), 9.49 (s, 1 H) | MS (DCI/NH$_3$) m/z 546 (M + H)$^+$ |
| 357 | 6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-2-yl)pyrimido[4,5-d]pyridazin-5(6H)-one | $^1$H NMR (300 MHz, DMSO-d$_6$): δ 0.79-1.41 (m, 4 H), 2.94 (d, J = 3.97 Hz, 3 H), 3.24 (s, 2 H), 3.82 (s, 3 H), 4.38 (s, 2 H), 6.84 (d, J = 7.93 Hz, 1 H), 7.54 (d, J = 9.12 Hz, 1 H), 7.60-7.74 (m, 3 H), 7.75-7.82 (m, 2 H), 7.85 (s, 1 H), 7.85 (s, 1 H) | MS (DCI/NH$_3$) m/z 559 (M + H)$^+$ |
| 358 | 6-(3,5-dichloropyridin-4-yl)-2-{[4-(4-methylpiperazin-1-yl)phenyl]amino}-8-(pyridin-4-yl)pyrimido[4,5-d]pyridazin-5(6H)-one | $^1$H NMR (300 MHz, DMSO-d$_6$): δ 2.85 (d, J = 4.41 Hz, 3 H), 3.03 (t, J = 11.53 Hz, 2 H), 3.09-3.25 (m, 2 H), 3.39-3.53 (m, 2 H), 3.82 (d, J = 12.89 Hz, 2 H), 7.00 (d, J = 8.48 Hz, 2 H), 7.59 (d, J = 8.82 Hz, 2 H), 8.05 (d, J = 4.41 Hz, 2 H), 8.82 (d, J = 6.10 Hz, 2 H), 8.99 (s, 2 H), 9.41 (s, 1 H) | MS (DCI/NH$_3$) m/z 561 (M + H)$^+$ |

TABLE 1-continued

| Ex | Name | ¹H NMR | MS |
|---|---|---|---|
| 359 | 6-(3,5-dichloropyridin-4-yl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one | ¹H NMR (300 MHz, DMSO-$d_6$): δ 0.83-1.48 (m, 4 H), 2.94 (d, J = 4.36 Hz, 3 H), 3.20 (s, 2 H), 3.95 (s, 3 H), 4.32 (s, 2 H), 6.98 (s, 1 H), 7.46 (s, 1 H), 7.64 (s, 1 H), 7.71 (s, 1 H), 7.74 (s, 1 H), 9.01 (s, 2 H), 9.45 (s, 1 H) | MS (DCI/NH$_3$) m/z 561 (M + H)⁺ |
| 360 | 6-(3,5-dichloropyridin-4-yl)-2-{[4-(4-methylpiperazin-1-yl)phenyl]amino}-8-(1,3-thiazol-5-yl)pyrimido[4,5-d]pyridazin-5(6H)-one | ¹H NMR (300 MHz, DMSO-$d_6$): δ 2.82 (s, 3 H), 2.97 (d, J = 10.17 Hz, 2 H), 3.16 (d, J = 15.94 Hz, 2 H), 3.40-3.63 (m, 2 H), 3.67-3.86 (m, 2 H), 6.97 (d, J = 8.82 Hz, 2 H), 7.62 (d, J = 8.82 Hz, 2 H), 8.11 (d, J = 3.39 Hz, 1 H), 8.35 (d, J = 3.39 Hz, 1 H), 8.49 (s, 2 H), 8.90 (s, 1 H) | MS (DCI/NH$_3$) m/z 567 (M + H)⁺ |
| 361 | 6-(3,5-dichloropyridin-4-yl)-8-(1-methyl-1H-imidazol-4-yl)-2-{[4-(4-methylpiperazin-1-yl)phenyl]amino}pyrimido[4,5-d]pyridazin-5(6H)-one | ¹H NMR (300 MHz, DMSO-$d_6$): δ 2.84 (d, J = 3.97 Hz, 3 H), 3.18 (d, J = 11.50 Hz, 2 H), 3.24-3.42 (m, 2 H) 3.76 (m, 2 H), 3.78-3.90 (m, 2 H), 3.96 (s, 3 H), 7.17 (d, J = 7.93 Hz, 2 H), 7.54 (d, J = 8.73 Hz, 2 H), 8.05 (s, 1 H), 9.00 (s, 2 H), 9.22 (s, 1 H), 9.39 (s, 1 H) | MS (DCI/NH$_3$) m/z 564 (M + H)⁺ |
| 362 | 6-(3,5-dichloropyridin-4-yl)-2-{[4-(4-methylpiperazin-1-yl)phenyl]amino}-8-(pyridin-2-yl)pyrimido[4,5-d]pyridazin-5(6H)-one | ¹H NMR (300 MHz, DMSO-$d_6$): δ 2.84 (d, J = 4.75 Hz, 3 H), 3.00 (t, J = 11.87 Hz, 2 H), 3.06-3.23 (m, 2 H), 3.45-3.62 (m, 2 H), 3.78 (d, J = 12.55 Hz, 2 H), 6.90 (d, J = 8.48 Hz, 2 H), 7.54-7.63 (m, 1 H), 7.68 (d, J = 8.82 Hz, 2 H), 7.87-7.95 (m, 1 H), 7.98-8.09 (m, 1 H), 8.84 (d, J = 4.07 Hz, 1 H), 8.98 (s, 2 H), 9.39 (s, 1 H) | MS (DCI/NH$_3$) m/z 561 (M + H)⁺ |
| 372 | 6-(3,5-dichloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one | ¹H NMR (300 MHz, DMSO-$d_6$): δ 0.98-1.20 (m, 4 H), 3.26 (s, 3 H), 3.99 (s, 2 H), 4.40 (s, 2 H), 6.93 (s, 1 H), 7.73 (d, J = 13.43 Hz, 2 H), 8.06 (s, 1 H), 9.01 (s, 2 H), 9.21 (s, 1 H), 9.44 (s, 1 H) | MS (DCI/NH$_3$) m/z 547 (M + H)⁺ |
| 373 | 6-(3-chloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one | ¹H NMR (300 MHz, DMSO-$d_6$): δ 1.06-1.25 (m, 4 H), 3.31 (s, 3 H), 4.04 (s, 2 H), 4.46 (s, 2 H), 6.93 (s, 1 H), 7.62-7.73 (m, 1 H), 7.82 (d, J = 5.19 Hz, 1 H), 8.14 (s, 1 H), 8.81 (d, J = 5.19 Hz, 1 H), 8.91 (s, 1 H), 9.11 (s, 1 H), 9.20 (s, 1 H), 9.43 (s, 1 H) | MS (DCI/NH$_3$) m/z 512 (M + H)⁺ |
| 374 | 2-{[4-(4-acetylpiperazin-1-yl)phenyl]amino}-6-(2,6-dichlorophenyl)-8-(pyridin-2-yl)pyrimido[4,5-d]pyridazin-5(6H)-one | ¹H NMR (300 MHz, DMSO-$d_6$): δ 2.05 (s, 3 H), 2.93-3.16 (m, 4 H), 3.54-3.64 (m, 4 H), 6.86 (d, J = 8.48 Hz, 2 H), 7.50-7.68 (m, 4 H), 7.69-7.81 (m, 2 H), 7.87 (d, J = 7.80 Hz, 1 H), 7.93-8.08 (m, 1 H), 8.82 (d, J = 3.73 Hz, 1 H), 9.37 (s, 1 H) | MS (DCI/NH$_3$) m/z 588 (M + H)⁺ |
| 375 | 2-[(2'-acetyl-2',3'-dihydro-1'H-spiro[cyclopropane-1,4'-isoquinolin]-7'-yl)amino]-6-(2,6-dichlorophenyl)-8-(pyridin-2-yl)pyrimido[4,5-d]pyridazin-5(6H)-one | ¹H NMR (300 MHz, DMSO-$d_6$): δ 0.83-0.98 (m, 4 H), 2.06 (s, 3 H), 3.51 (s, 2 H), 4.50 (s, 2 H), 6.74 (d, J = 8.48 Hz, 1 H), 7.33-7.49 (m, 1 H), 7.56-7.70 (m, 3 H), 7.72-7.80 (m, 2 H), 7.88 (d, J = 7.80 Hz, 1 H), 8.05 (t, J = 7.80 Hz, 1 H), 8.83 (s, 1 H), 9.43 (s, 1 H) | MS (DCI/NH$_3$) m/z 585 (M + H)⁺ |
| 376 | 6-(2,6-dichlorophenyl)-2-({4-[4-(methylsulfonyl)piperazin-1-yl]phenyl}amino)-8-(pyridin-2-yl)pyrimido[4,5-d]pyridazin-5(6H)-one | ¹H NMR (300 MHz, DMSO-$d_6$): δ 2.94 (s, 3 H), 3.14-3.34 (m, 8 H), 6.94 (d, J = 7.12 Hz, 2 H), 7.58-7.69 (m, 4 H), 7.71-7.81 (m, 2 H), 7.92 (s, 1 H), 8.06 (t, J = 6.95 Hz, 1 H), 8.85 (d, J = 4.75 Hz, 1 H), 9.39 (s, 1 H) | MS (DCI/NH$_3$) m/z 624 (M + H)⁺ |
| 377 | 6-(2,6-dichlorophenyl)-2-{[2'-(methylsulfonyl)-2',3'-dihydro-1'H-spiro[cyclopropane-1,4'- | ¹H NMR (300 MHz, DMSO-$d_6$): δ 0.85-1.09 (m, 4 H), 2.93 (s, 3 H), | MS (DCI/NH$_3$) |

| Ex | Name | ¹H NMR | MS |
|---|---|---|---|
| | isoquinolin]-7'-yl]amino}-8-(pyridin-2-yl)pyrimido[4,5-d]pyridazin-5(6H)-one | 3.26 (s, 2 H), 4.24 (s, 2 H), 6.74 (d, J = 8.48 Hz, 1 H), 7.42 (d, J = 8.14 Hz, 1 H), 7.54-7.68 (m, 3 H), 7.71-7.80 (m, 2 H), 7.76-7.95 (m, 1 H), 7.95-8.14 (m, 1 H), 8.82 (d, J = 4.41 Hz, 1 H), 9.44 (s, 1 H) | m/z 621 (M + H)⁺ |
| 378 | 2-{[4-(4-acetylpiperazin-1-yl)phenyl]amino}-6-(2,6-dichlorophenyl)-8-(pyridin-4-yl)pyrimido[4,5-d]pyridazin-5(6H)-one | ¹H NMR (300 MHz, DMSO-d₆): δ 2.06 (s, 3 H), 3.02-3.29 (m, 8 H), 6.99 (d, J = 8.54 Hz, 2 H), 7.58 (d, J = 8.54 Hz, 2 H), 7.61-7.70 (m, 1 H), 7.78 (d, J = 8.24 Hz, 2 H), 8.14 (d, J = 3.97 Hz, 2 H), 8.85 (d, J = 6.10 Hz, 2 H), 9.40 (s, 1 H) | MS (DCI/NH₃) m/z 588 (M + H)⁺ |
| 379 | 2-[(2'-acetyl-2',3'-dihydro-1'H-spiro[cyclopropane-1,4'-isoquinolin]-7'-yl)amino]-6-(2,6-dichlorophenyl)-8-(pyridin-4-yl)pyrimido[4,5-d]pyridazin-5(6H)-one | ¹H NMR (300 MHz, DMSO-d₆): δ 0.92-1.03 (m, 4 H), 2.52 (s, 3 H), 3.51 (s, 2 H), 4.62 (s, 2 H), 6.84 (d, J = 8.54 Hz, 1 H), 7.43 (d, J = 8.24 Hz, 1 H), 7.61 (s, 1 H), 7.63-7.69 (m, 1 H), 7.79 (d, J = 8.24 Hz, 2 H), 8.14 (s, 2 H), 8.87 (d, J = 5.80 Hz, 2 H), 9.47 (s, 1 H) | MS (DCI/NH₃) m/z 585 (M + H)⁺ |
| 380 | 6-(2,6-dichlorophenyl)-2-({4-[4-(methylsulfonyl)piperazin-1-yl]phenyl}amino)-8-(pyridin-4-yl)pyrimido[4,5-d]pyridazin-5(6H)-one | ¹H NMR (300 MHz, DMSO-d₆): δ 2.94 (s, 3 H), 3.26 (d, J = 4.27 Hz, 8 H), 7.00 (d, J = 8.54 Hz, 2 H), 7.58 (d, J = 8.54 Hz, 2 H), 7.62-7.68 (m, 1 H), 7.78 (d, J = 8.24 Hz, 2 H), 8.14 (d, J = 4.58 Hz, 2 H), 8.86 (d, J = 5.80 Hz, 2 H), 9.40 (s, 1 H) | MS (DCI/NH₃) m/z 624 (M + H)⁺ |
| 381 | 6-(2,6-dichlorophenyl)-2-{[2'-(methylsulfonyl)-2',3'-dihydro-1'H-spiro[cyclopropane-1,4'-isoquinolin]-7'-yl]amino}-8-(pyridin-4-yl)pyrimido[4,5-d]pyridazin-5(6H)-one | ¹H NMR (300 MHz, DMSO-d₆): δ 0.90-1.11 (m, 4 H), 2.95 (s, 3 H), 3.31 (s, 2 H), 4.36 (s, 2 H), 6.84 (d, J = 8.54 Hz, 1 H), 7.48 (d, J = 8.24 Hz, 1 H), 7.56 (s, 1 H), 7.60-7.72 (m, 1 H), 7.79 (d, J = 8.24 Hz, 2 H), 8.28 (s, 2 H), 8.94 (d, J = 5.80 Hz, 2 H), 9.47 (s, 1 H) | MS (DCI/NH₃) m/z 621 (M + H)⁺; |
| 382 | 6-(3-chloropyridin-4-yl)-2-{[4-(4-methylpiperazin-1-yl)phenyl]amino}-8-(pyridin-4-yl)pyrimido[4,5-d]pyridazin-5(6H)-one | ¹H NMR (300 MHz, DMSO-d₆): δ 2.82 (s, 3 H), 3.02-3.26 (m, 4 H), 3.82 (d, J = 11.60 Hz, 4 H), 7.03 (d, J = 8.85 Hz, 2 H), 7.58 (d, J = 8.54 Hz, 2 H), 7.86 (d, J = 4.88 Hz, 1 H), 8.35 (d, J = 3.36 Hz, 2 H), 8.80 (d, J = 4.88 Hz, 1 H), 8.92-9.02 (m, 3 H), 9.41 (s, 1 H) | MS (DCI/NH₃) m/z 526 (M + H)⁺; |
| 383 | 6-(3-chloropyridin-4-yl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one | ¹H NMR (300 MHz, DMSO-d₆): δ 1.08 (d, 4 H), 3.44 (s, 2 H), 4.24 (s, 2 H), 6.88 (d, J = 8.54 Hz, 1 H), 7.50-7.59 (m, 2 H), 7.86 (d, J = 4.88 Hz, 1 H), 8.80 (d, J = 5.19 Hz, 1 H), 8.90 (d, J = 5.19 Hz, 2 H), 8.95 (s, 1 H), 9.46 (s, 1 H), 9.51 (s, 2 H) | MS (DCI/NH₃) m/z 509 (M + H)⁺ |
| 384 | 6-(3-chloropyridin-4-yl)-2-{[4-(4-methylpiperazin-1-yl)phenyl]amino}-8-(pyridin-2-yl)pyrimido[4,5-d]pyridazin-5(6H)-one | ¹H NMR (300 MHz, DMSO-d₆): δ 2.82 (d, J = 3.97 Hz, 3 H), 3.01-3.10 (m, 2 H), 3.11-3.21 (m, 2 H), 3.34-3.48 (m, 2 H), 3.77 (d, J = 12.21 Hz, 2 H), 6.91 (d, J = 7.93 Hz, 2 H), 7.53-7.72 (m, 3 H), 7.85 (d, J = 4.88 Hz, 1 H), 8.00 (d, J = 7.32 Hz, 1 H), 8.11 (s, 1 H), 8.78 (d, J = 5.19 Hz, 1 H), 8.89 (s, 1 H), 8.94 (s, 1 H), 9.39 (s, 1 H) | MS (DCI/NH₃) m/z 526 (M + H)⁺ |
| 385 | 6-(3-chloropyridin-4-yl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one | ¹H NMR (300 MHz, DMSO-d₆): δ 0.99-1.13 (m, 4 H), 3.22 (s, 2 H), 4.11 (s, 2 H), 6.78 (d, J = 6.41 Hz, 1 H), 7.50-7.64 (m, 2 H), 7.70 (d, J = 3.97 Hz, 1 H), 7.85 (d, J = 5.19 Hz, 1 H), 7.98 (m, 1 H), 8.15 (d, J = 6.41 Hz, 2 H), 8.79 (d, J = 4.88 Hz, 1 H), 8.87 (m, 1 H), 8.94 (s, 1 H), 9.45 (s, 1 H) | MS (DCI/NH₃) m/z 509 (M + H)⁺; |
| 386 | 8-cyclopropyl-6-(2,6-dichlorophenyl)-2-{[4-(4-methylpiperazin-1-yl)phenyl]amino}pyrimido[4,5-d]pyridazin-5(6H)-one | ¹H NMR (300 MHz, DMSO-d₆): δ 0.82-0.93 (m, 2 H), 1.01-1.10 (m, 2 H), 2.64-2.79 (m, 1 H), 2.87 (s, 3 H), 2.97 (d, J = 12.21 Hz, 2 H), 3.07-3.27 (m, 2 H), 3.45 (d, 2 H), 3.83 (d, J = 12.51 Hz, 2 H), 7.06 (d, J = 8.85 Hz, 2 H), 7.54-7.63 (m, 1 | MS (DCI/NH₃) m/z 523 (M + H)⁺ |

TABLE 1-continued

| Ex | Name | ¹H NMR | MS |
|---|---|---|---|
| | | H), 7.68-7.73 (m, 2 H), 7.77-7.89 (m, 2 H), 9.31 (s, 1 H) | |
| 387 | 6-(2,6-dichlorophenyl)-8-(difluoromethyl)-2-{[4-(4-methylpiperazin-1-yl)phenyl]amino}pyrimido[4,5-d]pyridazin-5(6H)-one | ¹H NMR (300 MHz, DMSO-$d_6$): δ 2.81 (s, 3 H), 3.17 (s, 3 H), 3.25-3.46 (m, 8 H), 7.04 (d, J = 9.16 Hz, 2 H), 7.65 (dd, J = 9.00, 7.48 Hz, 1 H), 7.74-7.79 (m, 2 H), 7.81 (d, J = 8.24 Hz, 2 H), 9.36 (s, 1 H) | MS (DCI/NH$_3$) m/z 523 (M + H)⁺ |
| 388 | 6-(2,6-dichlorophenyl)-8-ethyl-2-{[4-(4-methylpiperazin-1-yl)phenyl]amino}pyrimido[4,5-d]pyridazin-5(6H)-one | ¹H NMR (300 MHz, DMSO-$d_6$): δ 1.24 (t, J = 7.34 Hz, 3 H), 2.68 (s, 3 H), 2.98 (q, J = 7.41 Hz, 2 H), 3.09-3.21 (m, 4 H), 3.22-3.41 (m, 4 H), 7.04 (d, J = 9.12 Hz, 2 H), 7.54-7.66 (m, 1 H), 7.68-7.77 (m, 2 H), 7.79 (d, J = 6.74 Hz, 2 H), 9.31 (s, 1 H) | MS (DCI/NH$_3$) m/z 511 (M + H)⁺ |
| 389 | 8-cyclopropyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (300 MHz, DMSO-$d_6$): δ 0.79-0.88 (m, 2 H), 0.86-0.97 (m, 4 H), 1.03-1.11 (m, 2 H), 2.32 (s, 3 H), 2.45 (s, 2 H), 2.66-2.78 (m, 1 H), 3.58 (s, 2 H), 6.74 (d, J = 8.54 Hz, 1 H), 7.53-7.66 (m, 3 H), 7.66-7.75 (m, 2 H), 9.33 (s, 1 H). | MS (DCI/NH$_3$) m/z 520 (M + H)⁺; |
| 390 | 8-cyclopropyl-6-(2,6-dichlorophenyl)-2-(1,2,3,4-tetrahydroisoquinolin-7-ylamino)pyrimido[4,5-d]pyridazin-5(6H)-one | ¹H NMR (300 MHz, DMSO-$d_6$): δ 0.81-0.96 (m, 2 H), 1.03-1.11 (m, 2 H), 2.74 (m, 1 H), 2.99 (t, J = 6.26 Hz, 2 H), 3.41 (m, 2 H), 4.31 (s, 2 H), 7.27 (d, J = 8.24 Hz, 1 H), 7.55-7.64 (m, 1 H), 7.68-7.75 (m, 2 H), 7.79 (d, J = 6.10 Hz, 2 H), 9.37 (s, 1 H) | MS (DCI/NH$_3$) m/z 480 (M + H)⁺ |
| 391 | 8-cyclopropyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one | ¹H NMR (300 MHz, DMSO-$d_6$): δ 0.78-0.97 (m, 2 H), 1.03-1.16 (m, 6 H), 2.67-2.82 (m, 1 H), 3.28 (s, 2 H), 4.42 (s, 2 H), 6.92 (d, J = 8.54 Hz, 1 H), 7.59 (dd, J = 8.85, 7.32 Hz, 1 H), 7.71 (d, J = 7.93 Hz, 2 H), 7.71-7.85 (m, 2 H), 9.37 (s, 1 H) | MS (DCI/NH$_3$) m/z 506 (M + H)⁺ |
| 392 | 8-cyclopropyl-6-(2,6-dichlorophenyl)-2-{[4-(piperazin-1-yl)phenyl]amino}pyrimido[4,5-d]pyridazin-5(6H)-one | ¹H NMR (300 MHz, DMSO-$d_6$): δ 0.79-0.92 (m, 2 H), 1.02-1.14 (m, 2 H), 2.64-2.84 (m, 1 H), 3.18-3.34 (m, 8 H), 7.05 (d, J = 9.16 Hz, 2 H), 7.51-7.63 (m, 1 H), 7.66-7.75 (m, 2 H), 7.75-7.98 (m, 2 H), 9.31 (s, 1 H) | MS (DCI/NH$_3$) m/z 509 (M + H)⁺ |
| 402 | 6-(2,6-dichlorophenyl)-8-ethyl-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (300 MHz, DMSO-$d_6$): δ 0.88-0.99 (m, 1 H), 1.14 (dd, J = 11.87, 4.75 Hz, 2 H), 1.27 (t, J = 7.46 Hz, 3 H), 1.35 (d, J = 5.43 Hz, 1 H), 2.94 (s, 3 H), 3.01 (q, J = 7.35 Hz, 2 H), 3.24 (s, 2 H), 4.49 (s, 2 H), 6.93 (d, J = 8.48 Hz, 1 H), 7.55-7.64 (m, 1 H), 7.67-7.88 (m, 4 H), 9.38 (s, 1 H) | MS (DCI/NH$_3$) m/z 507 (M + H)⁺ |
| 403 | 6-(2,6-dichlorophenyl)-8-ethyl-2-(1,2,3,4-tetrahydroisoquinolin-7-ylamino)pyrimido[4,5-d]pyridazin-5(6H)-one | ¹H NMR (300 MHz, DMSO-$d_6$): δ 1.26 (t, J = 7.46 Hz, 3 H), 2.99 (t, J = 7.29 Hz, 2 H), 3.27-3.36 (m, 2 H), 3.34-3.44 (m, 2 H), 4.30 (s, 2 H), 7.26 (d, J = 8.48 Hz, 1 H), 7.55-7.64 (m, 1 H), 7.68 (d, J = 8.82 Hz, 1 H), 7.70-7.76 (m, 2 H), 7.77-7.84 (m, 1 H), 9.38 (s, 1 H) | MS (DCI/NH$_3$) m/z 467 (M + H)⁺ |
| 404 | 6-(2,6-dichlorophenyl)-2-(2',3'-dihydro-1'H-spiro[cyclopropane-1,4'-isoquinolin]-7'-ylamino)-8-ethylpyrimido[4,5-d]pyridazin-5(6H)-one | ¹H NMR (300 MHz, DMSO-$d_6$): δ 1.10 (d, J = 7.54 Hz, 4 H), 1.26 (t, J = 7.34 Hz, 3 H), 3.01 (q, J = 7.41 Hz, 2 H), 3.23-3.29 (m, 2 H), 4.40 (s, 2 H), 6.91 (d, J = 8.73 Hz, 1 H), 7.56-7.63 (m, 1 H), 7.66 (d, J = 8.73 Hz, 1 H), 7.71-7.76 (m, 2 H), 7.77-7.87 (m, 1 H), 9.37 (s, 1 H) | MS (DCI/NH$_3$) m/z 518 (M + H)⁺ |

TABLE 1-continued

| Ex | Name | ¹H NMR | MS |
|---|---|---|---|
| 405 | 6-(2,6-dichlorophenyl)-8-(difluoromethyl)-2-{[4-(piperazin-1-yl)phenyl]amino}pyrimido[4,5-d]pyridazin-5(6H)-one | ¹H NMR (300 MHz, DMSO-$d_6$): δ 3.08-3.28 (m, 4 H), 3.28-3.44 (m, 5 H), 7.03 (d, J = 9.16 Hz, 2 H), 7.60-7.70 (m, 1 H), 7.75-7.78 (m, 2 H), 7.81 (d, J = 3.05 Hz, 2 H) 9.36 (s, 1 H) | MS (DCI/NH$_3$) m/z 519 (M + H)⁺ |
| 406 | 6-(2,6-dichlorophenyl)-2-{[2-(dimethylamino)-2,3-dihydro-1H-inden-5-yl]amino}-8-ethylpyrimido[4,5-d]pyridazin-5(6H)-one | ¹H NMR (300 MHz, DMSO-$d_6$): δ 1.27 (t, J = 7.34 Hz, 3 H), 2.81 (s, 6 H), 2.99 (q, J = 7.41 Hz, 2 H), 3.20-3.31 (m, 4 H), 4.05-4.17 (m, 1 H), 7.28 (d, J = 8.33 Hz, 1 H), 7.56-7.62 (m, 1 H), 7.68 (d, J = 7.54 Hz, 1 H), 7.71-7.74 (m, 2 H), 7.80-7.88 (m, 1 H), 9.37 (s, 1 H) | MS (DCI/NH$_3$) m/z 495 (M + H)⁺ |
| 407 | 6-(2,6-dichlorophenyl)-8-(difluoromethyl)-2-(2',3'-dihydro-1'H-spiro[cyclopropane-1,4'-isoquinolin]-7'-ylamino)pyrimido[4,5-d]pyridazin-5(6H)-one | ¹H NMR (300 MHz, DMSO-$d_6$): δ 1.04-1.19 (m, 4 H), 3.27 (s, 2 H), 4.38 (s, 2 H), 6.90 (d, J = 8.82 Hz, 1 H), 7.59-7.63 (m, 1 H), 7.63-7.70 (m, 1 H), 7.76-7.80 (m, 2 H), 7.92 (d, J = 5.43 Hz, 1 H), 9.42 (s, 1 H) | MS (DCI/NH$_3$) m/z 515 (M + H)⁺ |
| 408 | 6-(2,6-dichlorophenyl)-8-(difluoromethyl)-2-{[2-(dimethylamino)-2,3-dihydro-1H-inden-5-yl]amino}pyrimido[4,5-d]pyridazin-5(6H)-one | ¹H NMR (300 MHz, DMSO-$d_6$): δ 2.81 (s, 6 H), 3.14-3.31 (m, 5 H), 3.99-4.23 (m, 1 H), 7.26-7.29 (m, 1 H), 7.60-7.72 (m, 2 H), 7.75-7.80 (m, 2 H), 7.89 (s, 1 H), 9.41 (s, 1 H) | MS (DCI/NH$_3$) m/z 518 (M + H)⁺ |
| 409 | 6-(2,6-dichlorophenyl)-8-ethyl-2-{[4-(piperazin-1-yl)phenyl]amino}pyrimido[4,5-d]pyridazin-5(6H)-one | ¹H NMR (300 MHz, DMSO-$d_6$): δ 1.24 (t, J = 7.46 Hz, 3 H), 2.98 (q, J = 7.46 Hz, 2 H), 3.22-3.29 (m, 8 H), 7.04 (d, J = 9.16 Hz, 2 H), 7.56-7.63 (m, 1 H), 7.69-7.75 (m, 2 H), 7.75-7.91 (m, 2 H), 9.31 (s, 1 H) | MS (DCI/NH$_3$) m/z 496 (M + H)⁺ |
| 410 | 6-(2,6-dichlorophenyl)-8-(difluoromethyl)-2-(1,2,3,4-tetrahydroisoquinolin-7-ylamino)pyrimido[4,5-d]pyridazin-5(6H)-one | ¹H NMR (300 MHz, DMSO-$d_6$): δ 2.99 (t, J = 5.95 Hz, 2 H), 3.23-3.26 (m, 1 H), 3.37-3.44 (m, 2 H), 4.28 (s, 2 H), 7.26 (d, J = 8.73 Hz, 1 H), 7.60-7.67 (m, 2 H), 7.74-7.80 (m, 2 H), 7.86-7.96 (m, 1 H), 9.43 (s, 1 H) | MS (DCI/NH$_3$) m/z 489 (M + H)⁺ |
| 411 | 6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (300 MHz, DMSO-$d_6$): δ 0.82-1.45 (m, 4 H), 2.94 (s, 3 H), 3.17 (s, 2 H), 4.16 (m, 1 H), 4.51 (s, 2 H), 6.92 (d, J = 8.73 Hz, 1 H), 7.62-7.72 (m, 2 H), 7.75-7.81 (m, 2 H), 7.81-7.91 (m, 1 H), 9.43 (s, 1 H) | MS (DCI/NH$_3$) m/z 529 (M + H)⁺ |
| 412 | 6-(2,6-dichlorophenyl)-2-{[4-(4-methylpiperazin-1-yl)phenyl]amino}-8-(trifluoromethyl)pyrimido[4,5-d]pyridazin-5(6H)-one | ¹H NMR (300 MHz, DMSO-$d_6$): δ 2.83 (s, 3 H), 2.96-3.11 (m, 2 H), 3.17 (s, 2 H), 3.39-3.60 (m, 2 H), 3.72-3.90 (m, 2 H), 7.04 (d, J = 9.16 Hz, 2 H), 7.60-7.71 (m, 1 H), 7.74-7.87 (m, 4 H), 9.37 (s, 1 H) | MS (DCI/NH$_3$) m/z 550 (M + H)⁺ |
| 413 | 6-(2,6-dichlorophenyl)-2-[(2'-methyl-2',3'-dihydro-1'H-spiro[cyclopropane-1,4'-isoquinolin]-7'-yl)amino]-8-(trifluoromethyl)pyrimido[4,5-d]pyridazin-5(6H)-one | ¹H NMR (300 MHz, DMSO-$d_6$): δ 0.88-1.02 (m, 1 H), 1.07-1.23 (m, 2 H), 1.30-1.46 (m, 1 H), 2.95 (s, 3 H), 3.26-3.30 (m, 2 H), 4.48 (s, 2 H), 6.92 (d, J = 8.82 Hz, 1 H), 7.62-7.74 (m, 2 H), 7.75-7.88 (m, 3 H), 9.45 (s, 1 H). | MS (DCI/NH$_3$) m/z 547 (M + H)⁺ |
| 414 | 2-{[4-(4-acetylpiperazin-1-yl)phenyl]amino}-6-(2,6-dichlorophenyl)-8-ethylpyrimido[4,5-d]pyridazin-5(6H)-one | ¹H NMR (300 MHz, DMSO-$d_6$): δ 1.24 (t, J = 7.34 Hz, 3 H), 2.05 (s, 3 H), 2.97 (q, J = 7.41 Hz, 2 H), 3.03-3.23 (m, 4 H), 3.38-3.63 (m, 4 H), 7.02 (d, J = 8.73 Hz, 2 H), 7.46-7.63 (m, 1 H), 7.66-7.87 (m, 4 H), 9.30 (s, 1 H) | MS (DCI/NH$_3$) m/z 538 (M + H)⁺ |
| 415 | 2-[(2'-acetyl-2',3'-dihydro-1'H-spiro[cyclopropane-1,4'-isoquinolin]-7'-yl)amino]-6-(2,6-dichlorophenyl)-8-(difluoromethyl)pyrimido[4,5-d]pyridazin-5(6H)-one | ¹H NMR (300 MHz, DMSO-$d_6$): δ 0.88-1.06 (m, 4 H), 2.06 (s, 3 H), 3.26-3.41 (m, 1 H), 3.55 (s, 2 H), 4.73 (s, 2 H), 6.86 (d, J = 8.33 Hz, 1 H), 7.52-7.71 (m, 2 H), 7.71-7.94 (m, 3 H), 9.40 (s, 1 H) | MS (DCI/NH$_3$) m/z 557 (M + H)⁺ |

TABLE 1-continued

| Ex | Name | $^1$H NMR | MS |
|---|---|---|---|
| 418 | 6-(2,6-dichlorophenyl)-2-{[4-(piperazin-1-yl)phenyl]amino}-8-(trifluoromethyl)pyrimido[4,5-d]pyridazin-5(6H)-one | $^1$H NMR (300 MHz, DMSO-$d_6$): δ 3.15-3.30 (m, 4 H), 3.30-3.39 (m, 4 H), 7.03 (d, J = 9.12 Hz, 2 H), 7.63-7.71 (m, 1 H), 7.74-7.91 (m, 4 H), 9.38 (s, 1 H) | MS (DCI/NH$_3$) m/z 537 (M + H)$^+$ |
| 419 | 6-(2,6-dichlorophenyl)-8-(fluoromethyl)-2-{[4-(4-methylpiperazin-1-yl)phenyl]amino}pyrimido[4,5-d]pyridazin-5(6H)-one | $^1$H NMR (300 MHz, DMSO-$d_6$): δ 2.88 (s, 3 H), 2.93-3.06 (m, 2 H), 3.13-3.25 (m, J = 4.58 Hz, 2 H), 3.49-3.68 (m, 2 H), 3.76-3.92 (m, 2 H), 5.66 (d, J = 47.00 Hz, 2 H), 7.06 (d, J = 6.71 Hz, 2 H), 7.48-7.67 (m, 1 H), 7.71-7.79 (m, 2 H), 7.80 (s, 2 H), 9.35 (s, 1 H) | MS (DCI/NH$_3$) m/z 515 (M + H)$^+$ |
| 420 | 6-(2,6-dichlorophenyl)-2-(2',3'-dihydro-1'H-spiro[cyclopropane-1,4'-isoquinolin]-7'-ylamino)-8-(trifluoromethyl)pyrimido[4,5-d]pyridazin-5(6H)-one | $^1$H NMR (300 MHz, DMSO-$d_6$): δ ppm 0.89-1.20 (m, 4 H), 3.29 (s, 2 H), 4.38 (s, 2 H), 6.91 (d, J = 8.73 Hz, 1 H), 7.51-7.72 (m, 2 H), 7.75-7.85 (m, 2 H), 7.88 (d, J = 7.14 Hz, 1 H), 9.44 (s, 1 H) | MS (DCI/NH$_3$) m/z 533 (M + H)$^+$ |
| 421 | 6-(2,6-dichlorophenyl)-2-(1,2,3,4-tetrahydroisoquinolin-7-ylamino)-8-(trifluoromethyl)pyrimido[4,5-d]pyridazin-5(6H)-one | $^1$H NMR (300 MHz, DMSO-$d_6$): δ 2.99 (t, J = 5.93 Hz, 2 H), 3.40 (t, J = 7.12 Hz, 2 H), 4.26 (s, 2 H), 7.26 (d, J = 8.48 Hz, 1 H), 7.61-7.75 (m, J = 9.16, 7.12 Hz, 2 H), 7.74-7.83 (m, 2 H), 7.83-7.96 (m, 1 H), 9.45 (s, 1 H) | MS (DCI/NH$_3$) m/z 507 (M + H)$^+$ |
| 422 | 6-(2,6-dichlorophenyl)-2-{[4-(pyrrolidin-3-yl)phenyl]amino}-8-(trifluoromethyl)pyrimido[4,5-d]pyridazin-5(6H)-one | $^1$H NMR (300 MHz, DMSO-$d_6$): δ 1.84-2.06 (m, 1 H), 2.28-2.46 (m, 1 H), 2.99-3.17 (m, 1 H), 3.15-3.34 (m, 1 H), 3.34-3.54 (m, 3 H), 7.37 (d, J = 8.48 Hz, 2 H), 7.53-7.72 (m, 1 H), 7.72-7.86 (m, 2 H), 7.83-8.00 (m, 2 H), 9.44 (s, 1 H) | MS (DCI/NH$_3$) m/z 521 (M + H)$^+$ |
| 423 | 6-(2,6-dichlorophenyl)-8-(methoxymethyl)-2-{[4-(4-methylpiperazin-1-yl)phenyl]amino}pyrimido[4,5-d]pyridazin-5(6H)-one | $^1$H NMR (300 MHz, DMSO-$d_6$): δ 2.86 (s, 3 H), 3.28 (s, 8 H), 3.38 (s, 3 H), 4.67 (s, 2 H), 7.00 (d, J = 8.85 Hz, 2 H), 7.58-7.67 (m, 1 H), 7.68-7.78 (m, 2 H), 7.79 (t, J = 7.63 Hz, 2 H), 9.31 (s, 1 H) | MS (DCI/NH$_3$) m/z 526 (M + H)$^+$ |
| 424 | 6-(2,6-dichlorophenyl)-8-(methoxymethyl)-2-{[4-(piperazin-1-yl)phenyl]amino}pyrimido[4,5-d]pyridazin-5(6H)-one | $^1$H NMR (300 MHz, DMSO-$d_6$): δ 3.23-3.30 (m, 4 H), 3.33 (d, J = 5.55 Hz, 4 H), 3.38 (s, 3 H), 4.67 (s, 2 H), 7.04 (d, J = 9.12 Hz, 2 H), 7.54-7.67 (m, 1 H), 7.70-7.77 (m, 2 H), 7.78-7.95 (m, 2 H), 9.33 (s, 1 H) | MS (DCI/NH$_3$) m/z 512 (M + H)$^+$ |
| 428 | 6-(2,6-dichlorophenyl)-2-(2',3'-dihydro-1'H-spiro[cyclopropane-1,4'-isoquinolin]-7'-ylamino)-8-(methoxymethyl)pyrimido[4,5-d]pyridazin-5(6H)-one | $^1$H NMR (300 MHz, DMSO-$d_6$): δ 1.03-1.16 (m, 4 H), 3.29 (s, 2 H), 3.37 (s, 3 H), 4.42 (s, 2 H), 4.72 (s, 2 H), 6.91 (d, J = 8.54 Hz, 1 H), 7.59-7.65 (m, 1 H), 7.66-7.73 (m, 1 H), 7.75 (d, J = 8.24 Hz, 2 H), 7.83-7.98 (m, 1 H), 9.39 (s, 1 H) | MS (DCI/NH$_3$) m/z 509 (M + H)$^+$ |
| 429 | 6-(2,6-dichlorophenyl)-8-(methoxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one | $^1$H NMR (300 MHz, DMSO-$d_6$): δ 0.90-0.99 (m, 1 H), 1.07-1.26 (m, 2 H), 1.29-1.42 (m, 1 H), 2.96 (s, 3 H), 3.28 (s, 2 H), 3.38 (s, 3 H), 4.50 (s, 2 H), 4.72 (s, 2 H), 6.92 (d, J = 8.85 Hz, 1 H), 7.58-7.65 (m, 1 H), 7.69-7.88 (m, 4 H), 9.40 (s, 1 H) | MS (DCI/NH$_3$) m/z 523 (M + H)$^+$ |
| 460 | 6-(2,6-dichlorophenyl)-8-ethyl-2-[(1,1,2-trimethyl-1,2,3,4-tetrahydroisoquinolin-6-yl)amino]pyrimido[4,5-d]pyridazin-5(6H)-one | $^1$H NMR (400 MHz, DMSO-$d_6$): δ 10.63 (br s, 1 H), 9.35 (s, 1 H), 8.07-7.04 (m, 6 H), 3.06-2.97 (m, 2 H), 2.76 (s, 4 H), 2.34 (s, 3 H), 1.32 (s, 6 H), 1.27 (t, J = 7.2 Hz, 3 H) | MS (ESI) m/z 509 (M + H)$^+$ |
| 461 | 6-(2,6-dichlorophenyl)-8-ethyl-2-[(1,1,2-trimethyl-1,2,3,4-tetrahydroisoquinolin-7-yl)amino]pyrimido[4,5-d]pyridazin-5(6H)-one | $^1$H NMR (400 MHz, DMSO-$d_6$): δ 10.62 (br s, 1 H), 9.35 (s, 1 H), 8.07-7.46 (m, 5 H), 7.05 (d, J = 8.4 Hz, 1 H), 3.03 (q, J = 7.6 Hz, 2 H), 2.74 (s, 4 H), 2.35 (s, 3 H), 1.38 (s, 6 H), 1.24 (t, J = 7.2 Hz, 3 H) | MS (ESI) m/z 509 (M + H)$^+$ |

TABLE 1-continued

| Ex | Name | $^1$H NMR | MS |
|---|---|---|---|
| 462 | 6-(2,6-dichlorophenyl)-2-[(4,4-dimethyl-1,2,3,4-tetrahydroisoquinolin-7-yl)amino]-8-ethylpyrimido[4,5-d]pyridazin-5(6H)-one | $^1$H NMR (400 MHz, DMSO-$d_6$): δ 10.64 (br s, 1 H), 9.34 (s, 1 H), 7.74-7.58 (m, 5 H), 7.35 (d, J = 8.4 Hz, 1 H), 3.86 (s, 2 H), 2.99 (q, J = 7.2 Hz, 2 H), 2.70 (s, 2 H), 1.27 (t, J = 7.2 Hz, 3 H), 1.22 (s, 6 H) | MS (ESI) m/z 495 (M + H)$^+$ |
| 463 | 6-(2,6-dichlorophenyl)-2-[(1,1-dimethyl-1,2,3,4-tetrahydroisoquinolin-7-yl)amino]-8-ethylpyrimido[4,5-d]pyridazin-5(6H)-one | $^1$H NMR (400 MHz, DMSO-$d_6$): δ 10.62 (br s, 1 H), 9.35 (s, 1 H), 8.03-7.42 (m, 5 H), 7.04 (d, J = 8.0 Hz, 1 H), 3.03 (q, J = 7.6 Hz, 2 H), 2.96 (t, J = 5.6 Hz, 2 H), 2.66 (t, J = 5.6 Hz, 2 H), 1.40 (s, 6 H), 1.25 (t, J = 7.2 Hz, 3 H) | MS (ESI) m/z 495 (M + H)$^+$ |
| 464 | 6-(2,6-dichlorophenyl)-8-ethyl-2-[(3-oxo-1,2,3,4-tetrahydroisoquinolin-7-yl)amino]pyrimido[4,5-d]pyridazin-5(6H)-one | $^1$H NMR (400 MHz, DMSO-$d_6$): δ 10.76 (br s, 1 H), 9.37 (s, 1 H), 8.02-7.58 (m, 6 H), 7.25 (dd, J = 25.6, 8.4 Hz, 1 H), 4.35 (d, J = 8.4 Hz, 2 H), 3.45 (d, J = 10.4 Hz, 2 H), 3.00 (q, J = 7.6 Hz, 2 H), 1.27 (t, J = 7.2 Hz, 3 H) | MS (ESI) m/z 481 (M + H)$^+$ |
| 465 | 6-(2,6-dichlorophenyl)-8-ethyl-2-({4-[(4-methylpiperazin-1-yl)methyl]phenyl}amino)pyrimido[4,5-d]pyridazin-5(6H)-one | $^1$H NMR (400 MHz, DMSO-$d_6$): δ 10.74 (br s, 1 H), 9.37 (s, 1 H), 7.84-7.58 (m, 5 H), 7.30 (d, J = 8.8 Hz, 2 H), 3.43 (s, 2 H), 3.00 (q, J = 7.6 Hz, 2 H), 2.43-2.25 (m, 8 H), 2.16 (s, 3 H), 1.25 (t, J = 7.2 Hz, 3 H) | MS (ESI) m/z 524 (M + H)$^+$ |
| 466 | 6-(2,6-dichlorophenyl)-2-[(1,1-dimethyl-1,2,3,4-tetrahydroisoquinolin-6-yl)amino]-8-ethylpyrimido[4,5-d]pyridazin-5(6H)-one | $^1$H NMR (400 MHz, DMSO-$d_6$): δ 10.76 (s, 1 H), 9.39 (s, 1 H), 9.27 (s, 1 H), 9.21 (s, 1 H), 8.10-7.23 (m, 6 H), 3.47 (d, J = 4.8 Hz, 2 H), 3.07-2.99 (m, 4 H), 1.70 (s, 6 H), 1.24 (t, J = 7.2 Hz, 3 H) | MS (ESI) m/z 495 (M + H)$^+$ |
| 468 | 2-({4-[(1R,4R)-2,5-diazabicyclo[2.2.1]hept-2-yl]phenyl}amino)-6-(2,6-dichlorophenyl)-8-ethylpyrimido[4,5-d]pyridazin-5(6H)-one | $^1$H NMR (400 MHz, DMSO-$d_6$): δ 10.54 (br s, 1 H), 9.28 (s, 1 H), 9.08 (s, 1 H), 8.58 (s, 1 H), 7.77-7.48 (m, 5 H), 6.72 (d, J = 8.0 Hz, 2 H), 4.63 (s, 1 H), 4.46 (s, 1 H), 3.63 (d, J = 8.4 Hz, 1 H), 3.27-3.19 (m, 3 H), 2.96 (q, J = 7.6 Hz, 2 H), 2.04 (dd, J = 10.4, 9.0 Hz, 2 H), 1.24 (t, J = 7.2 Hz, 3 H) | MS (ESI) m/z 508 (M + H)$^+$ |
| 469 | 6-(2,6-dichlorophenyl)-8-ethyl-2-{[3-methyl-4-(4-methyl-1,4-diazepan-1-yl)phenyl]amino}pyrimido[4,5-d]pyridazin-5(6H)-one | $^1$H NMR (400 MHz, DMSO-$d_6$): δ 10.59 (s, 1 H), 9.32 (s, 1 H), 7.77-7.57 (m, 5 H), 7.08 (d, J 8.8 Hz, 1 H), 3.12-3.08 (m, 4 H), 2.98 (q, J = 7.6 Hz, 2 H), 2.69-2.64 (m, 4 H), 2.31 (s, 3 H), 2.28 (s, 3 H), 1.89-1.83 (m, 2 H), 1.26 (t, J = 7.2 Hz, 3 H) | MS (ESI) m/z 538 (M + H)$^+$ |
| 470 | 6-(2,6-dichlorophenyl)-8-ethyl-2-{[4-(3-oxopiperazin-1-yl)phenyl]amino}pyrimido[4,5-d]pyridazin-5(6H)-one | $^1$H NMR (400 MHz, DMSO-$d_6$): δ 10.59 (br s, 1 H), 9.30 (s, 1 H), 8.03 (br s, 1 H), 7.77-7.57 (m, 5 H), 6.98 (d, J = 9.2 Hz, 2 H), 3.71 (s, 2 H), 3.42-3.37 (m, 2 H), 3.34-3.28 (m, 2 H), 2.97 (q, J = 7.6 Hz, 2 H), 1.24 (t, J = 7.2 Hz, 3 H) | MS (ESI) m/z 510 (M + H)$^+$ |
| 473 | 6-(2,6-dichlorophenyl)-8-(difluoromethyl)-2-(1,2,3,4-tetrahydroisoquinolin-6-ylamino)pyrimido[4,5-d]pyridazin-5(6H)-one | $^1$H NMR (300 MHz, DMSO-$d_6$): δ 2.49 (s, 3 H), 3.01 (s, 2 H), 3.36-3.44 (m, 1 H), 4.26 (s, 2 H), 7.08-7.43 (m, 2 H), 7.64 (d, J = 5.49 Hz, 1 H), 7.71-7.81 (m, 2 H), 7.85-8.03 (m, 1 H), 9.42 (d, J = 0.31 Hz, 1 H) | MS (DCI/NH$_3$) m/z 489 (M + H)$^+$ |
| 474 | 6-(2,6-dichlorophenyl)-8-(difluoromethyl)-2-[(2-methyl-1,2,3,4-tetrahydroisoquinolin-6-yl)amino]pyrimido[4,5-d]pyridazin-5(6H)-one | $^1$H NMR (300 MHz, DMSO-$d_6$): δ 2.87 (s, 3 H), 2.89 (d, J = 3.97 Hz, 2 H), 3.14-3.21 (m, J = 5.16 Hz, 1 H), 3.23-3.34 (m, 2 H), 3.68 (s, 2 H), 7.06-7.13 (m, 1 H), 7.51-7.62 (m, 1 H), 7.62-7.68 (m, 1 H), 7.73-7.79 (m, 2 H), 7.80-7.87 (m, 1 H), 9.40 (s, 1 H) | MS (DCI/NH$_3$) m/z 489 (M + H)$^+$ |

TABLE 1-continued

| Ex | Name | ¹H NMR | MS |
|---|---|---|---|
| 475 | 6-(2,6-dichlorophenyl)-8-(difluoromethyl)-2-[(2-methyl-1,2,3,4-tetrahydroisoquinolin-7-yl)amino]pyrimido[4,5-d]pyridazin-5(6H)-one | ¹H NMR (300 MHz, DMSO-d₆): δ 2.44 (s, 3 H), 2.68-2.78 (m, 2 H), 2.80-2.89 (m, J = 5.16 Hz, 3 H), 3.61 (s, 2 H), 7.06-7.20 (m, 1 H), 7.55 (d, J = 6.74 Hz, 1 H), 7.60-7.70 (m, 1 H), 7.71-7.82 (m, 3 H), 9.40 (s, 1 H) | MS (DCI/NH₃) m/z 503 (M + H)⁺ |
| 476 | 2-[(2-acetyl-1,2,3,4-tetrahydroisoquinolin-6-yl)amino]-6-(2,6-dichlorophenyl)-8-(difluoromethyl)pyrimido[4,5-d]pyridazin-5(6H)-one | ¹H NMR (300 MHz, DMSO-d₆): δ 2.09 (s, 3 H), 2.71-2.81 (m, 1 H), 2.88 (t, J = 5.59 Hz, 2 H), 3.68 (t, J = 5.93 Hz, 2 H), 4.58 (s, 2 H), 7.20 (d, J = 8.48 Hz, 1 H), 7.56-7.70 (m, 2 H), 7.74-7.90 (m, 3 H), 9.40 (s, 1 H) | MS (DCI/NH₃) m/z 531 (M + H)⁺ |
| 477 | 2-[(2-acetyl-1,2,3,4-tetrahydroisoquinolin-7-yl)amino]-6-(2,6-dichlorophenyl)-8-(difluoromethyl)pyrimido[4,5-d]pyridazin-5(6H)-one | ¹H NMR (300 MHz, DMSO-d₆): δ 2.10 (s, 3 H), 2.70-2.78 (m, 1 H), 2.85 (t, J = 5.76 Hz, 2 H), 3.67 (t, J = 5.93 Hz, 2 H), 4.61 (s, 2 H), 7.19 (d, J = 8.14 Hz, 1 H), 7.57-7.70 (m, 2 H), 7.72-7.82 (m, 3 H), 9.40 (s, 1 H) | MS (DCI/NH₃) m/z 531 (M + H)⁺ |
| 478 | 6-(2,6-dichlorophenyl)-8-(difluoromethyl)-2-[(4,4-dimethyl-1,2,3,4-tetrahydroisoquinolin-7-yl)amino]pyrimido[4,5-d]pyridazin-5(6H)-one | ¹H NMR (300 MHz, DMSO-d₆): δ 1.36 (s, 6 H), 3.24-3.28 (m, 1 H), 3.50-3.74 (m, 2 H), 4.28 (s, 2 H), 7.51 (d, J = 8.48 Hz, 1 H), 7.60-7.73 (m, 2 H), 7.75-7.79 (m, 2 H), 7.89 (dd, J = 4.07, 2.37 Hz, 1 H), 9.43 (s, 1 H) | MS (DCI/NH₃) m/z 517 (M + H)⁺ |
| 479 | 6-(2,6-dichlorophenyl)-8-(difluoromethyl)-2-{[4-(piperidin-3-yl)phenyl]amino}pyrimido[4,5-d]pyridazin-5(6H)-one | ¹H NMR (300 MHz, DMSO-d₆): δ 1.66-1.81 (m, 2 H), 1.91 (d, J = 8.82 Hz, 2 H), 2.87-2.97 (m, J = 10.17 Hz, 1 H), 2.97-3.12 (m, 1 H), 3.30-3.36 (m, 2 H), 3.68-4.01 (m, 2 H), 7.32 (d, J = 8.48 Hz, 2 H), 7.75-7.80 (m, 2 H), 7.89 (dd, J = 4.24, 2.20 Hz, 1 H), 8.36-8.55 (m, 1 H), 8.80 (d, J = 11.19 Hz, 1 H), 9.42 (s, 1 H) | MS (DCI/NH₃) m/z 517 (M + H)⁺ |
| 485 | 6-(2,6-dichlorophenyl)-8-(difluoromethyl)-2-[(1,1,2-trimethyl-2,3-dihydro-1H-isoindol-5-yl)amino]pyrimido[4,5-d]pyridazin-5(6H)-one | ¹H NMR (300 MHz, DMSO-d₆): δ 1.20 (s, 6 H), 2.37 (s, 3 H), 3.85 (s, 2 H), 7.21 (d, J = 8.14 Hz, 1 H), 7.44-7.52 (m, 1 H), 7.61-7.68 (m, 1 H), 7.74-7.79 (m, 2 H), 7.81-7.91 (m, 2 H), 9.39 (s, 1 H) | MS (DCI/NH₃) m/z 517 (M + H)⁺ |
| 486 | 6-(2,6-dichlorophenyl)-8-(difluoromethyl)-2-{[4-(1-methylpiperidin-3-yl)phenyl]amino}pyrimido[4,5-d]pyridazin-5(6H)-one | ¹H NMR (300 MHz, DMSO-d₆): δ 1.53-1.74 (m, 2 H), 1.71-1.87 (m, 2 H), 1.85-2.05 (m, 2 H), 2.80 (s, 3 H), 2.86-3.04 (m, 2 H), 3.05-3.14 (m, 1 H), 7.28-7.34 (m, 2 H), 7.63-7.68 (m, 1 H), 7.75-7.80 (m, 2 H), 7.83-7.98 (m, 2 H), 9.42 (s, 1 H) | MS (DCI/NH₃) m/z 531 (M + H)⁺ |
| 492 | 6-(2,6-dichlorophenyl)-8-ethyl-2-[(2-methyl-1,2,3,4-tetrahydroisoquinolin-6-yl)amino]pyrimido[4,5-d]pyridazin-5(6H)-one | ¹H NMR (400 MHz, DMSO-d₆): δ 10.67 (br s, 1 H), 9.35 (s, 1 H), 7.77-7.56 (m, 5 H), 7.06 (d, J = 8.4 Hz, 1 H), 3.47 (s, 2 H), 2.98 (q, J = 7.6 Hz, 2 H), 2.84 (t, J = 5.6 Hz, 2 H), 2.61 (t, J = 5.6 Hz, 2 H), 2.35 (s, 3 H), 1.26 (t, J = 7.6 Hz, 3 H) | MS (ESI) m/z 481 (M + H)⁺ |
| 493 | 6-(2,6-dichlorophenyl)-8-ethyl-2-[(2-methyl-1,2,3,4-tetrahydroisoquinolin-7-yl)amino]pyrimido[4,5-d]pyridazin-5(6H)-one | ¹H NMR (400 MHz, DMSO-d₆): δ 10.83 (br s, 1 H), 10.18 (br s, 1 H), 9.39 (s, 1 H), 7.78-7.59 (m, 5 H), 7.29 (d, J = 8.4 Hz, 1 H), 4.49-4.35 (m, 2 H), 3.68-3.47 (m, 2 H), 3.07 (s, 2 H), 3.00 (q, J = 7.6 Hz, 2 H), 2.96 (s, 3 H), 1.28 (t, J = 7.6 Hz, 3 H) | MS (ESI) m/z 481 (M + H)⁺ |
| 494 | 6-(2,6-dichlorophenyl)-8-ethyl-2-[(2-methyl-2,3-dihydro-1H-isoindol-5-yl)amino]pyrimido[4,5-d]pyridazin-5(6H)-one | ¹H NMR (400 MHz, DMSO-d₆): δ 10.72 (br s, 1 H), 9.36 (s, 1 H), 7.82-7.58 (m, 5 H), 7.38 (d, J = 8.0 Hz, 1 H), 3.86 (s, 2 H), 3.82 (s, 2 H), 2.98 (q, J = 7.6 Hz, 2 H), 2.51 (s, 3 H), 1.25 (t, J = 7.6 Hz, 3 H) | MS (ESI) m/z 467 (M + H)⁺ |

Example 190

3-[6-(2,6-dichlorophenyl)-2-{[4-(4-methylpiperazin-1-yl)phenyl]amino}-5-oxo-5,6-dihydropyrimido[4,5-d]pyridazin-8-yl]benzoic acid

Example 190A methyl 3-(6-(2,6-dichlorophenyl)-2-(4-(4-methylpiperazin-1-yl)phenylamino)-5-oxo-5,6-dihydropyridazino[4,5-d]pyrimidin-8-yl)benzoate A solution of Example 72 (20 mg, 0.031 mmol) in methanol (4 ml) was added to a mixture of Pd-dppf (Heraeus, 1.148 mg, 1.569 μmol) and triethylamine (8.75 μl, 0.063 mmol) in a 50 mL pressure bottle. The mixture was pressurized with carbon monoxide (60 psi), and stirred at 80° C. for 4 hours. The volatiles were removed and the residue was purified by flash chromatography eluted with 30% ethyl acetate in hexane. MS (DCI/NH$_3$) m/z 616 (M+H)$^+$.

Example 190B 3-(6-(2,6-dichlorophenyl)-2-(4-(4-methylpiperazin-1-yl)phenylamino)-5-oxo-5,6-dihydropyrimido[4,5-d]pyridazin-8-yl)benzoic acid The title compound was prepared as described in Example 225A, substituting Example 190A for Example 222. MS (DCI/NH$_3$) m/z 603 (M+H)$^+$; $^1$H NMR (400 MHz, DMSO-d$_6$): δ 2.84 (s, 3H), 3.03 (d, J=11.19 Hz, 2H), 3.11-3.23 (m, 2H), 3.50 (d, J=9.16 Hz, 2H), 3.75 (d, J=9.83 Hz, 2H), 6.89 (d, J=7.12 Hz, 2H), 7.48-7.70 (m, 4H), 7.71-7.84 (m, 3H), 8.10 (d, J=7.80 Hz, 2H), 9.39 (s, 1H).

Example 191

3-[6-(2,6-dichlorophenyl)-2-{[4-(4-methylpiperazin-1-yl)phenyl]amino}-5-oxo-5,6-dihydropyrimido[4,5-d]pyridazin-8-yl]-N-methylbenzamide The title compound was prepared as described in Example 225B, substituting Example 190 for Example 225A and methylamine for pyrrolidine. MS (DCI/NH$_3$) m/z 615 (M+H)$^+$; $^1$H NMR (400 MHz, DMSO-d$_6$): δ 2.78 (d, J=4.76 Hz, 3H), 2.87 (s, 3H), 2.88-2.99 (m, 2H), 3.07-3.25 (m, 2H), 3.50-3.60 (m, 2H), 3.75 (d, J=13.09 Hz, 2H), 6.84 (d, J=8.33 Hz, 2H), 7.52-7.70 (m, 4H), 7.71-7.83 (m, 3H), 7.96 (d, J=7.54 Hz, 2H), 9.40 (s, 1H).

Example 192

6-(2,6-dichlorophenyl)-8-{3-[(4-methylpiperazin-1-yl)carbonyl]phenyl}-2-{[4-(4-methylpiperazin-1-yl)phenyl]amino}pyrimido[4,5-d]pyridazin-5(6H)-one The title compound was prepared as described in Example 225B, substituting Example 190 for Example 225A and 1-methylpiperazine for pyrrolidine. MS (DCI/NH$_3$) m/z 684 (M+H)$^+$; $^1$H NMR (400 MHz, DMSO-d$_6$): δ 2.79 (s, 3H), 2.88 (s, 3H), 2.97 (d, J=12.30 Hz, 2H), 3.07-3.29 (m, 2H), 3.43-3.95 (m, 12H), 6.90-7.03 (m, 2H), 7.59-7.69 (m, 4H), 7.70-7.81 (m, 3H), 8.14 (d, J=6.74 Hz, 2H), 9.40 (s, 1H).

Example 200

8-[1-(2-chloroethyl)-1H-pyrazol-4-yl]-6-(2,6-dichlorophenyl)-2-{[4-(4-methylpiperazin-1-yl)phenyl]amino}pyrimido[4,5-d]pyridazin-5(6H)-one

Example 200A ethyl 4-(1-(2-chloroethyl)-1H-pyrazole-4-carbonyl)-2-(methylthio)pyrimidine-5-carboxylate The title compound was prepared as described in Example 60A, substituting 1-(2-chloroethyl)-1H-pyrazole-4-carbaldehyde for picolinaldehyde. MS (DCI/NH$_3$) m/z 355 (M+H)$^+$.

Example 200B ethyl 4-(1-(2-chloroethyl)-1H-pyrazole-4-carbonyl)-2-(4-(4-methylpiperazin-1-yl)phenylamino)pyrimidine-5-carboxylate The title compound was prepared as described in Example 6C, substituting Example 200A for Example 6B. MS (DCI/NH$_3$) m/z 498 (M+H)$^+$.

Example 200C

8-[1-(2-chloroethyl)-1H-pyrazol-4-yl]-6-(2,6-dichlorophenyl)-2-{[4-(4-methylpiperazin-1-yl)phenyl]amino}pyrimido[4,5-d]pyridazin-5(6H)-one The title compound was prepared as described in Example 6D, substituting Example 200B for Example 6C and 2,6-dichlorophenylhydrazine for methylhydrazine. MS (DCI/NH$_3$) m/z 612 (M+H)$^+$; $^1$H NMR (300 MHz, DMSO-D6) δ ppm 2.89 (s, 3H), 2.99 (t, J=12.29 Hz, 2H), 3.19 (d, J=15.07 Hz, 2H), 3.37-3.68 (m, 2H), 3.87 (d, J=12.69 Hz, 2H), 3.93-4.14 (m, 2H), 4.30-4.56 (m, 2H), 7.11 (d, J=8.33 Hz, 2H), 7.56-7.61 (m, 4H), 7.70-7.80 (m, 3H), 9.35 (s, 1H).

Example 202

6-(2,6-dichlorophenyl)-8-{1-[2-(ethylamino)ethyl]-1H-pyrazol-4-yl}-2-{[4-(4-methylpiperazin-1-yl)phenyl]amino}pyrimido[4,5-d]pyridazin-5(6H)-one To a solution of Example 200 (40 mg, 0.065 mmol) in N,N-dimethylformamide (2 mL) was added KI (83 mg, 0.65 mmol), K$_2$CO$_3$ (47 mg, 0.65 mmol) and ethylamine (30 mg, 0.65 mmol) successively. The mixture was stirred at 80° C. overnight and concentrated. The residue was purified by HPLC (Zorbax C-18, 0.1% TFA/CH$_3$CN/H$_2$O) to yield the title compound as a TFA salt. MS (DCI/NH$_3$) m/z 619 (M+H)$^+$; $^1$H NMR (300 MHz, DMSO-d$_6$) δ 1.14 (q, J=7.23 Hz, 3H), 2.89 (s, 3H), 2.98 (t, J=10.85 Hz, 4H), 3.09-3.26 (m, 2H), 3.35-3.53 (m, 2H), 3.53 (s, 2H), 3.85 (d, J=13.22 Hz, 2H), 4.45 (t, J=14.07 Hz, 2H), 7.08 (d, J=8.82 Hz, 2H), 7.53-7.67 (m, 4H), 7.69-7.81 (m, 3H), 9.36 (s, 1H).

Example 211

6-(2,6-dichlorophenyl)-8-{1-[2-(methylamino) ethyl]-1H-pyrazol-4-yl}-2-{[4-(4-methylpiperazin-1-yl)phenyl]amino}pyrimido[4,5-d]pyridazin-5(6H)-one The title compound was prepared as described in Example 202, substituting methylamine for ethylamine. MS (DCI/NH$_3$) m/z 605 (M+H)$^+$; $^1$H NMR (300 MHz, DMSO-d$_6$) δ 2.56 (d, J=5.76 Hz, 3H), 2.57-2.61 (m, 2H), 2.89 (s, 3H), 2.93-3.06 (m, 2H), 3.10-3.27 (m, 2H), 3.41 (d, J=3.39 Hz, 2H), 3.55 (d, J=11.53 Hz, 2H), 3.85 (d, J=13.22 Hz, 2H), 7.09 (d, J=9.16 Hz, 2H), 7.54-7.65 (m, 4H), 7.72-7.77 (m, 3H), 9.36 (s, 1H).

Example 212

6-(2,6-dichlorophenyl)-8-{1-[2-(dimethylamino) ethyl]-1H-pyrazol-4-yl}-2-{[4-(4-methylpiperazin-1-yl)phenyl]amino}pyrimido[4,5-d]pyridazin-5(6H)-one The title compound was prepared as described in Example 202, substituting dimethylamine for ethylamine. MS (DCI/NH$_3$) m/z 618 (M+H)$^+$; $^1$H NMR (300 MHz, DMSO-d$_6$) δ 2.81 (s, 6H), 2.89 (s, 3H), 2.99 (d, J=11.90 Hz, 2H), 3.18 (q, J=9.65 Hz, 2H), 3.55 (d, J=12.29 Hz, 4H), 3.85 (d, J=12.29 Hz, 2H), 4.55 (d, J=15.07 Hz, 2H), 7.08 (d, J=8.72 Hz, 2H), 7.54-7.65 (m, 4H), 7.71-7.79 (m, 3H), 9.36 (s, 1H).

Example 213

6-(2,6-dichlorophenyl)-2-{[4-(4-methylpiperazin-1-yl)phenyl]amino}-8-{1-[2-(piperidin-1-yl)ethyl]-1H-pyrazol-4-yl}pyrimido[4,5-d]pyridazin-5(6H)-one The title compound was prepared as described in Example 202, substituting piperidine for ethylamine. MS (DCI/NH$_3$) m/z 658 (M+H)$^+$; $^1$H NMR (300 MHz, DMSO-d$_6$) δ 1.26-1.44 (m, 2H), 1.54-1.72 (m, 4H), 1.75-1.89 (m, 4H), 2.89 (s, 3H), 2.93-3.05 (m, 2H), 3.12-3.27 (m, 2H), 3.38-3.65 (m, 4H), 3.85 (d, J=12.70 Hz, 2H), 4.47-4.79 (m, 2H), 7.08 (d, J=9.12 Hz, 2H), 7.52-7.69 (m, 4H), 7.69-7.84 (m, 3H), 9.36 (s, 1H).

Example 214

6-(2,6-dichlorophenyl)-8-{1-[2-(4-methylpiperazin-1-yl)ethyl]-1H-pyrazol-4-yl}-2-{[4-(4-methylpiperazin-1-yl)phenyl]amino}pyrimido[4,5-d]pyridazin-5(6H)-one The title compound was prepared as described in Example 202, substituting 1-methylpiperazine for ethylamine. MS (DCI/NH$_3$) m/z 674 (M+H)$^+$; $^1$H NMR (300 MHz, DMSO-d$_6$) δ 2.19-2.46 (m, 2H), 2.74 (s, 3H), 2.85 (m, 2H), 2.89 (s, 3H), 3.00 (d, J=12.29 Hz, 4H), 3.19-3.26 (m, 4H), 3.27-3.42 (m, 2H), 3.56 (d, J=11.50 Hz, 2H), 3.80-3.95 (m, 2H), 4.15-4.39 (m, 2H), 7.10 (d, J=7.54 Hz, 2H), 7.48-7.66 (m, 4H), 7.70-7.78 (m, 3H), 9.36 (s, 1H).

Example 215

6-(2,6-dichlorophenyl)-8-{3-[(4-methylpiperazin-1-yl)methyl]phenyl}-2-{[4-(4-methylpiperazin-1-yl)phenyl]amino}pyrimido[4,5-d]pyridazin-5(6H)-one

Example 215A ethyl 4-(3-(dimethoxymethyl)benzoyl)-2-(methylthio)pyrimidine-5-carboxylate The title compound was prepared as described in Example 60A, substituting 3-(dimethoxymethyl)benzaldehyde for picolinaldehyde. MS (DCI/NH$_3$) m/z 377 (M+H)$^+$.

Example 215B ethyl 4-(3-(dimethoxymethyl)benzoyl)-2-(4-(4-methylpiperazin-1-yl)phenylamino)pyrimidine-5-carboxylate The title compound was prepared as described in Example 6C, substituting Example 215A for Example 6B. MS (DCI/NH$_3$) m/z 520 (M+H)$^+$.

Example 215C ethyl 4-(3-formylbenzoyl)-2-(4-(4-methylpiperazin-1-yl)phenylamino)pyrimidine-5-carboxylate A solution of Example 215B (200 mg, 0.54 mmol) in dichloromethane (20 ml) was added TFA (5 mL). The mixture was stirred at 40° C. overnight. The reaction mixture was concentrated and the crude product was used in the next step without further purification. MS (DCI/NH$_3$) m/z 474 (M+H)$^+$.

Example 215D ethyl 4-(3-((4-methylpiperazin-1-yl)methyl)benzoyl)-2-(4-(4-methylpiperazin-1-yl)phenylamino) pyrimidine-5-carboxylate A solution of Example 215C (100 mg, 0.2 mmol) in dioxane (5 mL) was added 1-methylpiperazine (40 mg, 0.4 mmol) and NaCNBH$_3$ (25 mg, 0.5 mmol). The reaction mixture was stirred at 70° C. for 2 days, and concentrated. The residue was purified by flash chromatography, eluted with 0-20% gradient methanol in methylene chloride to yield the title compound. MS (DCI/NH$_3$) m/z 557 (M+H).

Example 215E 6-(2,6-dichlorophenyl)-8-{3-[(4-methylpiperazin-1-yl)methyl]phenyl}-2-{[4-(4-methylpiperazin-1-yl)phenyl]amino}pyrimido[4,5-d]pyridazin-5(6H)-one The title compound was prepared as described in Example 6D, substituting Example 215D for Example 6C and 2,6-dichlorophenylhydrazine for methylhydrazine. MS (DCI/NH$_3$) m/z 670 (M+H)$^+$; $^1$H NMR (300 MHz, DMSO-d$_6$) δ 2.75 (s, 3H), 2.88 (s, 3H), 2.91-3.02 (m, 4H), 3.07-3.25 (m, 4H), 3.25-3.44 (m, 2H), 3.54 (d, J=11.50 Hz, 4H), 3.67-3.87 (m, 4H), 6.93 (d, J=6.74 Hz, 2H), 7.46-7.69 (m, 5H), 7.73-7.81 (m, 3H), 7.96 (d, J=7.14 Hz, 1H), 9.39 (s, 1H).

Example 216

8-[3-(azetidin-1-ylcarbonyl)phenyl]-6-(2,6-dichlorophenyl)-2-{[4-(4-methylpiperazin-1-yl)phenyl]amino}pyrimido[4,5-d]pyridazin-5(6H)-one The title compound was prepared as described in Example 225B, substituting Example 190 for Example 225A and azetidine for pyrrolidine. MS (DCI/NH$_3$) m/z 641 (M+H)$^+$; $^1$H NMR (300 MHz, DMSO-d$_6$) δ 2.13-2.31 (m, 2H), 2.87 (s, 3H), 2.88-2.98 (m, 2H), 3.06-3.29 (m, 4H), 3.54 (d, J=12.29 Hz, 2H), 3.79 (d, J=11.90 Hz, 2H), 4.04 (t, J=7.54 Hz, 2H), 6.90 (t, J=7.73 Hz, 2H), 7.55-7.69 (m, 4H), 7.72-7.82 (m, 3H), 7.95-8.21 (m, 2H), 9.39 (s, 1H).

Example 218

2-(4-(4-aminophenyl)piperazin-1-yl)-8-(pyridin-2-yl)-6-(pyridin-4-yl)pyridazino[4,5-d]pyrimidin-5(6H)-one

Example 218A ethyl 2-(methylthio)-4-picolinoylpyrimidine-5-carboxylate

The title compound was prepared as described in Example 6B, substituting picolinoyl chloride for 3-phenylpropanoyl chloride. MS (DCI/NH$_3$) m/z 304 (M+H)$^+$.

Example 218B 2-(4-(4-aminophenyl)piperazin-1-yl)-8-(pyridin-2-yl)-6-(pyridin-4-yl)pyridazino[4,5-d]pyrimidin-5(6H)-one To a solution of Example 218A (3.4 g, 11.21 mmol) in dichloromethane (40 ml) was added 3-chloroperoxybenzoic acid (2.73 g, 13.45 mmol) portionwise. After the addition, the reaction mixture was stirred at 25° C. for 15 hours. Aqueous NaHCO$_3$ solution was then added and the mixture was extracted with dichloromethane (30 mL×3). The combined organic layers were washed with brine, dried over Na$_2$SO$_4$, filtered, and concentrated in vacuo. The residue was dissolved in 2-propanol, and was added 4-(piperazin-1-yl)aniline (2.38 g, 13.45 mmol) and TFA (127 mg, 1.12 mmol) at room temperature. The reaction mixture was heated up to 120° C. and stirred at this temperature for 15 h. After cooling, the volatiles were removed and the residue was purified by flash chromatography (40-95% gradient methanol in water) to give the title compound. MS (ESI) m/z 478 (M+H)$^+$; $^1$H NMR (400 MHz, CDCl$_3$) δ 9.43 (s, 1H), 8.81 (d, J=4.8 Hz, 1H), 8.71 (dd, J=2.0, 4.8 Hz, 2H), 7.92-7.85 (m, 4H), 7.46-7.42 (m, 1H), 6.83 (d, J=8.8 Hz, 2H), 6.67 (d, J=9.2 Hz, 2H), 4.18 (br s, 2H), 3.99 (br s, 2H), 3.49 (br s, 1H), 3.18-3.00 (m, 4H).

Example 219

8-(2-acetylpyridin-4-yl)-6-(2,6-dichlorophenyl)-2-{[4-(4-methylpiperazin-1-yl)phenyl]amino}pyrimido[4,5-d]pyridazin-5(6H)-one The title compound was prepared as described in Example 175E, substituting 2-chloroisonicotinoyl chloride for 6-chloropicolinoyl chloride. MS (DCI/NH$_3$) m/z 602 (M+H)$^+$; $^1$H NMR (400 MHz, CD$_3$OD) δ 2.71 (s, 3H), 2.99 (s, 3H), 3.02-3.08 (m, 2H), 3.60-3.67 (m, 2H), 3.78-3.85 (m, 2H), 6.93 (d, J=8.24 Hz, 2H), 7.51-7.58 (m, 3H), 7.61-7.66 (m, 2H), 8.15 (d, J=3.66 Hz, 1H), 8.58 (s, 1H), 8.77 (d, J=4.58 Hz, 1H), 9.38 (s, 1H).

Example 222 methyl 4-[6-(2,6-dichlorophenyl)-2-{[4-(4-methylpiperazin-1-yl)phenyl]amino}-5-oxo-5,6-dihydropyrimido[4,5-d]pyridazin-8-yl]pyridine-2-carboxylate The title compound was prepared as described in Example 175D, substituting 2-chloroisonicotinoyl chloride for 6-chloropicolinoyl chloride. MS (DCI/NH$_3$) m/z 617 (M+H)$^+$; $^1$H NMR (400 MHz, CD$_3$OD) δ 3.02 (s, 3H), 3.24-3.28 (m, 2H), 3.87-3.90 (m, 2H), 4.14-4.17 (m, 4H), 4.67 (s, 3H), 7.61 (d, J=8.85 Hz, 2H), 8.31 (d, J=8.85 Hz, 2H), 8.44 (dd, J=8.85, 7.63 Hz, 1H), 8.57 (d, J=7.93 Hz, 2H), 8.92 (d, J=3.97 Hz, 1H), 9.30 (s, 1H), 9.67 (d, J=4.88 Hz, 1H), 10.17 (s, 1H), 11.44 (s, 1H).

Example 225

6-(2,6-dichlorophenyl)-2-{[4-(4-methylpiperazin-1-yl)phenyl]amino}-8-[2-(pyrrolidin-1-ylcarbonyl)pyridin-4-yl]pyrimido[4,5-d]pyridazin-5(6H)-one

Example 225A 4-(6-(2,6-dichlorophenyl)-2-(4-(4-methylpiperazin-1-yl)phenylamino)-5-oxo-5,6-dihydropyrimido[4,5-d]pyridazin-8-yl)picolinic acid To a solution of Example 222 (0.36 g, 0.583 mmol) in THF (8 mL) was added lithium hydroxide monohydrate (0.049 g, 1.166 mmol) in water (8 mL). Methanol was added until a transparent solution formed (8 mL). This mixture was stirred at room temperature for 2 hours and acidified to pH 5 with 2N aqueous HCl solution. The mixture was concentrated and the formed solid was collected by filtration, washed with water and dried to give the title compound. MS (DCI/NH$_3$) m/z 604 (M+H)$^+$.

Example 225B 6-(2,6-dichlorophenyl)-2-{[4-(4-methylpiperazin-1-yl)phenyl]amino}-8-[2-(pyrrolidin-1-ylcarbonyl)pyridin-4-yl]pyrimido[4,5-d]pyridazin-5(6H)-one To a solution of Example 225A (30 mg, 0.050 mmol) and pyrrolidine (5.3 mg, 0.075 mmol) in anhydrous N,N-dimethylformamide (2 mL) was added 1-ethyl-3-[3-(dimethylamino)propyl]-carbodiimide hydrochloride (14.30 mg, 0.075 mmol), 1-hydroxybenzotriazole hydrate (11.42 mg, 0.075 mmol) and triethylamine (0.021 mL, 0.149 mmol). The solution was stirred at room temperature overnight, concentrated and purified by flash chromatography (0-15% gradient methanol in CH$_2$Cl$_2$) to give the title compound. MS (DCI/NH$_3$) m/z 656 (M+H)$^+$; $^1$H NMR (400 MHz, DMSO-d$_6$) δ 1.83-1.88 (m, 4H), 2.23 (s, 3H), 2.44-2.48 (m, 2H), 3.08-3.12 (m, 2H), 3.33 (m, 4H), 3.52 (t, J=6.71 Hz, 2H), 3.66-3.71 (m, 2H), 6.88 (d, J=8.54 Hz, 2H), 7.55 (d, J=8.85 Hz, 1H), 7.64 (dd, J=8.85, 7.63 Hz, 1H), 7.75-7.79 (m, 2H), 8.06 (d, J=3.97 Hz, 1H), 8.17 (s, 1H), 8.76 (d, J=5.19 Hz, 1H), 9.38 (s, 1H), 10.64 (s, 1H).

Example 235

8-[1-(2-aminoethyl)-1H-pyrazol-3-yl]-6-(2,6-dichlorophenyl)-2-{[4-(4-methylpiperazin-1-yl)phenyl]amino}pyrimido[4,5-d]pyridazin-5(6H)-one

Example 235A ethyl 4-(1-(2-(tert-butoxycarbonylamino)ethyl)-1H-pyrazole-3-carbonyl)-2-(methylthio)pyrimidine-5-carboxylate The title compound was prepared as described in Example 60A, substituting tert-butyl 2-(3-formyl-1H-pyrazol-1-yl)ethylcarbamate for picolinaldehyde. MS (DCI/NH$_3$) m/z 436 (M+H)$^+$.

Example 235B ethyl 4-(1-(2-(tert-butoxycarbonylamino)ethyl)-1H-pyrazole-3-carbonyl)-2-(4-(4-methylpiperazin-1-yl)phenylthio)pyrimidine-5-carboxylate The title compound was prepared as described in Example 60B, substituting Example 235A for Example 60A. MS (DCI/NH$_3$) m/z 596 (M+H)$^+$.

Example 235C 8-(1-(2-aminoethyl)-1H-pyrazol-3-yl)-6-(2,6-dichlorophenyl)-2-(4-(4-methylpiperazin-1-yl)phenylthio)pyrimido[4,5-d]pyridazin-5(6H)-one The title compound was prepared as described in Example 6D, substituting Example 235B for Example 6C and 2,6-dichlorophenylhydrazine for methylhydrazine. MS (DCI/NH3) m/z 591 (M+H)$^+$; $^1$H NMR (300 MHz, DMSO-d$_6$) δ 2.89 (s, 3H), 2.98 (d, J=12.29 Hz, 2H), 3.14-3.23 (m, 2H), 3.32 (d, J=5.16 Hz, 2H), 3.53-3.62 (m, 2H), 3.83 (d, J=12.69 Hz, 2H), 4.40-4.51 (m, 2H), 7.01 (d, J=8.33 Hz, 2H), 7.60-7.68 (m, 3H), 7.72-7.80 (m, 3H), 7.94 (s, 1H), 9.37 (s, 1H).

Example 237

6-(2,6-dichlorophenyl)-2-{[4-(piperazin-1-yl)phenyl]amino}-8-[3-(piperidin-1-ylmethyl)phenyl]pyrimido[4,5-d]pyridazin-5(6H)-one

Example 237A ethyl 4-(3-formylbenzoyl)-2-(methylthio)pyrimidine-5-carboxylate To a solution of Example 215A (500 mg, 1.32 mmol) in dichloromethane (20 ml) was added TFA (5 mL). The mixture was stirred at 40° C. overnight. The reaction mixture was concentrated and the crude product was used in the next step without further purification. MS (DCI/NH$_3$) m/z 331 (M+H)$^+$.

Example 237B ethyl 2-(4-(4-(tert-butoxycarbonyl)piperazin-1-yl)phenylamino)-4-(3-formylbenzoyl)pyrimidine-5-carboxylate The title compound was prepared as described in Example 60B, substituting Example 237A for Example 60A and tert-butyl 4-(4-aminophenyl)piperazine-1-carboxylate for 4-(4-methylpiperazin-1-yl)aniline. MS (DCI/NH$_3$) m/z 560 (M+H).

Example 237C ethyl 2-(4-(4-(tert-butoxycarbonyl)piperazin-1-yl)phenylamino)-4-(3-(piperidin-1-ylmethyl)benzoyl)pyrimidine-5-carboxylate The title compound was prepared as described in Example 215D, substituting Example 237B for Example 215C and piperidine for 1-methylpiperazine. MS (DCI/NH$_3$) m/z 629 (M+H)$^+$.

Example 237D 6-(2,6-dichlorophenyl)-2-(4-(piperazin-1-yl)phenylamino)-8-(3-(piperidin-1-ylmethyl)phenyl)pyrimido[4,5-d]pyridazin-5(6H)-one The title compound was prepared as described in Example 6D, substituting Example 237C for Example 6C and 2,6-dichlorophenylhydrazine for methylhydrazine. MS (DCI/NH3) m/z 642 (M+H)$^+$; $^1$H NMR (300 MHz, DMSO-d$_6$) δ 1.15-1.46 (m, 2H), 1.49-1.73 (m, 2H), 1.78 (d, J=11.53 Hz, 2H), 2.81-2.98 (m, 2H), 3.21-3.43 (m, 8H), 3.73-3.99 (m, 2H), 4.33 (s, 2H), 6.93 (d, J=5.76 Hz, 2H), 7.54-7.68 (m, 5H), 7.74-7.79 (m, 2H), 7.90 (s, 1H), 8.08-8.22 (m, 1H), 9.40 (s, 1H).

Example 248

4-[6-(2,6-dichlorophenyl)-2-{[4-(4-methylpiperazin-1-yl)phenyl]amino}-5-oxo-5,6-dihydropyrimido[4,5-d]pyridazin-8-yl]-N,N-dimethylpyridine-2-carboxamide The title compound was prepared as described in Example 225B, substituting dimethylamine for pyrrolidine. MS (DCI/NH$_3$) m/z 631 (M+H)$^+$; $^1$H NMR (300 MHz, DMSO-d$_6$): δ 2.23 (s, 3H), 2.45-2.48 (m, 4H), 3.00 (s, 3H), 3.03 (s, 3H), 3.08-3.13 (m, 4H), 6.90 (d, J=8.85 Hz, 2H), 7.55 (d, J=8.54 Hz, 2H), 7.60-7.68 (m, 1H), 7.75-7.79 (m, 2H), 7.99 (s, 1H), 8.04 (d, J=4.88 Hz, 1H), 8.74 (d, J=5.19 Hz, 1H), 9.37 (s, 1H), 10.63 (s, 1H).

Example 250

6-(2,6-dichlorophenyl)-8-[2-(2-hydroxypropan-2-yl)pyridin-4-yl]-2-{[4-(4-methylpiperazin-1-yl)phenyl]amino}pyrimido[4,5-d]pyridazin-5(6H)-one The title compound was prepared as described in Example 175E, substituting 2-chloroisonicotinoyl chloride for 6-chloropicolinoyl chloride. MS (DCI/NH$_3$) m/z 618 (M+H)$^+$; $^1$H NMR (400 MHz, CD$_3$OD) δ 2.65 (s, 6H), 2.98 (s, 3H), 3.04-3.14 (m, 2H), 3.26-3.31 (m, 2H), 3.61-3.66 (m, 2H), 3.82-3.88 (m, 2H), 7.03 (d, J=7.02 Hz, 2H), 7.52-7.60 (m, 3H), 7.64-7.69 (m, 2H), 8.49-8.57 (m, 2H), 8.72 (d, J=5.49 Hz, 2H), 9.42 (s, 1H).

Example 259

8-[1-(2-aminoethyl)-1H-pyrazol-3-yl]-6-(2,6-dichlorophenyl)-2-{[4-(piperazin-1-yl)phenyl]amino}pyrimido[4,5-d]pyridazin-5(6H)-one

Example 259A ethyl 2-(4-(4-(tert-butoxycarbonyl)piperazin-1-yl)phenylamino)-4-(1-(2-(tert-butoxycarbonylamino)ethyl)-1H-pyrazole-3-carbonyl)pyrimidine-5-carboxylate The title compound was prepared as described in Example 60B, substituting Example 235A for Example 60A and tert-butyl 4-(4-aminophenyl)piperazine-1-carboxylate for 4-(4-aminophenyl)piperazine. MS (DCI/NH$_3$) m/z 682 (M+H)$^+$.

Example 259B 8-(1-(2-aminoethyl)-1H-pyrazol-3-yl)-6-(2,6-dichlorophenyl)-2-(4-(piperazin-1-yl)phenylthio)pyrimido[4,5-d]pyridazin-5(6H)-one The title compound was prepared as described in Example 6D, substituting Example 259A for Example 6C and 2,6-dichlorophenylhydrazine for methylhydrazine. MS (DCI/NH$_3$) m/z 577 (M+H)$^+$; $^1$H NMR (300 MHz, DMSO-d$_6$): δ 2.39-2.50 (m, 2H), 2.69-2.76 (m, 2H), 3.25-3.33 (m, 6H), 4.40-4.53 (m, 2H), 7.00 (d, J=8.82 Hz, 2H), 7.59-7.68 (m, 2H), 7.70-7.81 (m, 3H), 7.85-7.98 (m, 2H), 9.37 (s, 1H).

Example 260

8-(2-chloropyridin-4-yl)-6-(2,6-dichlorophenyl)-2-{[4-(4-methylpiperazin-1-yl)phenyl]amino}pyrimido[4,5-d]pyridazin-5(6H)-one

Example 260A 8-(2-chloropyridin-4-yl)-6-(2,6-dichlorophenyl)-2-(methylthio)pyrimido[4,5-d]pyridazin-5(6H)-one The title compound was prepared as described in Example 175B, substituting 2-chloroisonicotinoyl chloride for 6-chloropicolinoyl chloride. MS (DCI/NH$_3$) m/z 451 (M+H)$^+$.

Example 260B 8-(2-chloropyridin-4-yl)-6-(2,6-dichlorophenyl)-2-{[4-(4-methylpiperazin-1-yl)phenyl]amino}pyrimido[4,5-d]pyridazin-5(6H)-one The title compound was prepared as described in Example 6C, substituting Example 260A for Example 6B. MS (DCI/NH$_3$) m/z 595 (M+H)$^+$; $^1$H NMR (500 MHz, DMSO-d$_6$) δ 2.88 (s, 3H), 2.94 (t, J=12.51 Hz, 2H), 3.16-3.25 (m, 2H), 3.52-3.58 (m, 2H), 3.79-3.85 (m, 2H), 7.02 (d, J=8.85 Hz, 2H), 7.59-7.66 (m, 2H), 7.74-7.79 (m, 2H), 7.83-7.87 (m, 1H), 8.09 (s, 1H), 8.56 (t, J=5.49 Hz, 1H), 9.40 (s, 1H), 9.72 (s, 1H), 10.71 (s, 1H).

Example 261

6-(2,6-dichlorophenyl)-8-{1-[2-(methylamino)ethyl]-1H-pyrazol-3-yl}-2-{[4-(4-methylpiperazin-1-yl)phenyl]amino}pyrimido[4,5-d]pyridazin-5(6H)-one The title compound was prepared as described in Example 215D, substituting Example 235 for Example 215C and methylamine for 1-methylpiperazine. MS (DCI/NH$_3$) m/z 605 (M+H)$^+$; $^1$H NMR (300 MHz, DMSO-d$_6$): δ 2.54-2.59 (m, 3H), 2.89 (s, 3H), 2.97 (d, J=11.90 Hz, 2H), 3.10-3.26 (m, 2H), 3.35-3.42 (m, 2H), 3.54 (d, J=11.90 Hz, 2H), 3.83 (d, J=13.88 Hz, 2H), 4.52 (t, J=6.15 Hz, 2H), 7.01 (d, J=8.33 Hz, 2H), 7.57-7.67 (m, 2H), 7.70-7.80 (m, 4H), 7.95 (s, 1H), 9.37 (s, 1H).

Example 266

6-(2,6-dichlorophenyl)-8-(1-methyl-1H-pyrazol-3-yl)-2-(1,2,3,4-tetrahydroisoquinolin-7-ylamino)pyrimido[4,5-d]pyridazin-5(6H)-one

Example 266A ethyl 4-(1-methyl-1H-pyrazole-3-carbonyl)-2-(methylthio)pyrimidine-5-carboxylate The title compound was prepared as described in Example 60A, substituting 1-methyl-1H-pyrazole-3-carbaldehyde for picolinaldehyde. MS (DCI/NH$_3$) m/z 307 (M+H)$^+$.

Example 266B ethyl 4-(1-methyl-1H-pyrazole-3-carbonyl)-2-(4-(4-methylpiperazin-1-yl)phenylamino)pyrimidine-5-carboxylate The title compound was prepared as described in Example 60B, substituting Example 266A for Example 60A. MS (DCI/NH$_3$) m/z 450 (M+H)$^+$.

Example 266C 6-(2,6-dichlorophenyl)-8-(1-methyl-1H-pyrazol-3-yl)-2-(4-(4-methylpiperazin-1-yl)phenylthio)pyridazino[4,5-d]pyrimidin-5(6H)-one The title compound was prepared as described in Example 6D, substituting Example 266B for Example 6C and 2,6-dichlorophenylhydrazine for methylhydrazine. MS (DCI/NH$_3$) m/z 580 (M+H)$^+$; $^1$H NMR (300 MHz, DMSO-d$_6$): δ 2.99 (t, J=5.95 Hz, 2H), 3.34-3.54 (m, 2H), 3.96 (s, 3H), 4.17-4.30 (m, 2H), 7.23 (d, J=8.33 Hz, 1H), 7.59-7.67 (m, 1H), 7.68-7.73 (m, 1H), 7.77 (d, J=7.93 Hz, 2H), 7.89 (d, J=1.98 Hz, 1H), 9.06-9.28 (m, 2H), 9.43 (s, 1H).

Example 270

6-(2,6-dichlorophenyl)-8-[1-(2-hydroxyethyl)-1H-pyrazol-3-yl]-2-{[4-(4-methylpiperazin-1-yl)phenyl]amino}pyrimido[4,5-d]pyridazin-5(6H)-one

Example 270A ethyl 4-(1-(2-(methoxymethoxy)ethyl)-1H-pyrazole-3-carbonyl)-2-(methylthio)pyrimidine-5-carboxylate The title compound was prepared as described in Example 60A, substituting 1-(2-(methoxymethoxy)ethyl)-1H-pyrazole-3-carbaldehyde for picolinaldehyde. MS (DCI/NH$_3$) m/z 381 (M+H)$^+$.

Example 270B ethyl 4-(1-(2-(methoxymethoxy)ethyl)-1H-pyrazole-3-carbonyl)-2-(4-(4-methylpiperazin-1-yl)phenylamino)pyrimidine-5-carboxylate The title compound was prepared as described in Example 60B, substituting Example 270A for Example 60A. MS (DCI/NH$_3$) m/z 524 (M+H)$^+$.

Example 270C 6-(2,6-dichlorophenyl)-8-(1-(2-hydroxyethyl)-1H-pyrazol-3-yl)-2-(4-(4-methylpiperazin-1-yl)phenylthio)pyrimido[4,5-d]pyridazin-5(6H)-one The title compound was prepared as described in Example 6D, substituting Example 270B for Example 60B and 2,6-dichlorophenylhydrazine for methylhydrazine. MS (DCI/NH$_3$) m/z 610 (M+H)$^+$; $^1$H NMR (300 MHz, DMSO-d$_6$): δ 2.85 (s, 3H), 2.91-3.10 (m, 2H), 3.09-3.25 (m, 2H), 3.40-3.64 (m, 4H), 3.71-3.94 (m, 2H), 4.21-4.39 (m, 2H), 4.60 (d, J=3.05 Hz, 1H), 6.75-7.12 (m, 3H), 7.55-7.72 (m, 4H), 7.71-7.80 (m, 2H), 9.37 (s, 1H).

Example 271

6-(2,6-dichlorophenyl)-2-{[4-(4-methylpiperazin-1-yl)phenyl]amino}-8-(pyrazin-2-yl)pyrimido[4,5-d]pyridazin-5(6H)-one

Example 271A ethyl 2-(methylthio)-4-(pyrazine-2-carbonyl)pyrimidine-5-carboxylate The title compound was prepared as described in Example 60A, substituting pyrazine-2-carbaldehyde for nicotinaldehyde. MS (DCI/NH$_3$) m/z 305 (M+H)$^+$.

Example 271B ethyl 2-(4-(4-methylpiperazin-1-yl)phenylamino)-4-(pyrazine-2-carbonyl)pyrimidine-5-carboxylate The title compound was prepared as described in Example 60B, substituting Example 271A for Example 60A. MS (DCI/NH$_3$) m/z 448 (M+H)$^+$.

Example 271C 6-(2,6-dichlorophenyl)-2-(4-(4-methylpiperazin-1-yl)phenylamino)-8-(pyrazin-2-yl)pyridazino[4,5-d]pyrimidin-5(6H)-one The title compound was prepared as described in Example 6D, substituting Example 271B for Example 6C and (2-chlorophenyl)hydrazine for methylhydrazine. MS (DCI/NH$_3$) m/z 561 (M+H)$^+$;
$^1$H NMR (300 MHz, DMSO-d$_6$): δ 2.87 (s, 3H), 2.89-3.00 (m, 2H), 3.09-3.33 (m, 2H), 3.53 (d, J=12.29 Hz, 2H), 3.79 (d, J=12.69 Hz, 2H), 6.91 (d, J=8.33 Hz, 2H), 7.51-7.72 (m, 3H), 7.73-7.85 (m, 2H), 8.82 (d, J=2.38 Hz, 1H), 8.93 (s, 1H), 9.13 (s, 1H), 9.40 (s, 1H).

Example 290

4-[6-(2,6-dichlorophenyl)-2-{[4-(4-methylpiperazin-1-yl)phenyl]amino}-5-oxo-5,6-dihydropyrimido[4,5-d]pyridazin-8-yl]benzoic acid The title compound was prepared as described in Example 190, substituting 4-bromobenzaldehyde for 3-bromobenzaldehyde. MS (DCI/NH$_3$) m/z 603 (M+H)$^+$; $^1$H NMR (300 MHz, DMSO-d$_6$): δ 3.27 (s, 3H), 3.30-3.40 (m, 4H), 3.73-4.16 (m, 4H), 6.98 (d, J=8.82 Hz, 2H), 7.51-7.79 (m, 3H), 7.95 (d, J=3.73 Hz, 2H), 8.60-8.71 (m, 2H), 8.71-8.80 (m, 2H), 9.38 (s, 1H).

Example 291

4-[6-(2,6-dichlorophenyl)-2-{[4-(4-methylpiperazin-1-yl)phenyl]amino}-5-oxo-5,6-dihydropyrimido[4,5-d]pyridazin-8-yl]-N,N-dimethylbenzamide The title compound was prepared as described in Example 225B, substituting Example 290 for Example 225A and dimethylamine for pyrrolidine. MS (DCI/NH$_3$) m/z 629 (M+H)$^+$; $^1$NMR (300 MHz, DMSO-d$_6$): δ 2.87 (s, 3H), 2.91-3.07 (m, 2H), 3.14-3.26 (m, 2H), 3.43 (s, 6H), 3.47-3.65 (m, 2H), 3.79 (d, J=12.69 Hz, 2H), 6.94 (d, J=7.14 Hz, 2H), 7.43-7.70 (m, 3H), 7.74-7.83 (m, 2H), 7.94 (d, J=8.33 Hz, 2H), 7.99-8.10 (m, 2H), 9.39 (s, 1H).

Example 292

N-cyclobutyl-4-[6-(2,6-dichlorophenyl)-2-{[4-(4-methylpiperazin-1-yl)phenyl]amino}-5-oxo-5,6-dihydropyrimido[4,5-d]pyridazin-8-yl]benzamide The title compound was prepared as described in Example 225B, substituting Example 290 for Example 225A and cyclobutanamine for pyrrolidine. MS (DCI/NH$_3$) m/z 656 (M+H)$^+$; $^1$NMR (300 MHz, DMSO-d$_6$): δ 1.62-1.80 (m, 2H), 2.02-2.17 (m, 2H), 2.19-2.31 (m, 2H), 2.88 (s, 3H), 2.97 (d, J=12.21 Hz, 2H), 3.10-3.28 (m, 2H), 3.35-3.65 (m, 2H), 3.81 (d, J=13.90 Hz, 2H), 4.34-4.55 (m, 1H), 6.95 (d, J=8.48 Hz, 2H), 7.48-7.68 (m, 3H), 7.72-7.82 (m, 2H), 7.90-8.12 (m, 2H), 8.72 (d, J=7.46 Hz, 2H), 9.39 (s, 1H).

Example 293

4-[6-(2,6-dichlorophenyl)-2-{[4-(4-methylpiperazin-1-yl)phenyl]amino}-5-oxo-5,6-dihydropyrimido[4,5-d]pyridazin-8-yl]-N-methylbenzamide The title compound was prepared as described in Example 225B, substituting Example 290 for Example 225A and methylamine for pyrrolidine. MS (DCI/NH$_3$) m/z 616 (M+H)$^+$; $^1$NMR (300 MHz, DMSO-d$_6$): δ 2.83 (s, 3H), 2.88 (d, J=3.17 Hz, 2H), 3.17 (m, 3H), 3.19-3.26 (m, 2H), 3.54 (d, J=11.50 Hz, 2H), 3.74-4.13 (m, 2H), 6.94 (d, J=7.93 Hz, 2H), 7.50-7.68 (m, 3H), 7.71-7.86 (m, 2H), 7.91-8.06 (m, 2H), 8.56 (d, J=4.76 Hz, 2H), 9.39 (s, 1H).

Example 299

6-(2-chloro-6-fluorophenyl)-8-(6-ethoxypyridin-2-yl)-2-{[4-(4-methylpiperazin-1-yl)phenyl]amino}pyrimido[4,5-d]pyridazin-5(6H)-one Example 299A ethyl 4-(6-fluoropicolinoyl)-2-(methylthio)pyrimidine-5-carboxylate The title compound was prepared as described in Example 60A, substituting 6-fluoropicolinaldehyde for picolinaldehyde. MS (DCI/NH$_3$) m/z 322 (M+H)$^+$.

Example 299B 6-(2-chloro-6-fluorophenyl)-8-(6-ethoxypyridin-2-yl)-2-(4-(4-methylpiperazin-1-yl)phenylamino)pyrimido[4,5-d]pyridazin-5(6H)-one To a solution of Example 299A (50 mg, 0.156 mmol) in dichloromethane (10 mL) was added meta-chloroperoxybenzoic acid (30 mg, 0.17 mmol) at 0 °C. The reaction mixture was stirred at the same temperature for 1 hour, and was partitioned between 10% sodium thiosulfate solution and ethyl acetate. The organic layer was washed with saturated sodium bicarbonate solution, dried over anhydrous sodium sulfate, filtered and concentrated under reduced pressure. The residue was dissolved in ethanol (3 mL), trasnsfered to a high pressure tube, and (2-chloro,6-florophenyl)hydrazine (55 mg, 0.33 mmol) was added. The high pressure vessel was sealed, and the mixture was heated at 110° C. overnight. After cooling, the crude product was directly separated by HPLC (Zorbax C-18, 0.1% TFA/CH$_3$CN/H$_2$O) to yield the title compound as TFA salt. MS (DCI/NH$_3$) m/z 588 (M+H)$^+$; $^1$H NMR (300 MHz, DMSO-d$_6$): δ 1.25 (t, J=6.35 Hz, 3H), 2.87 (s, 3H), 2.90-2.96 (m, 2H), 3.10-3.27 (m, 2H), 3.53 (d, J=12.29 Hz, 2H), 3.70-3.99 (m, 2H), 4.23-4.31 (m, 2H), 6.84 (d, J=6.35 Hz, 2H), 6.98 (d, J=8.33 Hz, 1H), 7.38 (d, J=7.14 Hz, 1H), 7.50-7.58 (m, 1H), 7.59-7.69 (m, 4H), 7.85-7.89 (m, 1H), 9.36 (s, 1H).

Example 300

6-(2,6-dichlorophenyl)-2-(2',3'-dihydro-1'H-spiro[cyclopropane-1,4'-isoquinolin]-7'-ylamino)-8-methylpyrimido[4,5-d]pyridazin-5(6H)-one Example 300A ethyl 4-(1-ethoxyvinyl)-2-(methylthio)pyrimidine-5-carboxylate A solution of ethyl 4-chloro-2-(methylthio)pyrimidine-5-carboxylate (10 g, 43.0 mmol), tributyl(1-ethoxyvinyl)stannane (16 ml, 47.3 mmol) and bis(triphenylphosphine)palladium dichloride (1.508 g, 2.149 mmol) in N,N-dimethylformamide (100 mL) was heated to 70° C. for 5 hours. After cooling, the mixture was treated with an aqueous solution of KF (6 g in 12 mL water) and stirred over the weekend at room temperature. The mixture was filtered through diatomaceous earth and washed with ethyl acetate. The filtrate was partitioned between ethyl acetate and brine. The organic phase was washed with brine twice and concentrated. The residue was separated by flash chromatography (0-20% gradient ethyl acetate in hexane) to give the title compound. MS (DCI/NH$_3$) m/z 269 (M+H)$^+$.

Example 300B ethyl 4-acetyl-2-(methylthio)pyrimidine-5-carboxylate

A solution of Example 300A (9.46 g, 35.3 mmol) in a mixture of ethanol (100 ml) and 10% HCl solution (21.42 ml, 70.5 mmol) was heated to 50° C. for 4 hours. The volatiles were then removed, and the residue was partitioned between ethyl acetate and water. The organic phase was washed with brine, and concentrated. The residue was purified by flash chromatography (5-50% gradient ethyl acetate in hexane) to give the title compound. MS (DCI/NH$_3$) m/z 241 (M+H)$^+$.

Example 300C 6-(2,6-dichlorophenyl)-8-methyl-2-(methylthio)pyrimido[4,5-d]pyridazin-5(6H)-one To a solution of Example 300B (1.53 g, 6.37 mmol) in 2,2,2-trifluoroethanol (40 mL) was added 2,6-dichlorophenylhydrazine hydrochloride (1.359 g, 6.37 mmol). This mixture was heated in a sealed tube at 140° C. overnight. The volatiles were removed and the residue was stirred between ethyl acetate and water. The formed solid material was collected by filtration, and washed with ethyl acetate and water to give the title compound. MS (DCI/NH$_3$) m/z 354 (M+H)$^+$.

Example 300D tert-butyl 7'-(6-(2,6-dichlorophenyl)-8-methyl-5-oxo-5,6-dihydropyrimido[4,5-d]pyridazin-2-ylamino)-1'H-spiro[cyclopropane-1,4'-isoquinoline]-2'(3'H)-carboxylate To a solution of Example 300C (1.68 g, 4.76 mmol) in anhydrous methylene chloride (60 mL) was added 3-chloroperoxybenzoic acid (1.17 g, 5.23 mmol) and the solution was stirred at room temperature for 2 hours. tert-Butyl 7'-amino-1'H-spiro[cyclopropane-1,4'-isoquinoline]-2'(3'H)-carboxylate (1.69 g, 6.18 mmol) was then added, and the solution was stirred at 45° C. overnight. After cooling, the mixture was separated by flash chromatography (15-60% gradient ethyl acetate in hexane) to give the title compound. MS (DCI/NH$_3$) m/z 580 (M+H)$^+$.

Example 300E 6-(2,6-dichlorophenyl)-2-(2',3'-dihydro-1'H-spiro[cyclopropane-1,4'-isoquinolin]-7'-ylamino)-8-methylpyrimido[4,5-d]pyridazin-5(6H)-one To a solution of Example 300D (2.688 g, 4.64 mmol) in methylene chloride (25 mL) was added TFA (5 mL) at room temperature. The reaction mixture was stirred at room temperature for 2 hours. The volatiles were removed, and the residue was treated with methanol (20 mL). Solid material precipitated and the mixture was stirred with an additional 10 mL of methanol. The solid was collected by filtration, washed with methanol and dried under vacuum to provide the title compound as TFA salt. The material was dissolved in a 1:4 mixture of methanol/CH$_2$Cl$_2$ (200 mL) and treated with 1 M HCl solution in ether (30 mL). Removal of the volatiles gave a solid which was dissolved in a mixture of methanol and CH$_2$Cl$_2$, and treated with HCl in ether again. Concentration of the mixture provided the title compound as HCl salt. MS (DCI/NH$_3$) m/z 479 (M+H)$^+$; $^1$H NMR (400 MHz, DMSO-d$_6$): δ 1.00 (m, 2H), 1.20 (m, 2H), 1.99 (s, 3H), 2.54 (s, 3H), 3.51-3.56 (m, 2H), 4.75 (d, J=17.70 Hz, 2H), 6.87 (dd, J=8.54, 4.88 Hz, 1H), 7.55-7.77 (m, 4H), 9.35 (s, 1H), 10.71 (s, 1H).

Example 303

6-(2-chloro-6-fluorophenyl)-8-(6-hydroxypyridin-2-yl)-2-{[4-(4-methylpiperazin-1-yl)phenyl]amino}pyrimido[4,5-d]pyridazin-5(6H)-one To a solution of Example 299A (50 mg, 0.156 mmol) in dichloromethane (10 mL) was added meta-chloroperoxybenzoic acid (30 mg, 0.17 mmol) at 0° C. The reaction mixture was stirred at the same temperature for 1 hour, and was partitioned between 10% sodium thiosulfate solution and ethyl acetate. The organic layer was washed with saturated sodium bicarbonate solution, dried over anhydrous sodium sulfate, filtered and concentrated under reduced pressure. The residue was dissolved in ethanol (3 mL), trasnsfered to a high pressure tube, and (2-chloro,6-florophenyl)hydrazine (55 mg, 0.33 mmol) was added. The high pressure vessel was sealed, and the mixture was heated at 110° C. overnight. After cooling, the crude product was directly separated by HPLC (Zorbax C-18, 0.1% TFA/CH$_3$CN/H$_2$O) to yield the title compound as TFA salt. MS (DCI/NH$_3$) m/z 559 (M+H)$^+$; $^1$H NMR (300 MHz, DMSO-d$_6$): δ 2.87 (s, 3H), 2.91-3.00 (m, 2H), 3.19 (d, J=9.92 Hz, 2H), 3.52 (m, 2H), 3.77 (d, J=12.69 Hz, 2H), 6.53 (d, J=8.33 Hz, 1H), 6.97 (d, J=7.93 Hz, 2H), 7.43-7.75 (m, 7H), 9.36 (s, 1H).

Example 323

6-(2,6-dichlorophenyl)-2-{[4-(4-methylpiperazin-1-yl)phenyl]amino}pyrimido[4,5-d]pyridazin-(6H)-one Example 323A ethyl 4-formyl-2-(methylthio)pyrimidine-5-carboxylate A solution of ethyl 4-methyl-2-(methylthio)pyrimidine-5-carboxylate in dioxane (330 mg, 1.56 mmol) was treated with SeO$_2$ (220 mg, 2.0 mmol) at 100° C. for 3 days. After cooling, the reaction mixture was concentrated and the residue was purified by flash chromatography (20% ethyl acetate in hexane) to provide the title compound. MS (DCI/NH$_3$) m/z 227 (M+H)$^+$.

Example 323B 6-(2,6-dichlorophenyl)-2-(methylthio)pyrimido[4,5-d]pyridazin-5(6H)-one The title compound was prepared as described in Example 6D, substituting Example 323A for Example 6C and 2,6-dichlorophenylhydrazine for methylhydrazine. MS (DCI/NH$_3$) m/z 340 (M+H)$^+$.

Example 323C 6-(2,6-dichlorophenyl)-2-(4-(4-methylpiperazin-1-yl)phenylamino)pyridazino[4,5-d]pyrimidin-5(6H)-one The title compound was prepared as described in Example 6C, substituting Example 323B for Example 6B. MS (DCI/NH$_3$) m/z 483 (M+H)$^+$; $^1$H NMR (300 MHz, DMSO-d$_6$): δ 2.78 (s, 3H), 3.15-3.32 (m, 8H), 7.03 (d, J=9.12 Hz, 2H), 7.56-7.65 (m, 2H), 7.70-7.79 (m, 3H), 8.39 (s, 1H), 9.31 (s, 1H).

Example 324

6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one The title compound was prepared as described in Example 6C, substituting Example 323B for Example 6B and 2'-methyl-2',3'-dihydro-1'H-spiro[cyclopropane-1,4'-isoquinolin]-7'-amine for 4-(4-methylpiperazin-1-yl)aniline. MS (DCI/NH$_3$) m/z 480 (M+H)$^+$; $^1$H NMR (300 MHz, DMSO-d$_6$): δ 0.79-1.01 (m, 4H), 2.34 (s, 3H), 3.31 (s, 2H), 3.63 (s, 2H), 6.73 (d, J=8.48 Hz, 1H), 7.51-7.56 (m, 1H), 7.57-7.64 (m, 1H), 7.71-7.78 (m, 2H), 7.83-7.92 (m, 1H), 8.44 (s, 1H), 9.33 (s, 1H).

Example 325

6-(2,6-dichlorophenyl)-2-{[4-(piperazin-1-yl)phenyl]amino}pyrimido[4,5-d]pyridazin-5(6H)-one Example 325A tert-butyl 4-(4-(6-(2,6-dichlorophenyl)-5-oxo-5,6-dihydropyrimido[4,5-d]pyridazin-2-ylamino)phenyl)piperazine-1-carboxylate The title compound was prepared as described in Example 6C, substituting Example 323B for Example 6B and tert-butyl 4-(4-aminophenyl)piperazine-1-carboxylate for 4-(4-methylpiperazin-1-yl)aniline. MS (DCI/NH$_3$) m/z 569 (M+H)$^+$.

Example 325B 6-(2,6-dichlorophenyl)-2-(4-(piperazin-1-yl)phenylamino)pyridazino[4,5-d]pyrimidin-5(6H)-one The title compound was prepared as described in Example 215C, substituting Example 215B for Example 325A. MS (DCI/NH$_3$) m/z 469 (M+H)$^+$; $^1$H NMR (300 MHz, DMSO-d$_6$): δ 3.26 (d, J=5.16 Hz, 4H), 3.32 (m, 4H), 7.03 (d, J=9.12 Hz, 2H), 7.54-7.65 (m, 1H), 7.67-7.79 (m, 2H), 8.40 (s, 1H), 8.69 (m, 2H), 9.31 (s, 1H).

Example 326

6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one Example 326A tert-butyl 7'-(6-(2,6-dichlorophenyl)-5-oxo-5,6-dihydropyrimido[4,5-d]pyridazin-2-ylamino)-1'H-spiro[cyclopropane-1,4'-isoquinoline]-2'(3'H)-carboxylate The title compound was prepared as described in Example 6C, substituting Example 323B for Example 6B and tert-butyl 7'-amino-1'H-spiro[cyclopropane-1,4'-isoquinoline]-2'(3'H)-carboxylate for 4-(4-methylpiperazin-1-yl)aniline. MS (DCI/NH$_3$) m/z 566 (M+H)$^+$.

Example 326B 6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one The title compound was prepared as described in Example 215C, substituting Example 326A for Example 215B. MS (DCI/NH$_3$) m/z 466 (M+H)$^+$; $^1$H NMR (300 MHz, DMSO-d$_6$): δ 1.11 (d, J=6.35 Hz, 4H), 3.17 (s, 2H), 4.43 (s, 2H), 6.89 (d, J=8.73 Hz, 2H), 7.50-7.66 (m, 1H), 7.69-7.81 (m, 2H), 8.48 (s, 1H), 9.24 (m, 2H), 9.37 (s, 1H).

Example 327

6-(2,6-dichlorophenyl)-2-(1,2,3,4-tetrahydroisoquinolin-7-ylamino)pyrimido[4,5-d]pyridazin-5(6H)-one

Example 327A tert-butyl 7-(6-(2,6-dichlorophenyl)-5-oxo-5,6-dihydropyrimido[4,5-d]pyridazin-2-ylamino)-3,4-dihydroisoquinoline-2(1H)-carboxylate The title compound was prepared as described in Example 6C, substituting Example 323B for Example 6B and tert-butyl 7-amino-3,4-dihydroisoquinoline-2(1H)-carboxylate for 4-(4-methylpiperazin-1-yl)aniline. MS (DCI/NH$_3$) m/z 540 (M+H)$^+$.

Example 327B 6-(2,6-dichlorophenyl)-2-(1,2,3,4-tetrahydroisoquinolin-7-ylamino)pyrimido[4,5-d]pyridazin-5(6H)-one The title compound was prepared as described in Example 215C, substituting Example 327A for Example 215B. MS (DCI/NH$_3$) m/z 440 (M+H)$^+$; $^1$H NMR (300 MHz, DMSO-d$_6$): δ 2.99 (t, J=6.15 Hz, 2H), 3.38 (m, 2H), 4.32 (s, 2H), 7.25 (d, J=8.33 Hz, 1H), 7.58-7.64 (m, 1H), 7.67 (d, J=8.33 Hz, 1H), 7.72-7.82 (m, 2H), 8.49 (s, 1H), 9.05 (m, 1H), 9.38 (s, 1H).

The following Examples were prepared essentially as described in Example 300, substituting the appropriate hydrazines in Example 300C and the appropriate anilines in Example 300D. Some products were purified by flash chromatography while others were purified by reverse-phase HPLC. Accordingly, some Examples were isolated as trifluoroacetic acid salts.

TABLE 2

| Ex | Name | $^1$H NMR | MS |
|---|---|---|---|
| 308 | 6-(2-chloro-6-fluorophenyl)-2-(2',3'-dihydro-1'H-spiro[cyclopropane-1,4'-isoquinolin]-7'-ylamino)-8-methylpyrimido[4,5-d]pyridazin-5(6H)-one | $^1$H NMR (300 MHz, DMSO-d$_6$): δ 1.10 (m, 2 H), 1.12-1.14 (m, 2 H), 2.54 (s, 3 H), 3.26-3.30 (m, 2 H), 4.40-4.45 (m, 2 H), 6.91 (d, J = 8.54 Hz, 1 H), 7.48-7.72 (m, 3 H), 7.81 (s, 1 H), 9.29-9.39 (m, 2 H), 10.78 (s, 1 H) | MS (DCI/NH$_3$) m/z 463 (M + H)$^+$ |
| 311 | 6-(2-chloro-6-fluorophenyl)-8-methyl-2-[(2,4,4-trimethyl-1,2,3,4-tetrahydroisoquinolin-7-yl)amino]pyrimido[4,5-d]pyridazin-5(6H)-one | $^1$H NMR (400 MHz, DMSO-d$_6$): δ 1.36 (s, 3 H), 1.38 (s, 3H), 2.55 (s, 3 H), 3.01 (s, 3 H), 3.25-3.33 (m, 2 H), 4.36-4.50 (m, 2 H), 7.50-7.69 (m, 3 H), 7.78 (s, 1 H), 9.37 (s, 1 H), 9.83 (s, 1 H), 10.82 (s, 1 H) | MS (DCI/NH$_3$) m/z 479 (M + H)$^+$ |
| 312 | 6-(2-chloro-6-fluorophenyl)-8-methyl-2-{[4-(4-methylpiperazin-1-yl)phenyl]amino}pyrimido[4,5-d]pyridazin-5(6H)-one | $^1$H NMR (400 MHz, DMSO-d$_6$): δ 2.87 (s, 3 H), 2.94-3.02 (m, 2 H), 3.15-3.21 (m, 2 H), 3.17 (s, 3 H), 3.79-3.85 (m, 2 H), 6.99-7.11 (m, 2 H), 7.47-7.67 (m, 3 H), 7.82 (s, 1 H), 9.30 (s, 1 H), 9.96 (s, 1 H), 10.63 (s, 1 H) | MS (DCI/NH$_3$) m/z 480 (M + H)$^+$ |
| 313 | 6-(2-chloro-6-fluorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one | $^1$H NMR (400 MHz, DMSO-d$_6$): δ 1.38 (m, 4 H), 2.55 (s, 3 H), 3.01 (s, 3 H), 4.37-4.48 (m, 2 H), 7.50-7.65 (m, 2 H), 7.69-7.73 (m, 1 H), 7.76-7.80 (m, 1 H), 7.88-7.91 (m, 2 H), 9.37-9.40 (m, 1 H), 9.67 (s, 1 H), 10.82 (s, 1 H) | MS (DCI/NH$_3$) m/z 477 (M + H)$^+$ |
| 314 | 6-(2,6-dichlorophenyl)-8-methyl-2-{[4-(4-methylpiperazin-1-yl)phenyl]amino}pyrimido[4,5-d]pyridazin-5(6H)-one | $^1$H NMR (400 MHz, DMSO-d$_6$): δ 2.52 (s, 3 H), 2.87 (s, 3 H), 2.97 (t, J = 12.21 Hz, 2 H), 3.14-3.21 (m, 2 H), 3.83 (d, J = 12.82 Hz, 2 H), 7.06 (d, J = 8.85 Hz, 2 H), 7.57-7.63 (m, 2 H), 7.72 (d, J = 7.93 Hz, 2 H), 7.80-7.86 (m, 1 H), 9.31 (s, 1 H), 9.94 (s, 1 H), 10.64 (s, 1 H) | MS (DCI/NH$_3$) m/z 496 (M + H)$^+$ |
| 349 | 6-(3-chloropyridin-2-yl)-2-(2',3'-dihydro-1'H-spiro[cyclopropane-1,4'-isoquinolin]-7'-ylamino)-8-methylpyrimido[4,5-d]pyridazin-5(6H)-one | $^1$H NMR (400 MHz, CD$_3$OD) δ 1.11-1.16 (m, 2 H), 1.22-1.26 (m, 2 H), 2.59 (s, 3 H), 3.37 (s, 2 H), 4.51 (s, 2 H), 6.90 (d, J = 8.85 Hz, 1 H), 7.62 (dd, J = 8.09, 4.73 Hz, | MS (ESI) m/z 446 (M + H)$^+$ |

TABLE 2-continued

| Ex | Name | ¹H NMR | MS |
|---|---|---|---|
| | | 1 H), 7.69-7.73 (m, 1 H), 7.78 (s, 1 H), 8.16 (dd, J = 7.93, 1.53 Hz, 1 H), 8.59 (dd, J = 4.88, 1.53 Hz, 1 H), 9.31 (s, 1 H) | |
| 351 | 6-(3-chloropyridin-2-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (400 MHz, CD₃OD) δ 0.93-0.97 (m, 2 H), 1.03-1.07 (m, 2 H), 2.46 (s, 3 H), 2.58 (s, 3 H), 2.63 (s, 2 H), 3.78 (s, 2 H), 6.77 (d, J = 8.54 Hz, 1 H), 7.61 (m, 3 H), 8.15 (dd, J = 7.93, 1.53 Hz, 1 H), 8.58 (dd, J = 4.58, 1.53 Hz, 1 H), 9.32 (s, 1 H) | MS (ESI) m/z 460 (M + H)⁺ |
| 363 | 6-(2,6-dichlorophenyl)-2-({2-methoxy-4-[4-(4-methylpiperazin-1-yl)piperidin-1-yl]phenyl}amino)-8-methylpyrimido[4,5-d]pyridazin-5(6H)-one | ¹H NMR (400 MHz, CD₃OD) δ 1.73 (dd, J = 11.75, 3.51 Hz, 2 H), 2.03 (m, 2 H), 2.55 (s, 3 H), 2.69 (s, 3 H), 2.67-2.83 (m, 4 H), 2.95-3.14 (m, 4 H), 3.80 (d, J = 12.51 Hz, 2 H), 3.92 (s, 3 H), 6.61-6.65 (m, 1 H), 6.71 (d, J = 2.44 Hz, 1 H), 7.48-7.54 (m, 1 H), 7.59-7.62 (m, 2 H), 8.19-8.25 (m, 1 H), 9.27 (s, 1 H) | MS (ESI) m/z 611 (M + H)⁺ |
| 364 | 6-(2,6-dichlorophenyl)-8-methyl-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-d₆) δ 10.66 (br s, 1 H), 9.34 (s, 1 H), 7.73-7.58 (m, 5 H), 7.36 (d, J = 8.4 Hz, 1 H), 3.49 (s, 2 H), 2.54 (s, 3 H), 2.35 (m, 5 H), 1.26 (s, 6 H) | MS (ESI) m/z 495 (M + H)⁺ |
| 365 | 6-(3-chloropyridin-2-yl)-8-methyl-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-d₆) δ 10.63 (s, 1 H), 9.32 (s, 1 H), 8.62 (dd, J = 4.8, 1.6 Hz, 1 H), 8.25 (dd, J = 8.0, 1.6 Hz, 1 H), 7.68-7.60 (m, 3 H), 7.35 (d, J = 8.4 Hz, 1 H), 3.48 (s, 2 H), 2.53 (s, 3 H), 2.35 (s, 2 H), 2.34 (s, 3 H), 1.26 (s, 6 H) | MS (ESI) m/z 462 (M + H)⁺ |
| 366 | 6-(2-chloro-6-fluorophenyl)-2-{[2-(dimethylamino)-2,3-dihydro-1H-inden-5-yl]amino}-8-methylpyrimido[4,5-d]pyridazin-5(6H)-one | ¹H NMR (400 MHz, DMSO-d₆) δ 10.64 (s, 1 H), 9.32 (s, 1 H), 7.77-7.49 (m, 5 H), 7.18 (d, J = 8.0 Hz, 1 H), 3.02-2.95 (m, 3 H), 2.81-2.71 (m, 2 H), 2.51 (s, 3 H), 2.20 (s, 6 H) | MS (ESI) m/z 465 (M + H)⁺ |
| 367 | 6-(3-chloropyridin-2-yl)-2-{[2-(dimethylamino)-2,3-dihydro-1H-inden-5-yl]amino}-8-methylpyrimido[4,5-d]pyridazin-5(6H)-one | ¹H NMR (400 MHz, DMSO-d₆) δ 10.64 (s, 1 H), 9.32 (s, 1 H), 8.61 (dd, J = 4.8, 1.6 Hz, 1 H), 8.25 (dd, J = 8.0, 1.6 Hz, 1 H), 7.79-7.76 (m, 1 H), 7.66 (dd, J = 8.0, 4.8 Hz, 1 H), 7.66-7.62 (m, 1 H), 7.19 (d, J = 8.4 Hz, 1 H), 3.09-2.97 (m, 3 H), 2.84-2.73 (m, 2 H), 2.51 (s, 3 H), 2.24 (s, 6 H) | MS (ESI) m/z 448 (M + H)⁺ |
| 368 | 6-(2-chloro-6-fluorophenyl)-8-methyl-2-(3-methyl-4-(4-methyl-1,4-diazepan-1-yl)phenylamino)pyrimido[4,5-d]pyridazin-5(6H)-one | ¹H NMR (400 MHz, DMSO-d₆) δ 10.60 (s, 1 H), 9.30 (s, 1 H), 7.66-7.49 (m, 5 H), 7.09 (d, J = 8.8 Hz, 1 H), 3.19-3.08 (m, 5 H), 2.91-2.88 (m, 4 H), 2.52 (s, 3 H), 2.48 (s, 3 H), 2.29 (s, 3 H), 1.98-1.91 (m, 2 H) | MS (ESI) m/z 507 (M + H)⁺ |
| 369 | 6-(3-chloropyridin-2-yl)-8-methyl-2-(3-methyl-4-(4-methyl-1,4-diazepan-1-yl)phenylamino)pyridazino[4,5-d]pyrimidin-5(6H)-one | ¹H NMR (400 MHz, DMSO-d₆) δ 10.58 (s, 1 H), 9.30 (s, 1 H), 8.61 (dd, J = 4.8, 1.6 Hz, 1 H), 8.25 (dd, J = 8.0, 1.6 Hz, 1 H), 7.76 (s, 1 H), 7.66 (dd, J = 8.0, 4.4 Hz, 2 H), 7.09 (d, J = 8.8 Hz, 1 H), 3.17 (t, J = 4.4 Hz, 2 H), 3.09 (t, J = 6.4 Hz, 2 H), 2.88-2.85 (m, 4 H), 2.52 (s, 3 H), 2.46 (s, 3 H), 2.29 (s, 3 H), 1.96-1.76 (m, 2 H) | MS (ESI) m/z 490 (M + H)⁺ |
| 370 | 6-(2,6-dichlorophenyl)-2-{[4,4-dimethyl-2-(2,2,2-trifluoroethyl)-1,2,3,4-tetrahydroisoquinolin-7-yl]amino}-8-methylpyrimido[4,5-d]pyridazin-5(6H)-one | ¹H NMR (300 MHz, DMSO-d₆) δ 1.26 (s, 6 H), 2.53 (s, 3 H), 2.66 (s, 2 H), 3.83 (s, 2 H), 7.37 (d, J = 8.48 Hz, 1 H), 7.54-7.75 (m, 4 H), 7.86-7.91 (m, 1 H), 9.34 (s, 1 H), 10.65 (s, 1 H) | MS (ESI) m/z 563 (M + H)⁺ |

TABLE 2-continued

| Ex | Name | $^1$H NMR | MS |
|---|---|---|---|
| 393 | 6-(2,6-dichlorophenyl)-8-methyl-2-{[4-(piperazin-1-yl)phenyl]amino}pyrimido[4,5-d]pyridazin-5(6H)-one | $^1$H NMR (400 MHz, DMSO-$d_6$) δ 10.58 (s, 1 H), 9.29 (s, 1 H), 7.76-7.73 (m, 2 H), 7.71 (d, J = 7.6 Hz, 2 H), 7.59 (dd, J = 8.8, 7.6 Hz, 1 H), 6.96 (d, J = 4.8 Hz, 2 H), 3.06 (t, J = 4.8 Hz, 4 H), 2.87 (t, J = 4.8 Hz, 4 H), 2.51 (s, 3 H) | MS (ESI) m/z 482 (M + H)$^+$ |
| 394 | 6-(2,6-dichlorophenyl)-8-methyl-2-(3-methyl-4-(4-methyl-1,4-diazepan-1-yl)phenylamino)pyrimido[4,5-d]pyridazin-5(6H)-one | $^1$H NMR (400 MHz, DMSO-$d_6$) δ 10.59 (s, 1 H), 9.31 (s, 1 H), 7.73-7.57 (m, 5 H), 7.08 (d, J 8.4 Hz, 1 H), 3.17-3.08 (m, 5 H), 2.75-2.72 (m, 4 H), 2.53 (s, 3 H), 2.36 (s, 3 H), 2.28 (s, 3 H), 1.91-1.85 (m, 2 H) | MS (ESI) m/z 523 (M + H)$^+$ |
| 395 | 6-(2,6-dichlorophenyl)-8-methyl-2-(1,2,3,4-tetrahydroisoquinolin-7-ylamino)pyrimido[4,5-d]pyridazin-5(6H)-one | $^1$H NMR (400 MHz, DMSO-$d_6$) δ 10.67 (s, 1 H), 9.34 (s, 1 H), 7.71 (d, J = 8.4 Hz, 2 H), 7.59 (dd, J = 8.8, 7.2 Hz, 2 H), 7.64-7.55 (m, 1 H), 7.09 (d, J = 8.4 Hz, 1 H), 3.94 (s, 2 H), 3.03 (t, J = 5.6 Hz, 2 H), 2.72 (t, J = 5.6 Hz, 2 H), 2.52 (s, 3 H) | MS (ESI) m/z 453 (M + H)$^+$ |
| 396 | 6-(2-chloro-6-fluorophenyl)-8-methyl-2-{[4-(piperazin-1-yl)phenyl]amino}pyrimido[4,5-d]pyridazin-5(6H)-one | $^1$H NMR (400 MHz, DMSO-$d_6$) δ 10.58 (s, 1 H), 9.28 (s, 1 H), 7.77-7.48 (m, 5 H), 6.96 (d, J = 8.8 Hz, 2 H), 3.06 (t, J = 4.8 Hz, 4 H), 2.88 (t, J = 4.8 Hz, 4 H), 2.52 (s, 3 H) | MS (ESI) m/z 466 (M + H)$^+$ |
| 397 | 6-(2,6-dichlorophenyl)-2-{[2-(dimethylamino)-2,3-dihydro-1H-inden-5-yl]amino}-8-methylpyrimido[4,5-d]pyridazin-5(6H)-one | $^1$H NMR (400 MHz, DMSO-$d_6$) δ 10.66 (s, 1 H), 9.33 (s, 1 H), 7.74-7.59 (m, 2 H), 7.72 (d, J = 8.4 Hz, 2 H), 7.59 (dd, J = 8.8, 7.6 Hz, 1 H), 7.18 (d, J = 7.6 Hz, 1 H), 3.09-2.97 (m, 3 H), 2.84-2.73 (m, 2 H), 2.51 (s, 3 H), 2.24 (s, 6 H) | MS (ESI) m/z 481 (M + H)$^+$ |
| 398 | 6-(2-chloro-6-fluorophenyl)-8-methyl-2-(1,2,3,4-tetrahydroisoquinolin-7-ylamino)pyrimido[4,5-d]pyridazin-5(6H)-one | $^1$H NMR (400 MHz, DMSO-$d_6$) δ 10.67 (s, 1 H), 9.33 (s, 1 H), 7.66-7.49 (m, 5 H), 7.11 (d, J = 8.4 Hz, 1 H), 3.96 (s, 2 H), 3.05 (t, J = 5.6 Hz, 2 H), 2.75-2.73 (m, 2 H), 2.52 (s, 3 H) | MS (ESI) m/z 437 (M + H)$^+$ |
| 399 | 6-(3-chloropyridin-2-yl)-8-methyl-2-{[4-(piperazin-1-yl)phenyl]amino}pyrimido[4,5-d]pyridazin-5(6H)-one | $^1$H NMR (400 MHz, DMSO-$d_6$) δ 10.57 (s, 1 H), 9.28 (s, 1 H), 8.61 (dd, J = 4.8, 1.6 Hz, 1 H), 8.25 (dd, J = 8.4, 1.6 Hz, 1 H), 7.78-7.51 (m, 3 H), 6.96 (d, J = 8.8 Hz, 2 H), 3.07-3.05 (m, 4 H), 2.89-2.87 (m, 4 H), 2.51 (s, 3 H) | MS (ESI) m/z 449 (M + H)$^+$ |
| 400 | 6-(3-chloropyridin-2-yl)-8-methyl-2-(1,2,3,4-tetrahydroisoquinolin-7-ylamino)pyrimido[4,5-d]pyridazin-5(6H)-one | $^1$H NMR (400 MHz, DMSO-$d_6$) δ 10.67 (s, 1 H), 9.33 (s, 1 H), 8.62 (dd, J = 4.8, 1.6 Hz, 1 H), 8.25 (dd, J = 8.0, 1.6 Hz, 1 H), 7.69-7.59 (m, 3 H), 7.13 (d, J = 8.4 Hz, 1 H), 4.01 (s, 2 H), 3.11 (t, J = 6.0 Hz, 2 H), 2.77 (t, J = 6.8 Hz, 2 H), 2.52 (s, 3 H) | MS (ESI) m/z 420 (M + H)$^+$ |
| 401 | 6-(2,6-dichlorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one | $^1$H NMR (400 MHz, DMSO-$d_6$) δ 0.83-0.87 (m, 2 H), 0.91-0.95 (m, 2 H), 2.33 (s, 3 H), 2.46 (s, 3 H), 2.53 (s, 2 H), 3.60 (s, 2 H), 6.74 (d, J = 8.54 Hz, 1 H), 7.56-7.62 (m, 2 H), 7.70-7.75 (m, 2 H), 9.33 (s, 1 H), 10.65 (s, 1 H) | MS (ESI) m/z 495 (M + H)$^+$ |
| 425 | 6-(2,6-dichlorophenyl)-2-({4-[4-(dimethylamino)piperidin-1-yl]phenyl}amino)-8-methylpyrimido[4,5-d]pyridazin-5(6H)-one | $^1$H NMR (400 MHz, DMSO-$d_6$) δ 2.29-2.34 (m, 4 H), 2.55 (s, 3 H), 2.76 (s, 6 H), 3.38-3.55 (m, 4 H), 3.77-3.82 (m, 2 H), 7.58-7.63 (m, 1 H), 7.64 (s, 1 H), 7.71-7.75 (m, 2 H), 7.96 (s, 1 H), 9.39 (s, 1 H), 10.88 (s, 1 H), 11.27 (s, 1 H) | MS (ESI) m/z 524 (M + H)$^+$ |
| 435 | 6-(2,6-dichlorophenyl)-8-methyl-2-[(2-methyl-1,2,3,4-tetrahydroisoquinolin-6-yl)amino]pyrimido[4,5-d]pyridazin-5(6H)-one | $^1$H NMR (400 MHz, DMSO-$d_6$): δ 10.65 (br s, 1 H), 9.34 (s, 1 H), 7.73-7.57 (m, 5 H), 7.06 (d, J = 8.0 Hz, 1 H), 3.46 (s, 2 H), 2.84 (t, J = 5.6 Hz, 2 H), 2.60 (t, J = 5.6 Hz, 2 H), 2.53 (s, 3 H), 2.34 (s, 3 H) | MS (ESI) m/z 467 (M + H$^+$) |

TABLE 2-continued

| Ex | Name | $^1$H NMR | MS |
|---|---|---|---|
| 438 | 6-(2,6-dichlorophenyl)-2-[(4,4-dimethyl-1,2,3,4-tetrahydroisoquinolin-7-yl)amino]-8-methylpyrimido[4,5-d]pyridazin-5(6H)-one | $^1$H NMR (400 MHz, DMSO-d$_6$) δ 10.63 (br s, 1 H), 9.33 (s, 1 H), 7.73-7.58 (m, 5 H), 7.34 (d, J = 8.8 Hz, 1 H), 3.86 (s, 2 H), 2.70 (s, 2 H), 2.53 (s, 3 H), 1.22 (s, 6 H) | MS (ESI) m/z 481 (M + H$^+$) |
| 439 | 2-[(2-acetyl-4,4-dimethyl-1,2,3,4-tetrahydroisoquinolin-7-yl)amino]-6-(2,6-dichlorophenyl)-8-methylpyrimido[4,5-d]pyridazin-5(6H)-one | $^1$H NMR (400 MHz, DMSO-d$_6$) δ 10.71 (br s, 1 H), 9.36 (s, 1 H), 7.74-7.43 (m, 5 H), 7.41 (dd, J = 8.4, 4.0 Hz, 1 H), 4.68 (d, J = 23.6 Hz, 2 H), 3.49 (d, J = 2.8 Hz, 2 H), 2.55 (s, 3 H), 2.12 (d, J = 14.0 Hz, 3 H), 1.23 (d, J = 22.8 Hz, 6 H) | MS (ESI) m/z 523 (M + H)$^+$ |
| 440 | 2-{[2-(cyclopropylcarbonyl)-4,4-dimethyl-1,2,3,4-tetrahydroisoquinolin-7-yl]amino}-6-(2,6-dichlorophenyl)-8-methylpyrimido[4,5-d]pyridazin-5(6H)-one | $^1$H NMR (400 MHz, DMSO-d$_6$): (two rotamers) δ 10.74 (br s, 1 H), 9.36 (s, 1 H), 7.74-7.58 (m, 5 H), 7.42 (d, J = 8.0 Hz, 1 H), 4.96 (s, 0.7 H), 4.69 (s, 1.4 H), 3.74 (s, 1.4 H), 3.6 (s, 0.7 H), 2.55 (s, 3 H), 2.18-2.10 (m, 1 H), 1.29 (s, 4.3 H), 1.24 (s, 2.3 H), 0.80-0.72 (m, 4 H) | MS (ESI) m/z 549 (M + H)$^+$ |
| 441 | 6-(2,6-dichlorophenyl)-2-{[4,4-dimethyl-2-(methylsulfonyl)-1,2,3,4-tetrahydroisoquinolin-7-yl]amino}-8-methylpyrimido[4,5-d]pyridazin-5(6H)-one | $^1$H NMR (400 MHz, DMSO-d$_6$): δ 10.74 (br s, 1 H), 9.36 (s, 1 H), 7.74-7.58 (m, 5 H), 7.45 (d, J = 8.4 Hz, 1 H), 4.36 (s, 2 H), 3.16 (s, 2 H), 3.00 (s, 3 H), 2.55 (s, 3 H), 1.29 (s, 6 H) | MS (ESI) m/z 559 (M + H)$^+$ |
| 442 | 6-(2,6-dichlorophenyl)-8-methyl-2-{[4-(3-oxopiperazin-1-yl)phenyl]amino}pyrimido[4,5-d]pyridazin-5(6H)-one | $^1$H NMR (400 MHz, DMSO-d$_6$): δ 10.62 (br s, 1 H), 9.30 (s, 1 H), 8.05 (br s, 1 H), 7.81-7.57 (m, 5 H), 6.99 (d, J = 8.4 Hz, 2 H), 3.71 (s, 2 H), 3.38-3.34 (m, 2 H), 3.34-3.28 (m, 2 H), 2.51 (s, 3 H) | MS (ESI) m/z 496 (M + H)$^+$ |
| 443 | 6-(2,6-dichlorophenyl)-8-methyl-2-[(1,1,2-trimethyl-1,2,3,4-tetrahydroisoquinolin-7-yl)amino]pyrimido[4,5-d]pyridazin-5(6H)-one | $^1$H NMR (400 MHz, DMSO-d$_6$): δ 10.62 (br s, 1 H), 9.34 (s, 1 H), 8.09-7.45 (m, 5 H), 7.05 (d, J = 8.4 Hz, 1 H), 2.74 (s, 4 H), 2.55 (s, 3 H), 2.34 (s, 3 H), 1.37 (s, 6 H) | MS (ESI) m/z 495 (M + H)$^+$ |
| 444 | 6-(2,6-dichlorophenyl)-2-[(1,1-dimethyl-1,2,3,4-tetrahydroisoquinolin-7-yl)amino]-8-methylpyrimido[4,5-d]pyridazin-5(6H)-one | $^1$H NMR (400 MHz, DMSO-d$_6$): δ 10.66 (br s, 1 H), 9.36 (s, 1 H), 8.07-7.46 (m, 5 H), 7.06 (d, J = 8.4 Hz, 1 H), 3.06 (t, J = 5.2 Hz, 2 H), 2.73 (t, J = 5.2 Hz, 2 H), 2.55 (s, 3H), 1.47 (s, 6 H) | MS (ESI) m/z 481 (M + H)$^+$ |
| 445 | 6-(2,6-dichlorophenyl)-8-methyl-2-({4-[4-(oxetan-3-yl)piperazin-1-yl]phenyl}amino)pyrimido[4,5-d]pyridazin-5(6H)-one | $^1$H NMR (400 MHz, DMSO-d$_6$) δ 2.52 (s, 3 H), 3.17 (m, 4 H), 3.51 (m, 4 H), 4.34-4.44 (m, 1 H), 4.72-4.82 (m, 4 H), 7.07 (d, J = 8.54 Hz, 2 H), 7.55-7.63 (m, 1 H), 7.70-7.74 (m, 2 H), 7.80-7.86 (m, 1 H), 9.31 (s, 1 H), 10.64 (d, J = 1.22 Hz, 1 H) | MS (ESI) m/z 538 (M + H)$^+$ |
| 446 | 6-(2,6-dichlorophenyl)-2-{[4-(hexahydropyrrolo[3,4-c]pyrrol-2(1H)-yl)phenyl]amino}-8-methylpyrimido[4,5-d]pyridazin-5(6H)-one | $^1$H NMR (500 MHz, DMSO-d$_6$): δ 2.50 (s, 3 H), 3.06-3.14 (m, 4 H), 3.25-3.29 (m, 2 H), 3.35 (m, 2 H), 3.46-3.50 (m, 2 H), 6.73 (d, J = 8.24 Hz, 2 H), 7.53-7.62 (m, 1 H), 7.68-7.77 (m, 2 H), 8.86-8.93 (m, 1 H), 9.27 (s, 1 H), 10.54 (s, 1 H) | MS (ESI) m/z 509 (M + H)$^+$ |
| 447 | 6-(3,5-dichloropyridin-4-yl)-2-(2',3'-dihydro-1'H-spiro[cyclopropane-1,4'-isoquinolin]-7'-ylamino)-8-methylpyrimido[4,5-d]pyridazin-5(6H)-one | $^1$H NMR (500 MHz, DMSO-d$_6$) δ 1.09-1.11 (m, 2 H), 1.11-1.13 (m, 2 H), 2.55 (s, 3 H), 3.29 (s, 2 H), 4.43 (s, 2 H), 6.92 (d, J = 8.85 Hz, 1 H), 7.68 (s, 1 H), 7.83 (s, 1 H), 8.94-8.97 (m, 1 H), 9.31 (s, 2 H), 9.38 (s, 1 H), 10.85 (s, 1 H) | MS (ESI) m/z 480 (M + H)$^+$ |
| 448 | 6-(3,5-dichloropyridin-4-yl)-8-methyl-2-(1,2,3,4-tetrahydroisoquinolin-6-ylamino)pyrimido[4,5-d]pyridazin-5(6H)-one | $^1$H NMR (500 MHz, DMSO-d$_6$): δ 2.55 (s, 3 H), 3.03 (t, J = 6.10 Hz, 2 H), 3.42 (t, J = 6.10 Hz, 2 H), 4.27 (s, 2 H), 7.25 (d, J = 8.54 Hz, 1 H), 7.69 (s, 1 H), 7.87 (s, 1 H), 8.93-8.98 (m, 1 H), 9.09 (s, 2 H), 9.40 (s, 1 H), 10.86 (s, 1 H) | MS (ESI) m/z 454 (M + H)$^+$ |
| 449 | 2-[(2-acetyl-1,2,3,4-tetrahydroisoquinolin-6-yl)amino]-6-(2,6-dichlorophenyl)-8-methylpyrimido[4,5-d]pyridazin-5(6H)-one | $^1$H NMR (400 MHz, DMSO-d$_6$) δ 2.09 (s, 3 H), 2.50 (s, 3 H), 2.87-2.92 (m, 2 H), 3.67 (t, J = 5.95 Hz, 2 H), 4.58 (s, 1 H), 4.63 (s, 1 H), 7.21 (d, J = 8.24 Hz, 1 H), | MS (ESI) m/z 496 (M + H)$^+$ |

TABLE 2-continued

| Ex | Name | ¹H NMR | MS |
|---|---|---|---|
| | | 7.58-7.61 (m, 1 H), 7.63-7.69 (m, 1 H), 7.72 (d, J = 7.93 Hz, 2 H), 7.78-7.83 (m, 1 H), 9.36 (s, 1 H), 10.72 (s, 1 H) | |
| 450 | 6-(2,6-dichlorophenyl)-8-methyl-2-{[2-(methylsulfonyl)-1,2,3,4-tetrahydroisoquinolin-6-yl]amino}pyrimido[4,5-d]pyridazin-5(6H)-one | ¹H NMR (400 MHz, DMSO-$d_6$): δ 2.54 (s, 3 H), 2.93-2.97 (m, 5 H), 3.45 (t, J = 5.95 Hz, 2 H), 4.36 (s, 2 H), 7.21 (d, J = 8.54 Hz, 1 H), 7.58-7.62 (m, 1 H), 7.67-7.70 (m, 1 H), 7.73 (d, J = 8.54 Hz, 2 H), 7.79-7.86 (m, 1 H), 9.37 (s, 1 H), 10.74 (s, 1 H) | MS (ESI) m/z 532 (M + H)⁺ |
| 451 | 6-(2,6-dichlorophenyl)-2-(2,3-dihydro-1H-isoindol-5-ylamino)-8-methylpyrimido[4,5-d]pyridazin-5(6H)-one | ¹H NMR (400 MHz, DMSO-$d_6$): δ 2.55 (s, 3 H), 4.52 (s, 2 H), 4.57 (s, 2 H), 7.43 (d, J = 8.24 Hz, 1 H), 7.57-7.63 (m, 1 H), 7.69-7.76 (m, 2 H), 7.79-7.84 (m, 1 H), 9.40 (s, 1 H), 9.54 (s, 1 H), 10.90 (s, 1 H) | MS (ESI) m/z 439 (M + H)⁺ |
| 452 | 6-(2,6-dichlorophenyl)-2-[(1,1-dimethyl-1,2,3,4-tetrahydroisoquinolin-6-yl)amino]-8-methylpyrimido[4,5-d]pyridazin-5(6H)-one | ¹H NMR (400 MHz, DMSO-$d_6$): δ 10.61 (br s, 1 H), 9.33 (s, 1 H), 8.03-7.02 (m, 6 H), 2.95 (q, J = 5.2 Hz, 2 H), 2.70-2.64 (m, 2 H), 2.53 (s, 3 H), 1.34 (s, 6 H) | MS (ESI) m/z 481 (M + H)⁺ |
| 453 | 6-(2,6-dichlorophenyl)-8-methyl-2-[(1,1,2-trimethyl-1,2,3,4-tetrahydroisoquinolin-6-yl)amino]pyrimido[4,5-d]pyridazin-5(6H)-one | ¹H NMR (400 MHz, DMSO-$d_6$): δ 10.64 (br s, 1 H), 9.34 (s, 1 H), 8.10-7.04 (m, 6 H), 2.74 (m, 4 H), 2.54 (s, 3 H), 2.33 (s, 3 H), 1.32 (s, 6 H) | MS (ESI) m/z 495 (M + H)⁺ |
| 454 | 6-(2,6-dichlorophenyl)-8-methyl-2-({4-[(4-methylpiperazin-1-yl)methyl]phenyl}amino)pyrimido[4,5-d]pyridazin-5(6H)-one | ¹H NMR (400 MHz, DMSO-$d_6$): δ 10.76 (br s, 1 H), 9.36 (s, 1 H), 7.85-7.58 (m, 5 H), 7.30 (d, J = 8.4 Hz, 2 H), 3.43 (s, 2 H), 2.54 (s, 3 H), 2.48-2.20 (m, 8 H), 2.15 (s, 3 H) | MS (ESI) m/z 510 (M + H)⁺ |
| 455 | 6-(2,6-dichlorophenyl)-8-methyl-2-{[4-(pyrrolidin-2-yl)phenyl]amino}pyrimido[4,5-d]pyridazin-5(6H)-one | ¹H NMR (400 MHz, DMSO-$d_6$): δ 10.71 (br s, 1 H), 9.35 (s, 1 H), 7.83-7.36 (m, 5 H), 7.20 (d, J = 8.8 Hz, 2 H), 4.01 (t, J = 7.6 Hz, 1 H), 3.04-2.86 (m, 2 H), 2.53 (s, 3 H), 2.14-2.06 (m, 1 H), 1.84-1.69 (m, 2 H), 1.54-1.45 (m, 1 H) | MS (ESI) m/z 467 (M + H)⁺ |
| 456 | 6-(2,6-dichlorophenyl)-8-methyl-2-{[4-(1-methylpiperidin-4-yl)phenyl]amino}pyrimido[4,5-d]pyridazin-5(6H)-one | ¹H NMR (400 MHz, DMSO-$d_6$): δ 10.72 (br s, 1 H), 9.35 (s, 1 H), 7.84-7.58 (m, 5 H), 7.26 (d, J = 8.0 Hz, 2 H), 2.86 (d, J = 11.2 Hz, 2 H), 2.53 (s, 3 H), 2.48-2.40 (m, 1 H), 2.19 (s, 3 H), 1.95 (td, J = 11.2, 2.4 Hz, 2 H), 1.75-1.60 (m, 4 H) | MS (ESI) m/z 495 (M + H)⁺ |
| 457 | 2-({4-[(1R,4R)-2,5-diazabicyclo[2.2.1]hept-2-yl]phenyl}amino)-6-(2,6-dichlorophenyl)-8-methylpyrimido[4,5-d]pyridazin-5(6H)-one | ¹H NMR (400 MHz, DMSO-$d_6$) δ 10.48 (br s, 1 H), 9.25 (s, 1 H), 7.73-7.42 (m, 5 H), 6.60 (d, J = 8.0 Hz, 2 H), 4.34 (s, 1 H), 3.67 (s, 1 H), 3.51 (d, J = 8.0 Hz, 2 H), 2.49 (s, 3 H), 2.93-2.84 (m, 3 H), 1.74 (dd, J = 8.8, 56.4 Hz, 2 H) | MS (ESI) m/z 494 (M + H)⁺ |
| 458 | 6-(2,6-dichlorophenyl)-8-methyl-2-{[4-(piperidin-4-yl)phenyl]amino}pyrimido[4,5-d]pyridazin-5(6H)-one | ¹H NMR (400 MHz, DMSO-$d_6$): δ 10.75 (br s, 1 H), 9.36 (s, 1 H), 8.72 (d, J = 9.2 Hz, 1 H), 8.47 (d, J = 9.6 Hz, 1 H), 7.86-7.58 (m, 5 H), 7.26 (d, J = 8.8 Hz, 2 H), 3.39 (d, J = 12.0 Hz, 2 H), 3.02 (q, J = 12.0 Hz, 2 H), 2.89-2.81 (m, 1 H), 2.54 (s, 3 H), 1.96 (d, J = 13.2 Hz, 2 H), 1.86-1.75 (m, 2 H) | MS (ESI) m/z 481 (M + H)⁺ |
| 459 | 6-(2,6-dichlorophenyl)-8-methyl-2-{[4-(piperidin-3-yl)phenyl]amino}pyrimido[4,5-d]pyridazin-5(6H)-one | ¹H NMR (400 MHz, DMSO-$d_6$): δ 10.78 (br s, 1 H), 9.37 (s, 1 H), 8.96 (d, J = 10.4 Hz, 1 H), 8.66 (d, J = 10.0 Hz, 1 H), 7.89-7.58 (m, 5 H), 7.33 (d, J = 8.4 Hz, 2 H), 3.32 (d, J = 10.0 Hz, 2 H), 3.05-3.00 (m, 1 H), 2.94-2.90 (m, 2 H), 2.55 (s, 3 H), 1.92 (d, J = 10.4 Hz, 2 H), 1.79-1.71 (m, 2 H) | MS (ESI) m/z 481 (M + H)⁺ |

TABLE 2-continued

| Ex | Name | ¹H NMR | MS |
|---|---|---|---|
| 467 | 6-(2,6-dichlorophenyl)-8-methyl-2-[(3-oxo-1,2,3,4-tetrahydroisoquinolin-7-yl)amino]pyrimido[4,5-d]pyridazin-5(6H)-one | ¹H NMR (400 MHz, DMSO-$d_6$): δ 10.75 (br s, 1 H), 9.36 (s, 1 H), 8.00-7.58 (m, 6 H), 7.25 (dd, J = 25.2, 8.4 Hz, 1 H), 4.35 (d, J = 10.8 Hz, 2 H), 3.45 (d, J = 13.6 Hz, 2 H), 2.54 (d, J = 2.4 Hz, 3 H) | MS (ESI) m/z 467 (M + H)⁺ |
| 471 | 6-(2,6-dichlorophenyl)-8-methyl-2-[(1,1,2-trimethyl-2,3-dihydro-1H-isoindol-5-yl)amino]pyrimido[4,5-d]pyridazin-5(6H)-one | ¹H NMR (400 MHz, DMSO-$d_6$): δ 1.44 (s, 3 H), 1.74 (s, 3 H), 2.55 (s, 3 H), 2.92 (d, J = 4.58 Hz, 3 H), 4.58-4.65 (m, 1 H), 4.71-4.78 (m, 1 H), 7.45 (d, J = 8.24 Hz, 1 H), 7.58-7.63 (m, 1 H), 7.72-7.74 (m, 1 H), 7.84-7.86 (m, 1 H), 7.96 (s, 1 H), 9.40 (s, 1 H), 10.43 (s, 1 H), 10.92 (s, 1 H) | MS (ESI) m/z 481 (M + H)⁺ |
| 472 | 2-[(7-chloro-1,2,3,4-tetrahydroisoquinolin-6-yl)amino]-6-(2,6-dichlorophenyl)-8-methylpyrimido[4,5-d]pyridazin-5(6H)-one | ¹H NMR (400 MHz, DMSO-$d_6$): δ 2.42 (s, 3 H), 3.01 (t, J = 6.10 Hz, 2 H), 3.38-3.42 (m, 2 H), 4.32 (s, 2 H), 7.51 (s, 1 H), 7.57-7.62 (m, 1 H), 7.70-7.74 (m, 2 H), 9.13 (s, 2 H), 9.33 (s, 1 H), 10.37 (s, 1 H) | MS (ESI) m/z 489 (M + H)⁺ |
| 480 | 6-(2,6-dichlorophenyl)-2-[(7-fluoro-1,2,3,4-tetrahydroisoquinolin-6-yl)amino]-8-methylpyrimido[4,5-d]pyridazin-5(6H)-one | ¹H NMR (400 MHz, DMSO-$d_6$): δ 2.44 (s, 3 H), 3.00 (t, J = 5.95 Hz, 2 H), 3.40-3.44 (m, 2 H), 4.31 (s, 2 H), 7.26 (d, J = 11.29 Hz, 1 H), 7.60 (dd, J = 8.85, 7.63 Hz, 1 H), 7.70-7.75 (m, 2 H), 9.17 (s, 2 H), 9.35 (s, 1 H), 10.48 (s, 1 H) | MS (ESI) m/z 471 (M + H)⁺ |
| 481 | 6-(2-chlorophenyl)-8-methyl-2-(1,2,3,4-tetrahydroisoquinolin-6-ylamino)pyrimido[4,5-d]pyridazin-5(6H)-one | ¹H NMR (400 MHz, DMSO-$d_6$): δ 2.52 (s, 3 H), 3.03 (t, J = 6.10 Hz, 2 H), 3.40-3.43 (m, 2 H), 4.25-4.29 (m, 2 H), 7.24 (d, J = 8.54 Hz, 1 H), 7.52-7.56 (m, 1 H), 7.60 (dd, J = 4.27, 2.14 Hz, 1 H), 7.67-7.71 (m, 2 H), 7.85-7.87 (m, 1 H), 9.10 (s, 2 H), 9.36 (s, 1 H), 10.73 (s, 1 H) | MS (ESI) m/z 419 (M + H)⁺ |
| 482 | 6-(2-chlorophenyl)-2-[(4,4-dimethyl-1,2,3,4-tetrahydroisoquinolin-7-yl)amino]-8-methylpyrimido[4,5-d]pyridazin-5(6H)-one | ¹H NMR (400 MHz, DMSO-$d_6$) δ 1.37 (s, 6 H), 2.54 (s, 3 H), 3.26 (s, 2 H), 4.31 (s, 2 H), 7.49-7.53 (m, 1 H), 7.54 (t, J = 3.36 Hz, 1 H), 7.58-7.61 (m, 1 H), 7.68-7.70 (m, 1 H), 7.75-7.79 (m, 1 H), 9.18 (s, 2 H), 9.36 (s, 1 H), 10.74 (s, 1 H) | MS (ESI) m/z 447 (M + H)⁺ |
| 483 | 6-(2-chlorophenyl)-8-methyl-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-$d_6$): δ 1.28 (s, 3 H), 1.33 (s, 3 H), 2.49 (s, 3 H), 2.94 (s, 3 H), 3.16-3.24 (m, 2 H), 4.29-4.42 (m, 2 H), 7.47 (d, J = 8.85 Hz, 1 H), 7.51-7.56 (m, 1 H), 7.64-7.68 (m, 2 H), 7.69-7.73 (m, 1 H), 9.31 (s, 1 H), 9.74 (s, 1 H), 10.76 (s, 1 H) | MS (ESI) m/z 495 (M + H)⁺ |
| 484 | 6-(2-chlorophenyl)-2-{[2-(dimethylamino)-2,3-dihydro-1H-inden-5-yl]amino}-8-methylpyrimido[4,5-d]pyridazin-5(6H)-one | ¹H NMR (400 MHz, DMSO-$d_6$): δ 2.49 (s, 3 H), 2.80 (d, J = 4.27 Hz, 6 H), 3.03-3.16 (m, 1 H), 3.22-3.34 (m, 1 H), 4.05-4.12 (m, 2 H), 7.23 (d, J = 8.24 Hz, 1 H), 7.55 (dd, J = 8.70, 7.48 Hz, 1 H), 7.66-7.70 (m, 2 H), 7.81 (s, 1 H), 9.31 (s, 1 H), 9.97 (s, 1 H), 10.70 (s, 1 H) | MS (ESI) m/z 446 (M + H)⁺ |
| 487 | 6-(3,5-dichloropyridin-4-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one | ¹H NMR (400 MHz, DMSO-$d_6$): δ 0.94 (s, 1 H), 1.07-1.12 (m, 1 H), 1.15-1.21 (m, 1 H), 1.34-1.39 (m, 1 H), 2.56 (s, 3 H), 2.96 (d, J = 2.14 Hz, 3 H), 3.25 (d, J = 11.90 Hz, 1 H), 3.55 (dd, J = 11.75, 8.09 Hz, 1 H), 4.46-4.52 (m, 1 H), 4.59-4.65 (m, 1 H), 6.93 (d, J = 8.54 Hz, 1 H), 7.71-7.83 (m, 2 H), 8.95 (s, 2 H), 9.39 (s, 1 H), 10.41 (s, 1 H), 10.88 (s, 1 H) | MS (ESI) m/z 494 (M + H)⁺ |
| 488 | 6-(3,5-dichloropyridin-4-yl)-8-methyl-2-[(1,1,2-trimethyl-2,3-dihydro-1H-isoindol-5-yl)amino]pyrimido[4,5-d]pyridazin-5(6H)-one | ¹H NMR (400 MHz, DMSO-$d_6$): δ 1.44 (s, 3 H), 1.74 (s, 3 H), 2.56 (s, 3 H), 2.92 (d, J = 4.88 Hz, 3 H), 4.57-4.64 (m, 1 H), 4.71-4.76 (m, 1 H), 7.45 (d, J = 8.24 Hz, 1 H), | MS (ESI) m/z 482 (M + H)⁺ |

TABLE 2-continued

| Ex | Name | ¹H NMR | MS |
|---|---|---|---|
| | | 7.82-7.88 (m, 1 H), 7.95 (s, 1 H), 8.95 (s, 1 H), 9.41 (s, 1 H), 10.39 (s, 1 H), 10.96 (s, 1 H) | |
| 489 | 6-(2,6-dichlorophenyl)-2-[(1,1-dimethyl-2,3-dihydro-1H-isoindol-5-yl)amino]-8-methylpyrimido[4,5-d]pyridazin-5(6H)-one | ¹H NMR (400 MHz, DMSO-$d_6$): δ 1.64 (s, 6 H), 2.55 (s, 3 H), 4.57-4.63 (m, 2 H), 7.43 (d, J = 8.24 Hz, 1 H), 7.58-7.64 (m, 1 H), 7.70-7.76 (m, 2 H), 7.87-7.95 (m, 1 H), 9.40 (s, 1 H), 9.50 (s, 2 H), 10.91 (s, 1 H) | MS (ESI) m/z 467 (M + H)⁺ |
| 490 | 6-(2,6-dichlorophenyl)-8-methyl-2-[(2-methyl-1,2,3,4-tetrahydroisoquinolin-7-yl)amino]pyrimido[4,5-d]pyridazin-5(6H)-one | ¹H NMR (400 MHz, DMSO-$d_6$): δ 10.83 (br s, 1 H), 10.24 (br s, 1 H), 9.39 (s, 1 H), 7.82-7.59 (m, 5 H), 7.29 (d, J = 7.6 Hz, 1 H), 4.49-4.38 (m, 2 H), 3.65-3.51 (m, 2 H), 3.07 (s, 2 H), 2.96 (s, 3 H), 2.55 (s, 3 H) | MS (ESI) m/z 467 (M + H)⁺ |
| 491 | 6-(2,6-dichlorophenyl)-8-methyl-2-[(2-methyl-2,3-dihydro-1H-isoindol-5-yl)amino]pyrimido[4,5-d]pyridazin-5(6H)-one | ¹H NMR (400 MHz, DMSO-$d_6$): δ 10.71 (br s, 1 H), 9.35 (s, 1 H), 7.82-7.58 (m, 5 H), 7.23 (d, J = 8.0 Hz, 1 H), 3.83 (s, 2 H), 3.79 (s, 2 H), 2.52 (s, 3 H), 2.49 (s, 3 H) | MS (ESI) m/z 453 (M + H)⁺ |
| 495 | 6-(2-chloro-6-methylphenyl)-8-methyl-2-(1,2,3,4-tetrahydroisoquinolin-7-ylamino)pyrimido[4,5-d]pyridazin-5(6H)-one | ¹H NMR (400 MHz, DMSO-$d_6$): δ 2.08 (s, 3 H), 2.49 (s, 3 H), 2.94 (t, J = 6.10 Hz, 2 H), 3.37 (t, J = 5.49 Hz, 2 H), 4.27 (s, 2 H), 7.21 (d, J = 8.54 Hz, 1 H), 7.34-7.41 (m, 2 H), 7.65 (d, J = 7.63 Hz, 1 H), 7.78 (s, 1 H), 9.09 (s, 2 H), 9.32 (s, 1 H), 10.69 (s, 1 H) | MS (ESI) m/z 433 (M + H)⁺ |
| 496 | 6-(2-chloro-6-methylphenyl)-8-methyl-2-(1,2,3,4-tetrahydroisoquinolin-6-ylamino)pyrimido[4,5-d]pyridazin-5(6H)-one | ¹H NMR (400 MHz, DMSO-$d_6$): δ 2.08 (s, 3 H), 2.49 (s, 3 H), 2.99 (t, J = 6.26 Hz, 2 H), 3.30-3.34 (m, 2 H), 4.22 (s, 2 H), 7.20 (d, J = 8.54 Hz, 1 H), 7.35-7.40 (m, 1 H), 7.44-7.48 (m, 1 H), 7.66 (d, J = 7.93 Hz, 1 H), 7.82 (s, 1 H), 9.04 (s, 2 H), 9.33 (s, 1 H), 10.69 (s, 1 H) | MS (ESI) m/z 433 (M + H)⁺ |
| 497 | 6-(2-chloro-6-methylphenyl)-2-[(4,4-dimethyl-1,2,3,4-tetrahydroisoquinolin-7-yl)amino]-8-methylpyrimido[4,5-d]pyridazin-5(6H)-one | ¹H NMR (400 MHz, DMSO-$d_6$): δ 1.31 (s, 6 H), 2.07 (s, 3 H), 2.49 (s, 3 H), 3.20 (s, 2 H), 4.25 (s, 2 H), 7.34-7.40 (m, 2 H), 7.42-7.48 (m, 2 H), 7.71 (s, 1 H), 9.14 (s, 2 H), 9.31 (s, 1 H), 10.69 (s, 1 H) | MS (ESI) m/z 461 (M + H)⁺ |
| 498 | 6-(2-chloro-6-methylphenyl)-8-methyl-2-[(2,4,4-trimethyl-1,2,3,4-tetrahydroisoquinolin-7-yl)amino]pyrimido[4,5-d]pyridazin-5(6H)-one | ¹H NMR (400 MHz, DMSO-$d_6$): δ 1.35 (s, 3 H), 1.40 (s, 3 H), 2.13 (s, 3 H), 2.55 (s, 3 H), 3.01 (s, 3 H), 3.27 (t, J = 11.14 Hz, 1 H), 3.51 (d, J = 12.51 Hz, 1 H), 4.34-4.50 (m, 2 H), 7.39-7.47 (m, 2 H), 7.50-7.57 (m, 2 H), 7.78 (s, 2 H), 9.38 (s, 1 H), 9.85 (s, 1 H), 10.78 (s, 1 H) | MS (ESI) m/z 475 (M + H)⁺ |
| 499 | 6-(2-chloro-6-methylphenyl)-2-{[2-(2-hydroxyethyl)-1,2,3,4-tetrahydroisoquinolin-7-yl]amino}-8-methylpyrimido[4,5-d]pyridazin-5(6H)-one | ¹H NMR (400 MHz, DMSO-$d_6$): δ 2.13 (s, 3 H), 2.54 (s, 3 H), 3.00-3.09 (m, 1 H), 3.15 (d, J = 15.56 Hz, 1 H), 3.34 (s, 2 H), 3.76 (t, 2 H), 3.85 (t, J = 5.19 Hz, 2 H), 4.39-4.47 (m, 1 H), 4.54-4.61 (m, 1 H), 7.28 (d, J = 8.54 Hz, 1 H), 7.38-7.54 (m, 3 H), 7.75 (d, J = 7.63 Hz, 2 H), 9.37 (s, 1 H), 10.01 (s, 1 H), 10.76 (s, 1 H) | MS (ESI) m/z 477 (M + H)⁺ |
| 500 | 6-(2-chloro-6-methylphenyl)-2-[(4-{4-[3-(dimethylamino)propyl]piperazin-1-yl}phenyl)amino]-8-methylpyrimido[4,5-d]pyridazin-5(6H)-one | ¹H NMR (400 MHz, DMSO-$d_6$): δ 2.04-2.10 (m, 2 H), 2.13 (s, 3 H), 2.49-2.52 (m, 3 H), 2.82 (s, 6 H), 2.97-3.05 (m, 2 H), 3.10-3.16 (m, 2 H), 3.18-3.25 (m, 2 H), 3.61 (s, 2 H), 3.84-3.90 (m, 2 H), 7.08 (d, J = 8.85 Hz, 2 H), 7.37-7.46 (m, 3 H), 7.48-7.52 (m, 1 H), 9.31 (s, 1 H), 9.91 (s, 1 H), 10.14 (s, 1 H), 10.59 (s, 1 H) | MS (ESI) m/z 547 (M + H)⁺ |
| 501 | 6-(2-chloro-6-methylphenyl)-8-methyl-2-({4-[(1-methylpiperidin-4-yl)amino]phenyl}amino)pyrimido[4,5-d]pyridazin-5(6H)-one | ¹H NMR (400 MHz, DMSO-$d_6$): δ 1.53-1.64 (m, 2 H), 1.88-1.97 (m, 2 H), 2.12 (s, 3 H), 2.48 (s, 3 H), 2.79 (s, 3 H), 3.01-3.10 (m, 2 H), 3.47 (t, J = 11.14 Hz, 2 H), | MS (ESI) m/z 490 (M + H)⁺ |

TABLE 2-continued

| Ex | Name | ¹H NMR | MS |
|---|---|---|---|
| | | 6.71 (t, J = 8.24 Hz, 1 H), 7.37-7.52 (m, 3 H), 7.67 (s, 1 H), 9.26 (s, 1 H), 9.49 (s, 1 H), 10.42 (s, 1 H) | |
| 502 | 6-(2-chloro-6-methylphenyl)-8-methyl-2-({4-[(1-methylpiperidin-4-yl)oxy]phenyl}amino)pyrimido[4,5-d]pyridazin-5(6H)-one | ¹H NMR (400 MHz, DMSO-d₆): δ 1.68-1.81 (m, 1 H), 1.99 (m, 1 H), 2.06-2.13 (m, 1 H), 2.13 (s, 3 H), 2.28 (m, 1 H), 2.49-2.52 (m, 3 H), 2.83 (dd, J = 12.66, 4.43 Hz, 3 H), 3.05-3.12 (m, 1 H), 3.14-3.23 (m, 1 H), 3.34 (d, J = 11.90 Hz, 1 H), 3.52 (d, J = 12.51 Hz, 1 H), 7.06 (dd, J = 16.94, 9.00 Hz, 1 H), 7.37-7.52 (m, 3 H), 7.84 (s, 1 H), 9.32 (s, 1 H), 9.59 (s, 1 H), 10.59 (s, 1 H) | MS (ESI) m/z 491 (M + H)⁺ |
| 503 | 6-(2,6-dichlorophenyl)-8-methyl-2-({4-[(1-methylpiperidin-4-yl)oxy]phenyl}amino)pyrimido[4,5-d]pyridazin-5(6H)-one | ¹H NMR (400 MHz, DMSO-d₆): δ 1.72-1.78 (m, 1 H), 1.92-2.02 (m, 1 H), 2.06-2.12 (m, 1 H), 2.25-2.31 (m, 1 H), 2.52 (s, 3 H), 2.83 (d, J = 10.07 Hz, 3 H), 3.09-3.20 (m, 1 H), 3.51 (s, 1 H), 4.51 (s, 1 H), 4.71 (s, 1 H), 7.01-7.09 (m, 2 H), 7.57-7.63 (m, 1 H), 7.69-7.76 (m, 2 H), 7.84 (s, 1 H), 9.33 (s, 1 H), 9.60 (s, 1 H), 10.66 (s, 1 H) | MS (ESI) m/z 511 (M + H)⁺ |
| 504 | 6-(2,6-dichlorophenyl)-8-methyl-2-{[3-(piperidin-1-yl)phenyl]amino}pyrimido[4,5-d]pyridazin-5(6H)-one | ¹H NMR (300 MHz, DMSO-d₆): δ 1.53-1.66 (m, 2 H), 1.68-1.85 (m, 4 H), 2.56 (s, 3 H), 3.15-3.50 (m, 4 H), 7.28-7.45 (m, 2 H), 7.50-7.65 (m, 2 H), 7.66-7.76 (m, 2 H), 7.89 (dd, J = 3.97, 2.44 Hz, 1 H), 9.38 (s, 1 H) | MS (DCI/NH₃) m/z 482 (M + H)⁺ |
| 505 | 6-(2,6-dichlorophenyl)-8-methyl-2-{[3-(morpholin-4-yl)phenyl]amino}pyrimido[4,5-d]pyridazin-5(6H)-one | ¹H NMR (300 MHz, DMSO-d₆): δ 2.49 (s, 3 H), 2.98-3.18 (m, 4 H), 3.63-3.78 (m, 4 H), 6.68 (d, J = 7.63 Hz, 1 H), 7.07-7.31 (m, 2 H), 7.45-7.62 (m, 2 H), 7.61-7.77 (m, 2 H), 9.31 (s, 1 H) | MS (DCI/NH₃) m/z 484 (M + H)⁺ |
| 506 | 6-(2,6-dichlorophenyl)-8-methyl-2-{[3-(piperazin-1-yl)phenyl]amino}pyrimido[4,5-d]pyridazin-5(6H)-one | ¹H NMR (300 MHz, DMSO-d₆): δ ppm 2.49 (s, 3 H), 3.11-3.28 (m, 8 H), 6.67-6.79 (m, 1 H), 7.16-7.33 (m, 1 H), 7.43-7.58 (m, 2 H), 7.59-7.76 (m, 3 H), 9.31 (s, 1 H) | MS (DCI/NH₃) m/z 483 (M + H)⁺ |
| 507 | 2-({3-[4-(3-chloropropyl)piperazin-1-yl]phenyl}amino)-6-(2,6-dichlorophenyl)-8-methylpyrimido[4,5-d]pyridazin-5(6H)-one | ¹H NMR (300 MHz, DMSO-d₆): δ 2.13-2.26 (m, 2 H), 2.55 (s, 3 H), 2.96-3.13 (m, 2 H), 3.18-3.34 (m, 4 H), 3.60-3.70 (m, 2 H), 3.76 (t, J = 6.26 Hz, 2 H), 3.81-3.97 (m, 2 H), 6.75-6.91 (m, 1 H), 7.17-7.31 (m, 2 H), 7.47-7.65 (m, 1 H), 7.67-7.78 (m, 3 H), 9.38 (s, 1 H) | MS (DCI/NH₃) m/z 559 (M + H)⁺ |
| 508 | 2-{[3-(4-cyclobutylpiperazin-1-yl)phenyl]amino}-6-(2,6-dichlorophenyl)-8-methylpyrimido[4,5-d]pyridazin-5(6H)-one | ¹H NMR (300 MHz, DMSO-d₆): δ 1.67-1.92 (m, 2 H), 2.13-2.35 (m, 4 H), 2.55 (s, 3 H), 3.00 (d, J = 8.48 Hz, 4 H), 3.37-3.58 (m, 1 H), 3.69-3.93 (m, 4 H), 6.70-6.87 (m, 1 H), 7.22-7.39 (m, 2 H), 7.56-7.65 (m, 1 H), 7.67-7.82 (m, 3 H), 9.37 (s, 1 H) | MS (DCI/NH₃) m/z 537 (M + H)⁺ |
| 509 | 6-(2,6-dichlorophenyl)-8-methyl-2-({3-[4-(tetrahydro-2H-pyran-4-yl)piperazin-1-yl]phenyl}amino)pyrimido[4,5-d]pyridazin-5(6H)-one | ¹H NMR (300 MHz, DMSO-d₆): δ 1.56-1.76 (m, 2 H), 2.04 (d, J = 11.87 Hz, 2 H), 2.55 (s, 3 H), 3.05 (d, J = 12.89 Hz, 2 H), 3.12-3.25 (m, 2 H), 3.32 (t, J = 11.19 Hz, 2 H), 3.45-3.58 (m, 1 H), 3.67 (d, J = 11.87 Hz, 2 H), 3.90 (d, J = 12.55 Hz, 4 H), 6.65-6.87 (m, 1 H), 7.22-7.34 (m, 2 H), 7.46-7.65 (m, 2 H), 7.65-7.76 (m, 2 H), 9.38 (s, 1 H) | MS (DCI/NH₃) m/z 566 (M + H)⁺ |
| 510 | 6-(2,6-dichlorophenyl)-2-({3-[4-(3-hydroxypropyl)piperazin-1-yl]phenyl}amino)-8-methylpyrimido[4,5-d]pyridazin-5(6H)-one | ¹H NMR (300 MHz, DMSO-d₆): δ 0.82 (d, J = 6.44 Hz, 2 H), 1.73-1.86 (m, J = 10.85 Hz, 2 H), 2.55 (s, 3 H), 3.11-3.24 (m, 4 H), 3.49 (t, J = 5.93 Hz, 4 H), 4.08 (q, J = 4.97 Hz, 2 H), 6.78 (d, J = 6.78 Hz, 1 H), 7.19-7.38 (m, 2 H), | MS (DCI/NH₃) m/z 540 (M + H)⁺ |

TABLE 2-continued

| Ex | Name | ¹H NMR | MS |
|---|---|---|---|
| | | 7.51-7.66 (m, 1 H), 7.67-7.80 (m, 3 H), 9.37 (s, 1 H) | |
| 511 | 6-(2,6-dichlorophenyl)-8-methyl-2-{[3-(4-methylpiperazin-1-yl)phenyl]amino}pyrimido[4,5-d]pyridazin-5(6H)-one | ¹H NMR (300 MHz, DMSO-d₆): δ 2.55 (s, 3 H), 2.87 (s, 3 H), 2.93-3.08 (m, 2 H), 3.11-3.29 (m, 2 H), 3.50-3.63 (m, 2 H), 3.86 (d, J = 12.89 Hz, 2 H), 6.73-6.84 (m, 1 H), 7.15-7.31 (m, 2 H), 7.51-7.64 (m, 1 H), 7.66-7.78 (m, 3 H), 9.38 (s, 1 H) | MS (DCI/NH₃) m/z 496 (M + H)⁺ |
| 512 | 6-(2,6-dichlorophenyl)-8-methyl-2-({3-[4-(oxetan-3-yl)piperazin-1-yl]phenyl}amino)pyrimido[4,5-d]pyridazin-5(6H)-one | ¹H NMR (300 MHz, DMSO-d₆): δ 2.38-2.47 (m, 4 H), 2.54 (s, 3 H), 3.14-3.24 (m, 4 H), 3.40-3.54 (m, 1 H), 4.48 (t, J = 6.10 Hz, 2 H), 4.57 (t, J = 6.44 Hz, 2 H), 6.62-6.82 (m, 1 H), 7.14-7.28 (m, 2 H), 7.53-7.62 (m, 1 H), 7.67-7.77 (m, 3 H), 9.35 (s, 1 H) | MS (DCI/NH₃) m/z 538 (M + H)⁺ |
| 513 | 6-(2,6-dichlorophenyl)-8-methyl-2-[(3-{[2-(morpholin-4-yl)ethyl]amino}phenyl)amino]pyrimido[4,5-d]pyridazin-5(6H)-one | ¹H NMR (300 MHz, DMSO-d₆): δ 2.41-2.45 (m, 4 H), 2.49-2.54 (m, 2 H), 2.55 (s, 3 H), 3.07-3.24 (m, 2 H), 3.52-3.67 (m, 4 H), 6.38 (d, J = 7.02 Hz, 1 H), 6.96-7.09 (m, 2 H), 7.52-7.67 (m, 1 H), 7.68-7.77 (m, 3 H), 9.33 (s, 1 H) | MS (DCI/NH₃) m/z 527 (M + H)⁺ |
| 514 | 6-(2,6-dichlorocyclohexa-1,5-dien-1-yl)-2-[(3-{[2-(dimethylamino)ethyl]amino}phenyl)amino]-8-methylpyrimido[4,5-d]pyridazin-5(6H)-one | ¹H NMR (300 MHz, DMSO-d₆): δ 2.19 (s, 6 H), 2.46 (t, J = 6.56 Hz, 2 H), 2.54 (s, 3 H), 3.13 (q, J = 6.41 Hz, 2 H), 6.39 (d, J = 7.02 Hz, 1 H), 6.99-7.11 (m, 2 H), 7.54-7.67 (m, 2 H), 7.72 (d, J = 8.24 Hz, 2 H), 9.33 (s, 1 H) | MS (DCI/NH₃) m/z 485 (M + H)⁺ |
| 515 | 6-(2,6-dichlorophenyl)-2-[(3-{4-[3-(dimethylamino)propyl]piperazin-1-yl}phenyl)amino]-8-methylpyrimido[4,5-d]pyridazin-5(6H)-one | ¹H NMR (300 MHz, DMSO-d₆): δ 2.00-2.14 (m, 2 H), 2.55 (s, 3 H), 2.81 (s, 6 H), 2.99-3.30 (m, 8 H), 3.42-3.64 (m, 2 H), 3.80-3.98 (m, 2 H), 6.69-7.02 (m, 1 H), 7.14-7.35 (m, 2 H), 7.50-7.63 (m, 1 H), 7.65-7.78 (m, 3 H), 9.38 (s, 1 H) | MS (DCI/NH₃) m/z 485 (M + H)⁺ |
| 516 | 6-(2,6-dichlorophenyl)-8-methyl-2-({3-[(1-methylpiperidin-4-yl)oxy]phenyl}amino)pyrimido[4,5-d]pyridazin-5(6H)-one | ¹H NMR (300 MHz, DMSO-d₆): δ 1.56-1.75 (m, 2 H), 1.84-2.01 (m, 2 H), 2.11-2.17 (m, 1 H), 2.19 (s, 3 H), 2.55 (s, 3 H), 2.61 (dd, J = 10.68, 4.58 Hz, 2 H), 4.26-4.46 (m, 2 H), 6.73-6.87 (m, 1 H), 7.20-7.30 (m, 2 H), 7.56-7.61 (m, 1 H), 7.69-7.75 (m, 3 H), 9.37 (s, 1 H) | MS (DCI/NH₃) m/z 511 (M + H)⁺ |
| 517 | 6-(2,6-dichlorophenyl)-2-[(4-{4-[3-(dimethylamino)propyl]piperazin-1-yl}phenyl)amino]-8-methylpyrimido[4,5-d]pyridazin-5(6H)-one | ¹H NMR (400 MHz, DMSO-d₆): δ 2.04-2.12 (m, 2 H), 2.50 (s, 3 H), 2.79 (s, 6 H), 2.95-3.02 (m, 2 H), 3.08-3.12 (m, 2 H), 3.16-3.20 (m, 2 H), 3.78-3.86 (m, 2 H), 7.05 (d, J = 8.54 Hz, 2 H), 7.54-7.59 (m, 1 H), 7.69 (d, J = 8.24 Hz, 2 H), 7.80 (m, 1 H), 9.29 (s, 1 H), 9.91 (s, 1 H), 10.62 (s, 1 H) | MS (ESI) m/z 567 (M + H)⁺ |
| 518 | 6-(2-chlorophenyl)-2-[(4-{4-[3-(dimethylamino)propyl]piperazin-1-yl}phenyl)amino]-8-methylpyrimido[4,5-d]pyridazin-5(6H)-one | ¹H NMR (400 MHz, DMSO-d₆): δ 2.08 (m, 2 H), 2.50 (s, 3 H), 2.85 (s, 6 H), 3.00 (m, 2 H), 3.14 (m, 2 H), 3.25 (m, 2 H), 3.80 (m, 2 H), 7.10 (m, 2 H), 7.55 (m, 1 H), 7.70 (m, 2 H), 7.80 (s, 1 H), 9.30 (s, 1 H), 9.92 (s, 1 H), 10.60 (s, 1 H) | MS (ESI) m/z 534 (M + H)⁺ |
| 519 | 6-(2,6-dichlorophenyl)-2-[(3-{[4-(dimethylamino)piperidin-1-yl]carbonyl}phenyl)amino]-8-methylpyrimido[4,5-d]pyridazin-5(6H)-one | ¹H NMR (300 MHz, DMSO-d₆): δ 1.44-1.69 (m, 2 H), 1.94-2.14 (m, 2 H), 2.54 (s, 3 H), 2.78 (s, 6 H), 3.37-3.56 (m, 1 H), 4.21-4.91 (m, 4 H), 7.16 (d, J = 7.46 Hz, 1 H), 7.38-7.57 (m, 1 H), 7.54-7.64 (m, 1 H), 7.68-7.77 (m, 2 H), 7.83-8.12 (m, 2 H), 9.41 (s, 1 H) | MS (DCI/NH₃) m/z 552 (M + H)⁺ |
| 524 | 6-(2-chloro-6-methylphenyl)-8-methyl-2-{[4-(piperidin-4-ylamino)phenyl]amino}pyrimido[4,5-d]pyridazin-5(6H)-one | ¹H NMR (400 MHz, DMSO-d₆): δ 1.52-1.61 (m, 2 H), 2.03-2.09 (m, 2 H), 2.12 (s, 3 H), 2.48 (s, 3 H), 2.96-3.07 (m, 2 H), 3.33 (d, J = 12.82 Hz, 2 H), 3.52-3.58 (m, 1 | MS (ESI) m/z 476 (M + H)⁺ |

TABLE 2-continued

| Ex | Name | ¹H NMR | MS |
|---|---|---|---|
|  |  | H), 6.73 (d, J = 8.85 Hz, 2 H), 7.38-7.52 (m, 3 H), 7.66 (s, 1 H), 8.41 (s, 1 H), 8.57 (s, 1 H), 9.25 (s, 1 H), 10.40 (s, 1 H) |  |
| 525 | 6-(2,6-dichlorophenyl)-8-methyl-2-{[4-(piperidin-4-ylamino)phenyl]amino}pyrimido[4,5-d]pyridazin-5(6H)-one | ¹H NMR (400 MHz, DMSO-d₆): δ 1.52-1.63 (m, 2 H), 2.07 (d, J = 11.29 Hz, 2 H), 2.50 (s, 3 H), 2.96-3.06 (m, 2 H), 3.33 (d, J = 12.82 Hz, 2 H), 3.52-3.59 (m, 1 H), 6.74 (d, J = 8.85 Hz, 2 H), 7.54-7.73 (m, 3 H), 8.45 (s, 1 H), 8.62 (s, 1 H), 9.26 (s, 1 H), 10.47 (s, 1 H) | MS (ESI) m/z 496 (M + H)⁺ |
| 526 | 6-(2-chlorophenyl)-8-methyl-2-{[4-(piperidin-4-ylamino)phenyl]amino}pyrimido[4,5-d]pyridazin-5(6H)-one | ¹H NMR (400 MHz, DMSO-d₆): δ 1.53-1.63 (m, 2 H), 2.07 (d, J = 11.60 Hz, 2 H), 2.47 (s, 3 H), 2.96-3.07 (m, 2 H), 3.33 (d, J = 12.51 Hz, 2 H), 3.51-3.58 (m, 1 H), 6.74 (d, J = 8.85 Hz, 2 H), 7.49-7.70 (m, 4 H), 8.45 (s, 1 H), 8.61 (s, 1 H), 9.24 (s, 1 H), 10.39 (s, 1 H) | MS (ESI) m/z 462 (M + H)⁺ |

6-(2,6-dichlorophenyl)-8-methyl-2-(1,2,3,4-tetrahydroisoquinolin-6-ylamino)pyrimido[4,5-d]pyridazin-5(6H)-one The title compound was prepared as described in Example 300, substituting tert-butyl 6-amino-3,4-dihydroisoquinoline-2(1H)-carboxylate for tert-butyl 7'-amino-1'H-spiro[cyclopropane-1,4'-isoquinoline]-2'(3'H)-carboxylate. MS (ESI) m/z 453 (M+H)⁺; ¹H NMR (500 MHz, DMSO-d₆) δ 2.54 (s, 3H), 3.04 (t, J=6.10 Hz, 2H), 3.37-3.41 (m, J=6.41 Hz, 2H), 4.22-4.27 (m, 2H), 7.25 (d, J=8.54 Hz, 1H), 7.57-7.63 (m, 1H), 7.69-7.75 (m, 2H), 7.83-7.89 (m, 1H), 9.34-9.40 (m, 2H), 10.80 (s, 1H).

Example 416

7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-carboxamide To a solution of Example 300E as TFA salt (50 mg, 0.071 mmol) in THF (3 mL) was added triethylamine (0.039 mL, 0.283 mmol) and trimethylsilyl isocyanate (0.014 mL, 0.106 mmol). The slurry was heated at 50° C. for 2 hours. The volatiles were removed, and the residue was stirred with 2 mL of DMSO. The insoluble fraction was diluted with water and filtered to give the first batch of product (9.3 mg). The soluble fraction was separated by HPLC (Zorbax, C-18, 250×2.54 column, Mobile phase A: 0.1% TFA in H₂O; B: 0.1% TFA in CH₃CN; 0-100% gradient) to provide title compound. MS (ESI) m/z 523 (M+H)⁺; ¹H NMR (400 MHz, DMSO-d₆) δ 0.93-0.97 (m, 4H), 2.55 (s, 3H), 3.41 (s, 2H), 4.62 (s, 2H), 6.06 (s, 1H), 6.84 (d, J=8.54 Hz, 1H), 7.56-7.64 (m, 2H), 7.69-7.79 (m, 2H), 9.35 (s, 1H), 10.71 (s, 1H).

Example 417

2-[(2'-acetyl-2',3'-dihydro-1'H-spiro[cyclopropane-1,4'-isoquinolin]-7'-yl)amino]-6-(2,6-dichlorophenyl)-8-methylpyrimido[4,5-d]pyridazin-5(6H)-one To a solution of Example 300E as HCl salt (5.47 g, 9.71 mmol) in N,N-dimethylformamide (60 mL) was added acetic acid (1.112 mL, 19.42 mmol), 1-hydroxybenzotriazole hydrate (2.23 g, 14.57 mmol), 1-ethyl-3-[3-(dimethylamino)propyl]-carbodiimide hydrochloride (2.79 g, 14.57 mmol), and triethylamine (6.77 mL, 48.6 mmol). The solution was stirred at room temperature over the weekend, and was partitioned between sodium bicarbonate solution and ethyl acetate. The organic phase was washed with sodium bicarbonate and brine, and concentrated. The residue was purified by flash chromatography (50-100% gradient ethyl acetate in hexane) to give the title compound. MS (ESI) m/z 521 (M+H)⁺; ¹H NMR (400 MHz, DMSO-d₆) δ 0.89-1.03 (m, 4H), 2.06 (s, 3H), 2.53-2.55 (m, 3H), 3.52-3.57 (m, 2H), 4.75 (m, 1H), 6.87 (dd, J=8.54, 4.88 Hz, 1H), 7.57-7.63 (m, 1H), 7.64-7.79 (m, 3H), 9.35 (s, 1H), 10.71 (d, J=1.83 Hz, 1H).

Example 426

6-(2,6-dichlorophenyl)-2-{[2'-(hydroxyacetyl)-2',3'-dihydro-1'H-spiro[cyclopropane-1,4'-isoquinolin]-7'-yl]amino}-8-methylpyrimido[4,5-d]pyridazin-5(6H)-one To a solution of Example 300E as the TFA salt (80 mg, 0.113 mmol) in N,N-dimethylformamide (2 mL) was added glycolic acid (13 mg, 0.170 mmol), 1-hydroxybenzotriazole hydrate (26 mg, 0.170 mmol), 1-ethyl-3-[3-(dimethylamino)propyl]-carbodiimide hydrochloride (33 mg, 0.170 mmol), and triethylamine (0.063 mL, 0.453 mmol). The mixture was stirred at room temperature overnight. The solvent was removed and the residue was stirred with methanol (2 mL). The formed solid was collected by filtration, washed with methanol and dried under vacuum to give the title compound. MS (ESI) m/z 538 (M+H)⁺; ¹H NMR (400 MHz, DMSO-d₆) δ 0.93-1.03 (m, 4H), 2.54 (s, 3H), 4.15 (d, J=5.49 Hz, 2H), 4.22 (d, J=5.19 Hz, 2H), 4.65-4.73 (m, 2H), 4.74-4.80 (m, 2H), 6.87 (d, J=8.54 Hz, 1H), 7.57-7.63 (m, 2H), 7.63-7.75 (m, 3H), 9.35 (s, 1H).

Example 427

6-(2,6-dichlorophenyl)-8-methyl-2-{[2'-(methylsulfonyl)-2',3'-dihydro-1'H-spiro[cyclopropane-1,4'-isoquinolin]-7'-yl]amino}pyrimido[4,5-d]pyridazin-5(6H)-one To a solution of Example 300E as TFA salt (80 mg, 0.113 mmol) in N,N-dimethylformamide (2 mL) was added triethylamine (0.063 mL, 0.453 mmol) and methanesulfonyl chloride (16 mg, 0.136 mmol). The mixture was stirred at room temperature overnight, and was concentrated. The residue was purified by HPLC (Zorbax, C-18, 250×2.54 column, Mobile phase A: 0.1% TFA in $H_2O$; B: 0.1% TFA in $CH_3CN$; 0-100% gradient) to provide the title compound as TFA salt. MS (ESI) m/z 557 $(M+H)^+$; $^1H$ NMR (400 MHz, DMSO-$d_6$) δ 0.94-1.01 (m, 2H), 1.03-1.10 (m, 2H), 2.54 (s, 3H), 2.93 (s, 3H), 3.31 (s, 2H), 4.51 (s, 2H), 6.87 (d, J=8.73 Hz, 1H), 7.55-7.64 (m, 1H), 7.65-7.79 (m, 3H), 9.36 (s, 1H), 10.73 (s, 1H).

Example 430

6-(2,6-dichlorophenyl)-8-(hydroxymethyl)-2-{[4-(piperazin-1-yl)phenyl]amino}pyrimido[4,5-d]pyridazin-5(6H)-one

Example 430A ethyl 4-(2-acetoxyacetyl)-2-(methylthio)pyrimidine-5-carboxylate The title compound was prepared as described in Example 6B, substituting 2-chloro-2-oxoethyl acetate for 3-phenylpropanoyl chloride. MS (DCI/$NH_3$) m/z 299 $(M+H)^+$.

Example 430B ethyl 4-(2-acetoxyacetyl)-2-(4-(4-(tert-butoxycarbonyl)piperazin-1-yl)phenylthio)pyrimidine-5-carboxylate The title compound was prepared as described in Example 6C, substituting Example 430A for Example 6B and tert-butyl 4-(4-aminophenyl)piperazine-1-carboxylate for 4-(4-methylpiperazin-1-yl)aniline. MS (DCI/$NH_3$) m/z 545 $(M+H)^+$.

Example 430C 6-(2,6-dichlorophenyl)-8-(hydroxymethyl)-2-{[4-(piperazin-1-yl)phenyl]amino}pyrimido[4,5-d]pyridazin-5(6H)-one The title compound was prepared as described in Example 6D, substituting Example 430B for Example 6B and 2,6-dichlorophenylhydrazine for methylhydrazine. MS (DCI/$NH_3$) m/z 499 $(M+H)^+$; $^1H$ NMR (300 MHz, DMSO-$d_6$): δ 3.23-3.29 (m, 4H), 3.32-3.36 (m, 4H), 4.79 (s, 2H), 7.04 (d, J=8.85 Hz, 2H), 7.55-7.67 (m, 1H), 7.70-7.78 (m, 2H), 7.79-7.88 (m, 2H), 9.32 (s, 1H).

Example 431

6-(2,6-dichlorophenyl)-8-(hydroxymethyl)-2-{[4-(4-methylpiperazin-1-yl)phenyl]amino}pyrimido[4,5-d]pyridazin-5(6H)-one

Example 431A ethyl 4-(2-acetoxyacetyl)-2-(4-(4-methylpiperazin-1-yl)phenylamino)pyrimidine-5-carboxylate The title compound was prepared as described in Example 6C, substituting Example 430A for Example 6B. MS (DCI/$NH_3$) m/z 442 $(M+H)^+$.

Example 431B 6-(2,6-dichlorophenyl)-8-(hydroxymethyl)-2-{[4-(4-methylpiperazin-1-yl)phenyl]amino}pyrimido[4,5-d]pyridazin-5(6H)-one The title compound was prepared as described in Example 6D, substituting Example 431A for Example 6C and 2,6-dichlorophenylhydrazine for methylhydrazine. MS (DCI/$NH_3$) m/z 513 $(M+H)^+$; $^1H$ NMR (300 MHz, DMSO-$d_6$): δ 2.87 (s, 3H), 2.92-3.02 (m, 2H), 3.08-3.24 (m, 2H), 3.49-3.61 (m, 2H), 3.75-3.87 (m, 2H), 4.79 (s, 2H) 7.05 (d, J=8.85 Hz, 2H), 7.58-7.62 (m, 1H), 7.73 (d, J=8.24 Hz, 2H), 7.79-7.86 (m, 2H), 9.32 (s, 1H).

Example 432

6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one

Example 432A ethyl 4-(2-acetoxyacetyl)-2-(2'-methyl-2',3'-dihydro-1'H-spiro[cyclopropane-1,4'-isoquinoline]-7'-ylamino)pyrimidine-5-carboxylate The title compound was prepared as described in Example 6C, substituting Example 430A for Example 6B and 2'-methyl-2',3'-dihydro-1'H-spiro[cyclopropane-1,4'-isoquinolin]-7'-amine for 4-(4-methylpiperazin-1-yl)aniline. MS (DCI/$NH_3$) m/z 439 $(M+H)^+$.

Example 432B 6-(2,6-dichlorophenyl)-8-(hydroxymethyl)-2-(2'-methyl-2',3'-dihydro-1'H-spiro[cyclopropane-1,4'-isoquinoline]-7'-ylamino)pyridazino[4,5-d]pyrimidin-5(6H)-one The title compound was prepared as described in Example 6D, substituting Example 432A for Example 6C and 2,6-dichlorophenylhydrazine for methylhydrazine. MS (DCI/$NH_3$) m/z 510 $(M+H)^+$; $^1H$ NMR (300 MHz, DMSO-$d_6$): δ 2.04 (s, 3H), 2.99 (t, J=6.15 Hz, 4H), 3.41 (s, 2H), 4.30 (s, 2H), 5.37 (s, 2H), 7.23 (d, J=8.73 Hz, 1H), 7.59-7.70 (m, 2H), 7.68-7.86 (m, 3H), 9.40 (s, 1H).

Example 433

6-(2,6-dichlorophenyl)-2-(2',3'-dihydro-1'H-spiro [cyclopropane-1,4'-isoquinolin]-7'-ylamino)-8-(hydroxymethyl)pyrimido[4,5-d]pyridazin-5(6H)-one

Example 433A tert-butyl 7'-(4-(2-acetoxyacetyl)-5-(ethoxycarbonyl) pyrimidin-2-ylamino)-1'H-spiro[cyclopropane-1,4'-isoquinoline]-2'(3'H)-carboxylate The title compound was prepared as described in Example 6C, substituting Example 430A for Example 6B and tert-butyl 7'-amino-1'H-spiro[cyclopropane-1,4'-isoquinoline]-2' (3'H)-carboxylate for 4-(4-methylpiperazin-1-yl)aniline. MS (DCI/NH$_3$) m/z 525 (M+H)$^+$.

Example 433B 6-(2,6-dichlorophenyl)-2-(2',3'-dihydro-1'H-spiro [cyclopropane-1,4'-isoquinoline]-7'-ylamino)-8-(hydroxymethyl)pyridazino[4,5-d]pyrimidin-5(6H)-one The title compound was prepared as described in Example 6D, substituting Example 433A for Example 6C and 2,6-dichlorophenylhydrazine for methylhydrazine. MS (DCI/NH$_3$) m/z 496 (M+H)$^+$; $^1$H NMR (300 MHz, DMSO-d$_6$): δ 1.05-1.16 (m, 4H), 3.28 (s, 3H), 4.41 (s, 2H), 4.80 (s, 2H), 5.36 (s, 2H), 6.90 (d, J=8.73 Hz, 1H), 7.53-7.67 (m, 2H), 7.70-7.79 (m, 2H), 7.83-8.06 (m, 1H), 9.38 (s, 1H).

Example 434

7-{[6-(2,6-dichlorophenyl)-8-methyl-5-oxo-5,6-dihydropyrimido[4,5-d]pyridazin-2-yl]amino}-3,4-dihydroisoquinoline-2 (1H)-sulfonamide

Example 434A (tert-butoxycarbonyl) {[4-(dimethylamino)pyridinium-1-yl]sulfonyl}azanide To a solution of t-butanol (2.6 mL, 27.2 mmol) in anhydrous methylene chloride (20 mL) was added dropwise chlorosulfonyl isocyanate (2.4 mL, 27.6 mL) at 0° C. over 15 minutes. After stirring for 15 minutes, 4-(dimethylamino) pyridine (6.9 g, 56.5 mmol) was then added. The cooling bath was removed, and more methylene chloride (100 mL) was added. The reaction mixture was stirred for 1 hour at room temperature. The mixture was diluted with 130 mL of dichloromethane and washed three times with water and finally with a saturated solution of NaCl in water. After drying with sodium sulfate, the organic layer was filtered and concentrated under vacuum. The product was used for the next step without further purification.

Example 434B

7-{[6-(2,6-dichlorophenyl)-8-methyl-5-oxo-5,6-dihydropyrimido[4,5-d]pyridazin-2-yl]amino}-3,4-dihydroisoquinoline-2 (1H)-sulfonamide To a solution of Example 371 as TFA salt (17 mg, 0.025 mmol) in CH$_2$Cl$_2$ (3 mL) was added triethylamine (7.6 mg, 0.075 mmol) and Example 434A (7.5 mg, 0.025 mmol) at room temperature.

The mixture was stirred at room temperature overnight. TFA (0.6 mL) was then added and the solution was stirred at room temperature for 1 hour. The mixture was concentrated and the residue was purified by HPLC (Zorbax, C-18, 250× 2.54 column, Mobile phase A: 0.1% TFA in H$_2$O; B: 0.1% TFA in CH$_3$CN; 0-100% gradient) to provide the title compound as TFA salt. MS (ESI) m/z 532 (M+H)$^+$; $^1$H NMR (400 MHz, DMSO-d$_6$) δ 2.54 (s, 3H), 2.94 (t, J=5.34 Hz, 2H), 3.29 (t, J=5.80 Hz, 2H), 4.19 (s, 2H), 6.92 (s, 1H), 7.19 (d, J=8.54 Hz, 1H), 7.56-7.63 (m, 1H), 7.67-7.80 (m, 3H), 9.36 (s, 1H), 10.72 (s, 1H).

Example 436

7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-sulfonamide The title compound was prepared as described in Example 434, substituting Example 300E for Example 371. MS (DCI/NH$_3$) m/z 557 (M+H)$^+$; $^1$H NMR (400 MHz, DMSO-d$_6$) δ 0.91-0.97 (m, 2H), 1.01-1.05 (m, 2H), 2.54 (s, 3H), 3.09 (s, 2H), 4.30 (s, 2H), 6.84 (d, J=8.54 Hz, 1H), 6.94 (s, 1H), 7.57-7.62 (m, 1H), 7.65-7.77 (m, 3H), 9.35 (s, 1H).

Example 437

6-(2,6-dichlorophenyl)-2-{[2-(2-hydroxy-2-methylpropanoyl)-1,2,3,4-tetrahydroisoquinolin-6-yl] amino}-8-methylpyrimido[4,5-d]pyridazin-5(6H)-one The title compound was prepared as described in Example 426, substituting Example 371 for Example 300E and 2-hydroxy-2-methylpropanoic acid for glycolic acid. MS (DCI/NH$_3$) m/z 541 (M+H)$^+$; $^1$H NMR (400 MHz, CD$_3$OD) δ 1.46 (s, 6H), 2.60 (s, 3H), 2.96 (s, 2H), 3.80-3.86 (m, 1H), 4.20-4.27 (m, 1H), 4.65-4.74 (m, 1H), 5.11-5.23 (m, 1H), 7.17 (d, J=8.54 Hz, 1H), 7.48-7.54 (m, 2H), 7.59-7.62 (m, 1H), 7.65-7.77 (m, 2H), 9.34 (s, 1H).

Example 520

3-{[6-(2,6-dichlorophenyl)-8-methyl-5-oxo-5,6-dihydropyrimido[4,5-d]pyridazin-2-yl]amino}-N-[4-(dimethylamino)cyclohexyl]benzamide The title compound was prepared as described in Example 225B, substituting Example 521 for Example 225A and N$^1$,N$^1$-dimethylcyclohexane-1,4-diamine for pyrrolidine. MS (DCI/NH$_3$) m/z 567 (M+H)$^+$; $^1$H NMR (300 MHz, DMSO-d$_6$): δ 1.54-1.72 (m, 2H), 1.74-1.87 (m, 4H), 1.90-2.08 (m, 2H), 2.57 (s, 3H), 2.76 (s, 6H), 3.13-3.28 (m, 1H), 4.05-4.17 (m, 1H), 7.50 (d, J=7.80 Hz, 1H), 7.55 (s, 1H), 7.60 (dd, J=8.82, 7.12 Hz, 1H), 7.70-7.75 (m, 2H), 7.96 (d, J=8.14 Hz, 1H), 8.14 (d, J=6.44 Hz, 1H), 9.40 (s, 1H).

Example 521

3-{[6-(2,6-dichlorophenyl)-8-methyl-5-oxo-5,6-dihydropyrimido[4,5-d]pyridazin-2-yl]amino}benzoic acid The title compound was prepared as described in Example 6C, substituting Example 300C for Example 6B and 3-aminobenzoic acid for 4-(4-methylpiperazin-1-yl)aniline. MS (DCI/NH$_3$) m/z 403 (M+H)$^+$; $^1$H NMR (300 MHz, DMSO-d$_6$): δ 2.75 (s, 3H), 7.59-7.68 (m, 1H), 7.70-7.81 (m, 3H), 8.03 (t, J=7.80 Hz, 1H), 8.14 (d, J=8.48 Hz, 1H), 8.81 (d, J=8.48 Hz, 1H), 9.90 (s, 1H).

Example 522

6-(2,6-dichlorophenyl)-8-methyl-2-({3-[(1-methylpiperidin-4-yl)amino]phenyl}amino)pyrimido[4,5-d]pyridazin-5(6H)-one The title compound was prepared as described in Example 6C, substituting Example 300C for Example 6B and 3-(4-methylpiperazin-1-yl)aniline for 4-(4-methylpiperazin-1-yl)aniline. MS (DCI/NH$_3$) m/z 511 (M+H)$^+$; $^1$H NMR (300 MHz, DMSO-d$_6$): δ 1.47-1.68 (m, 2H), 1.88-2.02 (m, 1H), 2.09-2.22 (m, 2H), 2.80 (s, 3H), 2.80 (s, 3H), 2.95-3.14 (m, 2H), 3.17-3.35 (m, 1H), 3.47 (s, 2H), 7.12 (d, J=17.63 Hz, 1H), 7.48-7.62 (m, 2H), 7.64-7.75 (m, 2H), 7.81-7.97 (m, 1H), 9.34 (s, 1H).

Example 523

3-{[6-(2,6-dichlorophenyl)-8-methyl-5-oxo-5,6-dihydropyrimido[4,5-d]pyridazin-2-yl]amino}-N-(1-methylpiperidin-4-yl)benzamide The title compound was prepared as described in Example 225B, substituting Example 521 for Example 225A and 1-methylpiperidin-4-amine for pyrrolidine. MS (DCI/NH$_3$) m/z 539; (M+H)$^+$; $^1$H NMR (300 MHz, DMSO-d$_6$): δ 1.67-1.86 (m, 2H), 1.94-2.13 (m, 2H), 2.58 (s, 3H), 2.79 (s, 3H), 2.98-3.21 (m, 3H), 3.47 (d, J=11.87 Hz, 2H), 7.48 (t, J=7.97 Hz, 1H), 7.53-7.68 (m, 2H), 7.67-7.77 (m, 2H), 7.84-7.94 (m, 1H), 8.47 (d, J=7.46 Hz, 1H), 9.41 (s, 1H).

Example 527

6-(2,6-dichlorophenyl)-2-[(3-{[4-(2-hydroxyethyl)piperazin-1-yl]carbonyl}phenyl)amino]-8-methylpyrimido[4,5-d]pyridazin-5(6H)-one The title compound was prepared as described in Example 225B, substituting Example 521 for Example 225A and 2-(piperazin-1-yl)ethanol for pyrrolidine. MS (DCI/NH$_3$) m/z 555 (M+H)$^+$; $^1$H NMR (300 MHz, DMSO-d$_6$): δ 2.55 (s, 3H), 3.20 (d, J=17.97 Hz, 4H), 3.42-4.02 (m, 8H), 7.21 (d, J=7.80 Hz, 1H), 7.51 (t, J=7.97 Hz, 1H), 7.55-7.67 (m, 2H), 7.67-7.77 (m, 2H), 7.90-8.12 (m, 1H), 9.42 (s, 1H).

Example 528

6-(2,6-dichlorophenyl)-8-methyl-2-({3-[(4-methylpiperazin-1-yl)carbonyl]phenyl}amino)pyrimido[4,5-d]pyridazin-5(6H)-one The title compound was prepared as described in Example 225B, substituting Example 521 for Example 225A and 1-methylpiperazine for pyrrolidine. MS (DCI/NH$_3$) m/z 525 (M+H)$^+$; $^1$H NMR (300 MHz, DMSO-d$_6$): δ 2.55 (s, 3H), 2.84 (s, 3H), 3.07-3.74 (m, 8H), 7.20 (d, J=7.46 Hz, 1H), 7.42-7.56 (m, 1H), 7.55-7.65 (m, 1H), 7.69-7.78 (m, 2H), 7.92-8.16 (m, 2H), 9.42 (s, 1H).

Example 529

6-(2,6-dichlorophenyl)-2-({3-[(1,1-dioxidothiomorpholin-4-yl)carbonyl]phenyl}amino)-8-methylpyrimido[4,5-d]pyridazin-5(6H)-one The title compound was prepared as described in Example 225B, substituting Example 521 for Example 225A and S,S-dioxithiomorpholine for pyrrolidine. MS (DCI/NH$_3$) m/z 560 (M+H)$^+$; $^1$H NMR (300 MHz, DMSO-d$_6$): δ 2.54 (s, 3H), 3.22-3.45 (m, 4H), 3.68-4.25 (m, 4H), 7.25 (d, J=7.80 Hz, 1H), 7.49 (t, J=7.97 Hz, 1H), 7.54-7.63 (m, 1H), 7.68-7.81 (m, 2H), 7.82-8.11 (m, 2H), 9.41 (s, 1H).

Example 530

3-{[6-(2,6-dichlorophenyl)-8-methyl-5-oxo-5,6-dihydropyrimido[4,5-d]pyridazin-2-yl]amino}-N-(piperidin-4-yl)benzamide Example 530A tert-butyl 4-(3-(6-(2,6-dichlorophenyl)-8-methyl-5-oxo-5,6-dihydropyrimido[4,5-d]pyridazin-2-ylamino)benzamido)piperidine-1-carboxylate The title compound was prepared as described in Example 225B, substituting Example 521 for Example 225A and tert-butyl 4-aminopiperidine-1-carboxylate for pyrrolidine. MS (DCI/NH$_3$) m/z 625 (M+H)$^+$.

Example 530B

3-{[6-(2,6-dichlorophenyl)-8-methyl-5-oxo-5,6-dihydropyrimido[4,5-d]pyridazin-2-yl]amino}-N-(piperidin-4-yl)benzamide The title compound was prepared as described in Example 215C, substituting Example 530A for Example 215B. MS (DCI/NH$_3$) m/z 525 (M+H)$^+$; $^1$NMR (300 MHz, DMSO-d$_6$): δ 1.57-1.80 (m, 2H), 1.87-2.08 (m, 2H), 2.58 (s, 3H), 2.89-3.18 (m, 4H), 3.98-4.27 (m, 1H), 7.48 (t, J=7.80 Hz, 1H), 7.60 (dd, J=8.99, 7.29 Hz, 2H), 7.67-7.77 (m, 2H), 7.76-7.97 (m, 1H), 8.45 (d, J=7.46 Hz, 1H), 9.40 (s, 1H).

Example 273

Wee1 Assay

Wee1 kinase was assayed using a time-resolved fluorescence equilibrium binding assay monitoring displacement of a rapidly reversible Oregon Green-labeled ATP-competitive kinase probe (N-(2-(2-(2-(4-(4-(5-chloro-4-(2-(1-hydroxycyclobutyl)thiazol-5-yl)-1H-pyrrolo[2,3-b]pyridin-2-yl)phenyl)piperazin-1-yl)ethoxy)ethoxy)ethyl)-2',7'-difluoro-3',6'-dihydroxy-3-oxo-3H-spiro[isobenzofuran-1,9'-xanthene]-5-carboxamide) by competitive Wee1 inhibitors. GST-tagged-Wee1 kinase (Carnabio #05-177, 2 nM final concentration), was mixed with fluorescent probe (300 nM final concentration, K$_d$=137 nM) and terbium-labeled anti-GST antibody (1 nM final concentration, Invitrogen #PV3551) and then inhibitor (0.003 to 10 micromolar) in final volume of 18 μl kinase buffer (20 mM HEPES, pH 7.5, 10 mM MgCl$_2$, 100 μM Na$_3$VO$_4$, 0.0075% Triton X-100, 1 mM DTT, 2% DMSO), incubated (1 hour) to allow attainment of equilibrium and time-resolved fluorescence measured using an Envision plate reader (Perkin Elmer; ex=337 nM, em=495/520 nM).

Table 1 depicts enzyme inhibition data ($K_i$) for exemplalry compounds.

| Example | Wee-1 inhibition Ki (uM) |
|---|---|
| 1 | 1.9 |
| 2 | 0.14 |
| 3 | 0.18 |
| 4 | 0.025 |
| 5 | 0.006 |
| 6 | 0.68 |
| 7 | 0.25 |
| 8 | 0.37 |
| 9 | 0.061 |
| 10 | >3.14 |
| 11 | 0.73 |
| 12 | 0.006 |
| 13 | 0.62 |
| 14 | 1.1 |
| 15 | 0.25 |
| 16 | 0.13 |
| 17 | 0.036 |
| 18 | 0.004 |
| 19 | 0.073 |
| 20 | 0.019 |
| 21 | 0.35 |
| 22 | 0.7 |
| 23 | 0.37 |
| 24 | 0.002 |
| 25 | 0.001 |
| 26 | 0.012 |
| 27 | 0.002 |
| 28 | 0.0008 |
| 29 | <0.001 |
| 30 | 0.001 |
| 31 | 0.0008 |
| 32 | 0.0006 |
| 33 | 0.0003 |
| 34 | 0.004 |
| 35 | 0.018 |
| 36 | 0.003 |
| 37 | 0.018 |
| 38 | 0.024 |
| 39 | 0.25 |
| 40 | 0.001 |
| 41 | 0.038 |
| 42 | 0.4 |
| 43 | 0.26 |
| 44 | 0.52 |
| 45 | 0.001 |
| 46 | 0.0003 |
| 47 | 0.24 |
| 48 | 0.0002 |
| 49 | 0.009 |
| 50 | 0.005 |
| 51 | 0.0004 |
| 52 | 0.001 |
| 53 | 0.0001 |
| 54 | 0.035 |
| 55 | 0.002 |
| 56 | 0.063 |
| 57 | 0.007 |
| 58 | 0.002 |
| 59 | 0.003 |
| 60 | 0.001 |
| 61 | <0.001 |
| 62 | 0.011 |
| 63 | 0.005 |
| 64 | 0.0003 |
| 65 | 0.001 |
| 66 | 0.004 |
| 67 | 0.014 |
| 68 | 0.014 |
| 69 | 0.00006 |
| 70 | 0.0001 |
| 71 | 0.0002 |
| 72 | 0.0005 |
| 73 | 0.003 |
| 74 | 0.001 |
| 75 | 0.00008 |
| 76 | 0.004 |
| 77 | 0.0007 |
| 78 | 0.048 |
| 79 | 0.71 |
| 80 | 0.027 |
| 81 | 0.004 |
| 82 | 0.009 |
| 83 | 0.0002 |
| 84 | 0.0001 |
| 85 | 0.0247 |
| 86 | 0.001 |
| 87 | 0.0001 |
| 88 | 0.005 |
| 89 | 0.00007 |
| 90 | 0.0002 |
| 91 | 0.0003 |
| 92 | 0.008 |
| 93 | 0.0001 |
| 94 | 0.0005 |
| 95 | 0.0001 |
| 96 | 0.0002 |
| 97 | 0.00006 |
| 98 | 0.0005 |
| 99 | 0.00009 |
| 100 | 0.014 |
| 101 | 0.00002 |
| 102 | 0.006 |
| 103 | 0.0002 |
| 104 | 0.0006 |
| 105 | 0.004 |
| 106 | 0.005 |
| 107 | 0.001 |
| 108 | 0.15 |
| 109 | >3.14 |
| 110 | >3.14 |
| 111 | 0.0025 |
| 112 | 0.014 |
| 113 | 0.0004 |
| 114 | 0.003 |
| 115 | 0.004 |
| 116 | 0.0004 |
| 117 | 0.003 |
| 118 | 0.001 |
| 119 | 0.001 |
| 120 | 0.001 |
| 121 | 0.003 |
| 122 | 0.0005 |
| 123 | 0.002 |
| 124 | 0.075 |
| 125 | >3.14 |
| 126 | 0.006 |
| 127 | 0.004 |
| 128 | 0.006 |
| 129 | >3.14 |
| 130 | 0.0004 |
| 131 | 0.0005 |
| 132 | 0.0007 |
| 133 | 0.003 |
| 134 | 0.0006 |
| 135 | 0.008 |
| 136 | 0.014 |
| 137 | 0.022 |
| 138 | 0.0015 |
| 139 | 0.005 |
| 140 | >3.14 |
| 141 | 0.007 |
| 142 | 0.057 |
| 143 | 0.039 |
| 144 | 0.002 |

| Example | Wee-1 inhibition Ki (uM) |
|---|---|
| 145 | 0.0003 |
| 146 | 0.003 |
| 147 | 0.012 |
| 148 | 0.016 |
| 149 | 0.00005 |
| 150 | 0.0001 |
| 151 | 0.00007 |
| 152 | 0.00004 |
| 153 | 0.00005 |
| 154 | 0.009 |
| 155 | 0.0004 |
| 156 | 0.00003 |
| 157 | 0.00005 |
| 158 | 0.0002 |
| 159 | 0.00006 |
| 160 | 0.0001 |
| 161 | 0.003 |
| 162 | 0.004 |
| 163 | 0.004 |
| 164 | 0.0005 |
| 165 | >3.14 |
| 166 | 0.0008 |
| 167 | 0.0004 |
| 168 | 0.002 |
| 169 | 0.002 |
| 170 | 0.0007 |
| 171 | 0.0006 |
| 172 | 0.0025 |
| 173 | 0.0004 |
| 174 | 0.0001 |
| 175 | 0.0002 |
| 176 | 0.036 |
| 177 | 0.019 |
| 178 | 0.002 |
| 179 | 0.0001 |
| 180 | 0.002 |
| 181 | 0.006 |
| 182 | 0.012 |
| 183 | 0.00002 |
| 184 | 0.00003 |
| 185 | 0.00004 |
| 186 | 0.00002 |
| 187 | 1.8 |
| 188 | 0.001 |
| 189 | 0.00002 |
| 190 | 0.00001 |
| 191 | 0.00003 |
| 192 | 0.00002 |
| 193 | 0.00002 |
| 194 | <0.001 |
| 195 | 0.00007 |
| 196 | 0.23 |
| 197 | 0.1 |
| 198 | 0.025 |
| 199 | 0.082 |
| 200 | 0.0003 |
| 201 | 0.0002 |
| 202 | 0.0003 |
| 203 | 0.0002 |
| 204 | 0.002 |
| 205 | 0.0002 |
| 206 | 0.0002 |
| 207 | 0.0001 |
| 208 | 0.002 |
| 209 | 0.0008 |
| 210 | 0.033 |
| 211 | 0.0006 |
| 212 | 0.0006 |
| 213 | 0.0006 |
| 214 | 0.0004 |
| 215 | 0.0002 |
| 216 | 0.0001 |
| 217 | 0.0001 |
| 218 | 0.48 |
| 219 | 0.0001 |
| 220 | 0.0004 |
| 221 | 0.0002 |
| 222 | 0.0002 |
| 223 | 0.0002 |
| 224 | 0.00007 |
| 225 | 0.0003 |
| 226 | <0.001 |
| 227 | <0.001 |
| 228 | 0.003 |
| 229 | 0.0002 |
| 230 | 0.005 |
| 231 | 0.0001 |
| 232 | 0.0002 |
| 233 | 0.0003 |
| 234 | 0.0003 |
| 235 | 0.0001 |
| 236 | <0.001 |
| 237 | 0.0002 |
| 238 | 0.034 |
| 239 | 0.025 |
| 240 | 0.0005 |
| 241 | 0.0001 |
| 242 | 0.05 |
| 243 | <0.001 |
| 244 | 0.0005 |
| 245 | 0.0007 |
| 246 | 0.0003 |
| 247 | 0.0002 |
| 248 | 0.0004 |
| 249 | 1.5 |
| 250 | 0.0002 |
| 251 | 0.0002 |
| 252 | 0.0004 |
| 253 | 0.00009 |
| 254 | 0.0003 |
| 255 | >3.14 |
| 256 | 0.0003 |
| 257 | 0.002 |
| 258 | 0.002 |
| 259 | 0.0002 |
| 260 | 0.0002 |
| 261 | 0.0003 |
| 262 | 0.59 |
| 263 | 0.0003 |
| 264 | 0.012 |
| 265 | 0.0002 |
| 266 | 0.0001 |
| 267 | 0.24 |
| 268 | 0.0001 |
| 269 | 0.058 |
| 270 | <0.001 |
| 271 | 0.0004 |
| 272 | 0.10 |
| 273 | 0.011 |
| 274 | 0.179 |
| 275 | 0.0032 |
| 276 | 0.0011 |
| 277 | 0.0012 |
| 278 | 0.00083 |
| 279 | 0.0012 |
| 280 | 0.00051 |
| 281 | 0.00053 |
| 282 | 0.058 |
| 283 | 0.030 |
| 284 | 0.00036 |
| 285 | 0.0084 |
| 286 | 0.0094 |
| 287 | 0.011 |
| 288 | 0.172 |
| 289 | 0.081 |
| 290 | 0.00033 |
| 291 | 0.00038 |
| 292 | 0.00048 |
| 293 | 0.00025 |
| 294 | 0.629 |

| Example | Wee-1 inhibition Ki (uM) |
|---|---|
| 295 | 0.501 |
| 296 | 0.00027 |
| 297 | 0.00019 |
| 298 | 0.0018 |
| 299 | 0.00099 |
| 300 | 0.00012 |
| 301 | 0.0027 |
| 302 | 0.00061 |
| 303 | 0.0028 |
| 304 | 0.61 |
| 305 | 0.84 |
| 306 | 0.050 |
| 307 | 0.0014 |
| 308 | 0.001 |
| 309 | 0.68 |
| 310 | 0.0036 |
| 311 | 0.001 |
| 312 | 0.0019 |
| 313 | 0.0026 |
| 314 | 0.0012 |
| 315 | 0.0019 |
| 316 | 0.0018 |
| 317 | 0.00038 |
| 318 | 0.00026 |
| 319 | 0.00039 |
| 320 | 0.00049 |
| 321 | 0.0008 |
| 322 | >3.14 |
| 323 | 0.00049 |
| 324 | 0.0002 |
| 325 | 0.0007 |
| 326 | 0.00053 |
| 327 | 0.00093 |
| 328 | 0.22 |
| 329 | 0.027 |
| 330 | 0.26 |
| 331 | 0.18 |
| 332 | 0.49 |
| 333 | 0.77 |
| 334 | 0.64 |
| 335 | 0.00021 |
| 336 | 0.00049 |
| 337 | 0.00022 |
| 338 | 0.00072 |
| 339 | 0.00071 |
| 340 | 0.00032 |
| 341 | 0.001 |
| 342 | 0.001 |
| 343 | 0.0069 |
| 344 | 0.00025 |
| 345 | 0.00034 |
| 346 | 0.00021 |
| 347 | 0.0065 |
| 348 | 0.0018 |
| 349 | 0.0005 |
| 350 | 0.0018 |
| 351 | 0.0011 |
| 352 | 0.012 |
| 353 | 0.016 |
| 354 | 0.74 |
| 355 | 0.0024 |
| 356 | 0.0010 |
| 357 | 0.00087 |
| 358 | 0.00047 |
| 359 | 0.0050 |
| 360 | 0.0024 |
| 361 | 0.0044 |
| 362 | 0.0018 |
| 363 | 0.040 |
| 364 | 0.00061 |
| 365 | 0.0029 |
| 366 | 0.00053 |
| 367 | 0.0037 |
| 368 | 0.00054 |
| 369 | 0.0018 |
| 370 | 0.035 |
| 371 | 0.0002 |
| 372 | 0.0037 |
| 373 | 0.069 |
| 374 | 0.00067 |
| 375 | 0.0012 |
| 376 | 0.0013 |
| 377 | 0.0013 |
| 378 | 0.00049 |
| 379 | 0.00045 |
| 380 | 0.00061 |
| 381 | 0.00081 |
| 382 | 0.0076 |
| 383 | 0.0011 |
| 384 | 0.013 |
| 385 | 0.0072 |
| 386 | 0.00048 |
| 387 | 0.0003 |
| 388 | 0.00033 |
| 389 | 0.00028 |
| 390 | 0.00041 |
| 391 | 0.00093 |
| 392 | 0.00027 |
| 393 | 0.001 |
| 394 | 0.001 |
| 395 | 0.001 |
| 396 | 0.001 |
| 397 | 0.001 |
| 398 | 0.001 |
| 399 | 0.018 |
| 400 | 0.0067 |
| 401 | 0.00022 |
| 402 | 0.00023 |
| 403 | 0.00021 |
| 404 | 0.00025 |
| 405 | 0.00079 |
| 406 | 0.0007 |
| 407 | 0.00021 |
| 408 | 0.00041 |
| 409 | 0.0010 |
| 410 | 0.0010 |
| 411 | 0.0010 |
| 412 | 0.0010 |
| 413 | 0.00034 |
| 414 | 0.00075 |
| 415 | 0.001 |
| 416 | 0.00019 |
| 417 | 0.00031 |
| 418 | 0.00035 |
| 419 | 0.00019 |
| 420 | 0.00045 |
| 421 | 0.0005 |
| 422 | 0.0004 |
| 423 | 0.0007 |
| 424 | 0.0004 |
| 425 | 0.00019 |
| 426 | 0.00011 |
| 427 | 0.00091 |
| 428 | 0.00024 |
| 429 | 0.00048 |
| 430 | 0.0002 |
| 431 | 0.00042 |
| 432 | 0.0002 |
| 433 | 0.00015 |
| 434 | 0.00035 |
| 435 | 0.00046 |
| 436 | 0.00065 |
| 437 | 0.0008 |
| 438 | 0.00018 |
| 439 | 0.00069 |
| 440 | 0.00082 |
| 441 | 0.00072 |
| 442 | 0.00046 |
| 443 | 0.0003 |
| 444 | 0.00016 |

-continued

| Example | Wee-1 inhibition Ki (uM) |
|---|---|
| 445 | 0.00033 |
| 446 | 0.00027 |
| 447 | 0.0004 |
| 448 | 0.0005 |
| 449 | 0.00055 |
| 450 | 0.00061 |
| 451 | 0.00019 |
| 452 | 0.00016 |
| 453 | 0.00036 |
| 454 | 0.0012 |
| 455 | 0.0005 |
| 456 | 0.0005 |
| 457 | 0.00028 |
| 458 | 0.00023 |
| 459 | 0.00017 |
| 460 | 0.00032 |
| 461 | 0.00068 |
| 462 | 0.00095 |
| 463 | 0.00055 |
| 464 | 0.0016 |
| 465 | 0.00088 |
| 466 | 0.00034 |
| 467 | 0.00047 |
| 468 | 0.00069 |
| 469 | 0.00063 |
| 470 | 0.00099 |
| 471 | 0.00016 |
| 472 | 0.0023 |
| 473 | 0.00038 |
| 474 | 0.00032 |
| 475 | 0.00024 |
| 476 | 0.00017 |
| 477 | 0.00067 |
| 478 | 0.00017 |
| 479 | 0.00029 |
| 480 | 0.0013 |
| 481 | 0.00073 |
| 482 | 0.00031 |
| 483 | 0.00055 |
| 484 | 0.00017 |
| 485 | 0.00015 |
| 486 | 0.00013 |
| 487 | 0.00027 |
| 488 | 0.00029 |
| 489 | 0.000089 |
| 490 | 0.00011 |
| 491 | 0.00026 |
| 492 | 0.00056 |
| 493 | 0.00086 |
| 494 | 0.00031 |
| 495 | 0.00016 |
| 496 | 0.00034 |
| 497 | 0.00026 |
| 498 | 0.00023 |
| 499 | 0.00021 |
| 500 | 0.00051 |
| 501 | 0.00032 |
| 502 | 0.00036 |
| 503 | 0.0001 |
| 504 | 0.0037 |
| 505 | 0.0027 |
| 506 | 0.00054 |
| 507 | 0.0024 |
| 508 | 0.002 |
| 509 | 0.0012 |
| 510 | 0.0011 |
| 511 | 0.00046 |
| 512 | 0.0014 |
| 513 | 0.0011 |
| 514 | 0.00041 |
| 515 | 0.00019 |
| 516 | 0.00036 |
| 517 | 0.00024 |
| 518 | 0.0007 |
| 519 | 0.00075 |

-continued

| Example | Wee-1 inhibition Ki (uM) |
|---|---|
| 520 | 0.00045 |
| 521 | 0.097 |
| 522 | 0.00013 |
| 523 | 0.0005 |
| 524 | 0.0003 |
| 525 | 0.0002 |
| 526 | 0.00048 |
| 527 | 0.0028 |
| 528 | 0.0024 |
| 529 | 0.0094 |
| 530 | 0.0003 |

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound of formula (I), or a pharmaceutically acceptable salt thereof;

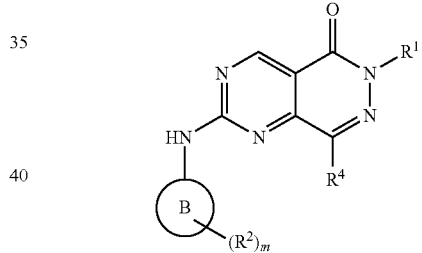

Formula (I)

B is 5-16 membered monocyclic, bicyclic, or tricyclic heterocyclyl; and m is 0, 1, 2, or 3;

$R^1$ is hydrogen, $C_{1-6}$ alkyl, $C_{2-6}$ alkenyl, $C_{2-6}$ alkynyl, aryl, heteroaryl, heterocyclyl, cycloalkyl, or cycloalkenyl; wherein the $R^1 C_{1-6}$ alkyl, $C_{2-6}$ alkenyl, and $C_{2-6}$ alkynyl are optionally substituted with 1, 2, or 3 substituents independently selected from the group consisting of halo, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, and $NR^bS(O)_2R^a$; wherein the $R^1$ aryl, heterocyclyl, cycloalkyl, and cycloalkenyl are optionally substituted with 1, 2, or 3 substituents independently selected from the group consisting of halo, $C_{1-6}$ alkyl, $C_{2-6}$ alkenyl, $C_{2-6}$ alkynyl, $C_{1-6}$ haloalkyl, —$C_{1-4}$-alkyl-$NR^eR^f$, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$;

$R^2$, at each occurrence, is independently selected from the group consisting of halo, CN, $C_{1-4}$ alkyl, $C_{2-6}$ alkenyl, $C_{2-6}$ alkynyl, $C_{1-4}$-haloalkyl, $C_{1-4}$ hydroxyalkyl, $C_{1-4}$ alkoxy, $C_{1-4}$ haloalkoxy, $C_{1-4}$-thioalkoxy, aryl, cycloalkyl, heteroaryl, heterocycloalkyl, aryl-$C_{1-6}$- alkyl-, cycloalkyl-$C_{1-6}$-alkyl-, heteroaryl-$C_{1-6}$-alkyl-, heterocycloalkyl-$C_{1-6}$-alkyl-, $NR^6R^7$—$C_{1-6}$-alkyl-, $OR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$, wherein the $R^2$ cycloalkyl, aryl, heterocycloalkyl, and heteroaryl, alone or part of another group, are optionally substituted with one, two, or three $R^3$;

$R^3$, at each occurrence, is independently selected from the group consisting of halo, $C_{1-4}$ alkyl, $C_{2-6}$ alkenyl, $C_{2-6}$ alkynyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, cycloalkyl, heteroaryl, heterocycloalkyl, aryl-($C_{1-4}$ alkyl)-, cycloalkyl-($C_{1-4}$ alkyl)-, heteroaryl-($C_{1-4}$ alkyl)-, heterocycloalkyl-($C_{1-4}$ alkyl)-, CN, $NO_2$, $OR^n$, $SR^n$, $C(O)R^n$, $C(O)NR^oR^p$, $C(O)OR^n$, $OC(O)R^n$, $OC(O)NR^oR^p$, $NR^oR^p$, $NR^oC(O)R^n$, $S(O)R^n$, $S(O)NR^oR^p$, $S(O)_2R^n$, $NR^oS(O)_2R^n$, and $S(O)_2NR^oR^p$, wherein the $R^3$ aryl, cycloalkyl, heteroaryl, and heterocycloalkyl, alone or as part of another group, are optionally substituted with one, two or three $R^8$;

$R^4$ is hydrogen, $C_{1-6}$ alkyl, $C_{1-6}$ haloalkyl, $C_{1-6}$ alkoxy-$C_{1-6}$-alkyl, $C_{1-6}$ hydroxyalkyl, $C_{2-6}$ alkenyl, $C_{2-6}$ alkynyl, $C_{1-6}$ haloalkyl, aryl, cycloalkyl, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, wherein the $R^4$ aryl, cycloalkyl, heteroaryl, and heterocycloalkyl, alone or part of another group, are optionally substituted with 1, 2, or 3 substituents independently selected from the group consisting of halo, $C_{1-6}$ alkyl, $C_{2-6}$ alkenyl, $C_{1-4}$ haloalkyl, alkoxy-$C_{1-6}$-alkyl-, hydroxy-$C_{1-6}$-alkyl-, heteroaryl, heterocycloalkyl, aryl-$C_{1-6}$-alkyl-, cycloalkyl-$C_{1-6}$-alkyl-, heteroaryl-$C_{1-6}$-alkyl-, heterocycloalkyl-$C_{1-6}$-alkyl-, $R^m$-heterocycloalkyl-$C_{1-6}$-alkyl-, CN, $NO_2$, $OR^g$, $SR^g$, $C(O)R^g$, $C(O)NR^hR^i$, $C(O)OR^g$, $OC(O)R^g$, $OC(O)NR^hR^i$, —$C_{1-6}$ alkyl-$NR^hR^i$, $NR^hR^i$, $NR^hC(O)R^g$, $NR^hR^iR^g$, $S(O)R^g$, $S(O)NR^hR^i$, $S(O)_2R^g$, $NR^hS(O)_2R^g$, and $S(O)_2NR^hR^i$; wherein the $R^4 C_{1-6}$ alkyl, $C_{2-6}$ alkenyl, and $C_{2-6}$ alkynyl, alone or part of another group, are optionally substituted with 1, 2, or 3 substituents independently selected from the group consisting of halo, CN, $NO_2$, $OR^j$, $SR^j$, $C(O)R^j$, $C(O)NR^kR^l$, $C(O)OR^j$, $OC(O)R^j$, $OC(O)NR^kR^l$, $NR^kR^l$, $NR^kC(O)R^j$, $S(O)R^j$, $S(O)NR^kR^l$, $S(O)_2R^j$, $NR^kS(O)_2R^j$, and $S(O)_2NR^kR^l$;

$R^5$ is independently selected from the group consisting of hydrogen, $C_{1-6}$ alkyl, $C_{1-6}$ hydroxyalkyl, $C_{2-6}$ alkenyl, $C_{2-6}$ alkynyl, $C_{1-6}$-haloalkyl, heteroaryl-$C_{1-6}$-alkyl-, heterocycloalkyl-$C_{1-6}$-alkyl-, aryl, cycloalkyl, heteroaryl, and heterocycloalkyl, wherein the $R^5$ cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^6$ and $R^7$, at each occurrence, are independently selected from the group consisting of hydrogen, $C_{1-6}$ alkyl, $C_{2-6}$ alkenyl, $C_{2-6}$ alkynyl, $C_{1-6}$-haloalkyl, $C_{1-6}$ hydroxyalkyl, $C_{1-4}$ dialkylamino-$C_{1-4}$ alkyl-, heteroaryl-$C_{1-6}$-alkyl-, heterocycloalkyl-$C_{1-6}$-alkyl-, aryl, cycloalkyl, heteroaryl, and heterocycloalkyl, wherein the $R^6$ and $R^7$ aryl, cycloalkyl, heteroaryl, and heterocycloalkyl, alone or as part of another group, are optionally substituted with 1, 2, or 3 substituents independently selected from the group consisting of halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^8$ is independently selected from the group consisting of halo, $C_{1-4}$ alkyl, $C_{1-4}$-alkylamino, $C_{1-4}$ dialkylamino-$C_{1-4}$ alkyl-, or 1-methylpiperazinyl;

$R^a$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^a$ aryl, cycloalkyl, heteroaryl, and heterocycloalkyl alone or as part of another group, are optionally substituted with one, two or three substituents independently selected from the group consisting of halo and $C_{1-4}$ alkyl;

$R^b$ and $R^c$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^b$ or $R^c$ aryl, cycloalkyl, heteroaryl, and heterocycloalkyl alone or as part of another group, are optionally substituted with one, two or three substituents independently selected from the group consisting of halo and $C_{1-4}$ alkyl;

$R^d$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^d$ aryl, cycloalkyl, heteroaryl, and heterocycloalkyl, alone or part of another group, are optionally substituted with 1, 2, or 3 substituents independently selected from the group consisting of halo and $C_{1-4}$ alkyl;

$R^e$ and $R^f$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^e$ or $R^f$ aryl, cycloalkyl, heteroaryl, and heterocycloalkyl alone or as part of another group, are optionally substituted with one, two or three substituents independently selected from the group consisting of halo and $C_{1-4}$ alkyl;

$R^g$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^g$ aryl, cycloalkyl, heteroaryl, and heterocycloalkyl alone or as part of another group, are optionally substituted with one, two or three substituents independently selected from the group consisting of halo and $C_{1-4}$ alkyl;

$R^h$ and $R^i$, at each occurrence, are independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^h$ or $R^i$ aryl, cycloalkyl, heteroaryl, and heterocycloalkyl alone or as part of another group, are optionally substituted with one, two or three substituents independently selected from the group consisting of halo and $C_{1-4}$ alkyl;

$R^j$, at each occurrence, is independently selected from the group consisting of hydrogen, $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl; wherein the $R^j$ aryl, cycloalkyl, heteroaryl, and heterocycloalkyl alone or as part of another group, are optionally substituted with one, two or three substituents independently selected from the group consisting of halo and $C_{1-4}$ alkyl;

R$^k$ and R$^l$, at each occurrence, are independently selected from the group consisting of hydrogen, C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl; wherein the R$^k$ or R$^l$ aryl, cycloalkyl, heteroaryl, and heterocycloalkyl alone or as part of another group, are optionally substituted with one, two or three substituents independently selected from the group consisting of halo and C$_{1-4}$ alkyl;

R$^n$, at each occurrence, is independently selected from the group consisting of hydrogen, C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl; wherein the R$^n$ aryl, cycloalkyl, heteroaryl, and heterocycloalkyl alone or as part of another group, are optionally substituted with one, two or three substituents independently selected from the group consisting of halo and C$_{1-4}$ alkyl;

R$^m$, at each occurrence, is independently selected from the group consisting of hydrogen, C$_{1-6}$ alkyl, C$_{2-6}$ alkenyl, C$_{2-6}$ alkynyl, —C(O)C$_{1-6}$ alkyl, and C$_{1-6}$ haloalkyl; and R$^o$ and R$^p$, at each occurrence, are independently selected from the group consisting of hydrogen, C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl; wherein the R$^o$ or R$^p$ aryl, cycloalkyl, heteroaryl, and heterocycloalkyl alone or as part of another group, are optionally substituted with one, two or three substituents independently selected from the group consisting of halo and C$_{1-4}$ alkyl.

2. The compound of claim 1 of formula (I), or a pharmaceutically acceptable salt thereof; wherein B is 5-16 membered monocyclic, bicyclic, or tricyclic heterocyclyl.

3. The compound of claim 1 of formula (I), or a pharmaceutically acceptable salt thereof; wherein B is 5-16 membered bicyclic, or tricyclic heterocyclyl; m is 1, 2, or 3; and R$^2$, at each occurrence, is independently selected from the group consisting of C$_{1-6}$-alkyl, C$_{1-4}$ alkoxy, heterocycloalkyl, NR$^6$R$^7$—C$_{1-6}$-alkyl-, C(O)R$^5$, and S(O)$_2$R$^5$; wherein the R$^2$ heterocycloalkyl is optionally substituted with one, two, or three R$^3$.

4. The compound of claim 1 of formula (I), or a pharmaceutically acceptable salt thereof; wherein R$^1$ is hydrogen, C$_{1-6}$ alkyl, C$_{2-6}$ alkenyl, aryl, heterocyclyl, or cycloalkyl; wherein the R$^1$ C$_{1-6}$ alkyl is optionally substituted with 1, 2, or 3 substituents independently selected from the group consisting of halo, CN, and OR$^a$; wherein the R$^1$ aryl is optionally substituted with 1, 2, or 3 substituents independently selected from the group consisting of halo, C$_{1-6}$ alkyl, C$_{1-6}$ haloalkyl, and OR$^d$.

5. The compound of claim 1 of formula (I), or a pharmaceutically acceptable salt thereof; wherein R$^1$ is aryl; wherein the R$^1$ aryl is optionally substituted with 1, 2, or 3 substituents independently selected from the group consisting of halo, C$_{1-6}$ alkyl, C$_{1-6}$ haloalkyl, and OR$^d$; and R$^d$ is C$_{1-6}$ alkyl.

6. The compound of claim 1 of formula (I), or a pharmaceutically acceptable salt thereof; wherein R$^1$ is

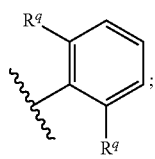

wherein each R$^q$ is independently selected from the group consisting of halo, C$_{1-6}$ alkyl, C$_{1-6}$ haloalkyl, and OR$^d$; and R$^d$ is C$_{1-6}$ alkyl.

7. The compound of claim 1 of formula (I), or a pharmaceutically acceptable salt thereof; wherein R$^4$ is aryl, cycloalkyl, heteroaryl, heterocycloalkyl, or aryl-C$_{1-6}$-alkyl; wherein the R$^4$ aryl, cycloalkyl, heteroaryl, and heterocycloalkyl, alone or part of another group, are optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$ alkyl-NR$^h$R$^i$, NR$^h$R$^i$ and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl and heterocycloalkyl are optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl.

8. The compound of claim 1 of formula (I), or a pharmaceutically acceptable salt thereof; wherein R$^4$ is heteroaryl; wherein the heteroaryl is optionally substituted with 1, 2, or 3 substituents independently selected from the group consisting of halo, C$_{1-6}$ alkyl, C$_{2-6}$ alkenyl, C$_{1-4}$ haloalkyl, alkoxy-C$_{1-6}$-alkyl-, hydroxy-C$_{1-6}$-alkyl-, heteroaryl, heterocycloalkyl, heterocycloalkyl-C$_{1-6}$-alkyl-, R$^m$-heterocycloalkyl-C$_{1-6}$-alkyl-, CN, OR$^g$, C(O)R$^g$, C(O)NR$^h$R$^i$, C(O)OR$^g$, —C$_{1-6}$ alkyl-NR$^h$R$^i$, NR$^h$R$^i$, and NR$^h$NR$^i$R$^g$; R$^g$, at each occurrence, is independently selected from the group consisting of hydrogen, C$_{1-6}$ alkyl, aryl, and heterocycloalkyl; wherein the R$^g$ aryl, is optionally substituted with one, two or three substituents independently selected from the group consisting of halo and C$_{1-4}$ alkyl; R$^h$ and R$^i$, at each occurrence, are independently selected from the group consisting of hydrogen, C$_{1-6}$ alkyl, cycloalkyl, heteroaryl, and heterocycloalkyl; and R$^m$, at each occurrence, is independently selected C$_{1-6}$ alkyl.

9. The compound of claim 1 selected from the group consisting of 6-(2-chlorophenyl)-2-[(2'-methyl-2',3'-dihydro-1'H-spiro[cyclopropane-1,4'-isoquinolin]-7'-yl)amino]-8-phenylpyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-3-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-2-yl)pyrimido[4,5-d]pyridazin-5(6H)-one;

6-allyl-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one;

6-(2-chlorophenyl)-2-[(2'-methyl-2',3'-dihydro-1'H-spiro[cyclopropane-1,4'-isoquinolin]-7'-yl)amino]-8-(2-thienyl)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(2-methylphenyl)-8-(2-thienyl)pyrimido[4,5-d]pyridazin-5(6H)-one;

6-allyl-8-(2-furyl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-(2-furyl)-2-[(2'-methyl-2',3'-dihydro-1'H-spiro[cyclopropane-1,4'-isoquinolin]-7'-yl)amino]-6-(2-methylphenyl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-4-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-pyrazol-3-yl)pyrimido[4,5-d]pyridazin-5(6H)-one;

6-allyl-2-[(2-methyl-1,2,3,4-tetrahydroisoquinolin-7-yl)amino]-8-(2-thienyl)pyrimido[4,5-d]pyridazin-5(6H)-one;

6-(2-methylphenyl)-2-[(2-methyl-1,2,3,4-tetrahydroisoquinolin-7-yl)amino]-8-(2-thienyl)pyrimido[4,5-d]pyridazin-5(6H)-one;

6-(2-chlorophenyl)-2-[(2-methyl-1,2,3,4-tetrahydroisoquinolin-7-yl)amino]-8-(2-thienyl)pyrimido[4,5-d]pyridazin-5(6H)-one;

6-(2-methylphenyl)-2-[(2-methyl-1,2,3,4-tetrahydroisoquinolin-7-yl)amino]-8-phenylpyrimido[4,5-d]pyridazin-5(6H)-one;

6-allyl-2-[(2'-methyl-2',3'-dihydro-1'H-spiro[cyclopropane-1,4'-isoquinolin]-7'-yl)amino]-8-phenylpyrimido[4,5-d]pyridazin-5(6H)-one;

2-[(2'-methyl-2',3'-dihydro-1'H-spiro[cyclopropane-1,4'-isoquinolin]-7'-yl)amino]-6-(2-methylphenyl)-8-phenylpyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(pyridin-4-yl)pyrimido[4,5-d]pyridazin-5(6H)-one;

6-(2,6-dichlorophenyl)-8-(pyridin-2-yl)-2-(1,2,3,4-tetrahydroisoquinolin-7-ylamino)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one;

6-(2,6-dichlorophenyl)-8-(pyridin-4-yl)-2-(1,2,3,4-tetrahydroisoquinolin-7-ylamino)pyrimido[4,5-d]pyridazin-5(6H)-one;

6-(2,6-dichlorophenyl)-8-(6-fluoropyridin-2-yl)-2-[(2'-methyl-2',3'-dihydro-1'H-spiro[cyclopropane-1,4'-isoquinolin]-7'-yl)amino]pyrimido[4,5-d]pyridazin-5(6H)-one;

2-[(2-methyl-1,2,3,4-tetrahydroisoquinolin-7-yl)amino]-8-phenyl-6-(prop-2-en-1-yl)pyrimido[4,5-d]pyridazin-5(6H)-one;

8-(furan-2-yl)-6-(2-methylphenyl)-2-[(2-methyl-1,2,3,4-tetrahydroisoquinolin-7-yl)amino]pyrimido[4,5-d]pyridazin-5(6H)-one;

2-[(4,4-dimethyl-1,2,3,4-tetrahydroisoquinolin-7-yl)amino]-8-(pyridin-2-yl)-6-(pyridin-4-yl)pyrimido[4,5-d]pyridazin-5(6H)-one;

8-(pyridin-2-yl)-6-(pyridin-4-yl)-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2-hydroxyethyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2-chlorophenyl)-2-[(2-methyl-1,2,3,4-tetrahydroisoquinolin-7-yl)amino]-8-phenylpyrimido[4,5-d]pyridazin-5(6H)-one;

6-(2,6-dichlorophenyl)-8-[4-(2-oxopyrrolidin-1-yl)phenyl]-2-(1,2,3,4-tetrahydroisoquinolin-7-ylamino)pyrimido[4,5-d]pyridazin-5(6H)-one;

6-(2,6-dichlorophenyl)-8-(pyrazin-2-yl)-2-(1,2,3,4-tetrahydroisoquinolin-7-ylamino)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one;

6-(2,6-dichlorophenyl)-8-(pyridin-4-yl)-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(6-fluoropyridin-2-yl)pyrimido[4,5-d]pyridazin-5(6H)-one;

8-(furan-2-yl)-2-[(2-methyl-1,2,3,4-tetrahydroisoquinolin-7-yl)amino]-6-(prop-2-en-1-yl)pyrimido[4,5-d]pyridazin-5(6H)-one;

6-cyclohexyl-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6,8-di(pyridin-2-yl)pyrimido[4,5-d]pyridazin-5(6H)-one;

6-(2,6-dichlorophenyl)-8-(1-methyl-1H-pyrazol-3-yl)-2-(1,2,3,4-tetrahydroisoquinolin-7-ylamino)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(propan-2-yl)-8-(pyridin-2-yl)pyrimido[4,5-d]pyridazin-5(6H)-one;

2-[(2'-methyl-2',3'-dihydro-1'H-spiro[cyclopropane-1,4'-isoquinolin]-7'-yl)amino]-6-(propan-2-yl)-8-(pyridin-4-yl)pyrimido[4,5-d]pyridazin-5(6H)-one;

8-cyclobutyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;

8-cyclobutyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;

2-[(4,4-dimethyl-1,2,3,4-tetrahydroisoquinolin-7-yl)amino]-6-(2-hydroxyethyl)-8-(pyridin-2-yl)pyrimido[4,5-d]pyridazin-5(6H)-one;

8-(pyridin-2-yl)-6-(pyridin-3-yl)-2-[(2,4,4-trimethyl-1,2,3,4-tetrahydroisoquinolin-7-yl)amino]pyrimido[4,5-d]pyridazin-5(6H)-one;

6-(2-hydroxypropyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-cyclohexyl-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6-(2-hydroxypropyl)-8-(pyridin-2-yl)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-methylpyrimido[4,5-d]pyridazin-5(6H)-one;

6-(piperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one;

2-[(4,4-dimethyl-1,2,3,4-tetrahydroisoquinolin-7-yl)amino]-6-(piperidin-4-yl)-8-(pyridin-2-yl)pyrimido[4,5-d]pyridazin-5(6H)-one;

2-[(4,4-dimethyl-1,2,3,4-tetrahydroisoquinolin-7-yl)amino]-6-(naphthalen-1-yl)-8-(pyridin-2-yl)pyrimido[4,5-d]pyridazin-5(6H)-one;

6-(2-chloro-6-fluorophenyl)-2-(2',3'-dihydro-1'H-spiro[cyclopropane-1,4'-isoquinolin]-7'-ylamino)-8-methylpyrimido[4,5-d]pyridazin-5(6H)-one;

6-(2-chloro-6-fluorophenyl)-8-methyl-2-[(2,4,4-trimethyl-1,2,3,4-tetrahydroisoquinolin-7-yl)amino]pyrimido[4,5-d]pyridazin-5(6H)-one;

6-(2-chloro-6-fluorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1,3-thiazol-5-yl)pyrimido[4,5-d]pyridazin-5(6H)-one, 6-(2,6-dichlorophenyl)-2-[(2'-methyl-2',3'-dihydro-1'H-spiro[cyclopropane-1,4'-isoquinolin]-7'-yl)amino]-8-(1,3-thiazol-5-yl)pyrimido[4,5-d]pyridazin-5(6H)-one;

6-(2,6-dichlorophenyl)-2-(1,2,3,4-tetrahydroisoquinolin-7-ylamino)-8-(1,3-thiazol-5-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1,3-thiazol-2-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;

6-(2,6-dichlorophenyl)-2-(1,2,3,4-tetrahydroisoquinolin-7-ylamino)pyrimido[4,5-d]pyridazin-5(6H)-one;

6-(1-methylpiperidin-4-yl)-8-(pyridin-2-yl)-2-[(2,4,4-trimethyl-1,2,3,4-tetrahydroisoquinolin-7-yl)amino]pyrimido[4,5-d]pyridazin-5(6H)-one;

2-[(4,4-dimethyl-1,2,3,4-tetrahydroisoquinolin-7-yl)amino]-6-(1-methylpiperidin-4-yl)-8-(pyridin-2-yl)pyrimido[4,5-d]pyridazin-5(6H)-one;

6-(2,6-dimethylcyclohexyl)-8-(pyridin-2-yl)-2-[(2,4,4-trimethyl-1,2,3,4-tetrahydroisoquinolin-7-yl)amino]pyrimido[4,5-d]pyridazin-5(6H)-one;

6-(2,6-dimethylcyclohexyl)-2-[(4,4-dimethyl-1,2,3,4-tetrahydroisoquinolin-7-yl)amino]-8-(pyridin-2-yl)pyrimido[4,5-d]pyridazin-5(6H)-one;

2-[(4,4-dimethyl-1,2,3,4-tetrahydroisoquinolin-7-yl)amino]-6-(1-methylpiperidin-3-yl)-8-(pyridin-2-yl)pyrimido[4,5-d]pyridazin-5(6H)-one;

6-(2-chloro-6-fluorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-[1-(propan-2-yl)-1H-pyrazol-4-yl]pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(2,6-dichlorophenyl)-8-(1-methyl-1H-imidazol-4-yl)-2-(1,2,3,4-tetrahydroisoquinolin-7-ylamino)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1,3-thiazol-2-yl)pyrimido[4,5-d]pyridazin-5(6H)-one;

6-(2,6-dichlorophenyl)-2-(1,2,3,4-tetrahydroisoquinolin-7-ylamino)-8-(1,3-thiazol-2-yl)pyrimido[4,5-d]pyridazin-5(6H)-one;

6-(3-chloropyridin-2-yl)-2-(2',3'-dihydro-1'H-spiro[cyclopropane-1,4'-isoquinolin]-7'-ylamino)-8-methylpyrimido[4,5-d]pyridazin-5(6H)-one;

6-(3-chloropyridin-2-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;

6-(3-chloropyridin-2-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(3-chloropyridin-2-yl)-8-(1-methyl-1H-imidazol-4-yl)-2-(1,2,3,4-tetrahydroisoquinolin-7-ylamino)pyrimido[4,5-d]pyridazin-5(6H)-one;

6-(2,6-dichlorophenyl)-2-(2',3'-dihydro-1'H-spiro[cyclopropane-1,4'-isoquinolin]-7'-ylamino)-8-(1-methyl-1H-imidazol-2-yl)pyrimido[4,5-d]pyridazin-5(6H)-one;

6-(2,6-dichlorophenyl)-2-[(2'-methyl-2',3'-dihydro-1'H-spiro[cyclopropane-1,4'-isoquinolin]-7'-yl)amino]-8-(1-methyl-1H-imidazol-2-yl)pyrimido[4,5-d]pyridazin-5(6H)-one;

6-(3,5-dichloropyridin-4-yl)-2-[(2'-methyl-2',3'-dihydro-1'H-spiro[cyclopropane-1,4'-isoquinolin]-7'-yl)amino]-8-(1-methyl-1H-imidazol-4-yl)pyrimido[4,5-d]pyridazin-5(6H)-one;

6-(2,6-dichlorophenyl)-8-methyl-2-[(2,4,4-trimethyl-1,2,3,4-tetrahydroisoquinolin-7-yl)amino]pyrimido[4,5-d]pyridazin-5(6H)-one;

6-(3-chloropyridin-2-yl)-8-methyl-2-[(2,4,4-trimethyl-1,2,3,4-tetrahydroisoquinolin-7-yl)amino]pyrimido[4,5-d]pyridazin-5(6H)-one;

6-(2,6-dichlorophenyl)-2-{[4,4-dimethyl-2-(2,2,2-trifluoroethyl)-1,2,3,4-tetrahydroisoquinolin-7-yl]amino}-8-methylpyrimido[4,5-d]pyridazin-5(6H)-one;

6-(2,6-dichlorophenyl)-8-methyl-2-(1,2,3,4-tetrahydroisoquinolin-6-ylamino)pyrimido[4,5-d]pyridazin-5(6H)-one;

6-(3,5-dichloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

6-(3-chloropyridin-4-yl)-2-(2',3'-dihydro-1'H-spiro[cyclopropane-1,4'-isoquinolin]-7'-ylamino)-8-(1-methyl-1H-imidazol-4-yl)pyrimido[4,5-d]pyridazin-5(6H)-one;

2-[(2'-acetyl-2',3'-dihydro-1'H-spiro[cyclopropane-1,4'-isoquinolin]-7'-yl)amino]-6-(2,6-dichlorophenyl)-8-(pyridin-2-yl)pyrimido[4,5-d]pyridazin-5(6H)-one;

6-(2,6-dichlorophenyl)-2-{[2'-(methylsulfonyl)-2',3'-dihydro-1'H-spiro[cyclopropane-1,4'-isoquinolin]-7'-yl]amino}-8-(pyridin-2-yl)pyrimido[4,5-d]pyridazin-5(6H)-one;

2-[(2'-acetyl-2',3'-dihydro-1'H-spiro[cyclopropane-1,4'-isoquinolin]-7'-yl)amino]-6-(2,6-dichlorophenyl)-8-(pyridin-4-yl)pyrimido[4,5-d]pyridazin-5(6H)-one;

6-(2,6-dichlorophenyl)-2-{[2'-(methylsulfonyl)-2',3'-dihydro-1'H-spiro[cyclopropane-1,4'-isoquinolin]-7'-yl]amino}-8-(pyridin-4-yl)pyrimido[4,5-d]pyridazin-5(6H)-one;

6-(3-chloropyridin-4-yl)-2-(2',3'-dihydro-1'H-spiro[cyclopropane-1,4'-isoquinolin]-7'-ylamino)-8-(pyridin-4-yl)pyrimido[4,5-d]pyridazin-5(6H)-one;

- 6-(3-chloropyridin-4-yl)-2-(2',3'-dihydro-1'H-spiro[cyclopropane-1,4'-isoquinolin]-7'-ylamino)-8-(pyridin-2-yl)pyrimido[4,5-d]pyridazin-5(6H)-one;
- 8-cyclopropyl-6-(2,6-dichlorophenyl)-2-[(2'-methyl-2',3'-dihydro-1'H-spiro[cyclopropane-1,4'-isoquinolin]-7'-yl)amino]pyrimido[4,5-d]pyridazin-5(6H)-one;
- 8-cyclopropyl-6-(2,6-dichlorophenyl)-2-(1,2,3,4-tetrahydroisoquinolin-7-ylamino)pyrimido[4,5-d]pyridazin-5(6H)-one,
- 8-cyclopropyl-6-(2,6-dichlorophenyl)-2-(2',3'-dihydro-1'H-spiro[cyclopropane-1,4'-isoquinolin]-7'-ylamino)pyrimido[4,5-d]pyridazin-5(6H)-one;
- 6-(2,6-dichlorophenyl)-8-methyl-2-(1,2,3,4-tetrahydroisoquinolin-7-ylamino)pyrimido[4,5-d]pyridazin-5(6H)-one;
- 6-(2-chloro-6-fluorophenyl)-8-methyl-2-(1,2,3,4-tetrahydroisoquinolin-7-ylamino)pyrimido[4,5-d]pyridazin-5(6H)-one;
- 6-(3-chloropyridin-2-yl)-8-methyl-2-(1,2,3,4-tetrahydroisoquinolin-7-ylamino)pyrimido[4,5-d]pyridazin-5(6H)-one;
- 6-(2,6-dichlorophenyl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;
- 6-(2,6-dichlorophenyl)-8-ethyl-2-[(2'-methyl-2',3'-dihydro-1'H-spiro[cyclopropane-1,4'-isoquinolin]-7'-yl)amino]pyrimido[4,5-d]pyridazin-5(6H)-one;
- 6-(2,6-dichlorophenyl)-8-ethyl-2-(1,2,3,4-tetrahydroisoquinolin-7-ylamino)pyrimido[4,5-d]pyridazin-5(6H)-one;
- 6-(2,6-dichlorophenyl)-2-(2',3'-dihydro-1'H-spiro[cyclopropane-1,4'-isoquinolin]-7'-ylamino)-8-ethylpyrimido[4,5-d]pyridazin-5(6H)-one;
- 6-(2,6-dichlorophenyl)-8-(difluoromethyl)-2-(2',3'-dihydro-1'H-spiro[cyclopropane-1,4'-isoquinolin]-7'-ylamino)pyrimido[4,5-d]pyridazin-5(6H)-one;
- 6-(2,6-dichlorophenyl)-8-(difluoromethyl)-2-(1,2,3,4-tetrahydroisoquinolin-7-ylamino)pyrimido[4,5-d]pyridazin-5(6H)-one;
- 6-(2,6-dichlorophenyl)-8-(difluoromethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
- 6-(2,6-dichlorophenyl)-2-[(2'-methyl-2',3'-dihydro-1'H-spiro[cyclopropane-1,4'-isoquinolin]-7'-yl)amino]-8-(trifluoromethyl)pyrimido[4,5-d]pyridazin-5(6H)-one;
- 2-[(2'-acetyl-2',3'-dihydro-1'H-spiro[cyclopropane-1,4'-isoquinolin]-7'-yl)amino]-6-(2,6-dichlorophenyl)-8-(difluoromethyl)pyrimido[4,5-d]pyridazin-5(6H)-one;
- 7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-carboxamide;
- 2-[(2'-acetyl-2',3'-dihydro-1'H-spiro[cyclopropane-1,4'-isoquinolin]-7'-yl)amino]-6-(2,6-dichlorophenyl)-8-methylpyrimido[4,5-d]pyridazin-5(6H)-one;
- 6-(2,6-dichlorophenyl)-2-(2',3'-dihydro-1'H-spiro[cyclopropane-1,4'-isoquinolin]-7'-ylamino)-8-(trifluoromethyl)pyrimido[4,5-d]pyridazin-5(6H)-one;
- 6-(2,6-dichlorophenyl)-2-(1,2,3,4-tetrahydroisoquinolin-7-ylamino)-8-(trifluoromethyl)pyrimido[4,5-d]pyridazin-5(6H)-one;
- 6-(2,6-dichlorophenyl)-2-{[2'-(hydroxyacetyl)-2',3'-dihydro-1'H-spiro[cyclopropane-1,4'-isoquinolin]-7'-yl]amino}-8-methylpyrimido[4,5-d]pyridazin-5(6H)-one;
- 6-(2,6-dichlorophenyl)-8-methyl-2-{[2'-(methylsulfonyl)-2',3'-dihydro-1'H-spiro[cyclopropane-1,4'-isoquinolin]-7'-yl]amino}pyrimido[4,5-d]pyridazin-5(6H)-one;
- 6-(2,6-dichlorophenyl)-2-(2',3'-dihydro-1'H-spiro[cyclopropane-1,4'-isoquinolin]-7'-ylamino)-8-(methoxymethyl)pyrimido[4,5-d]pyridazin-5(6H)-one;
- 6-(2,6-dichlorophenyl)-8-(methoxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
- 6-(2,6-dichlorophenyl)-8-(hydroxymethyl)-2-[(2'-methyl-2',3'-dihydro-1'H-spiro[cyclopropane-1,4'-isoquinolin]-7'-yl)amino]pyrimido[4,5-d]pyridazin-5(6H)-one;
- 6-(2,6-dichlorophenyl)-2-(2',3'-dihydro-1'H-spiro[cyclopropane-1,4'-isoquinolin]-7'-ylamino)-8-(hydroxymethyl)pyrimido[4,5-d]pyridazin-5(6H)-one;
- 7-{[6-(2,6-dichlorophenyl)-8-methyl-5-oxo-5,6-dihydropyrimido[4,5-d]pyridazin-2-yl]amino}-3,4-dihydroisoquinoline-2(1H)-sulfonamide;
- 6-(2,6-dichlorophenyl)-8-methyl-2-[(2-methyl-1,2,3,4-tetrahydroisoquinolin-6-yl)amino]pyrimido[4,5-d]pyridazin-5(6H)-one;
- 7'-{[6-(2,6-dichlorophenyl)-8-methyl-5-oxo-5,6-dihydropyrimido[4,5-d]pyridazin-2-yl]amino}-1'H-spiro[cyclopropane-1,4'-isoquinoline]-2'(3'H)-sulfonamide;
- 6-(2,6-dichlorophenyl)-2-{[2-(2-hydroxy-2-methylpropanoyl)-1,2,3,4-tetrahydroisoquinolin-6-yl]amino}-8-methylpyrimido[4,5-d]pyridazin-5(6H)-one;
- 6-(2,6-dichlorophenyl)-2-[(4,4-dimethyl-1,2,3,4-tetrahydroisoquinolin-7-yl)amino]-8-methylpyrimido[4,5-d]pyridazin-5(6H)-one;
- 2-[(2-acetyl-4,4-dimethyl-1,2,3,4-tetrahydroisoquinolin-7-yl)amino]-6-(2,6-dichlorophenyl)-8-methylpyrimido[4,5-d]pyridazin-5(6H)-one;
- 2-{[2-(cyclopropylcarbonyl)-4,4-dimethyl-1,2,3,4-tetrahydroisoquinolin-7-yl]amino}-6-(2,6-dichlorophenyl)-8-methylpyrimido[4,5-d]pyridazin-5(6H)-one;
- 6-(2,6-dichlorophenyl)-2-{[4,4-dimethyl-2-(methylsulfonyl)-1,2,3,4-tetrahydroisoquinolin-7-yl]amino}-8-methylpyrimido[4,5-d]pyridazin-5(6H)-one;
- 6-(2,6-dichlorophenyl)-8-methyl-2-[(1,1,2-trimethyl-1,2,3,4-tetrahydroisoquinolin-7-yl)amino]pyrimido[4,5-d]pyridazin-5(6H)-one;
- 6-(2,6-dichlorophenyl)-2-[(1,1-dimethyl-1,2,3,4-tetrahydroisoquinolin-7-yl)amino]-8-methylpyrimido[4,5-d]pyridazin-5(6H)-one;
- 6-(3,5-dichloropyridin-4-yl)-2-(2',3'-dihydro-1'H-spiro[cyclopropane-1,4'-isoquinolin]-7'-ylamino)-8-methylpyrimido[4,5-d]pyridazin-5(6H)-one;
- 6-(3,5-dichloropyridin-4-yl)-8-methyl-2-(1,2,3,4-tetrahydroisoquinolin-6-ylamino)pyrimido[4,5-d]pyridazin-5(6H)-one;
- 2-[(2-acetyl-1,2,3,4-tetrahydroisoquinolin-6-yl)amino]-6-(2,6-dichlorophenyl)-8-methylpyrimido[4,5-d]pyridazin-5(6H)-one;
- 6-(2,6-dichlorophenyl)-8-methyl-2-{[2-(methylsulfonyl)-1,2,3,4-tetrahydroisoquinolin-6-yl]amino}pyrimido[4,5-d]pyridazin-5(6H)-one;
- 6-(2,6-dichlorophenyl)-2-(2,3-dihydro-1H-isoindol-5-ylamino)-8-methylpyrimido[4,5-d]pyridazin-5(6H)-one;
- 6-(2,6-dichlorophenyl)-2-[(1,1-dimethyl-1,2,3,4-tetrahydroisoquinolin-6-yl)amino]-8-methylpyrimido[4,5-d]pyridazin-5(6H)-one;
- 6-(2,6-dichlorophenyl)-8-methyl-2-[(1,1,2-trimethyl-1,2,3,4-tetrahydroisoquinolin-6-yl)amino]pyrimido[4,5-d]pyridazin-5(6H)-one;
- 6-(2,6-dichlorophenyl)-8-ethyl-2-[(1,1,2-trimethyl-1,2,3,4-tetrahydroisoquinolin-6-yl)amino]pyrimido[4,5-d]pyridazin-5(6H)-one;

6-(2,6-dichlorophenyl)-8-ethyl-2-[(1,1,2-trimethyl-1,2,3,4-tetrahydroisoquinolin-7-yl)amino]pyrimido[4,5-d]pyridazin-5(6H)-one;
6-(2,6-dichlorophenyl)-2-[(4,4-dimethyl-1,2,3,4-tetrahydroisoquinolin-7-yl)amino]-8-ethylpyrimido[4,5-d]pyridazin-5(6H)-one;
6-(2,6-dichlorophenyl)-2-[(1,1-dimethyl-1,2,3,4-tetrahydroisoquinolin-7-yl)amino]-8-ethylpyrimido[4,5-d]pyridazin-5(6H)-one;
6-(2,6-dichlorophenyl)-8-ethyl-2-[(3-oxo-1,2,3,4-tetrahydroisoquinolin-7-yl)amino]pyrimido[4,5-d]pyridazin-5(6H)-one;
6-(2,6-dichlorophenyl)-2-[(1,1-dimethyl-1,2,3,4-tetrahydroisoquinolin-6-yl)amino]-8-ethylpyrimido[4,5-d]pyridazin-5(6H)-one;
6-(2,6-dichlorophenyl)-8-methyl-2-[(3-oxo-1,2,3,4-tetrahydroisoquinolin-7-yl)amino]pyrimido[4,5-d]pyridazin-5(6H)-one;
6-(2,6-dichlorophenyl)-8-methyl-2-[(1,1,2-trimethyl-2,3-dihydro-1H-isoindol-5-yl)amino]pyrimido[4,5-d]pyridazin-5(6H)-one;
2-[(7-chloro-1,2,3,4-tetrahydroisoquinolin-6-yl)amino]-6-(2,6-dichlorophenyl)-8-methylpyrimido[4,5-d]pyridazin-5(6H)-one;
6-(2,6-dichlorophenyl)-8-(difluoromethyl)-2-(1,2,3,4-tetrahydroisoquinolin-6-ylamino)pyrimido[4,5-d]pyridazin-5(6H)-one;
6-(2,6-dichlorophenyl)-8-(difluoromethyl)-2-[(2-methyl-1,2,3,4-tetrahydroisoquinolin-6-yl)amino]pyrimido[4,5-d]pyridazin-5(6H)-one;
6-(2,6-dichlorophenyl)-8-(difluoromethyl)-2-[(2-methyl-1,2,3,4-tetrahydroisoquinolin-7-yl)amino]pyrimido[4,5-d]pyridazin-5(6H)-one;
2-[(2-acetyl-1,2,3,4-tetrahydroisoquinolin-6-yl)amino]-6-(2,6-dichlorophenyl)-8-(difluoromethyl)pyrimido[4,5-d]pyridazin-5(6H)-one;
2-[(2-acetyl-1,2,3,4-tetrahydroisoquinolin-7-yl)amino]-6-(2,6-dichlorophenyl)-8-(difluoromethyl)pyrimido[4,5-d]pyridazin-5(6H)-one;
6-(2,6-dichlorophenyl)-8-(difluoromethyl)-2-[(4,4-dimethyl-1,2,3,4-tetrahydroisoquinolin-7-yl)amino]pyrimido[4,5-d]pyridazin-5(6H)-one;
6-(2,6-dichlorophenyl)-2-[(7-fluoro-1,2,3,4-tetrahydroisoquinolin-6-yl)amino]-8-methylpyrimido[4,5-d]pyridazin-5(6H)-one;
6-(2-chlorophenyl)-8-methyl-2-(1,2,3,4-tetrahydroisoquinolin-6-ylamino)pyrimido[4,5-d]pyridazin-5(6H)-one;
6-(2-chlorophenyl)-2-[(4,4-dimethyl-1,2,3,4-tetrahydroisoquinolin-7-yl)amino]-8-methylpyrimido[4,5-d]pyridazin-5(6H)-one;
6-(2-chlorophenyl)-8-methyl-2-[(2,4,4-trimethyl-1,2,3,4-tetrahydroisoquinolin-7-yl)amino]pyrimido[4,5-d]pyridazin-5(6H)-one;
6-(2,6-dichlorophenyl)-8-(difluoromethyl)-2-[(1,1,2-trimethyl-2,3-dihydro-1H-isoindol-5-yl)amino]pyrimido[4,5-d]pyridazin-5(6H)-one;
6-(3,5-dichloropyridin-4-yl)-8-methyl-2-[(2'-methyl-2',3'-dihydro-1'H-spiro[cyclopropane-1,4'-isoquinolin]-7'-yl)amino]pyrimido[4,5-d]pyridazin-5(6H)-one;
6-(3,5-dichloropyridin-4-yl)-8-methyl-2-[(1,1,2-trimethyl-2,3-dihydro-1H-isoindol-5-yl)amino]pyrimido[4,5-d]pyridazin-5(6H)-one;
6-(2,6-dichlorophenyl)-2-[(1,1-dimethyl-2,3-dihydro-1H-isoindol-5-yl)amino]-8-methylpyrimido[4,5-d]pyridazin-5(6H)-one;
6-(2,6-dichlorophenyl)-8-methyl-2-[(2-methyl-1,2,3,4-tetrahydroisoquinolin-7-yl)amino]pyrimido[4,5-d]pyridazin-5(6H)-one;
6-(2,6-dichlorophenyl)-8-methyl-2-[(2-methyl-2,3-dihydro-1H-isoindol-5-yl)amino]pyrimido[4,5-d]pyridazin-5(6H)-one;
6-(2,6-dichlorophenyl)-8-ethyl-2-[(2-methyl-1,2,3,4-tetrahydroisoquinolin-6-yl)amino]pyrimido[4,5-d]pyridazin-5(6H)-one;
6-(2,6-dichlorophenyl)-8-ethyl-2-[(2-methyl-1,2,3,4-tetrahydroisoquinolin-7-yl)amino]pyrimido[4,5-d]pyridazin-5(6H)-one;
6-(2,6-dichlorophenyl)-8-ethyl-2-[(2-methyl-2,3-dihydro-1H-isoindol-5-yl-amino]pyrimido[4,5-d]pyridazin-5(6H)-one;
6-(2-chloro-6-methylphenyl)-8-methyl-2-(1,2,3,4-tetrahydroisoquinolin-7-ylamino)pyrimido[4,5-d]pyridazin-5(6H)-one;
6-(2-chloro-6-methylphenyl)-8-methyl-2-(1,2,3,4-tetrahydroisoquinolin-6-ylamino)pyrimido[4,5-d]pyridazin-5(6H)-one;
6-(2-chloro-6-methylphenyl)-2-[(4,4-dimethyl-1,2,3,4-tetrahydroisoquinolin-7-yl)amino]-8-methylpyrimido[4,5-d]pyridazin-5(6H)-one;
6-(2-chloro-6-methylphenyl)-8-methyl-2-[(2,4,4-trimethyl-1,2,3,4-tetrahydroisoquinolin-7-yl)amino]pyrimido[4,5-d]pyridazin-5(6H)-one;
6-(2-chloro-6-methylphenyl)-2-{[2-(2-hydroxyethyl)-1,2,3,4-tetrahydroisoquinolin-7-yl]amino}-8-methylpyrimido[4,5-d]pyridazin-5(6H)-one;
and pharmaceutically acceptable salts thereof.

10. A pharmaceutical composition comprising a compound, or a pharmaceutically acceptable salt thereof, of claim 1 and pharmaceutically acceptable excipient.

* * * * *